(12) United States Patent
Wang et al.

(10) Patent No.: US 9,644,021 B2
(45) Date of Patent: May 9, 2017

(54) BOVINE FUSION ANTIBODIES

(71) Applicant: The California Institute for Biomedical Research, La Jolla, CA (US)

(72) Inventors: Feng Wang, Carlsbad, CA (US); Yong Zhang, San Diego, CA (US); Peter G. Schultz, La Jolla, CA (US)

(73) Assignee: THE CALIFORNIA INSTITUTE FOR BIOMEDICAL RESEARCH, La Jolla, CA (US)

( * ) Notice: Subject to any disclaimer, the term of this patent is extended or adjusted under 35 U.S.C. 154(b) by 0 days.

(21) Appl. No.: 14/152,441

(22) Filed: Jan. 10, 2014

(65) Prior Publication Data

US 2014/0227267 A1 Aug. 14, 2014

Related U.S. Application Data

(60) Provisional application No. 61/751,598, filed on Jan. 11, 2013.

(51) Int. Cl.
| | | |
|---|---|---|
| *C07K 16/00* | (2006.01) | |
| *C07K 16/28* | (2006.01) | |
| *C07K 14/575* | (2006.01) | |
| *C07K 14/605* | (2006.01) | |
| *C07K 14/61* | (2006.01) | |
| *C07K 14/635* | (2006.01) | |
| *C07K 14/64* | (2006.01) | |
| *C07K 14/81* | (2006.01) | |
| *C07K 7/08* | (2006.01) | |

(52) U.S. Cl.
CPC ............... *C07K 16/00* (2013.01); *C07K 7/08* (2013.01); *C07K 14/575* (2013.01); *C07K 14/5759* (2013.01); *C07K 14/605* (2013.01); *C07K 14/61* (2013.01); *C07K 14/635* (2013.01); *C07K 14/64* (2013.01); *C07K 14/811* (2013.01); *C07K 16/2869* (2013.01); *C07K 2317/565* (2013.01); *C07K 2318/10* (2013.01); *C07K 2319/00* (2013.01); *C07K 2319/30* (2013.01)

(58) Field of Classification Search
None
See application file for complete search history.

(56) References Cited

U.S. PATENT DOCUMENTS

| | | |
|---|---|---|
| 6,498,020 B1 | 12/2002 | Walker et al. |
| 6,740,747 B2 | 5/2004 | Kaushik et al. |
| 7,166,697 B1 | 1/2007 | Galanis et al. |
| 7,196,185 B2 | 3/2007 | Kaushik et al. |
| 7,575,893 B2 | 8/2009 | Simmons |
| 7,592,010 B2 | 9/2009 | Rosen et al. |
| 7,977,071 B2 | 7/2011 | Nuttall et al. |
| 2003/0088074 A1 | 5/2003 | Hamers et al. |
| 2003/0170646 A1 | 9/2003 | Kaushik et al. |
| 2003/0232395 A1 | 12/2003 | Hufton |
| 2006/0160995 A1 | 7/2006 | Baker et al. |
| 2006/0275254 A1 | 12/2006 | Kim et al. |
| 2008/0152586 A1 | 6/2008 | Hudson et al. |
| 2009/0286964 A1 | 11/2009 | Gegg et al. |
| 2009/0304580 A1 | 12/2009 | Goldenberg et al. |
| 2010/0136032 A1 | 6/2010 | Weinberg et al. |
| 2010/0311119 A1 | 12/2010 | Hermans et al. |
| 2011/0172125 A1 | 7/2011 | Ladner |
| 2011/0269938 A1 | 11/2011 | Nuttall et al. |
| 2012/0128672 A1 | 5/2012 | Keer |
| 2012/0302737 A1 | 11/2012 | Christensen et al. |
| 2014/0050720 A1 | 2/2014 | Smider et al. |
| 2014/0086871 A1 | 3/2014 | Smider et al. |

(Continued)

FOREIGN PATENT DOCUMENTS

| | | |
|---|---|---|
| EP | 2194066 A1 | 6/2010 |
| EP | 2322228 A1 | 5/2011 |
| WO | WO-8907142 A1 | 8/1989 |

(Continued)

OTHER PUBLICATIONS

Wynne et al. (International Journal of Obesity, 30: 1729-1736, 2006).*
Brumeanu et al. (J. Exp. Med., 178: 1795-1799, 1993).*
Roche et al. (J. Dairy Sci., 92: 5769-5801, 2009).*
NCBI, PDB accession No. 4K3D_H (Jul. 3, 2013).
Almagro et al., Characterization of a High-Affinity Human Antibody with a Disulfide bridge in the Third Complementarity-Determining Region of the Heavy Chain. J. Mol. Recognit. 25:125-135 (2012).

(Continued)

*Primary Examiner* — Brad Duffy
*Assistant Examiner* — Nelson B Moseley, II
(74) *Attorney, Agent, or Firm* — Wilson Sonsini Goodrich & Rosati

(57) ABSTRACT

Disclosed herein are immunoglobulin constructs comprising at least one immunoglobulin domain or fragment thereof; and a therapeutic polypeptide or derivative or variant thereof attached to or inserted into said immunoglobulin domain. Also provided are immunoglobulin constructs comprising a mammalian immunoglobulin heavy chain comprising at least a portion of a knob domain in the complementarity-determining region 3 (CDR3H) or fragment thereof; and a therapeutic polypeptide attached to or inserted into said knob domain of the CDR3H. Also provided are immunoglobulin constructs comprising a mammalian immunoglobulin heavy chain comprising at least a portion of a stalk domain in the complementarity-determining region 3 (CDR3H) or fragment thereof; and a therapeutic polypeptide attached to or inserted into said stalk domain of the CDR3H. Also described herein are methods and compositions comprising the immunoglobulin constructs described herein for treatment and prevention of a disease or condition in a subject.

19 Claims, 2 Drawing Sheets

(56) References Cited

U.S. PATENT DOCUMENTS

| | | |
|---|---|---|
| 2015/0011431 A1 | 1/2015 | Smider et al. |
| 2016/0237156 A1 | 8/2016 | Wang et al. |

FOREIGN PATENT DOCUMENTS

| | | |
|---|---|---|
| WO | WO-9320210 A1 | 10/1993 |
| WO | WO-9418221 A1 | 8/1994 |
| WO | WO-0103737 A1 | 1/2001 |
| WO | WO-0222809 A2 | 3/2002 |
| WO | WO-03030821 A2 | 4/2003 |
| WO | WO-03085086 A2 | 10/2003 |
| WO | WO-2005007809 A2 | 1/2005 |
| WO | WO 2010/028791 A1 | 3/2010 |
| WO | WO-2011044542 A1 | 4/2011 |
| WO | WO-2012169822 A2 | 12/2012 |
| WO | WO 2013/106485 | 7/2013 |
| WO | WO-2013106489 A1 | 7/2013 |

OTHER PUBLICATIONS

Berens, et al. Use of a single VH family and long CDR3s in the variable region of cattle Ig heavy chains. Int Immunol. Jan. 1997;9(1):189-199.

Collis et al., Analysis of the Antigen Combining Site: Correlations Between Length and Sequence Composition of the Hypervariable Loops and the Nature of the Antigen. J. Mol. Biol. 325: 337-354 (2003).

Ekiert et al., Cross-Neutralization of Influenza A viruses mediated by a Single Antibody Loop. Nature. 489: 526-532 (2012).

Elsik et al., The Genome Sequence of Taurine Cattle: A window to ruminant biology and evolution. Science. 324 (5926): 522-528 (2009).

Henderson et al., 2007, Structure of an IgNAR-AMA1 Complex: Targeting a Conserved Hydrophobic Cleft Broadens Malarial Strain Recognition. Structure. 15: 1452-1466 (2007).

Hosseini, et al. Duplicated copies of the bovine JH locus contribute to the Ig repertoire. Int Immunol. Jun. 2004;16(6):843-852.

Kaushik, et al., Somatic hypermutations and isotype restricted exceptionally long CDR3H contribute to antibody diversification in cattle. Vet Immunol Immunopathol. Jan. 15, 2009;127(1-2):106-13.

Kaushik, et al., Novel Insight into Antibody Diversification from Cattle. Veterinary Immunology and Immunopathology. 87: 347-350 (2002).

Koti, et al. Novel atypical nucleotide insertions specifically at VH-DH junction generate exceptionally long CDR3H in cattle antibodies. Mol Immunol. Jul. 2010;47(11-12):2119-2128.

Koti et al., Organization of DH-Gene Locus is Distinct in Cattle. Dev Biol. (Basel) 132: 307-313 (2008).

Krause et al, An insertion mutation that distorts antibody binding site architecture enhances function of a human antibody. MBio 2(1):e00345-10 (2011).

Lopez et al., A Single VH Family and long CDR3 are the targets for Hypermutation in Bovine Immunoglobulin Heavy Chains. Immunological Reviews. 162: 55-66 (1998).

McLellan et al., Structure of HIV-1 gp120 V1/V2 domain with broadly neutralizing antibody PG9. Nature. 480 (7377): 336-343 (2011).

NCBI, GenBank Accession No. DM113215.1, Jun. 18, 2009.

Nuttall et al, Design and expression of soluble CTLA-4 variable domain as a scaffold for the display of functional polypeptides. Proteins: Structure, Function and Genetics. 36: 217-227 (1999).

PCT/US2014/011043 Search Report and Written Opinion dated May 1, 2014.

Pejchal et al., Structure and Function of Broadly Reactive Antibody PG16 Reveal an H3 Subdomain that Mediates Potent Neutralization of HIV-1. PNAS. 107(25): 11483-11488 (2010).

Saini, et al. Exceptionally long CDR3H region with multiple cysteine residues in functional bovine IgM antibodies. Eur J Immunol. Aug. 1999;29(8):2420-2426.

Saini, et al. Extensive CDR3H length heterogeneity exists in bovine foetal VDJ rearrangements. Scand J Immunol. Feb. 2002;55(2):140-148.

Saini, et al., Bovine IgM antibodies with exceptionally long complementarity-determining region 3 of the heavy chain share unique structural properties conferring restricted VH + Vlambda pairings. Int Immunol. 15(7): 845-853 (2003).

Saphire et al., Crystal Structure of a Neutralizing Human IgG Against HIV-1: A Template for Vaccine Design. Science. 293: 1155-1159 (2001).

Shojaei, et al., Unusually long Germline DH Genes Contribute to Large Sized CDR3H in Bovine Antibodies. Mol Immunol. 40: 61-67 (2003).

Wang, et al., Reshaping Antibody Diversity. Cell. 153: 1379-1393 (2013).

Zaghouani, et al. Engineered immunoglobulin molecules as vehicles for T cell epitopes. Int Rev Immunol. 1993;10(2-3):265-78.

Zhang, et al. An Antibody with a Variable-Region Coiled-Coil "Knob" Domain. Angew. Chem. Int. Ed. 53: 132-135 (2014).

Zhang, et al. An Antibody CDR3-Erythropoietin Fusion Protein. ACS Chem. Biol. 8:2117-2121 (2013).

Zhang, et al., Functional Antibody CDR3 fusion proteins with enhanced pharmalogical properties. Agnew. Chem. Int. Ed. 52: 8295-8298 (2013).

Zhao et al., The Bovine Antibody Repertoire. Dev Comp Immunol. 30: 175-186 (2006).

Zhong et al, Small antibody fusion proteins with complementarity-determining regions and lidamycin for tumor targeting therapy. Oncol Lett. 5: 1183-188 (2013).

Casset et al. A peptide mimetic of an anti-CD4 monoclonal antibody by rational design Biochemical and Biophysical Research Communications, vol. 307, pp. 198-205 (2003).

Chen et al.Selection and analysis of an Optimized Anti-VEGF Antibody: Structure of an Affinity-matured Fab in Complex with Antigen Journal of Molecular Biology, vol. 293, pp. 865-881(1999).

Co-pending U.S. Appl. No. 14/760,115, filed Jul. 9, 2015.

Ngo, J. Thomas et al. Computational Complexity, Protein Structure Prediction, and the Levinthal Paradox, Birkhauser, pp. 433-440, 492-495, 1994.

Paul, W.E. Fundamental Immunology, Third Edition (textbook). Fv Structure and Diversity in Three Dimensions pp. 292-295; Raven Press, New York (1993).

U.S. Appl. No. 13/737,910 Final Office Action Dated Jun. 4, 2015.

U.S. Appl. No. 13/737,910 Office Action Dated Oct. 16, 2014.

Wells, James A. Additivity of Mutational Effects in Proteins, vol. 29, No. 37, pp. 8509-8517 (Sep. 18, 1990).

Xiao-Qing Qiu et al., Small antibody mimetics comprising two complementarity-determining regions and a framework region for tumor targeting. Nature Biotechnology Aug. 2007, vol. 25, No. 8, pp. 921-929.

Chain H, Crystal Structure of Bovine Antibody Blv5b8 With Ultralong Cdr H3.Accessed PDB: 4K3E-H NCBI Feb. 12, 2016 (http://www.ncbi.nlm.nih.gov/protein/4K3E_H).

Edgar. MUSCLE: multiple sequence alignment with high accuracy and high throughput. Nucleic Acids Res. 32(5):1792-1797 (2004).

Glaser, et al Novel antibody hinge regions for efficient production of CH2 domain-deleted antibodies. The Journal of Biological Chemistry, vol. 280, No. 50, pp. 41494-41503 (2005).

Immunoglobulin heavy chain variable region BF1H1, partial [Bos taurus]. Accessed from GenBank: AAC71038.1. NCBI on Feb. 12, 2016 (http://ncbi.nlm.nig.gov/protein/AAC71038.1).

Immunoglobulin light chain variable region, partial [Bos taurus] GenBank: AAB81517.1 Accessed via NCBI Feb. 12, 2016 (http://ncbi.nlm.nih.gov/protein/2555151).

Immunoglobulin light chain variable region, partial [Bos taurus]. Accessed Feb. 12, 2016 via NCBI GenBank: AAB66580.1 (http://ncbi.nlm.nih.gov/protein/2323408).

Nuttall et al. Selection and affinity maturation of IgNAR variable domains targeting Plasmodium falciparum AMA1.Protein: Structure, Function and Biioinformatics. vol. 55, Issue 1 Apr. 2004, pp. 187-197.

(56) References Cited

OTHER PUBLICATIONS

Simmons et al. Shark IgNAR antibody mimotopes target a murine immunoglobulin through extended CDR3 loop structures. Proteins: Structure, Function and Bioinformatics vol. 71, Issue 1 Apr. 2008, pp. 119-130.

Streltsov et al. Crystal Structure of the Amyloid p3 Fragment Provides a Model for Oligomer Formation in Alzheimers Disease The Journal of Neuroscience, Jan. 26, 2011, 31(4):1419-1426, 1419 (with Supplemental Data).

Qin W. et al. Fusion protein of CDR mimetic peptide with Fc inhibit TNF-alpha induced cytotoxicity, Molecular Immunology, 43(6); 660-666 (Feb. 1, 2006).

Yang Xi et al. The three complementarity-determining region-like loops in the second extracellular domain of human Fc alpha/mu receptor contribute to its binding of IgA and Igm. Immunobiology,Urban Und Fischer Verlag, DE, 218(5); 798-809 (Oct. 4, 2012).

Inoue Hidetoshi et al. Affinity transfer to a human protein by CDR3 grafting of camelid VHH, Protein Science: A Publication of the Protein Society. vol. 20, No. 12. Dec. 2011, pp. 1971-1981.

Pistillo MP et al. Molecular Characterization and Applications of Recombinant scFv Antibodies to CD152 Co-Stimulatory Molecule, Tissue Antigens, Munksgaard, Copenhagen, DK, vol. 55, No. 3, Mar. 1, 2000, pp. 229-238.

Ramsland PA et al. Incorporation of long CDR3s into V domains: implications for the structural evolution of the antibody-combining site, Experimental and Clinical Immunogenetics, S. Karger, Basel, CH, vol. 18, No. 4, Jan. 1, 2001, pp. 176-198.

Li, Tengfei et al. Cell-penetrating anti-GFAP VHH and corresponding fluorescent fusion protein VHH-GFP spontaneously cross the blood-brain barrier and specifically recognize astrocytes: application to brain imaging. The FASEB Journal 26:1-11 (Oct. 2012).

U.S. Appl. No. 14/760,115 Non-final Office Action Mailed Feb. 10, 2017.

\* cited by examiner

R: reduced condition; N: non-reduced condition

BOVINE FUSION ANTIBODIES

CROSS-REFERENCE TO RELATED APPLICATIONS

This application claims the benefit of U.S. Provisional Application No. 61/751,598, filed Jan. 11, 2013, which is incorporated by reference herein in its entirety.

SEQUENCE LISTING

The instant application contains a Sequence Listing which has been submitted in ASCII format via EFS-Web and is hereby incorporated by reference in its entirety. Said ASCII copy, created on Apr. 3, 2014, is named 41135-703-201-SL.txt and is 93.4 Kilobytes in size.

In compliance with 37 C.F.R. §1.71(g)(1), disclosure is made that the claimed invention was made pursuant to a Joint Research Agreement as defined in 35 U.S.C. 103(c)(3), that was in effect on or before the date the claimed invention was made, and as a result of activities undertaken within the scope of the Joint Research Agreement, by or on the behalf of The California Institute for Biomedical Research and The Scripps Research Institute.

SEQUENCE LISTING

The instant application contains a Sequence Listing which has been submitted in ASCII format via EFS-Web and is hereby incorporated by reference in its entirety. Said ASCII copy, created on Apr. 3, 2014, is named 41135-703-201-SL.txt and is 93.4 Kilobytes in size.

FIELD OF THE INVENTION

Described herein are immunoglobulin constructs comprising at least a portion of an ultralong CDR3, methods of making such constructs, pharmaceutical compositions and medicaments comprising such constructs, and methods of using such constructs and compositions to prevent, inhibit, and/or treat a disease or condition in a subject.

BACKGROUND

Antibodies are natural proteins that the vertebrate immune system forms in response to foreign substances (antigens), primarily for defense against infection. For over a century, antibodies have been induced in animals under artificial conditions and harvested for use in therapy or diagnosis of disease conditions, or for biological research. Each individual antibody producing cell produces a single type of antibody with a chemically defined composition, however, antibodies obtained directly from animal serum in response to antigen inoculation actually comprise an ensemble of non-identical molecules (e.g., polyclonal antibodies) made from an ensemble of individual antibody producing cells.

Some bovine antibodies have unusually long VH CDR3 sequences compared to other vertebrates. For example, about 10% of IgM contains "ultralong" CDR3 sequences, which can be up to 61 amino acids long. These unusual CDR3s often have multiple cysteines. Functional VH genes form through a process called V(D)J recombination, wherein the D-region encodes a significant proportion of CDR3. A unique D-region encoding an ultralong sequence has been identified in cattle. Ultralong CDR3s are partially encoded in the cattle genome, and provide a unique characteristic of their antibody repertoire in comparison to humans. Kaushik et al. (U.S. Pat. Nos. 6,740,747 and 7,196,185) disclose several bovine germline D-gene sequences unique to cattle stated to be useful as probes and a bovine VDJ cassette stated to be useful as a vaccine vector.

SUMMARY OF THE INVENTION

In some embodiments is a recombinant antibody or fragment thereof, wherein at least a portion of the recombinant antibody or fragment thereof is based on or derived from at least a portion of an ultralong CDR3.

In some embodiments is an antibody or fragment thereof comprising: (a) a first antibody sequence, wherein at least a portion of the first antibody sequence is derived from at least a portion of an ultralong CDR3; (b) a non-antibody sequence; and (c) optionally, a second antibody sequence, wherein at least a portion of the second antibody sequence is derived from at least a portion of an ultralong CDR3.

The antibodies disclosed herein may be a chimeric, human engineered, or humanized antibody. The antibodies disclosed herein may be a bovinized or fully bovine antibody. The antibodies disclosed herein may comprise a Fab, a scFv, dsFv, diabody, $(dsFv)_2$, minibody, flex minibody or bi-specific fragment. The antibodies disclosed herein may be an isolated antibody.

The antibodies disclosed herein may further comprise a non-antibody sequence. The non-antibody sequence may be derived from a mammal. The mammal may be a bovine, human, or non-bovine mammal. The antibodies disclosed herein may comprise a non-antibody sequence derived from a non-bovine animal. The non-bovine animal may be a scorpion. The non-bovine animal may be a lizard. The lizard may be a gila monster. The non-antibody sequence may be a derived from a growth factor. The growth factor may be a GCSF, GMCSF or FGF21. The GCSF may be a bovine GCSF. Alternatively, the GCSF may be a human GCSF. The GMCSF and/or the FGF21 may be from a human. The non-antibody sequence may be a derived from a cytokine. The cytokine may be a beta-interferon. The non-antibody sequence may be a derived from a hormone. The hormone may be an exendin-4, GLP-1, parathyroid hormone or erythropoietin. The GLP-1 and/or erythropoietin may be from a human. The non-antibody sequence may be a derived from a toxin. The toxin may be a Moka1, Mamba1, Amgen1, 550 peptide or VM-24. The non-antibody sequence may be derived from or based on a synthetic peptide. The synthetic peptide may be oxyntomodulin. The non-antibody sequences disclosed herein may replace at least a portion of the ultralong CDR3. The non-antibody sequences disclosed herein may be inserted into the sequence of the ultralong CDR3.

The antibodies disclosed herein may comprise an ultralong CDR3 may be based on or derived from a cow ultralong CDR3. At least a portion of the antibodies disclosed herein may be from a mammal. At least a portion of the first antibody sequence and/or at least a portion of the second antibody sequence of the antibodies disclosed herein may be from a mammal. The mammal may be a bovine, human or non-bovine mammal.

The antibodies disclosed herein may comprise 3 or more amino acids in length. The antibodies disclosed herein may comprise a sequence that is based on or derived from an ultralong CDR3 disclosed herein. The antibodies disclosed herein may comprise 1 or more amino acid residues based on or derived from a stalk domain of the ultralong CDR3. The antibodies disclosed herein may comprise 1 or more amino acid residues based on or derived from a knob domain of the ultralong CDR3.

At least a portion of the antibodies disclosed herein may be based on or derived from at least a portion of an ultralong CDR3 disclosed herein. The portion of the antibody based on or derived from at least a portion of the ultralong CDR3 is 20 or fewer amino acids in length. The portion of the antibody based on or derived from at least a portion of the ultralong CDR3 is 3 or more amino acids in length The antibodies disclosed herein may comprise 1 or more conserved motifs derived from a stalk domain of the ultralong CDR3. The one or more conserved motifs derived from the stalk. The 1 or more conserved motifs derived from the stalk domain of the ultralong CDR3 may comprise any of the stalk domain conserved motifs disclosed herein. The 1 or more conserved motifs derived from the stalk domain of the ultralong CDR3 may comprise any of the stalk domain conserved motifs disclosed in Table 4 (SEQ ID NOS: 18-47).

The portion of the ultralong CDR3s disclosed herein may comprise at least a portion of a stalk domain of the ultralong CDR3, at least a portion of the knob domain of the ultralong CDR3, or a combination thereof.

The antibodies disclosed herein may comprise a sequence selected from any one of SEQ ID NOS: 18-47. The antibodies disclosed herein may comprise a sequence that is 50% or more homologous to a sequence selected from any one of SEQ ID NOS: 18-24 and 34-37.

A portion of any of the antibodies disclosed herein may be based on or derived from at least a portion of a single ultralong CDR3 sequence. A portion of the antibodies disclosed herein may be based on or derived from at least a portion of two or more different ultralong CDR3 sequences.

In any of the embodiments disclosed herein, the portion of the ultralong CDR3 may be based on or derived from a BLV1H12 ultralong CDR3 sequence. The portion of the ultralong CDR3 based on or derived from a sequence that may be 50% or more homologous to a BLV1H12 ultralong CDR3 sequence. The portion of the ultralong CDR3 may be based on or derived from a BLV5B8, BLVCV1, BLV5D3, BLV8C11, BF1H1, or F18 ultralong CDR3 sequence. The portion of the ultralong CDR3 based on or derived from a sequence that may be 50% or more homologous to a BLV5B8, BLVCV1, BLV5D3, BLV8C11, BF1H1, or F18 ultralong CDR3 sequence.

The antibodies disclosed herein may comprise a first and/or second antibody sequence that is 3 or more amino acids in length. A portion of the first antibody sequence derived from at least a portion of the ultralong CDR3 and/or the portion of the second antibody sequence derived from at least a portion of the ultralong CDR3 may be 20 or fewer amino acids in length. A portion of the first antibody sequence may be derived from at least a portion of the ultralong CDR3 and/or the portion of the second antibody sequence may be derived from at least a portion of the ultralong CDR3 is 3 or more amino acids in length.

In any of the embodiments disclosed herein, the first and/or second antibody sequences comprise 1 or more amino acid residues may be based on or derived from a stalk domain of the ultralong CDR3. The first and/or second antibody sequences may comprise 1 or more amino acid residues based on or derived from a knob domain of the ultralong CDR3. The 1 or more amino acid residues derived from the knob domain of the ultralong CDR3 may be a serine and/or cysteine residue. The first and/or second antibody sequences may comprise 1 or more conserved motifs derived from a stalk domain of the ultralong CDR3. The one or more conserved motifs derived from the stalk domain of the ultralong CDR3 may comprise a sequence selected from any one of SEQ ID NOS: 18-47.

In any of the embodiments disclosed herein, the portion of the first antibody sequence derived from at least a portion of the ultralong CDR3 and/or the portion of the second antibody sequence derived from at least a portion of the ultralong CDR3 may comprise a sequence selected from any one of SEQ ID NOS: 18-47. The portion of the first antibody sequence derived from at least a portion of the ultralong CDR3 and/or the portion of the second antibody sequence derived from at least a portion of the ultralong CDR3 may comprise a sequence that is 50% or more homologous to a sequence selected from any one of SEQ ID NOS: 18-24 and 34-37. The portion of the first antibody sequence derived from at least a portion of the ultralong CDR3 may comprise a sequence selected from any one of SEQ ID NOS: 18-33. The portion of the first antibody sequence derived from at least a portion of the ultralong CDR3 may comprise a sequence that is 50% or more homologous to a sequence selected from any one of SEQ ID NOS: 18-24.

In any of the embodiments disclosed herein, the portion of the second antibody sequence derived from at least a portion of the ultralong CDR3 may comprise a sequence selected from any one of SEQ ID NOS: 34-47. The portion of the second antibody sequence derived from at least a portion of the ultralong CDR3 may comprise a sequence that is 50% or more homologous to a sequence selected from any one of SEQ ID NOS: 34-37. The portion of the first antibody sequence derived from at least a portion of the ultralong CDR3 and the portion of the second antibody sequence derived from at least a portion of the ultralong CDR3 may be derived from the same ultralong CDR3 sequence.

In any of the embodiments disclosed herein, the portion of the first antibody sequence derived from at least a portion of the ultralong CDR3 and the portion of the second antibody sequence derived from at least a portion of the ultralong CDR3 are derived from two or more different ultralong CDR3 sequences. The portions of the ultralong CDR3 of the first and/or second antibody sequences may be based on or derived from a BLV1H12 ultralong CDR3 sequence. The portions of the ultralong CDR3 of the first and/or second antibody sequences may be based on or derived from a sequence that is 50% or more homologous to a BLV1H12 ultralong CDR3 sequence. The portions of the ultralong CDR3 of the first and/or second antibody sequences may be based on or derived from a BLV5B8, BLVCV1, BLV5D3, BLV8C11, BF1H1, or F18 ultralong CDR3 sequence. The portions of the ultralong CDR3 of the first and/or second antibody sequences may be based on or derived from a sequence that is 50% or more homologous to a BLV5B8, BLVCV1, BLV5D3, BLV8C11, BF1H1, or F18 ultralong CDR3 sequence.

In any of the embodiments disclosed herein, the ultralong CDR3 is based on or derived from an ultralong CDR3 that is 35 or more amino acids in length. The ultralong CDR3 may be based on or derived from an ultralong CDR3 comprising 3 or more cysteine residues.

In any of the embodiments disclosed herein, the ultralong CDR3 is based on or derived from an ultralong CDR3 comprises one or more cysteine motifs. The one or more cysteine motifs may be selected from the group consisting of SEQ ID NOS: 48-102. The one or more cysteine motifs may be selected from a cysteine motif disclosed in Table 5.

The antibodies disclosed herein may be based on or derived from an ultralong CDR3 that is 35 or more amino acids in length. The antibodies disclosed herein may be based on or derived from an ultralong CDR3 comprising 3 or more cysteine residues. The antibodies disclosed herein may be based on or derived from an ultralong CDR3 comprises 1 or more cysteine motifs.

The antibodies disclosed herein may comprise an ultralong CDR3 that is 35 or more amino acids in length. The antibodies disclosed herein may comprise an ultralong CDR3 comprising 3 or more cysteine residues. The antibodies disclosed herein may comprise an ultralong CDR3 comprising 1 or more cysteine motifs.

In any of the embodiments disclosed herein, the ultralong CDR3 is a heavy chain CDR3. The ultralong CDR3 may comprise an amino acid sequence derived from or based on a non-human DH sequence. The ultralong CDR3 may comprise an amino acid sequence derived from or based on a JH sequence. The ultralong CDR3 may comprise an amino acid sequence derived from or based on a non-human VH sequence; an amino acid sequence derived from or based on a non-human DH sequence; and/or an amino acid sequence derived from or based on a JH sequence. The ultralong CDR3 may comprise an additional amino acid sequence comprising at least about two amino acid residues positioned between the VH derived amino acid sequence and the DH derived amino acid sequence.

Any of the antibodies disclosed herein may comprise a sequence based on or derived from a sequence selected from SEQ ID NOS: 9-14, the antibody or binding fragment thereof encoded by the DNA sequence based on or derived from any of SEQ ID NOS:2-7. Any of the antibodies disclosed herein may comprise a sequence based on or derived from a sequence selected from SEQ ID NO:8, the antibody or binding fragment thereof encoded by the DNA sequence based on or derived from SEQ ID NO:1.

Any of the ultralong CDR3s disclosed herein may comprise a sequence based on or derived from a sequence selected from SEQ ID NOS: 9-14. Any of the antibodies disclosed herein may comprise a sequence based on or derived from a sequence selected from SEQ ID NO:8. Any of the ultralong CDR3s disclosed herein may be encoded by a DNA sequence that is derived from or based on SEQ ID NOS: 2-7. Any of the antibodies disclosed herein may comprise a portion encoded by a DNA sequence that is derived from or based on SEQ ID NO: 1.

Any of the antibodies disclosed herein may comprise one or more linkers. The one or more linkers may comprise a sequence disclosed in Table 3. Any of the antibodies disclosed herein may comprise first linker sequence. Any of the antibodies disclosed herein may comprise second linker sequence. The first and second linker sequences comprise the same sequence. The first and second linker sequences comprise different sequences. The first and/or second linker sequences may be the same length. The first and/or second linker sequences may be different lengths. The first and/or second linker sequences may be 3 or more amino acids in length.

The first and/or second linker sequence may attach the non-antibody sequence to the portion based on or derived from the portion of the ultralong CDR3. The first and/or second linker sequences may attach the non-antibody sequence to the first antibody sequence. The first and/or second linker sequences may attach the non-antibody sequence to the second antibody sequence. The first and/or second linker sequences may be adjacent to a non-antibody sequence, a portion of an ultralong CDR3 sequence, a cleavage site sequence, an antibody sequence, or a combination thereof.

The first and/or second linker sequences may comprise one or more glycine residues. The first and/or second linker sequences may comprise two or more consecutive glycine residues. The first and/or second linker sequences may comprise one or more serine residues. The first and/or second linker sequences may comprise one or more polar amino acid residues. The one or more polar amino acid residues may be selected from serine, threonine, asparagine, or glutamine. The polar amino acid residues may comprise uncharged side chains. The first and/or second linker sequences may comprise the sequence $(GGGGS)_n$, wherein n=1 to 5; the sequence GGGSGGGGS; the sequence GGGGSGGGS; or a combination thereof.

Any of the antibodies disclosed herein may comprise one or more cleavage sites. The one or more cleavage sites comprise a recognition site for a protease. The protease may be a Factor Xa or thrombin. The one or more cleavage sites may comprise an amino acid sequence of IEGR (SEQ ID NO: 104).

The one or more cleavage site may be between a first antibody sequence and the non-antibody sequence. The one or more cleavage sites may be between a second antibody sequence and the non-antibody sequence. The one or more cleavage sites may be between the one or more linkers and the non-antibody sequence. The one or more cleavage sites may be between a first antibody sequence and the one or more linkers. The one or more cleavage sites may be between a second antibody sequence and the one or more linkers. The one or more cleavage sites may be adjacent to a non-antibody sequence, a portion of an ultralong CDR3 sequence, a linker sequence, an antibody sequence, or a combination thereof.

In some embodiments is a library of antibodies or binding fragments thereof, wherein the antibodies or binding fragments thereof comprise an ultralong CDR3.

In some embodiments is a library of antibodies or binding fragments thereof, wherein the antibodies or binding fragments thereof comprise any of the antibodies disclosed herein.

In some embodiments is a nucleic acid library comprising a plurality of polynucleotides comprising sequences coding for antibodies or binding fragments thereof, wherein the antibodies or binding fragments thereof comprise an ultralong CDR3.

In some embodiments is a nucleic acid library comprising a plurality of polynucleotides comprising sequences coding for antibodies or binding fragments thereof, wherein the antibodies or binding fragments thereof comprise any of the antibodies disclosed herein.

In some embodiments is a polynucleotide comprising a nucleic acid sequence that encodes a variable region, wherein the variable region comprises an ultralong CDR3.

In some embodiments is a vector comprising a polynucleotide, wherein the polynucleotide comprises a nucleic acid sequence that encodes a variable region, wherein the variable region comprises an ultralong CDR3.

In some embodiments is a host cell comprising a polynucleotide, wherein the polynucleotide comprises a nucleic acid sequence that encodes a variable region, wherein the variable region comprises an ultralong CDR3.

In some embodiments is a polynucleotide comprising a nucleic acid sequence that encodes the antibody or binding fragment thereof of any of the antibodies disclosed herein.

In some embodiments is a vector comprising a polynucleotide, wherein the polynucleotide comprises a nucleic acid sequence that encodes the antibody or binding fragment thereof of any of the antibodies disclosed herein.

In some embodiments is a host cell comprising a polynucleotide, wherein the polynucleotide comprises a nucleic acid sequence that encodes the antibody or binding fragment thereof of any of the antibodies disclosed herein.

In some embodiments is a method of producing an antibody or binding fragment thereof comprising an ultralong CDR3 or fragment thereof comprising culturing a host cell comprising a polynucleotide, wherein the polynucleotide comprises a nucleic acid sequence that encodes the antibody or binding fragment thereof of any of the antibodies disclosed herein under conditions wherein the polynucleotide sequence is expressed and the antibody or binding fragment thereof comprising an ultralong CDR3 or fragment thereof is produced. The method may further comprise recovering the antibody or binding fragment thereof comprising the ultralong CDR3 or fragment thereof from the host cell culture.

In some embodiments is a pharmaceutical composition comprising any of the antibodies disclosed herein.

In some embodiments is a pharmaceutical composition comprising (a) an antibody or fragment thereof comprising sequence based on or derived from at least a portion of an ultralong CDR3; and (b) a pharmaceutically acceptable excipient.

In some embodiments is a method of treating a disease or condition in a subject in need thereof comprising administering to the mammal a therapeutically effective amount of any of the antibodies disclosed herein. In some instances, the antibodies disclosed herein comprise an ultralong CDR3 sequence and a non-antibody sequence. In some instances, the non-antibody sequence is selected from the group comprising Moka1, Vm24, human GLP-1, Exendin-4, beta-interferon, human EPO, human FGF21, human GMCSF, human interferon-beta, bovine GCSF, human GCSF and a derivative or variant thereof.

The disease or condition may be selected from the group comprising autoimmune disease, heteroimmune disease or condition, inflammatory disease, pathogenic infection, thromboembolic disorder, respiratory disease or condition, metabolic disease, central nervous system (CNS) disorder, bone disease, cancer, blood disorder, obesity, diabetes, osteoporosis, anemia, or pain.

The disease or condition may benefit from the modulation of an ion channel. The ion channel may be selected from the group comprising a potassium ion channel, sodium ion channel, or acid sensing ion channel. The ion channel may be selected from the group comprising Kv1.3 ion channel, Nav1.7 ion channel and acid sensing ion channel (ASIC).

The disease or condition would benefit from the modulation of a receptor. The receptor may be selected from the group comprising GLP1R, GCGR, EPO receptor, FGFR, FGF21R, CSFR, GMCSFR, and GCSFR.

The disease or condition may be mastitis.

The subject may be a mammal. The mammal may be a bovine or human.

In any or all of the above or below disclosure (e.g., antibodies, uses, or methods) or embodiments utilizing an antibody comprising an ultralong CDR3, any antibody comprising an ultralong CDR3 may be used including, for example, any of the above mentioned antibodies comprising an ultralong CDR3.

BRIEF DESCRIPTION OF THE DRAWINGS

The foregoing summary, as well as the following detailed description of the disclosure, may be better understood when read in conjunction with the appended figures. For the purpose of illustrating the disclosure, shown in the figures are embodiments which are presently preferred. It should be understood, however, that the disclosure is not limited to the precise arrangements, examples and instrumentalities shown.

FIG. 1A shows a ribbon diagram of bovine G-CSF attached to the knob domain of a heavy chain region of bovine BLV1H12 antibody. FIG. 1B shows a cartoon depicting the BLV1H12 antibody.

FIG. 2A shows a Western blot of harvest supernatant of BLV1H12 fusion with 550 peptide, Amgen1 and Mamba1. FIG. 2B shows an SDS PAGE of purified BLV1H12 fusion with 550, Amgen1 and Mamba.

DETAILED DESCRIPTION OF THE INVENTION

Figure 1:
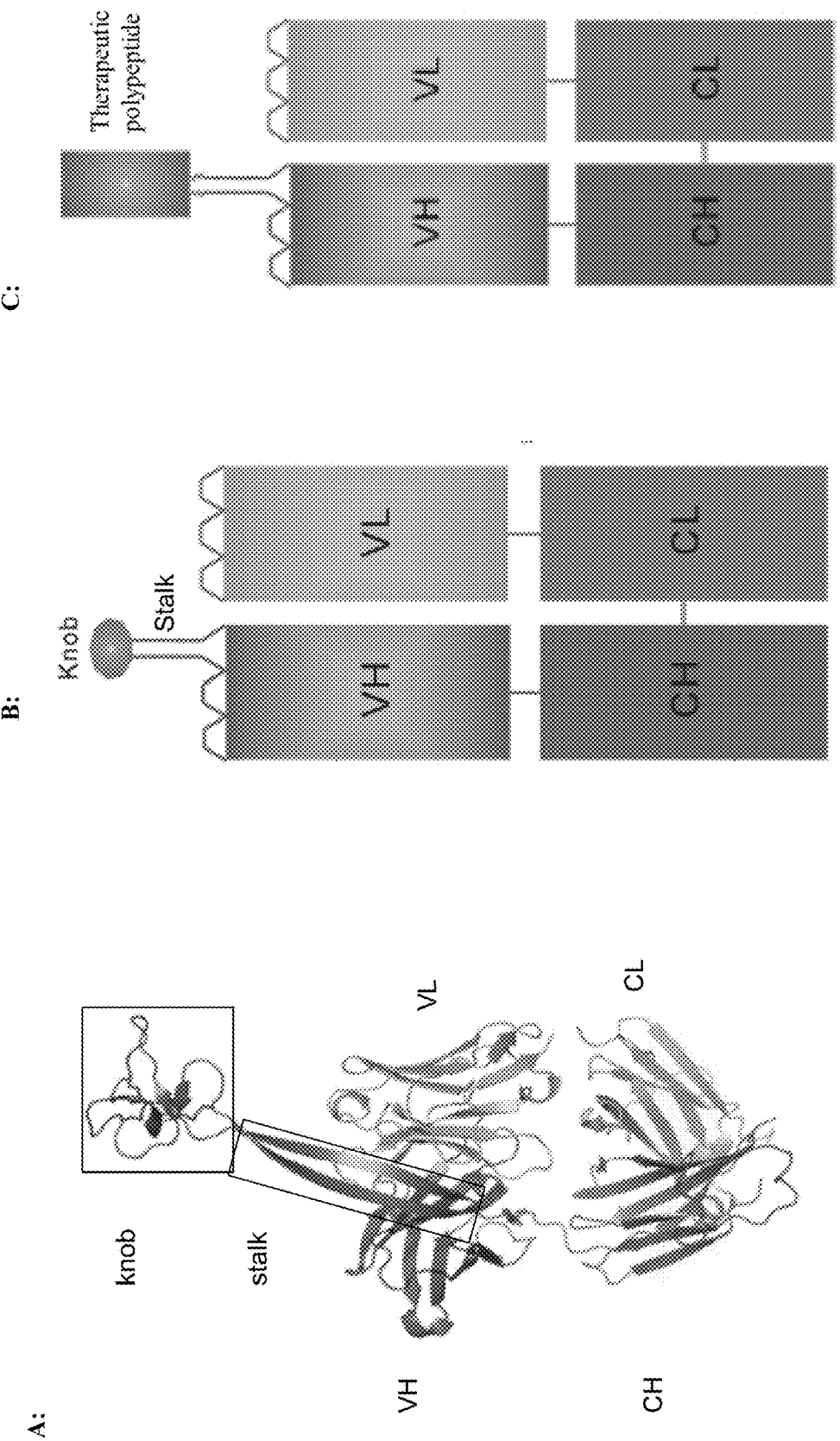
FIG. 1A-1B depict schemes showing insertion of therapeutic polypeptide into the ultralong CDR3 region of a heavy chain region of bovine BLV1H12 antibody to design an immunoglobulin construct described herein.
FIG. 1C shows a cartoon depicting a therapeutic polypeptide inserted into the ultralong CDR3 region of an immunoglobulin heavy chain region, said insertion can be with or without a linker of sequence.

Disclosed herein are antibodies and fragments thereof. Generally, the antibodies and fragments thereof comprise at least a portion of an ultralong CDR3. The portion of the ultralong CDR3 may be derived from or based on an ultralong CDR3 sequence. The portion of the ultralong CDR3 may be derived from or based on a stalk domain of an ultralong CDR3 sequence. Alternatively, or additionally, the portion of the ultralong CDR3 may be derived from or based on a knob domain of an ultralong CDR3 sequence. The antibodies and fragments thereof may further comprise one or more therapeutic polypeptides. The therapeutic polypeptides may be inserted into the portion of the ultralong CDR3. The therapeutic polypeptides may replace one or more amino acid residues in the amino acid sequence of the portion of the ultralong CDR3. The therapeutic polypeptides may replace one or more nucleotides in the nucleic acid sequence of the portion of the ultralong CDR3. Alternatively, the therapeutic polypeptides may be conjugated or attached to the portion of the ultralong CDR3. The antibodies and fragments disclosed herein may further comprise one or more linkers. Additionally, the antibodies and fragments disclosed herein further comprise a cleavage site. A portion of the antibodies and fragments disclosed herein may be based on or derived from an antibody sequence from a different animal or specie from with the ultralong CDR3 is derived. For example, the ultralong CDR3 may be derived from or based on a bovine antibody sequence and the additional and another portion of the antibody sequence may be derived from or based on a non-bovine antibody sequence. Further details of the antibodies and fragments thereof are described herein.

The present disclosure provides antibodies or immunoglobulin constructs comprising ultralong CDR3 sequences or portions thereof.

In an embodiment, the present disclosure provides an antibody comprising at least a portion of an ultralong CDR3. The portion of the ultralong CDR3 may be derived from or based on an ultralong CDR3 that is 35 amino acids in length or more (e.g., 40 or more, 45 or more, 50 or more, 55 or more, 60 or more).

The portion of the ultralong CDR3 may comprise at least a portion of a knob domain of an ultralong CDR3, at least a portion of a stalk domain of an ultralong CDR3, or a combination thereof. The portion of the knob domain of the ultralong CDR3 may comprise one or more conserved motifs derived from the knob domain of the ultralong CDR3. The one or more conserved motifs derived from the knob domain of the ultralong CDR3 may comprise one or more cysteine motifs disclosed herein.

The portion of the stalk domain of the ultralong CDR3 may comprise one or more conserved motifs derived from the stalk domain of the ultralong CDR3.

The portion of the ultralong CDR3 may comprise at least 3 cysteine residues or more. The portion of the ultralong CDR3 may comprise 4 or more, 6 or more, 8 or more, 9 or more, 10 or more, 11 or more, 12 or more, 13 or more, 14 or more, or 15 or more cysteine residues. The antibody may comprise one or more cysteine motifs.

The CDR3 may be 35 amino acids in length or more. The ultralong CDR3 may comprise at least a portion of a knob domain of a CDR3, at least a portion of a stalk domain of a CDR3, or a combination thereof. The portion of the knob domain of the CDR3 may comprise one or more conserved motifs derived from the knob domain of the ultralong CDR3. The portion of the stalk domain of the CDR3 may comprise one or more conserved motifs derived from the stalk domain of the ultralong CDR3. Alternatively, or additionally, the antibody comprises at least 3 cysteine residues or more. The antibody can comprise one or more cysteine motifs.

In another embodiment, the present disclosure provides an antibody comprising an ultralong CDR3, wherein the CDR3 is 35 amino acids in length or more and comprises at least 3 cysteine residues or more, including, for example, 4 or more, 6 or more, and 8 or more.

In some instances, the antibodies disclosed herein further comprise a non-ultralong CDR3 antibody sequence. The non-ultralong CDR3 antibody sequence typically does not comprise an ultralong CDR3 sequence. The non-ultralong CDR3 antibody sequence may comprise at least a portion of a heavy chain, a portion of a light chain, or a combination thereof. The amino acid sequence identity of the non-ultralong CDR3 antibody peptide sequence to the ultralong CDR3 peptide sequence may be about 40% or less, about 35% or less, about 30% or less, about 25% or less, about 20% or less, about 15% or less, 10% or less, about 5% or less, about 3% or less, or about 1% or less.

A portion of the antibodies disclosed herein may be derived from or based on a mammalian antibody. Alternatively, or additionally, a portion of the antibodies disclosed herein may be derived from or based on a non-mammalian antibody. For example, a portion of the antibodies disclosed herein may be derived from or based on a bovine antibody. The antibody may comprise at least a portion of a BLV1H12 and/or BLVCV1 antibody. Alternatively, or additionally, the antibody comprises at least a portion of a BLV5D3, BLV8C11, BF1H1, BLV5B8 and/or F18 antibody. The antibody may comprise at least a portion of a human antibody. The antibody may be a chimeric, recombinant, engineered, synthetic, humanized, fully human, or human engineered antibody. Alternatively, or additionally, the antibody may be a bovinized, bovine engineered or fully bovine antibody.

The portion of the ultralong CDR3 may be derived from or based on a bovine ultralong CDR3 sequence. Alternatively, the portion of the ultralong CDR3 sequence may be derived from or based on a camelid or shark CDR3 sequence.

The antibodies disclosed herein may comprise antibody sequences from two or more different antibodies. The two or more different antibodies may be from the same species. For example, the specie may be a bovine specie, human specie, or murine specie. The two or more different antibodies may be from the same type of animal. For example the two or more different antibodies may be from a cow. The two or more different antibodies may be from a human. Alternatively, the two or more different antibodies are from different species. For example, the two or more different antibodies are from a human specie and bovine specie. In another example, the two or more different antibodies are from a bovine specie and a non-bovine specie. In another example, the two or more different antibodies are from a human specie and a non-human specie.

In some instances, the antibodies disclosed herein further comprise a non-antibody sequence. In some embodiments, the antibodies disclosed herein comprise a portion of an ultralong CDR3 and a non-antibody sequence. The portion of the ultralong CDR3 can comprise any of the ultralong CDR3s or portions thereof disclosed herein. The non-antibody sequence may be inserted into the portion of the ultralong CDR3. The non-antibody sequence may be adjacent to a portion of the ultralong CDR3, non-bovine sequence, linker, cleavage site, or any combination thereof. Alternatively, the non-antibody sequence is conjugated or attached to the portion of the ultralong CDR3.

In another embodiment, the antibodies disclosed herein comprise an ultralong CDR3, wherein the ultralong CDR3 comprises a non-antibody sequence.

The non-antibody sequence may be derived from any protein family including, but not limited to, chemokines, growth factors, peptides, cytokines, cell surface proteins, serum proteins, toxins, extracellular matrix proteins, clotting factors, secreted proteins, etc. The non-antibody sequence may be derived from a therapeutic polypeptide. As used herein, the terms "non-antibody sequence", "non-antibody peptide" and "therapeutic polypeptide" may be used interchangeably. The non-antibody sequence may be of human. For example, the non-antibody sequence may be derived from or based on a parathyroid hormone. Alternatively, the non-antibody sequence may be of non-human origin. The non-human origin may be a bovine, rodent, snake, lizard, bird, fish, turtle, etc. The non-antibody sequence may be based on or derived from a snake peptide. For example, the non-antibody sequence may comprise Mamba1. The non-antibody sequence may comprise a synthetic sequence. For example, the non-antibody sequence may comprise oxynthomodulin, 550 peptide, or Amgen1.

The non-antibody sequence may comprise a portion of a non-antibody protein such as a peptide or domain. The non-antibody sequence of an ultralong CDR3 may contain mutations from its natural sequence, including amino acid changes (e.g., substitutions), insertions or deletions. Engineering additional amino acids at the junction between the non-antibody sequence may be done to facilitate or enhance proper folding of the non-antibody sequence within the antibody.

In some instances, the antibodies disclosed herein may comprise a portion based on or derived from a non-bovine sequence. The portion based on or derived from the non-bovine sequence may be inserted into the portion of the ultralong CDR3. Alternatively, the portion based on or derived from the non-bovine sequence may be conjugated or attached to the portion of the ultralong CDR3. The portion based on or derived from the non-bovine sequence may be adjacent the portion of the ultralong CDR3.

In some instances, the antibodies disclosed herein further comprise a non-bovine sequence. In some embodiments, the antibodies disclosed herein comprise a portion of an ultralong CDR3 and a non-bovine sequence. The portion of the ultralong CDR3 can comprise any of the ultralong CDR3s or portions thereof disclosed herein. The non-bovine sequence may be inserted into the portion of the ultralong CDR3. The non-bovine sequence may be adjacent to a portion of the ultralong CDR3, non-antibody sequence, linker, cleavage site, or any combination thereof. Alternatively, the non-bovine sequence is conjugated or attached to the ultralong CDR3 sequence.

The non-bovine sequence can be derived from or based on at least a portion of an antibody sequence. The antibody sequence can encode at least a portion of a variable region, at least a portion of a constant region or a combination thereof.

In some instances, the antibodies disclosed herein further comprise one or more linkers. The one or more linkers may be inserted into the portion of the ultralong CDR3. The one or more linkers may be adjacent to an ultralong CDR3, non-antibody sequence, non-ultralong antibody sequence, cleavage site, or a combination thereof. The one or more linkers may comprise an amino acid sequence of (GGGGS)$_n$ (SEQ ID NO: 103) wherein n=1 to 5. Alternatively, or additionally, the one or more linker comprise an amino acids sequence of GGGSGGGGS or GGGGSGGGS.

In some instances, the antibodies disclosed herein bind to one or more targets. The non-antibody sequence of the antibody may bind to the one or more target. Alternatively, or additionally, a variable region of the antibody may bind to the one or more targets. The target may be a protein target. The protein target may be a transmembrane protein target. Such transmembrane targets may include, but are not limited to, GPCRs, ion channels, transporters, and cell surface receptors.

Provided herein is an immunoglobulin construct comprising a mammalian immunoglobulin heavy chain comprising at least a portion of complementarity-determining region 3 (CDR3H); and a therapeutic polypeptide, wherein the therapeutic polypeptide is inserted into or replaces at least a portion of the CDR3H. The immunoglobulin construct may comprise one or more linkers. The one or more linkers can connect the therapeutic polypeptide to the heavy chain. In some embodiments, the linker comprises an amino acid sequence of (GGGGS)$_n$ (SEQ ID NO: 103) wherein n=1 to 5. Alternatively, or additionally, the linker comprises an amino acid sequence of GGGSGGGGS or GGGGSGGGS. The therapeutic polypeptide may be a synthetic peptide. The therapeutic polypeptide may modulate a receptor. The therapeutic polypeptide may be a receptor agonist. Alternatively, the therapeutic polypeptide is a receptor antagonist. The therapeutic polypeptide may be a hormone. In some instances, the therapeutic polypeptide is selected from the group comprising oxyntomodulin, 550 peptide, Amgen1, Mamba1, and parathyroid hormone. Provided herein are immunoglobulin constructs comprising a mammalian immunoglobulin heavy chain comprising a knob domain in the complementarity-determining region 3 (CDR3H) or fragment thereof; and a therapeutic polypeptide attached to said knob domain of the CDR3H, wherein said mammalian immunoglobulin is a bovine immunoglobulin. In some embodiments, the bovine immunoglobulin is a BLV1H12 antibody. In some embodiments of the immunoglobulin constructs described herein, at least a portion of the knob domain is replaced by the therapeutic polypeptide. The knob domain of the CDR3H may comprise one or more conserved motifs derived from the knob domain of the ultralong CDR3H. The immunoglobulin construct may further comprise at least a portion of a stalk domain in the CDR3H. The portion of the stalk domain of the CDRH3 may comprise one or more conserved motifs derived from the stalk domain of the ultralong CDR33H.

Further provided herein are antibodies or fragments thereof comprising a stalk domain in the complementarity-determining region 3 (CDR3H) or fragment thereof; and a therapeutic polypeptide. In some instances, the complementarity-determining region 3 (CDR3H) is derived from a bovine ultralong CDR3H. The therapeutic polypeptide can be any of the therapeutic polypeptides disclosed herein. For example, the therapeutic polypeptide is Moka1, Vm24, GLP-1, Exendin-4, human EPO, human FGF21, human GMCSF, or human interferon-beta. The therapeutic polypeptide can be attached to the stalk domain. In some instances, the antibody or fragment thereof further comprises a linker. The linker can attach the therapeutic polypeptide to the stalk domain. Alternatively, or additionally, the antibody or fragment thereof further comprises at least a portion of a knob domain in the CDR3H. In some instances, the linker attaches the therapeutic polypeptide to the knob domain. In some instances, the knob domain is attached to the stalk domain. The portion of the knob domain of the CDR3 may comprise one or more conserved motifs derived from the knob domain of the ultralong CDR3. The stalk domain of the CDR3 may comprise one or more conserved motifs derived from the stalk domain of the ultralong CDR3.

In some instances, an antibody or fragment thereof is provided herein. The antibody or fragment thereof can comprise at least one immunoglobulin domain or fragment thereof; and a therapeutic polypeptide or derivative or variant thereof. The therapeutic polypeptide, or derivative or variant thereof can be attached to the immunoglobulin domain. In some instances, the therapeutic polypeptide is Moka1, Vm24, GLP-1, Exendin-4, human EPO, human FGF21, human GMCSF, human interferon-beta, or derivative or variant thereof. In some embodiments, the immunoglobulin domain is an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. In some instances, the immunoglobulin domain is from an engineered antibody or recombinant antibody. In other instances, the immunoglobulin domain is from a humanized, human engineered or fully human antibody. In certain embodiments, the mammalian antibody is a bovine antibody. In other instances, the mammalian antibody is a human antibody. In other instances, the mammalian antibody is a murine antibody. In some instances, the immunoglobulin domain is a heavy chain region comprising a knob domain in the complementarity-determining region 3 (CDR3H) or fragment thereof. The therapeutic polypeptide can be attached to the knob domain. Alternatively, or additionally, the immunoglobulin domain is a heavy chain region comprising a stalk domain in the complementarity-determining region 3 (CDR3H) or fragment thereof. In some instances, the therapeutic polypeptide is attached to the stalk domain. In some instances, the antibody or fragment thereof further comprises a linker. The linker can attach the therapeutic polypeptide to the immunoglobulin domain or fragment thereof. The knob domain of the CDR3 may comprise one or more conserved motifs derived from the knob domain of the ultralong CDR3. The stalk domain of the CDR3 may comprise one or more conserved motifs derived from the stalk domain of the ultralong CDR3.

Provided herein is an immunoglobulin construct comprising at least one immunoglobulin domain or fragment thereof; and a G-CSF polypeptide or derivative or variant thereof attached to said immunoglobulin domain. In some embodiments, the immunoglobulin domain is an immunoglobulin A, an immunoglobulin D, an immunoglobulin E, an immunoglobulin G, or an immunoglobulin M. In some embodiments, the immunoglobulin domain is an immunoglobulin heavy chain region or fragment thereof. In an embodiment, the immunoglobulin domain is from a mammalian or chimeric antibody. In other instances, the immunoglobulin domain is from a humanized, human engineered or fully human antibody. In certain embodiments, the mammalian antibody is a bovine antibody. In some instances, the mammalian antibody is a human antibody. In other instances, the mammalian antibody is a murine antibody. In an embodiment, the immunoglobulin domain is a heavy chain region comprising a knob domain in the complementarity-determining region 3 (CDR3H) or fragment thereof. In an embodiment, the G-CSF polypeptide is attached to the knob domain. The immunoglobulin domain may be a heavy chain region comprising a stalk domain in the complementarity-determining region 3 (CDR3H) or fragment thereof. The G-CSF polypeptide may be attached to the stalk domain. The knob domain of the CDR3 may comprise one or more conserved motifs derived from the knob domain of the ultralong CDR3. The stalk domain of the CDR3 may comprise one or more conserved motifs derived from the stalk domain of the ultralong CDR3.

In certain embodiments, provided is an immunoglobulin construct comprising at least one immunoglobulin domain or fragment thereof; and a G-CSF polypeptide or derivative or variant thereof attached to said immunoglobulin domain, wherein said G-CSF polypeptide is a bovine G-CSF polypeptide or derivative or variant thereof. In certain embodiments provided herein is a pharmaceutical composition comprising an immunoglobulin construct provided herein, and a pharmaceutically acceptable carrier. In certain embodiments is provided a method of preventing or treating a disease in a mammal in need thereof comprising administering a pharmaceutical composition described herein to said mammal. The immunoglobulin domain may be a heavy chain region comprising a knob domain in the complementarity-determining region 3 (CDR3H) or fragment thereof. The G-CSF polypeptide may be attached to the knob domain. The immunoglobulin domain may be a heavy chain region comprising a stalk domain in the complementarity-determining region 3 (CDR3H) or fragment thereof. The G-CSF polypeptide may be attached to the stalk domain. The knob domain of the CDR3 may comprise one or more conserved motifs derived from the knob domain of the ultralong CDR3. The stalk domain of the CDR3 may comprise one or more conserved motifs derived from the stalk domain of the ultralong CDR3.

In some embodiments is an antibody or fragment thereof comprising: (a) a first antibody sequence, wherein at least a portion of the first antibody sequence is derived from at least a portion of an ultralong CDR3; and (b) a non-antibody sequence. The antibody or fragment thereof may further comprise a second antibody sequence, wherein at least a portion of the second antibody sequence is derived from at least a portion of an ultralong CDR3. The ultralong CDR3 from which the first antibody sequence and/or second antibody sequence may be derived from a ruminant. The ruminant can be a cow. At least a portion of the first antibody sequence and/or at least a portion of the second antibody sequence can be derived from a mammal. The mammal may be a bovine. Alternatively, the mammal is a non-bovine mammal, such as a human. The first and/or second antibody sequences may be 3 or more amino acids in length. The amino acids may be consecutive amino acids. Alternatively, the amino acids are non-consecutive amino acids. The first and/or second antibody sequences may comprise a bovine antibody sequence comprising 3 or more amino acids in length. The bovine antibody may be a BLVH12, BLV5B8, BLVCV1, BLV5D3, BLV8C11, BF1H1, or F18 antibody. The first and/or second antibody sequences may comprise a human antibody sequence comprising 3 or more amino acids in length. The portion of the first antibody sequence derived from at least a portion of the ultralong CDR3 and/or the portion of the second antibody sequence derived from at least a portion of the ultralong CDR3 can be 20 or fewer amino acids in length. The portion of the first antibody sequence derived from at least a portion of the ultralong CDR3 and/or the portion of the second antibody sequence derived from at least a portion of the ultralong CDR3 may be 3 or more amino acids in length. The first and/or second antibody sequences can comprise 1 or more, 2 or more, 3 or more, 4 or more, 5 or more, 6 or more, 7 or more, 8 or more, 9 or more, 10 or more, 15 or more, 20 or more, 30 or more, or 40 or more amino acid residues derived from a knob domain of the ultralong CDR3. The 1 or more amino acid residues derived from the knob domain of the ultralong CDR3 may be a serine and/or cysteine residue. The first and/or second antibody sequences may comprise 1 or more, 2 or more, 3 or more, 4 or more, 5 or more, 6 or more, 7 or more, 8 or more, 9 or more, or 10 or more amino acid residues derived from a stalk domain of the ultralong CDR3. The first and/or second antibody sequences may comprise 1 or more, 2 or more, 3 or more, 4 or more, or 5 or more conserved motifs derived from a stalk domain of the ultralong CDR3. The one or more conserved motifs derived from the stalk domain of the ultralong CDR3 may comprise a sequence selected from any one of SEQ ID NOS: 18-47. The portion of the first antibody sequence derived from at least a portion of the ultralong CDR3 and/or the portion of the second antibody sequence derived from at least a portion of the ultralong CDR3 may comprise a sequence selected from any one of SEQ ID NOS: 18-47. The portion of the first antibody sequence derived from at least a portion of the ultralong CDR3 and/or the portion of the second antibody sequence derived from at least a portion of the ultralong CDR3 may comprise a sequence that is 50% or more homologous to a sequence selected from any one of SEQ ID NOS: 18-24 and 34-37. The portion of the first antibody sequence derived from at least a portion of the ultralong CDR3 may comprise a sequence selected from any one of SEQ ID NOS: 18-33. The portion of the first antibody sequence derived from at least a portion of the ultralong CDR3 may comprise a sequence that is 50% or more homologous to a sequence selected from any one of SEQ ID NOS: 18-24. The portion of the first antibody sequence derived from at least a portion of the ultralong CDR3 may comprise a sequence that is 50% or more homologous to a sequence selected from any one of SEQ ID NOS: 22-24. The portion of the second antibody sequence derived from at least a portion of the ultralong CDR3 may comprise a sequence selected from any one of SEQ ID NOS: 34-47. The portion of the second antibody sequence derived from at least a portion of the ultralong CDR3 may comprise a sequence that may be 50% or more homologous to a sequence selected from any one of SEQ ID NOS: 34-37. The portion of the first antibody sequence derived from at least a portion of the ultralong CDR3 and the portion of the second antibody sequence derived from at least a portion of the ultralong CDR3 may be derived from the same ultralong CDR3 sequence. The portion of the first antibody sequence derived from at least a portion of the ultralong CDR3 and the portion of the second antibody sequence derived from at least a portion of the ultralong CDR3 may be derived from two or more different ultralong CDR3 sequences. The portions of the ultralong CDR3 of the first and/or second antibody sequences may be based on or derived from a BLV1H12 ultralong CDR3 sequence. The portions of the ultralong CDR3 of the first and/or second antibody sequences may be based on or derived from a BLV5B8, BLVCV1, BLV5D3, BLV8C11, BF1H1, or F18 ultralong CDR3 sequence. The antibody may further comprise one or more linker sequences.

The present disclosure also provides antibodies that comprise a heavy chain polypeptide, wherein the heavy chain polypeptide comprises at least a portion of an ultralong CDR3 sequence. The heavy chain polypeptide may comprise a polypeptide sequence of any one of SEQ ID NOS: 9-14. The heavy chain polypeptide may comprise a polypeptide sequence encoded by the DNA of any one of SEQ ID NOS: 2-7. Also provided are antibodies comprising a heavy chain polypeptide, wherein the heavy chain polypeptide comprises an ultralong CDR3 sequence and the heavy chain polypeptide sequences are substantially similar to those polypeptide sequences provided by any one of SEQ ID NOS: 9-14. A heavy chain polypeptide sequence may be considered substantially similar to a polypeptide sequence provided by any one of SEQ ID NOS: 9-14 where the heavy chain polypeptide sequence shares 60%, 70%, 80%, 90%, 95%, 99%, or more nucleic acid identity to a nucleotide sequence provided by any one of SEQ ID NOS: 9-14. The antibodies may further comprise a light chain polypeptide. The light chain polypeptide may comprise a polypeptide sequence of SEQ ID NO: 8. The light chain polypeptide may comprise a polypeptide sequence encoded by the DNA sequence based on or derived from SEQ ID NO:1. Also provided are antibodies further comprising a light chain polypeptide, wherein the light chain polypeptide comprises an ultralong CDR3 sequence and the light chain polypeptide sequences are substantially similar to those polypeptide sequences provided by SEQ ID NO: 8. A light chain polypeptide sequence may be considered substantially similar to a polypeptide sequence provided by SEQ ID NO: 1 where the light chain polypeptide sequence shares 60%, 70%, 80%, 90%, 95%, 99%, or more nucleic acid identity to a nucleotide sequence provided by any one of SEQ ID NO: 1. The antibody may have therapeutic activity in an animal. The antibody can have therapeutic activity in infectious disease in a subject. The antibody may comprise a monoclonal antibody, polyclonal antibody, chimeric antibody, recombinant antibody, engineered antibody, or synthetic antibody. The antibody may comprise a mammalian antibody. The antibody may comprise a bovine antibody. The antibody may comprise a G-CSF polypeptide, or derivative or variant thereof. The antibody may comprise a mammalian G-CSF polypeptide, or derivative or variant thereof. The antibody may comprise a bovine G-CSF, or derivative or variant thereof. In some embodiments, a pharmaceutical composition of therapeutic formulation comprises an antibody described herein and a pharmaceutically acceptable carrier. In certain embodiments, the antibody is used in a method of treating a subject in need thereof, with a therapeutically effective amount of the antibody or a pharmaceutical composition described herein. In some embodiments, a nucleic acid molecule or a complement thereof encodes a therapeutic immunoglobulin described herein.

Genetic Sequences

The present disclosure provides genetic sequences (e.g., genes, nucleic acids, polynucleotides) encoding antibodies comprising ultralong CDR3 sequences or portions thereof. The present disclosure provides genetic sequences (e.g., genes, nucleic acids, polynucleotides) encoding antibodies comprising the knob domain and/or knob domain of ultralong CDR3 sequences. In another embodiment, the present disclosure provides genetic sequences encoding an antibody or immunoglobulin construct described herein.

The present disclosure also provides genetic sequences (e.g., genes, nucleic acids, polynucleotides) encoding an ultralong CDR3 or portion thereof. The present disclosure also provides genetic sequences (e.g., genes, nucleic acids, polynucleotides) encoding the knob domain and/or knob domain of an ultralong CDR3.

In an embodiment, the present disclosure provides genetic sequences encoding an antibody comprising an ultralong CDR3. The ultralong CDR3 may be 35 amino acids in length or more (e.g., 40 or more, 45 or more, 50 or more, 55 or more, 60 or more). The ultralong CDR3 may comprise at least a portion of a knob domain of a CDR3, at least a portion of a stalk domain of a CDR3, or a combination thereof. Such an antibody may comprise at least 3 cysteine residues or more (e.g., 4 or more, 6 or more, 8 or more) within the ultralong CDR3. The antibody may comprise one or more cysteine motifs. The antibody may comprise a non-antibody sequence within the ultralong CDR3. Alternatively, or additionally, the antibody comprises a non-bovine sequence. The antibody may further comprise an antibody sequence. The antibody may comprise a cytotoxic agent or therapeutic polypeptide. The cytotoxic agent or therapeutic polypeptide may be conjugated to the ultralong CDR3. The antibody may bind to a target. The target may be a protein target, such as a transmembrane protein target.

In another embodiment, the present disclosure provides genetic sequences encoding an antibody comprising an ultralong CDR3, wherein the CDR3 is 35 amino acids in length or more and is derived from or based on a non-human sequence. The genetic sequences encoding the ultralong CDR3 may be derived from any species that naturally produces ultralong CDR3 antibodies, including ruminants such as cattle (*Bos taurus*). Alternatively, the ultralong CDR3 sequence may be derived from a camelid or shark CDR3 sequence.

In another embodiment, the present disclosure provides genetic sequences encoding an antibody comprising an ultralong CDR3, wherein the CDR3 comprises a non-antibody protein sequence. The genetic sequences encoding the non-antibody protein sequences may be derived from any protein family including, but not limited to, chemokines, growth factors, peptides, cytokines, cell surface proteins, serum proteins, toxins, extracellular matrix proteins, clotting factors, secreted proteins, etc. The non-antibody sequence may be derived from a therapeutic polypeptide. The non-antibody protein sequence may be of human or non-human origin. The non-antibody sequence may comprise a synthetic sequence. The non-antibody sequence may comprise a portion of a non-antibody protein such as a peptide or domain. The non-antibody protein sequence of an ultralong CDR3 may contain mutations from its natural sequence, including amino acid changes (e.g., substitutions), insertions or deletions. Engineering additional amino acids at the junction between the non-antibody sequence may be done to facilitate or enhance proper folding of the non-antibody sequence within the antibody. The CDR3 may be 35 amino acids in length or more. The ultralong CDR3 may comprise at least a portion of a knob domain of a CDR3, at least a portion of a stalk domain of a CDR3, or a combination thereof. Alternatively, or additionally, the antibody comprises at least 3 cysteine residues or more. The antibody can comprise one or more cysteine motifs.

In another embodiment, the present disclosure provides genetic sequences encoding an antibody comprising an ultralong CDR3 and a non-bovine sequence. The ultralong CDR3 can be derived from a ruminant. The ruminant can be a bovine. The non-bovine sequence can be derived from or based on a non-bovine mammal sequence. For example, the non-bovine sequence can be derived from or based on a human, mouse, rat, sheep, dog, and/or goat sequence. The non-bovine sequence can be within the ultralong CDR3. Alternatively, the non-bovine sequence is linked or attached to the ultralong CDR3 sequence. The non-bovine sequence can be derived from or based on at least a portion of an antibody sequence. The antibody sequence can encode a variable region, constant region or a combination thereof. The CDR3 may be 35 amino acids in length or more. The ultralong CDR3 may comprise at least a portion of a knob domain of a CDR3, at least a portion of a stalk domain of a CDR3, or a combination thereof. Alternatively, or additionally, the antibody comprises at least 3 cysteine residues or more. The antibody can comprise one or more cysteine motifs.

In another embodiment, the present disclosure provides genetic sequences encoding an antibody comprising an ultralong CDR3, wherein the CDR3 is 35 amino acids in length or more and comprises at least 3 cysteine residues or more, including, for example, 4 or more, 6 or more, and 8 or more.

In another embodiment, the present disclosure provides genetic sequences encoding an antibody comprising an ultralong CDR3 wherein the CDR3 is 35 amino acids in length or more and comprises at least 3 cysteine residues or more and wherein the ultralong CDR3 is a component of a multispecific antibody. The multispecific antibody may be bispecific or comprise greater valencies.

In another embodiment, the present disclosure provides genetic sequences encoding an antibody comprising an ultralong CDR3, wherein the CDR3 is 35 amino acids in length or more and comprises at least 3 cysteine residues or more, wherein the ultralong CDR3 is a component of an immunoconjugate.

In another embodiment, the present disclosure provides genetic sequences encoding an antibody comprising an ultralong CDR3 wherein the CDR3 is 35 amino acids in length or more and comprises at least 3 cysteine residues or more and wherein the antibody comprising an ultralong CDR3 binds to a transmembrane protein target. Such transmembrane targets may include, but are not limited to, GPCRs, ion channels, transporters, and cell surface receptors.

In another embodiment, the present disclosure provides genetic sequences encoding an antibody comprising an ultralong CDR3, wherein the antibody comprising an ultralong CDR3 binds to a transmembrane protein target. Such transmembrane targets may include, but are not limited to, GPCRs, ion channels, transporters, and cell surface receptors. The CDR3 may be 35 amino acids in length or more. The ultralong CDR3 may comprise at least a portion of a knob domain of a CDR3, at least a portion of a stalk domain of a CDR3, or a combination thereof. Alternatively, or additionally, the antibody comprises at least 3 cysteine residues or more. The antibody can comprise one or more cysteine motifs.

In another embodiment, the present disclosure provides genetic sequences encoding an antibody or fragment thereof comprising: (a) a first antibody sequence, wherein at least a portion of the first antibody sequence is derived from at least a portion of an ultralong CDR3; and (b) a non-antibody sequence. The antibody or fragment thereof may further comprise a second antibody sequence, wherein at least a portion of the second antibody sequence is derived from at least a portion of an ultralong CDR3. The ultralong CDR3 from which the first antibody sequence and/or second antibody sequence may be derived from a ruminant. The ruminant can be a cow. At least a portion of the first antibody sequence and/or at least a portion of the second antibody sequence can be derived from a mammal. The mammal may be a bovine. Alternatively, the mammal is a non-bovine mammal, such as a human. The first and/or second antibody sequences may be 3 or more amino acids in length. The amino acids may be consecutive amino acids. Alternatively, the amino acids are non-consecutive amino acids. The first and/or second antibody sequences may comprise a bovine antibody sequence comprising 3 or more amino acids in length. The bovine antibody may be a BLVH12, BLV5B8, BLVCV1, BLV5D3, BLV8C11, BF1H1, or F18 antibody. The first and/or second antibody sequences may comprise a human antibody sequence comprising 3 or more, 4 or more, 5 or more, 6 or more, 7 or more, 8 or more, 9 or more, 10 or more, 15 or more, 20 or more, 30 or more, 40 or more, 50 or more, 60 or more, or 70 or more amino acids in length. The portion of the first antibody sequence derived from at least a portion of the ultralong CDR3 and/or the portion of the second antibody sequence derived from at least a portion of the ultralong CDR3 can be 20 or fewer amino acids in length. The portion of the first antibody sequence derived from at least a portion of the ultralong CDR3 and/or the portion of the second antibody sequence derived from at least a portion of the ultralong CDR3 may be 3 or more amino, 4 or more, 5 or more, 6 or more, 7 or more, 8 or more, 9 or more, 10 or more, 15 or more, or 20 or more acids in length. The first and/or second antibody sequences can comprise 1 or more, 2 or more, 3 or more, 4 or more, 5 or more, 6 or more, 7 or more, 8 or more, 9 or more, 10 or more, 15 or more, 20 or more, 30 or more, or 40 or more amino acid residues derived from a knob domain of the ultralong CDR3. The 1 or more amino acid residues derived from the knob domain of the ultralong CDR3 may be a serine and/or cysteine residue. The first and/or second antibody sequences may comprise 1 or more, 2 or more, 3 or more, 4 or more, 5 or more, 6 or more, 7 or more, 8 or more, 9 or more, or 10 or more amino acid residues derived from a stalk domain of the ultralong CDR3. The first and/or second antibody sequences may comprise 1 or more, 2 or more, 3 or more, 4 or more, or 5 or more conserved motifs derived from a stalk domain of the ultralong CDR3. The one or more conserved motifs derived from the stalk domain of the ultralong CDR3 may comprise a sequence selected from any one of SEQ ID NOS: 18-47. The portion of the first antibody sequence derived from at least a portion of the ultralong CDR3 and/or the portion of the second antibody sequence derived from at least a portion of the ultralong CDR3 may comprise a sequence selected from any one of SEQ ID NOS: 18-47. The portion of the first antibody sequence derived from at least a portion of the ultralong CDR3 and/or the portion of the second antibody sequence derived from at least a portion of the ultralong CDR3 may comprise a sequence that is 50% or more homologous to a sequence selected from any one of SEQ ID NOS: 18-24 and 34-37. The portion of the first antibody sequence derived from at least a portion of the ultralong CDR3 may comprise a sequence selected from any one of SEQ ID NOS: 18-33. The portion of the first antibody sequence derived from at least a portion of the ultralong CDR3 may comprise a sequence that is 50% or more homologous to a sequence selected from any one of SEQ ID NOS: 18-24. The portion of the first antibody sequence derived from at least a portion of the ultralong CDR3 may comprise a sequence that is 50% or more homologous to a sequence selected from any one of SEQ ID NOS: 22-24. The portion of the second antibody sequence derived from at least a portion of the ultralong CDR3 may comprise a sequence selected from any one of SEQ ID NOS: 34-47. The portion of the second antibody sequence derived from at least a portion of the ultralong CDR3 may comprise a sequence that may be 50% or more homologous to a sequence selected from any one of SEQ ID NOS: 34-37. The portion of the first antibody sequence derived from at least a portion of the ultralong CDR3 and the portion of the second antibody sequence derived from at least a portion of the ultralong CDR3 may be derived from the same ultralong CDR3 sequence. The portion of the first antibody sequence derived from at least a portion of the ultralong CDR3 and the portion of the second antibody sequence derived from at least a portion of the ultralong CDR3 may be derived from two or more different ultralong CDR3 sequences. The portions of the ultralong CDR3 of the first and/or second antibody sequences may be based on or derived from a BLV1H12 ultralong CDR3 sequence. The portions of the ultralong CDR3 of the first and/or second antibody sequences may be based on or derived from a BLV5B8, BLVCV1, BLV5D3, BLV8C11, BF1H1, or F18 ultralong CDR3 sequence. The antibody may further comprise one or more linker sequences.

The present disclosure also provides isolated genetic sequences (e.g., genes, nucleic acids, polynucleotides, oligonucleotides) such as genetic sequences encoding antibodies that comprise a heavy chain polypeptide, wherein the heavy chain polypeptide comprises at least a portion of an ultralong CDR3 sequence. The heavy chain polypeptide may comprise a polypeptide sequence of any one of SEQ ID NOS: 9-14. The heavy chain polypeptide may comprise a polypeptide sequence encoded by the DNA of any one of SEQ ID NOS: 2-7. Also provided are isolated genetic sequences (e.g., genes, nucleic acids, polynucleotides, oligonucleotides) such as genetic sequences encoding antibodies comprising a heavy chain polypeptide, wherein the heavy chain polypeptide comprises an ultralong CDR3 sequence and the heavy chain polypeptide sequences are substantially similar to those polypeptide sequences provided by any one of SEQ ID NOS: 9-14. A heavy chain polypeptide sequence may be considered substantially similar to a polypeptide sequence provided by any one of SEQ ID NOS: 9-14 where the heavy chain polypeptide sequence shares 60%, 70%, 80%, 90%, 95%, 99%, or more nucleic acid identity to a nucleotide sequence provided by any one of SEQ ID NOS: 9-14 or hybridizes to any one of SEQ ID NOS: 9-14 under stringent hybridization conditions. The isolated genetic sequences (e.g., genes, nucleic acids, polynucleotides, oligonucleotides) such as genetic sequences encoding antibodies may further comprise a light chain polypeptide. The light chain polypeptide may comprise a polypeptide sequence of SEQ ID NO: 8. The light chain polypeptide may comprise a polypeptide sequence encoded by the DNA sequence based on or derived from SEQ ID NO:1. Also provided are isolated genetic sequences (e.g., genes, nucleic acids, polynucleotides, oligonucleotides) such as genetic sequences encoding antibodies further comprising a light chain polypeptide, wherein the light chain polypeptide comprises an ultralong CDR3 sequence and the light chain polypeptide sequences are substantially similar to those polypeptide sequences provided by SEQ ID NO: 8. A light chain polypeptide sequence may be considered substantially similar to a polypeptide sequence provided by SEQ ID NO: 1 where the light chain polypeptide sequence shares 60%, 70%, 80%, 90%, 95%, 99%, or more nucleic acid identity to a nucleotide sequence provided by any one of SEQ ID NO: 1 or hybridizes to SEQ ID NOS: 1 under stringent hybridization conditions.

Libraries and Arrays

The present disclosure provides collections, libraries and arrays of antibodies comprising ultralong CDR3 sequences. In some embodiments, members of the collections, libraries, or arrays may exhibit sequence diversity.

In an embodiment, the present disclosure provides a library or an array of antibodies comprising ultralong CDR3 sequences wherein at least two members of the library or array differ in the positions of at least one of the cysteines in the ultralong CDR3 sequence. Structural diversity may be enhanced through different numbers of cysteines in the ultralong CDR3 sequence (e.g., at least 3 or more cysteine residues such as 4 or more, 6 or more and 8 or more) and/or through different disulfide bond formation, and hence different loop structures.

In another embodiment, the present disclosure provides for a library or an array of antibodies comprising ultralong CDR3 sequences wherein at least two members of the library or the array differ in at least one amino acid located between cysteines in the ultralong CDR3. In this regard, members of the library or the array can contain cysteines in the same positions of CDR3, resulting in similar overall structural folds, but with fine differences brought about through different amino acid side chains. Such libraries or arrays may be useful for affinity maturation.

In another embodiment, the present disclosure provides libraries or arrays of antibodies comprising ultralong CDR3 sequences wherein at least two of the ultralong CDR3 sequences differ in length (e.g., 35 amino acids in length or more such as 40 or more, 45 or more, 50 or more, 55 or more and 60 or more). The amino acid and cysteine content may or may not be altered between the members of the library or the array. Different lengths of ultralong CDR3 sequences may provide for unique binding sites, including, for example, due to steric differences, as a result of altered length.

In another embodiment, the present disclosure provides libraries or arrays of antibodies comprising ultralong CDR3 sequences wherein at least two members of the library differ in the human framework used to construct the antibody comprising an ultralong CDR3.

In another embodiment, the present disclosure provides libraries or arrays of antibodies comprising ultralong CDR3 sequences wherein at least two members of the library or the array differ in having a non-antibody protein sequence that comprises a portion of the ultralong CDR3. Such libraries or arrays may contain multiple non-antibody protein sequences, including for chemokines, growth factors, peptides, cytokines, cell surface proteins, serum proteins, toxins, extracellular matrix proteins, clotting factors, secreted proteins, viral or bacterial proteins, etc. The non-antibody protein sequence may be of human or non-human origin and may be comprised of a portion of a non-antibody protein such as a peptide or domain. The non-antibody protein sequence of the ultralong CDR3 may contain mutations from its natural sequence, including amino acid changes (e.g., substitutions), or insertions or deletions. Engineering additional amino acids at the junction between the non-antibody sequence within the ultralong CDR3 may be done to facilitate or enhance proper folding of the non-antibody sequence within the antibody.

In another embodiment, the present disclosure provides libraries or arrays of antibodies comprising ultralong CDR3 sequences wherein at least two members of the library or the array differ in having a non-bovine sequence. The non-bovine sequence can be derived from or based on a non-bovine mammal sequence. For example, the non-bovine sequence can be derived from or based on a human, mouse, rat, sheep, dog, and/or goat sequence. The non-bovine sequence can be within the ultralong CDR3. Alternatively, the non-bovine sequence is linked or attached to the ultralong CDR3 sequence. The non-bovine sequence can be derived from or based on at least a portion of an antibody sequence. The antibody sequence can encode a variable region, constant region or a combination thereof.

In another embodiment, the present disclosure provides libraries or arrays of antibodies comprising ultralong CDR3 sequences wherein at least two members of the library or array differ in having a cytotoxic agent or therapeutic polypeptide that is conjugated to the ultralong CDR3. The cytotoxic agent or therapeutic polypeptide may include, but is not limited to, a chemotherapeutic agent, a drug, a growth inhibitory agent, a toxin (e.g., an enzymatically active toxin of bacterial, fungal, plant, or animal origin, or fragments thereof), or a radioactive isotope (e.g., a radioconjugate). The cytotoxic agent or therapeutic polypeptide can be encoded by a non-antibody sequence.

In another embodiment, the present disclosure provides libraries or arrays of antibodies comprising ultralong CDR3 sequences wherein at least two members of the library or array differ in binding to targets. The target can be a protein target. The protein target can be a transmembrane protein target. Such transmembrane targets may include, but are not limited to, GPCRs, ion channels, transporters, and cell surface receptors.

The libraries or the arrays of the present disclosure may be in several formats well known in the art. The library or the array may be an addressable library or an addressable array. The library or array may be in display format, for example, the antibody sequences may be expressed on phage, ribosomes, mRNA, yeast, or mammalian cells.

Cells

The present disclosure provides cells comprising genetic sequences encoding antibodies comprising ultralong CDR3 sequences or portions thereof. The present disclosure provides cells comprising genetic sequences encoding antibodies comprising at least a portion of a knob domain or at least a portion of a knob domain of an ultralong CDR3 sequence.

The present disclosure provides cells comprising genetic sequences (e.g., genes, nucleic acids, polynucleotides) encoding an ultralong CDR3 or portion thereof. The present disclosure also provides cells comprising genetic sequences (e.g., genes, nucleic acids, polynucleotides) encoding the knob domain and/or knob domain of an ultralong CDR3.

In an embodiment, the present disclosure provides cells expressing an antibody comprising an ultralong CDR3. The cells may be prokaryotic or eukaryotic, and an antibody comprising an ultralong CDR3 may be expressed on the cell surface or secreted into the media. When displayed on the cell surface an antibody preferentially contains a motif for insertion into the plasmid membrane such as a membrane spanning domain at the C-terminus or a lipid attachment site. For bacterial cells, an antibody comprising an ultralong CDR3 may be secreted into the periplasm. When the cells are eukaryotic, they may be transiently transfected with genetic sequences encoding an antibody comprising an ultralong CDR3. Alternatively, a stable cell line or stable pools may be created by transfecting or transducing genetic sequences encoding an antibody comprising an ultralong CDR3 by methods well known to those of skill in the art. Cells can be selected by fluorescence activated cell sorting (FACS) or through selection for a gene encoding drug resistance. Cells useful for producing antibodies comprising ultralong CDR3 sequences include prokaryotic cells like *E. coli*, eukaryotic cells like the yeasts *Saccharomyces cerevisiae* and *Pichia pastoris*, insect cells (e.g., Sf9, Hi5), chinese hamster ovary (CHO) cells, monkey cells like COS-1, or human cells like HEK-293, HeLa, SP-1.

Library Methods

The present disclosure provides methods for making libraries comprising antibodies comprising ultralong CDR3 sequences. Methods for making libraries of spatially addressed libraries are described in WO 2010/054007. Methods of making libraries in yeast, phage, *E. coli*, or mammalian cells are well known in the art.

The present disclosure also provides methods of screening libraries of antibodies comprising ultralong CDR3 sequences.

General Techniques

The present disclosure relies on routine techniques in the field of recombinant genetics. Basic texts disclosing the general methods of use in this present disclosure include Sambrook and Russell, Molecular Cloning: A Laboratory Manual 3d ed. (2001); Kriegler, Gene Transfer and Expression: A Laboratory Manual (1990); and Ausubel et al., Current Protocols in Molecular Biology (1994).

For nucleic acids, sizes are given in either kilobases (Kb) or base pairs (bp). These are estimates derived from agarose or polyacrylamide gel electrophoresis, from sequenced nucleic acids, or from published DNA sequences. For proteins, sizes are given in kilo-Daltons (kD) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage and Caruthers, Tetrahedron Letters, 22:1859-1862 (1981), using an automated synthesizer, as described in Van Devanter et al., Nucleic Acids Res., 12:6159-6168 (1984). Purification of oligonucleotides is by either native polyacrylamide gel electrophoresis or by anion-exchange chromatography as described in Pearson & Reanier, J. Chrom., 255:137-149 (1983). The sequence of the cloned genes and synthetic oligonucleotides can be verified after cloning using, e.g., the chain termination method for sequencing double-stranded templates of Wallace et al., Gene, 16:21-26 (1981).

The nucleic acids encoding recombinant polypeptides of the present disclosure may be cloned into an intermediate vector before transformation into prokaryotic or eukaryotic cells for replication and/or expression. The intermediate vector may be a prokaryote vector such as a plasmid or shuttle vector.

Antibodies with UltraLong CDR3 Sequences

In an embodiment, bovine antibodies are identified and/or produced. Multiple techniques exist to identify and/or produce antibodies.

Antibodies of the present disclosure may be isolated by screening including, high-throughput screening, of combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in Methods in Molecular Biology 178:1-37 (O'Brien et al., ed., Human Press, Totowa, N.J., 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, N.J., 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004). Such screening may be iterative until a hit is obtained.

In certain phage display methods, repertoires of VH and VL genes are separately cloned by polymerase chain reaction (PCR) and recombined randomly in phage libraries, which can then be screened for antigen-binding phage as described in Winter et al., Ann. Rev. Immunol., 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Phage display libraries of bovine antibodies may be a source of bovine antibody gene sequences, including ultralong CDR3 sequences.

Typically, a non-human antibody is humanized to reduce immunogenicity to humans, while retaining the specificity and affinity of the parental non-human antibody. Generally, a humanized antibody comprises one or more variable domains in which CDRs (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the CDR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing SDR (a-CDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005); Klimka et al., Br. J. Cancer, 83:252-260 (2000) (describing the "guided selection" approach to FR shuffling); and Studnicka et al., U.S. Pat. No. 5,766,886.

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., Biol. Chem. 272:10678-10684 (1997) and Rosok et al., J. Biol. Chem. 271:22611-22618 (1996)).

Antibodies with ultralong CDR3 sequences may also include non-antibody sequences, such as cytokines, therapeutic polypeptides or growth factors, into the CDR3 region. The resultant antibody can be effective in treating or preventing a disease or condition. For example, an antibody comprising an ultralong CDR3 inhibits tumor metastasis. In some embodiments, the cytokine, therapeutic polypeptide or growth factor may be shown to have an antiproliferative effect on at least one cell population. Alternatively, or additionally, the resultant antibody modulates the expression or activity of a target (e.g., protein target, transmembrane protein target). For example, an antibody comprising an ultralong CDR3 inhibits or blocks an ion channel. The non-antibody sequence may be a hormone, a lymphokine, an interleukin, a chemokines, a cytokine, a peptide toxin, and combinations thereof. Such cytokines, therapeutic polypeptides, toxins, lymphokines, growth factors, or other hematopoietic factors include In some embodiments, the therapeutic polypeptide is a mammalian G-CSF, a growth hormone, a leptin, a α-interferon, a β-interferon, a λ-interferon, a GM-CSF, a IL-11, a IL-10, a moka1 (e.g., Moka, mokatoxin-1), or a VM-24. In some embodiments, the therapeutic polypeptide is a glucagon-like peptide 1 (GLP-1), exendin-4 (Ex-4), erythropoietin (EPO), or fibroblast growth factor (FGF21). The G-CSF may be a bovine G-CSF. The G-CSF, GM-CSF, EPO, FGF21, (3-interferon and GLP-1 may be from a human. The non-antibody sequence may be derived from or based on oxyntomodulin. The non-antibody sequence may be derived from or based on Mamba1. The non-antibody sequence may be derived from or based on Amgen1. The non-antibody sequence may be derived from or based on a 550 peptide. The non-antibody sequence may be derived from or based on a parathyroid hormone. The parathyroid hormone may be a human parathyroid hormone.

The antibodies disclosed herein may comprise one or more sequences based on or derived from a mammalian, avian, reptilian, amphibian, fish, insect, bug, or arachnid sequence. Mammals include, but are not limited to, cows, bison, buffalo, humans, mice, dogs, cats, sheep, goats, or rabbits. Avians include, but are not limited to, chicken, geese, doves, eagles, sparrows, and pigeons. Reptiles include, but are not limited to, lizards, gators, snakes, and turtles. Amphibians include, but are not limited to, frogs, salamanders, toads, and newts. Fish include, but are not limited to, tuna, salmon, whales, and sharks. Insects, bugs, and arachnids include, but are not limited to, flies, mosquitoes, spiders, and scorpions. The non-antibody sequence may be based on or derived from a bovine or human sequence. Alternatively, the non-antibody sequence is based on or derived from a lizard or scorpion sequence. The lizard may be a gila monster.

In some embodiments, the non-antibody sequence is linked to an end of an ultralong CDR3 sequence. For example, the non-antibody sequence can be linked to the 5' end or 3' end of the ultralong CDR3 nucleotide sequence. In another example, the non-antibody sequence can be linked to the N-terminus or C-terminus of the ultralong CDR3 peptide sequence.

In another embodiment, the non-antibody sequence is inserted within an ultralong CDR3 sequence. For example, the non-antibody sequence is inserted between the stalk domain of an ultralong CDR3 sequence. The non-antibody sequence can be inserted within the stalk domain of an ultralong CDR3 sequence. In another example, the non-antibody sequence is inserted between the stalk domain and the knob domain of an ultralong CDR3 sequence. Alternatively, the non-antibody sequence is inserted within the knob domain of an ultralong CDR3 sequence.

In some embodiments, the non-antibody sequence replaces at least a portion of an ultralong CDR3 sequence. The non-antibody sequence can replace about 1 or more, 2 or more, 3 or more, 4 or more, 5 or more, 10 or more, 15 or more, 20 or more, 25 or more, 30 or more, 35 or more, 40 or more, 45 or more, 50 or more, 55 or more amino acids of the ultralong CDR3 peptide sequence. The non-antibody sequence can replace about 10% or more, 20% or more, 30% or more, 40% or more, 50% or more, 55% or more, 60% or more, 65% or more, 70% or more, 75% or more, 80% or more, 85% or more, 90% or more, 95% or more of the ultralong CDR3 peptide sequence. The non-antibody sequence can replace at least a portion of a knob domain of an ultralong CDR3. The non-antibody sequence can replace about 5 or more, 10 or more, 15 or more, 20 or more, 25 or more, 30 or more, 35 or more, 40 or more, 45 or more amino acids of the knob domain of an ultralong CDR3 peptide sequence. The non-antibody sequence can replace about 10% or more, 20% or more, 30% or more, 40% or more, 50% or more, 55% or more, 60% or more, 65% or more, 70% or more, 75% or more, 80% or more, 85% or more, 90% or more, 95% or more of the knob domain of the ultralong CDR3 peptide sequence. The non-antibody sequence can replace at least a portion of a stalk domain of an ultralong CDR3. The non-antibody sequence can replace about 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more amino acids of the stalk domain of an ultralong CDR3 peptide sequence. The non-antibody sequence can replace about 10% or more, 20% or more, 30% or more, 40% or more, 50% or more, 55% or more, 60% or more, 65% or more, 70% or more, 75% or more, 80% or more, 85% or more, 90% or more, 95% or more of the stalk domain of the ultralong CDR3 peptide sequence. The amino acids may be consecutive amino acids. Alternatively, the amino acids are non-consecutive amino acids. The ultralong CDR3 may comprise one or more conserved motifs. The conserved motifs may be stalk domain conserved motifs as disclosed herein. Alternatively, the conserved motifs may be knob domain conserved motifs as disclosed herein.

In some embodiments, the non-antibody sequence replaces at least a portion of an ultralong CDR3 sequence. The non-antibody sequence can replace about 5 or more, 10 or more, 15 or more, 20 or more, 25 or more, 30 or more, 40 or more, 50 or more, 55 or more, 60 or more, 70 or more, 80 or more, 90 or more, 100 or more, 110 or more, 120 or more, 130 or more, 140 or more, 150 or more, 160 or more, 170 or more nucleotides of the ultralong CDR3 nucleotide sequence. The non-antibody sequence can replace about 10% or more, 20% or more, 30% or more, 40% or more, 50% or more, 55% or more, 60% or more, 65% or more, 70% or more, 75% or more, 80% or more, 85% or more, 90% or more, 95% or more of the ultralong CDR3 nucleotide sequence. The non-antibody sequence can replace at least a portion of a knob domain of an ultralong CDR3. The non-antibody sequence can replace about 5 or more, 10 or more, 15 or more, 20 or more, 25 or more, 30 or more, 40 or more, 50 or more, 55 or more, 60 or more, 70 or more, 80 or more, 90 or more, 100 or more, 110 or more, 120 or more, 130 or more, 140 or more nucleotides of the knob domain of an ultralong CDR3 nucleotide sequence. The non-antibody sequence can replace about 10% or more, 20% or more, 30% or more, 40% or more, 50% or more, 55% or more, 60% or more, 65% or more, 70% or more, 75% or more, 80% or more, 85% or more, 90% or more, 95% or more of the knob domain of the ultralong CDR3 nucleotide sequence. The non-antibody sequence can replace at least a portion of a stalk domain of an ultralong CDR3. The non-antibody sequence can replace about 5 or more, 10 or more, 15 or more, 20 or more, 25 or more, 30 or more, 35 or more, 40 or more, 45 or more, 50 or more, 55 or more, 60 or more, 65 or more, 70 or more nucleotides of the stalk domain of an ultralong CDR3 nucleotide sequence. The non-antibody sequence can replace about 10% or more, 20% or more, 30% or more, 40% or more, 50% or more, 55% or more, 60% or more, 65% or more, 70% or more, 75% or more, 80% or more, 85% or more, 90% or more, 95% or more of the stalk domain of the ultralong CDR3 nucleotide sequence. The nucleotides may be consecutive nucleotides. Alternatively, the nucleotides are non-consecutive nucleotides. The ultralong CDR3 may comprise one or more conserved motifs. The conserved motifs may be stalk domain conserved motifs as disclosed herein. Alternatively, the conserved motifs may be knob domain conserved motifs as disclosed herein.

An antibody comprising an ultralong CDR3 sequence and a non-antibody sequence may further comprise one or more cleavage sites between the ultralong CDR3 sequence and the non-antibody sequence. The one or more cleavage sites may be in front of the N-terminus of the non-antibody peptide sequence. For example, a cleavage site is inserted at the N-terminus of the non-antibody peptide sequence and at the C-terminus of the ultralong CDR3 peptide sequence. Alternatively, the one or more cleave sites are behind the C-terminus of the non-antibody peptide sequence. For example the cleavage site is inserted at the C-terminus of the non-antibody peptide sequence and at the N-terminus of the ultralong CDR3 peptide sequence. The one or more cleavage sites may flank both the N-terminus and the C-terminus of the non-antibody peptide sequence. The one or more cleavage sites may be upstream of the non-antibody nucleotide sequence. For example, the one or more cleavage sites may be at the 5' end of the non-antibody nucleotide sequence and at the 3' end of the ultralong CDR3 nucleotide sequence. The one or more cleavage sites may be downstream of the non-antibody nucleotide sequence. For example, the one or more cleavage sites may be at the 3' end of the non-antibody nucleotide sequence and at the 5' end of the ultralong CDR3 nucleotide sequence. The one or more cleavage sites may flank both the 5' end and the 3' end of the non-antibody nucleotide sequence. The one or more cleavage sites may directly flank the non-antibody sequence. For example, there are zero nucleotides or amino acids between the cleavage site sequence and the non-antibody sequence. Alternatively, the one or more cleavage sites may indirectly flank the non-antibody sequence. For example, there are one or more nucleotides between the cleavage site nucleotide sequence and the non-antibody nucleotide sequence. There may be 2 or more, 3 or more, 4 or more, 5 or more, 6 or more, 7 or more, 8 or more, 9 or more, 10 or more, 12 or more, 15 or more, 20 or more nucleotides between the cleavage site nucleotide sequence and the non-antibody nucleotide sequence. In another example, there are one or more amino acids between the cleavage site peptide sequence and the non-antibody peptide sequence. There may be 2 or more, 3 or more, 4 or more, 5 or more, 6 or more, 7 or more, 8 or more, 9 or more, 10 or more, 12 or more, 15 or more, 20 or more amino acids between the cleavage site peptide sequence and the non-antibody peptide sequence. The cleavage site may be adjacent to the sequence based on or derived from the ultralong CDR3 sequence, linker sequence, non-antibody sequence, non-bovine sequence, or a combination thereof. The cleavage site may be between the sequence based on or derived from the ultralong CDR3 sequence and the linker sequence. The cleavage site may be between the sequence based on or derived from the ultralong CDR3 sequence and the non-antibody sequence. The cleavage site may be between the linker sequence and the non-antibody sequence. The cleavage site may be for a protease. The protease may be a serine protease, threonine protease, cysteine protease, aspartate protease, or metalloprotease. The protease may include, but is not limited to, Factor Xa protease, chymotrypsin-like protease, trypsin-like protease, elastase-like protease, subtilisin-like protease, actinidain, bromelain, calpains, caspases, cathepsins, Mir1-CP, papain, HIV-1 protease, chymosin, renin, cathepsin D, pepsin, plasmepsin, nepenthesin, metalloexopeptidases, and metalloendopeptidases. The cleavage site may be a cleavage site for Factor Xa or thrombin. For example, the cleavage site may comprise the amino acid sequence of IEGR (SEQ ID NO: 104). Alternatively, the cleavage site is for a nuclease. The antibody comprising the ultralong CDR3 sequence and non-antibody sequence may be cleaved by one or more proteases. Cleavage of the antibody by the one or more protease can result in release of one or more ends of the non-antibody peptide from the ultralong CDR3 region of the antibody. For example, cleavage of the antibody results in release of the N-terminus of the non-antibody peptide from the ultralong CDR3 region. Alternatively, cleavage of the antibody results in release of the C-terminus of the non-antibody peptide from the ultralong CDR3 region.

The non-antibody sequence may be linked to the ultralong CDR3 sequence via one or more linkers. The non-antibody sequence may be inserted with an ultralong CDR3 sequence. In some instances, two or more linkers are used to link the non-antibody sequence to the ultralong CDR3 sequence. The two or more linkers may comprise the same sequence. Alternatively, the two or more linkers comprise different sequences. The one or more linker sequences may be the same length. The one or more linker sequences may be different lengths. The one or more linker sequences may be 3 or more, 4 or more, 5 or more, 6 or more, 7 or more, 8 or more, 9 or more or 10 or more amino acids in length. The one or more linker sequences may comprise 1 or more, 2 or more, 3 or more, 4 or more, 5 or more, 6 or more, 7 or more, 8 or more, 9 or more, or 10 or more glycine residues. The one or more linker sequences may comprise 2 or more, 3 or more, 4 or more, or 5 or more consecutive glycine residues. The one or more linker sequences may comprise 1 or more serine residues. The one or more linker sequences may comprise 1 or more, 2 or more, 3 or more, 4 or more, or 5 or more polar amino acid residues. The polar amino acid residues may be selected from serine, threonine, asparagine, or glutamine. The polar amino acid residues may comprise uncharged side chains. The linkers may be attached to the N-terminal, C-terminal, or both N- and C-termini of the non-antibody peptide sequence. The linkers may be attached to the 5'-end, 3'-end, or both the 5'- and 3' ends of the non-antibody nucleotide sequence. In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Alternatively, the linker comprises an amino acid sequence of (GGGGS)$_n$ (SEQ ID NO: 103), wherein n=1 to 5. The linker may comprise an amino acid sequence of GGGSGGGGS (SEQ ID NO: 15) or GGGGSGGGS (SEQ ID NO: 16). Amino acid residues which comprise an amino acid linker component include those occurring naturally, as well as minor amino acids and non-naturally occurring amino acids including analogs, such as citrulline. Amino acid linker components can be designed and optimized in their selectivity for enzymatic cleavage by a particular enzymes, for example, a tumor-associated protease, cathepsin B, C and D, or a plasmin protease.

The ultralong CDR3 may be based on or derived from a single ultralong CDR3 sequence. Alternatively, the ultralong CDR3 is based on or derived from two or more ultralong CDR3 sequences. The two or more ultralong CDR3 sequences may be from the same animal. Alternatively, the two or more ultralong CDR3 sequences are from two or more different animals.

The ultralong CDR3 may comprise at least a portion of a stalk domain of an ultralong CDR3. The antibodies disclosed herein may comprise 1 or more, 2 or more, 3 or more, 4 or more, 5 or more, 6 or more 7 or more, 8 or more, 9 or more, or 10 or more amino acids derived from or based on the stalk domain of the ultralong CDR3. The antibodies disclosed herein may comprise 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, or 2 or fewer amino acids derived from or based the stalk domain of the ultralong CDR3. The amino acids may be consecutive amino acids. Alternatively, the amino acids are non-consecutive amino acids. The antibodies disclosed herein may comprise a sequence that is 50% or more, 60% or more, 70% or more, 80% or more, 85% or more, 90% or more, 95% or more, 97% or more, 99% or more, or 100% homologous the sequence of the stalk domain of the ultralong CDR3. The ultralong CDR3 may comprise one or more conserved motifs derived from or based on a stalk domain of the ultralong CDR3. The antibodies disclosed herein may comprise 1 or more, 2 or more, 3 or more, 4 or more, or 5 or more conserved motifs derived from or based on the stalk domain of the ultralong CDR3. The one or more conserved motifs derived from or based on the stalk domain of the ultralong CDR3 may comprise a sequence selected from any one of SEQ ID NOS: 18-47. The antibodies disclosed herein may comprise a sequence that is 50% or more, 60% or more, 70% or more, 80% or more, 85% or more, 90% or more, 95% or more, 97% or more, 99% or more, or 100% homologous to a sequence selected from any one of SEQ ID NOS: 18-24 and 34-37. The antibodies disclosed herein may comprise a sequence that is 50% or more, 60% or more, 70% or more, 80% or more, 85% or more, 90% or more, 95% or more, 97% or more, 99% or more, or 100% homologous to a sequence selected from any one of SEQ ID NOS: 22-24.

The one or more conserved motifs derived from or based on the stalk domain of the ultralong CDR3 may comprise a CT(T/S)VHQ (SEQ ID NO: 105) motif. Alternatively, the one or more conserved motifs derived from or based on the stalk domain of the ultralong CDR3 comprise a CT(T/S)VHQX$_n$ (SEQ ID NO: 106) motif. N may be between 1 to 8, between 1 to 7, between 1 to 6, between 1 to 5, between 1 to 4, or between 1 to 3. The one or more conserved motifs derived from or based on the stalk domain of the ultralong CDR3 may comprise a CX$^1$ X$^2$ X$^3$X$^4$Q (SEQ ID NO: 107) motif. X$^1$ may be a T, S, A, or G residue. X$^2$ may be a T, S, A, P, or I residue. X$^3$ may be a V or K residue. X$^4$ may be an H, K, or Y residue. The one or more conserved motifs derived from or based on the stalk domain of the ultralong CDR3 may comprise an X$^1$ X$^2$VHQ (SEQ ID NO: 108) motif. X$^1$ may be a T, S, A, or G residue. X$^2$ may be a T, S, A, P or I residue. The one or more conserved motifs derived from or based on the stalk domain of the ultralong CDR3 may comprise a CX$^1$X$^2$VHQ (SEQ ID NO: 109) motif. X$^1$ may be a T, S, A, or G residue. X$^2$ may be a T, S, A, P or I residue. The one or more conserved motifs derived from or based on the stalk domain of the ultralong CDR3 may comprise an X$^1$X$^2$VX$^3$Q (SEQ ID NO: 110) motif. X$^1$ may be a T, S, A, or G residue. X$^2$ may be a T, S, A, P or I residue. X$^3$ may be an H, Y or K residue. The one or more conserved motifs derived from or based on the stalk domain of the ultralong CDR3 may comprise a CX$^1$ X$^2$VX$^3$Q (SEQ ID NO: 111) motif. X$^1$ may be a T, S, A, or G residue. X$^2$ may be a T, S, A, P or I residue. X$^3$ may be an H, Y or K residue. The one or more conserved motifs derived from or based on the stalk domain of the ultralong CDR3 may comprise an X$^1$X$^2$KKQ (SEQ ID NO: 112) motif. X$^1$ may be a T, S, A, or G residue. X$^2$ may be a T, S, A, P or I residue. The one or more conserved motifs derived from or based on the stalk domain of the ultralong CDR3 may comprise a CX$^1$X$^2$KKQ (SEQ ID NO: 113) motif. X$^1$ may be a T, S, A, or G residue. X$^2$ may be a T, S, A, P or I residue.

The one or more conserved motifs derived from or based on the stalk domain of the ultralong CDR3 may comprise an YX$^1$YX$^2$ (SEQ ID NO: 114) motif. X$^1$ may be a T, S, N, or I residue. X$^2$ may be an E or D residue. The one or more conserved motifs derived from or based on the stalk domain of the ultralong CDR3 may comprise an YX$^1$YX$^2$Y (SEQ ID NO: 115) motif. X$^1$ may be an L, S, T, or R residue. X$^2$ may be a T, S, N or I residue. The one or more conserved motifs derived from or based on the stalk domain of the ultralong CDR3 may comprise an YX$^1$YX$^2$YX$^3$ (SEQ ID NO: 116) motif. X$^1$ may be an L, S, T, or R residue. X$^2$ may be a T, S, N or I residue. X$^3$ may be an E or D residue. The one or more conserved motifs derived from or based on the stalk domain of the ultralong CDR3 may comprise an YX$^1$YX$^2$YX$^3$X$^4$ (SEQ ID NO: 117) motif. X$^1$ may be an L, S, T, or R residue. X$^2$ may be a T, S, N or I residue. X$^3$ may be an E or D residue. X$^4$ may be an H, W, N, F, I or Y residue. The one or more conserved motifs derived from or based on the stalk domain of the ultralong CDR3 may comprise an Y(E/D)X (SEQ ID NO: 118) motif. X may be an H, W, N, F, I or Y residue. The one or more conserved motifs derived from or based on the stalk domain of the ultralong CDR3 may comprise an XY(E/D) (SEQ ID NO: 119) motif. X may be a T, S, N or I residue. The one or more conserved motifs derived from or based on the stalk domain of the ultralong CDR3 may comprise an Y(E/D)X$^1$X$_n$W (SEQ ID NO: 120) motif. X$^1$ may be an H, W, N, F, I or Y residue. N is between 1 to 4, between 1 to 3 or between 1 to 2. The one or more conserved motifs derived from or based on the stalk domain of the ultralong CDR3 may comprise an Y(E/D)X$^1$X$^2$X$^3$X$^4$X$^5$W (SEQ ID NO: 121) motif. X$^1$ may be an H, W, N, F, I or Y residue. X$^2$ may be an Y, H, G, or N residue. X3 may be a V, I, or A residue. X$^4$ may be a D, N, T, or E residue. X$^5$ may be an A, V, S, or T residue.

The antibodies disclosed herein may comprise a first conserved motif derived from or based on the stalk domain of the ultralong CDR3 selected from any of SEQ ID NOS: 18-33 and a second conserved motif derived from or based on the stalk domain of the ultralong CDR3 selected from any of SEQ ID NOS: 34-47. The antibodies disclosed herein may comprise a first conserved motif derived from or based on the stalk domain of the ultralong CDR3 selected from a group comprising CT(T/S)VHQX$_n$ (SEQ ID NO: 122), CX$^1$X$^2$X$^3$X$^4$Q (SEQ ID NO: 27), X$^1$X$^2$VHQ. (SEQ ID NO: 28), CX$^1$X$^2$VHQ (SEQ ID NO: 29), X$^1$X$^2$VX$^3$Q (SEQ ID NO: 30), CX$^1$X$^2$VX$^3$Q (SEQ ID NO: 31), X$^1$X$^2$KKQ (SEQ ID NO: 32), and CX$^1$X$^2$KKQ (SEQ ID NO: 33) and a second conserved motif derived from or based on the stalk domain of the ultralong CDR3 selected from the group comprising YX$^1$YX$^2$ (SEQ ID NO: 38), YX$^1$YX$^2$Y (SEQ ID NO: 39), YX$^1$YX$^2$YX$^3$ (SEQ ID NO: 40), YX$^1$YX$^2$YX$^3$X$^4$ (SEQ ID NO: 41), Y(E/D)X (SEQ ID NO: 123), XY(E/D) (SEQ ID NO: 124), Y(E/D)X$^1$X$_n$W (SEQ ID NO: 125), and Y(E/D)X$^1$X$^2$X$^3$X$^4$X$^5$W (SEQ ID NO: 126).

The ultralong CDR3 may comprise at least a portion of a knob domain of an ultralong CDR3. The antibodies disclosed herein may comprise 1 or more, 2 or more, 3 or more, 4 or more, 5 or more, 6 or more 7 or more, 8 or more, 9 or more, or 10 or more amino acids derived from or based on the knob domain of the ultralong CDR3. The antibodies disclosed herein may comprise 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, or 2 or fewer amino acids derived from or based the knob domain of the ultralong CDR3. The amino acids may be consecutive amino acids. Alternatively, the amino acids are non-consecutive amino acids. The antibodies disclosed herein may comprise a sequence that is 50% or more, 60% or more, 70% or more, 80% or more, 85% or more, 90% or more, 95% or more, 97% or more, 99% or more, or 100% homologous the sequence of the knob domain of the ultralong CDR3. The ultralong CDR3 may comprise one or more conserved motifs derived from or based on a knob domain of the ultralong CDR3. The antibodies disclosed herein may comprise 1 or more, 2 or more, 3 or more, 4 or more, or 5 or more conserved motifs derived from or based on the knob domain of the ultralong CDR3. The one or more conserved motifs derived from or based on the knob domain may comprise a cysteine motif as disclosed herein. Alternatively, or additionally, one or more conserved motifs derived from or based on the knob domain comprises a C(P/S)DG (SEQ ID NO: 127) motif.

The antibodies disclosed herein may comprise a sequence based on or derived from a mammal. The mammal may be a bovine. Alternatively, the mammal is a non-bovine mammal, such as a human. The antibody sequences may be 3 or more, 4 or more, 5 or more, 6 or more, 7 or more, 8 or more, 9 or more, 10 or more, 11 or more, 12 or more, 15 or more, 20 or more, 25 or more, 30 or more, 35 or more, 40 or more 45 or more, 50 or more, 55 or more, 60 or more, 65 or more 70 or more, 80 or more, 90 or more, 100 or more, 110 or more, 120 or more, 130 or more, 140 or more, 150 or more, 160 or more, 170 or more, 180 or more 190 or more, 200 or more, 220 or more, 230 or more, 240 or more 250 or more, 260 or more, 270 or more, 280 or more, 290 or more or 300 or more amino acids in length. The amino acids may be consecutive amino acids. Alternatively, the amino acids are non-consecutive amino acids.

The antibody sequences may comprise a bovine antibody sequence comprising 3 or more, 4 or more, 5 or more, 6 or more, 7 or more, 8 or more, 9 or more, 10 or more, 11 or more, 12 or more, 15 or more, 20 or more, 25 or more, 30 or more, 35 or more, 40 or more 45 or more, 50 or more, 55 or more, 60 or more, 65 or more 70 or more, 80 or more, 90 or more, 100 or more, 110 or more, 120 or more, 130 or more, 140 or more, 150 or more, 160 or more, 170 or more, 180 or more 190 or more, 200 or more, 220 or more, 230 or more, 240 or more 250 or more 260 or more, 270 or more, 280 or more, 290 or more or 300 or more amino acids in length. The bovine antibody may be a BLVH12, BLV5B8, BLVCV1, BLV5D3, BLV8C11, BF1H1, or F18 antibody. The antibody sequences may comprise a human antibody sequence comprising 3 or more, 4 or more, 5 or more, 6 or more, 7 or more, 8 or more, 9 or more, 10 or more, 11 or more, 12 or more, 15 or more, 20 or more, 25 or more, 30 or more, 35 or more, 40 or more 45 or more, 50 or more, 55 or more, 60 or more, 65 or more 70 or more, 80 or more, 90 or more, 100 or more, 110 or more, 120 or more, 130 or more, 140 or more, 150 or more, 160 or more, 170 or more, 180 or more 190 or more, 200 or more, 220 or more, 230 or more, 240 or more 250 or more 260 or more, 270 or more, 280 or more, 290 or more or 300 or more amino acids in length. The amino acids may be consecutive amino acids. Alternatively, the amino acids are non-consecutive amino acids.

The antibody sequence based on or derived from at least a portion of the ultralong CDR3 can be 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, or 5 or fewer amino acids in length. The antibody sequence based on or derived from at least a portion of the ultralong CDR3 may be 3 or more, 4 or more, 5 or more, 6 or more, 7 or more, 8 or more, 9 or more, 10 or more, 11 or more, 12 or more, 13 or more, 14 or more, or 15 or more amino acids in length. The amino acids may be consecutive amino acids. Alternatively, the amino acids are non-consecutive amino acids.

The antibody sequence based on or derived from at least a portion of the ultralong CDR3 can contain 1 or more, 2 or more, 3 or more, 4 or more, 5 or more, 6 or more, 7 or more, 8 or more, 9 or more, 10 or more, 15 or more, 20 or more, 25 or more, 30 or more, 35 or more, 40 or more, 50 or more, 60 or more, 70 or more, 80 or more, 90 or more, or 100 or more nucleic acid modifications or alterations in the nucleotide sequence of the ultralong CDR3 from which it is based on or derived from. The modifications and/or alterations may comprise substitutions, deletions, and/or insertions. Substitutions may comprise replacing one nucleic acid with another nucleic acid. The nucleic acid may be a natural nucleic acid or a non-natural nucleic acid.

The antibody sequence based on or derived from at least a portion of the ultralong CDR3 can contain 1 or more, 2 or more, 3 or more, 4 or more, 5 or more, 6 or more, 7 or more, 8 or more, 9 or more, 10 or more, 15 or more, 20 or more, 25 or more, 30 or more, 35 or more, 40 or more, 50 or more, or 60 or more amino acid modifications or alterations in the peptide sequence of the ultralong CDR3 from which it is based on or derived from. The modifications and/or alterations may comprise substitutions, deletions, and/or insertions. Substitutions may comprise replacing one amino acid with another amino acid. The amino acids to be substituted may contain one or more similar features to the amino acid by which it is replaced. The features may include, but are not limited to, size, polarity, hydrophobicity, acidity, side chain, and bond formations. The amino acid may be a natural amino acid or a non-natural amino acid.

In certain embodiments, the half-life of an antibody described herein is greater than the half-life of the un-conjugated therapeutic peptide or un-conjugated non-antibody peptide that is incorporated in the antibody. In some embodiments, the half-life of an antibody provided herein is greater than 4 hours when administered to a subject. In certain embodiments, the half-life of an antibody provided herein is greater than 4 hours, greater than 6 hours, greater than 12 hours, greater than 24 hours, greater than 36 hours, greater than 2 days, greater than 3 days, greater than 4 days, greater than 5 days, greater than 6 days, greater than 7 days, greater than 8 days, greater than 9 days, greater than 10 days, greater than 11 days, greater than 12 days, greater than 13 days, or greater than 14 days when administered to a subject. In some instances, the subject is a mammal. In some embodiments, the subject is a mouse or a bovine. In other instances, the subject is a human. In certain embodiments, a pharmaceutical composition comprising the antibody is administered to the subject once a day, every two days, every three days, every 4 days, every 7 days, every 10 days, every 14 days, every 21 days, every 28 days, every 2 months, or every three months.

The antibodies may be modified or altered to reduce immunogenicity. For example, the sequence of a partially bovine or non-bovine antibody may be modified or altered to reduce immunogenicity to humans. A non-human antibody may be humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

The antibodies comprising an ultralong CDR3 as disclosed herein are preferably monoclonal. Also encompassed within the scope of the disclosure are Fab, Fab', Fab'-SH and F(ab')$_2$ fragments of the antibodies comprising an ultralong CDR3 as provided herein. These antibody fragments can be created by traditional means, such as enzymatic digestion, or may be generated by recombinant techniques. Such antibody fragments may be chimeric or humanized. These fragments are useful for the diagnostic and therapeutic purposes set forth below.

Monoclonal antibodies are obtained from a population of substantially homogeneous antibodies, e.g., the individual antibodies comprising the population are identical except for possible naturally occurring mutations that may be present in minor amounts. Thus, the modifier "monoclonal" indicates the character of the antibody as not being a mixture of discrete antibodies.

The antibodies comprising an ultralong CDR3 as disclosed herein can be made using a hybridoma cell-based method first described by Kohler et al., Nature, 256:495 (1975), or may be made by recombinant DNA methods.

Hybridoma cells can be generated by fusing B cells producing a desired antibody with an immortalized cell line, usually a myeloma cell line, so that the resulting fusion cells will be an immortalized cell line that secrets a particular antibody. By the same principle, myeloma cells can be first transfected with a nucleic acid encoding a germline antibody V region and can be screened for the expression of the germline V region. Those myeloma cells with highest level of proteolytic light chain expression can be subsequently fused with B cells that produce an antibody with desired target protein specificity. The fusion cells will produce two types of antibodies: one is a heterologous antibody containing an endogenous antibody chain (either heavy or light) operably joined to the recombinant germline V region (either heavy or light), and the other is the same antibody that the parental B cells would secrete (e.g. both endogenous heavy and light chains). The operably joined heterologous heavy and light chains can be isolated by conventional methods such as chromatography and identification can be confirmed by target protein binding assays, assays identifying a unique tag of the germline polypeptide, or endopeptidase activity assays described in other sections of this disclosure. In some cases, where the heterologous antibody is the predominant type in quantity among the two types of antibodies, such isolation may not be needed.

The hybridoma cells may be seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, myeloma cell lines may be murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, pp. 51-63 (Marcel Dekker, Inc., New York, 1987)).

Culture medium in which hybridoma cells are growing is assayed for production of antibodies comprising an ultralong CDR3. For example, the binding specificity of monoclonal antibodies produced by hybridoma cells may be determined by immunoprecipitation or by an in vitro binding assay, such as an enzyme-linked immunoadsorbent assay (ELISA).

The binding affinity of the monoclonal antibody can, for example, be determined by the Scatchard analysis of Munson et al., Anal. Biochem., 107:220 (1980).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

The antibodies comprising an ultralong CDR3 as disclosed herein may be made by using combinatorial libraries to screen for synthetic antibody clones with the desired activity or activities. For example, synthetic antibody clones are selected by screening phage libraries containing phage that display various fragments of antibody variable regions (e.g., scFv or Fab) fused to phage coat protein. Such phage libraries may be panned, for example, by affinity chromatography against the desired antigen. Clones expressing antibody fragments capable of binding to the desired antigen may be adsorbed to the antigen and thus separated from the non-binding clones in the library. The binding clones may then be eluted from the antigen, and can be further enriched by additional cycles of antigen adsorption/elution. Any of the antibodies comprising an ultralong CDR3 as disclosed herein may be obtained by designing a suitable antigen screening procedure to select for the phage clone of interest followed by construction of a full length antibody comprising an ultralong CDR3 clone using the VH and VL (e.g., from scFv or Fab) sequences from the phage clone of interest and suitable constant region (Fc) sequences described in Kabat et al., Sequences of Proteins of Immunological Interest, Fifth Edition, NIH Publication 91-3242, Bethesda Md. (1991), vols. 1-3.

The antigen-binding domain of an antibody is formed from two variable (V) regions, one each from the light (VL) and heavy (VH) chains, that both present three hypervariable loops or complementarity-determining regions (CDRs). Variable domains may be displayed functionally on phage, either as single-chain Fv (scFv, also referred to as single-chain antibody (SCA)) fragments, in which VH and VL are covalently linked through a short, flexible peptide, or as Fab fragments, in which they are each fused to a constant domain and interact non-covalently, as described in Winter et al., Ann. Rev. Immunol., 12: 433-455 (1994). scFv or SCA encoding phage clones and Fab encoding phage clones may be separately or collectively referred to as "Fv phage clones" or "Fv clones".

Repertoires of VH and VL genes may be separately cloned by polymerase chain reaction (PCR) and recombined randomly in phage libraries, which can then be searched for antigen-binding clones as described in Winter et al., Ann. Rev. Immunol., 12: 433-455 (1994). Libraries from immunized sources provide high-affinity antibodies to the immunogen without the requirement of constructing hybridomas. Alternatively, the naive repertoire may be cloned to provide a single source of human antibodies to a wide range of non-self and also self antigens without any immunization as described by Griffiths et al., EMBO J. 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, J. Mol. Biol., 227: 381-388 (1992).

Filamentous phage is used to display antibody fragments by fusion to the minor coat protein pIII. Protein pIII may include truncated forms of pIII. The antibody fragments can be displayed as single chain Fv fragments, in which VH and VL domains are connected on the same polypeptide chain by a flexible polypeptide spacer, (e.g., as described by Marks et al., J. Mol. Biol., 222: 581-597 (1991)), or as Fab fragments, in which one chain is fused to pIII (e.g., a truncated pIII) and the other is secreted into the bacterial host cell periplasm where assembly of a Fab-coat protein structure which becomes displayed on the phage surface by displacing some of the wild type coat proteins, (e.g., as described in Hoogenboom et al., Nucl. Acids Res., 19: 4133-4137 (1991)).

Nucleic acid encoding antibody variable gene segments (including VH and VL segments) are recovered from the cells of interest and and may be amplified or copies made by recombinant DNA techniques (e.g., Kunkel mutagenesis). For example, in the case of rearranged VH and VL gene libraries, the desired DNA may be obtained by isolating genomic DNA or mRNA from lymphocytes followed by polymerase chain reaction (PCR) with primers matching the 5' and 3' ends of rearranged VH and VL genes as described in Orlandi et al., Proc. Natl. Acad. Sci. (USA), 86: 3833-3837 (1989), thereby making diverse V gene repertoires for expression. The V genes may be amplified from cDNA and genomic DNA, with back primers at the 5' end of the exon encoding the mature V-domain and forward primers based within the J-segment as described in Orlandi et al. (1989) and in Ward et al., Nature, 341: 544-546 (1989). For amplifying from cDNA, back primers can also be based in the leader exon as described in Jones et al., Biotechnol., 9: 88-89 (1991), and forward primers within the constant region as described in Sastry et al., Proc. Natl. Acad. Sci. (USA), 86: 5728-5732 (1989). To enhance or maximize complementarity, degeneracy may be incorporated in the primers as described in Orlandi et al. (1989) or Sastry et al. (1989). Library diversity may be enhanced or maximized by using PCR primers targeted to each V-gene family in order to amplify available VH and VL arrangements present in the immune cell nucleic acid sample, for example, as described in the method of Marks et al., J. Mol. Biol., 222: 581-597 (1991) or as described in the method of Orum et al., Nucleic Acids Res., 21: 4491-4498 (1993). For cloning of the amplified DNA into expression vectors, rare restriction may can be introduced within the PCR primer as a tag at one end as described in Orlandi et al. (1989), or by further PCR amplification with a tagged primer as described in Clackson et al., Nature, 352: 624-628 (1991).

Repertoires of synthetically rearranged V genes may be derived in vitro from V gene segments. Most of the human VH-gene segments have been cloned and sequenced (e.g., reported in Tomlinson et al., J. Mol. Biol., 227: 776-798 (1992)), and mapped (e.g., reported in Matsuda et al., Nature Genet., 3: 88-94 (1993); these cloned segments (including all the major conformations of the H1 and H2 loop) may be used to generate diverse VH gene repertoires with PCR primers encoding H3 loops of diverse sequence and length as described in Hoogenboom and Winter, J. Mol. Biol., 227: 381-388 (1992). VH repertoires may also be made with all the sequence diversity focused in a long H3 loop of a single length as described in Barbas et al., Proc. Natl. Acad. Sci. USA, 89: 4457-4461 (1992). Human Vκ and Vλ segments have been cloned and sequenced (reported in Williams and Winter, Eur. J. Immunol., 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, J. Mol. Biol., 227: 381-388 (1992).

Repertoires of antibody fragments may be constructed by combining VH and VL gene repertoires together in several ways. Each repertoire may be created in different vectors, and the vectors recombined in vitro, for example, as described in Hogrefe et al., Gene, 128: 119-126 (1993), or in vivo by combinatorial infection, for example, the loxP system described in Waterhouse et al., Nucl. Acids Res., 21: 2265-2266 (1993). The in vivo recombination approach exploits the two-chain nature of Fab fragments to overcome the limit on library size imposed by E. coli transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about $10^{12}$ clones). Both vectors contain in vivo recombination signals so that the VH and VL genes are recombined onto a single replicon and are co-packaged into phage virions. These large libraries may provide large numbers of diverse antibodies of good affinity ($K_d^{-1}$ of about $10^{-8}$M).

Alternatively, the repertoires may be cloned sequentially into the same vector, for example, as described in Barbas et al., Proc. Natl. Acad. Sci. USA, 88: 7978-7982 (1991), or assembled together by PCR and then cloned, for example, as described in Clackson et al., Nature, 352: 624-628 (1991). PCR assembly may also be used to join VH and VL DNAs with DNA encoding a flexible peptide spacer to form single chain Fv (scFv) repertoires. In yet another technique, "in cell PCR assembly" may be used to combine VH and VL genes within lymphocytes by PCR and then clone repertoires of linked genes as described in Embleton et al., Nucl. Acids Res., 20: 3831-3837 (1992).

The antibodies produced by naive libraries (either natural or synthetic) can be of moderate affinity ($K_d^{-1}$ of about $10^6$ to $10^7 M^{-1}$), but affinity maturation may also be mimicked in vitro by constructing and reselecting from secondary libraries as described in Winter et al. (1994), supra. For example, mutation can be introduced at random in vitro by using error-prone polymerase (reported in Leung et al., Technique, 1: 11-15 (1989)) in the method of Hawkins et al., J. Mol. Biol., 226: 889-896 (1992) or in the method of Gram et al., Proc. Natl. Acad. Sci. USA, 89: 3576-3580 (1992). Additionally, affinity maturation may be performed by randomly mutating one or more CDRs, for example, using PCR with primers carrying random sequence spanning the CDR of interest, in selected individual Fv clones and screening for higher affinity clones. WO 9607754 described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., Biotechnol., 10: 779-783 (1992). This technique allows the production of antibodies and antibody fragments with affinities in the $10^{-9}$M range.

The phage library samples are contacted with an immobilized protein under conditions suitable for binding of at least a portion of the phage particles with the adsorbent. Normally, the conditions, including pH, ionic strength, temperature and the like are selected to mimic physiological conditions. The phages bound to the solid phase are washed and then eluted by acid, e.g., as described in Barbas et al., Proc. Natl. Acad. Sci. USA, 88: 7978-7982 (1991), or by alkali, (e.g., as described in Marks et al., J. Mol. Biol., 222: 581-597 (1991)), or by antigen competition, (e.g., in a procedure similar to the antigen competition method of Clackson et al., Nature, 352: 624-628 (1991)). Phages may be enriched 20-1,000-fold in a single round of selection.

Moreover, the enriched phages may be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) may be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) may be promoted by use of long washes and monovalent phage display as described in Bass et al., Proteins, 8: 309-314 (1990) and in WO 92/09690, and a low coating density of antigen as described in Marks et al., Biotechnol., 10: 779-783 (1992).

DNA encoding the hybridoma-derived monoclonal antibodies or phage display Fv clones disclosed herein is readily isolated and sequenced using conventional procedures (e.g., by using oligonucleotide primers designed to specifically amplify the heavy and light chain coding regions of interest from hybridoma or phage DNA template). Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of the desired monoclonal antibodies in the recombinant host cells. Recombinant expression in bacteria of antibody-encoding DNA has been described by Better et al., U.S. Pat. No. 6,204,023 (see also, e.g., Skerra et al., Curr. Opinion in Immunol., 5: 256 (1993) and Pluckthun, Immunol. Revs, 130: 151 (1992)).

DNA encoding Fv clones as disclosed herein may be combined with known DNA sequences encoding heavy chain and/or light chain constant regions (e.g., the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions may be obtained from any human or animal species. A Fv clone derived from the variable domain DNA of one animal (such as human) species and then fused to constant region DNA of another animal species to form coding sequence(s) for "hybrid", full length heavy chain and/or light chain is included in the definition of "chimeric" and "hybrid" antibody as used herein. In a preferred Fv clone embodiment, a Fv clone derived from human variable DNA is fused to human constant region DNA to form coding sequence(s) for all human, full or partial length heavy and/or light chains.

DNA encoding an antibody comprising an ultralong CDR3 derived from a hybridoma disclosed herein may also be modified, for example, by substituting the coding sequence for human heavy- and light-chain constant domains in place of homologous murine sequences derived from the hybridoma clone (e.g., as in the method of Morrison et al., Proc. Natl. Acad. Sci. USA, 81: 6851-6855 (1984)). DNA encoding a hybridoma or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies disclosed herein.

Antibody Genes and Proteins

The present disclosure provides antibody genes and proteins including, for example, chimeric, recombinant, engineered, synthetic, hybrid, bovine, fully bovine, bovinized, human, fully human or humanized antibody genes or proteins that comprise an ultralong CDR3 sequence. The antibodies disclosed herein may selectively or specifically bind to an epitope of a target protein. In some embodiments, the antibody may be an antagonist (e.g., blocking) antibody or an agonist antibody.

The variable region of the heavy and light chains are encoded by multiple germline gene segments separated by non-coding regions, or introns, and often are present on different chromosomes. For example, the genes for the human immunoglobulin heavy chain region contains approximately 65 variable (VH) genes, 27 Diversity (DH) genes, and 6 Joining (JH) genes. The human kappa (κ) and lambda (λ) light chains are also each encoded by a similar number of VL and JL gene segments, but do not include any D gene segments. Exemplary VH, DH, JH and VL (Vκ or Vλ) and JL (Jκ or Jλ) germline gene segments are set forth in WO 2010/054007.

During B cell differentiation germline DNA is rearranged whereby one DH and one JH gene segment of the heavy chain locus are recombined, which is followed by the joining of one VH gene segment forming a rearranged VDJ gene that encodes a VH chain. The rearrangement occurs only on a single heavy chain allele by the process of allelic exclusion. Allelic exclusion is regulated by in-frame or "productive" recombination of the VDJ segments, which occurs in only about one-third of VDJ recombinations of the variable heavy chain. When such productive recombination events first occur in a cell, this result in production of a µ heavy chain that gets expressed on the surface of a pre-B cell and transmits a signal to shut off further heavy chain recombination, thereby preventing expression of the allelic heavy chain locus. The surface-expressed µ heavy chain also acts to activate the kappa (κ) locus for rearrangement. The lambda (λ) locus is only activated for rearrangement if the κ recombination is unproductive on both loci. The light chain rearrangement events are similar to the heavy chain, except that only the VL and JL segments are recombined. Before primary transcription of each, the corresponding constant chain gene is added. Subsequent transcription and RNA splicing leads to mRNA that is translated into an intact light chain or heavy chain.

The variable regions of antibodies confer antigen binding and specificity due to recombination events of individual germline V, D and J segments, whereby the resulting recombined nucleic acid sequences encoding the variable region domains differ among antibodies and confer antigen-specificity to a particular antibody. The variation, however, is limited to three complementarity determining regions (CDR1, CDR2, and CDR3) found within the N-terminal domain of the heavy (H) and (L) chain variable regions. The CDRs are interspersed with regions that are more conserved, termed "framework regions" (FR). The extent of the framework region and CDRs has been precisely defined (see e.g., Kabat, E. A. et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917). Each VH and VL is typically composed of three CDRs and four FRs arranged from the amino terminus to carboxy terminus in the following order: FR1, CDR1, FR2, CDR2, FR3, CDR3 and FR4. Sequence variability among VL and VH domains is generally limited to the CDRs, which are the regions that form the antigen binding site. For example, for the heavy chain, generally, VH genes encode the N-terminal three framework regions, the first two complete CDRs and the first part of the third CDR), the DH gene encodes the central portion of the third CDR, and the JH gene encodes the last part of the third CDR and the fourth framework region. For the light chain, the VL genes encode the first CDR and second CDR. The third CDR (CDRL3) is formed by the joining of the VL and JL gene segments. Hence, CDRs 1 and 2 are exclusively encoded by germline V gene segment sequences. The VH and VL chain CDR3s form the center of the Ag-binding site, with CDRs 1 and 2 form the outside boundaries; the FRs support the scaffold by orienting the H and L CDRs. On average, an antigen binding site typically requires at least four of the CDRs make contact with the antigen's epitope, with CDR3 of both the heavy and light chain being the most variable and contributing the most specificity to antigen binding (see, e.g., Janis Kuby, Immunology, Third Edition, New York, W.H. Freeman and Company, 1998, pp. 115-118). CDRH3, which includes all of the D gene segment, is the most diverse component of the Ab-binding site, and typically plays a critical role in defining the specificity of the Ab. In addition to sequence variation, there is variation in the length of the CDRs between the heavy and light chains.

The constant regions, on the other hand, are encoded by sequences that are more conserved among antibodies. These domains confer functional properties to antibodies, for example, the ability to interact with cells of the immune system and serum proteins in order to cause clearance of infectious agents. Different classes of antibodies, for example IgM, IgD, IgG, IgE and IgA, have different constant regions, allowing them to serve distinct effector functions.

These natural recombination events of V, D, and J, can provide nearly $2\times10^7$ different antibodies with both high affinity and specificity. Additional diversity is introduced by nucleotide insertions and deletions in the joining segments and also by somatic hypermutation of V regions. The result is that there are approximately $10^{10}$ antibodies present in an individual with differing antigen specificities.

Antibody Fragments

The present disclosure encompasses antibody fragments. In certain circumstances there are advantages of using antibody fragments, rather than whole antibodies. The smaller size of the fragments allows for rapid clearance, and may lead to improved access to solid tumors. Antibody fragments include, but are not limited to, Fab, Fab', Fab'-SH, F(ab')2, Fv, Fv', Fd, Fd', scFv, hsFv fragments, and diabodies, and other fragments described below. For a review of certain antibody fragments, see Hudson et al. Nat. Med. 9:129-134 (2003). For a review of scFv fragments, see, e.g., Pluckthun, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9: 129134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516). Antibody fragments can be made by various techniques, including but not limited to proteolytic digestion of an intact antibody as well as production by recombinant host cells (e.g. E. coli or phage), as described herein.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. coli, thus allowing the facile production of large amounts of these fragments (see, e.g., U.S. Pat. No. 6,204,023). Antibody fragments can be isolated from antibody phage libraries as discussed above. Alternatively, Fab'-SH fragments can be directly recovered from E. coli and chemically coupled to form F(ab')$_2$ fragments (see, e.g., Carter et al., Bio/Technology 10: 163-167 (1992)). According to another approach, F(ab')$_2$ fragments can be isolated directly from recombinant host cell culture. Fab and F(ab')$_2$ fragment with increased in vivo half-life comprising a salvage receptor binding epitope residues (see, e.g., in U.S. Pat. No. 5,869,046). Other techniques for the production of antibody fragments will be apparent to the skilled practitioner. In other embodiments, the antibody of choice is a single chain Fv fragment (scFv or single chain antibody (SCA)). See WO 93/16185; U.S. Pat. Nos. 5,571,894; and 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, Supra. The antibody fragment may also be a "linear antibody", for example, as described in U.S. Pat. No. 5,641,870. Such linear antibody fragments may be monospecific or bispecific.

Humanized Antibodies

The present disclosure provides humanized antibodies comprising an ultralong CDR3. Humanized antibodies may include human engineered antibodies (see, e.g., Studnicka et al. (1994) Protein Eng. 7(6) 805-814; and U.S. Pat. No. 5,766,886). Various methods for humanizing non-human antibodies are known in the art. For example, a humanized antibody can have one or more amino acid residues introduced into it from a source which is human or non-human. Humanization may be performed following the method of Studnicka (see, e.g., Studnicka et al. (1994) Protein Eng. 7(6) 805-814; and U.S. Pat. No. 5,766,886), including the preparation of modified antibody variable domains. Humanization may alternatively be performed following the method of Winter and co-workers (Jones et al. (1986) Nature 321:522-525; Riechmann et al. (1988) Nature 332:323-327; Verhoeyen et al. (1988) Science 239:1534-1536), by substituting hypervariable region sequences for the corresponding sequences of a human antibody. Accordingly, such "humanized" or "human engineered" antibodies are chimeric antibodies, including wherein substantially less than an intact human variable domain has been substituted by or incorporated into the corresponding sequence from a non-human species. For example, humanized antibodies may be human antibodies in which some hypervariable region residues and possibly some FR residues are substituted by residues from analogous sites in rodent antibodies. Alternatively, humanized or human engineered antibodies may be non-human (e.g., rodent) antibodies in which some residues are substituted by residues from analogous sites in human antibodies (see, e.g., Studnicka et al. (1994) Protein Eng. 7(6) 805-814; and U.S. Pat. No. 5,766,886).

The choice of human variable domains, both light and heavy, to be used in making the humanized antibodies is important to reduce antigenicity. For example, to the so-called "best-fit" method, the sequence of the variable domain of a rodent antibody is screened against the entire library of known human variable-domain sequences. The human sequence which is closest to that of the rodent is then accepted as the human framework for the humanized antibody (Sims et al. (1993) J. Immunol. 151:2296; Chothia et al. (1987) J. Mol. Biol. 196:901). Another method uses a particular framework derived from the consensus sequence of all human antibodies of a particular subgroup of light or heavy chains. The same framework may be used for several different humanized antibodies (Carter et al. (1992) Proc. Natl. Acad. Sci. USA, 89:4285; Presta et al. (1993) J. Immunol., 151:2623).

It is further important that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, e.g., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

In some embodiments, the humanized antibodies comprising an ultralong CDR3 may be deimmunized. Methods of deimmunizing an antibody or protein are well known in the art. The immunogenicity of therapeutic proteins such as antibodies is thought to result from the presence of T-cell epitopes which can bind MHC class II molecules and generate a proliferative and cytokine response in CD4+ helper T-cells. These CD4+ helper cells then collaborate with B-cells to generate an antibody response against the therapeutic protein. Removal of the T-cell epitopes are thought to be key steps in deimmunizing a recombinant protein. T-cell epitopes can be predicted by in silico algorithms that identify residues required for binding MHC. Alternatively, epitopes can be identified directly by utilizing peripheral blood mononuclear cells from panels of human donors and measuring their response against the therapeutic protein when incubated with antigen presenting cells. Such in silico and in vitro systems are well known in the art [Jones T D, Crompton L J, Carr F J, Baker M P. Methods Mol Biol. 2009; 525:405-23, Deimmunization of monoclonal antibodies; and Baker M, and Jones T D. The identification and removal of immunogenicity in therapeutic proteins. *Curr.* *Opin. Drug Discovery Dev.* 2007; (2007); 10(2): 219-227]. When peptides are identified that bind MHC II or otherwise stimulate CD4+ cell activation, the residues of the peptide can be mutated one by one and tested for T-cell activation until a mutation is found which disrupts MHC II binding and T-cell activation. Such mutations, when found in an individual peptide, can be encoded directly in the recombinant therapeutic protein. Incubation of the whole protein with antigen presenting cells will not induce a significant CD4+ response, indicating successful deimmunization.

Bovine Antibodies

The present disclosure provides for bovine antibodies comprising an ultralong CDR3. The bovine antibodies may be recombinant antibodies, engineered antibodies, synthetic antibodies, bovinized antibodies, or fully bovine antibodies. Bovinized antibodies may include bovine engineered antibodies. Methods for producing a bovinized antibody may comprise introducing one or more amino acid residues into it from a source which is a bovine. In some instances, methods for producing a bovinized antibody may comprise introducing one or more amino acid residues into it from a source which is a non-bovine. Bovinization may be performed by preparing a modified antibody variable domains. Alternatively, bovinization may be performed by substituting hypervariable region sequences for the corresponding sequences of a bovine antibody. Accordingly, such "bovinized" or "bovine engineered" antibodies are chimeric antibodies. Chimeric antibodies may include antibodies wherein substantially less than an intact bovine variable domain has been substituted by or incorporated into the corresponding sequence from a non-bovine species. Bovinized or bovine engineered antibodies may be bovine antibodies in which some hypervariable region residues and constant region residues are substituted by residues from analogous sites in non-bovine antibodies. Alternatively, bovinized, bovine engineered or fully bovine antibodies may be non-bovine (e.g., human) antibodies in which some residues are substituted by residues from analogous sites in bovine antibodies. For example, a bovine immunoglobuline region can be used to replace a non-bovine (e.g., human, rodent) immunoglobulin region to produce a fully bovine, bovinized or bovine engineered antibody.

Bispecific Antibodies

Bispecific antibodies are monoclonal, preferably human or humanized, antibodies that have binding specificities for at least two different antigens. For example, one of the binding specificities may be for a first antigen and the other may be for any other antigen. Exemplary bispecific antibodies may bind to two different epitopes of the same protein. Bispecific antibodies may also be used to localize cytotoxic agents to cells which express a particular protein. These antibodies possess a binding arm specific for the particular protein and an arm which binds the cytotoxic agent (e.g., saporin, anti-interferon-α, vinca alkaloid, ricin A chain, methotrexate or radioactive isotope hapten). Bispecific antibodies may be prepared as full length antibodies or antibody fragments (e.g., F(ab')$_2$ bispecific antibodies).

Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature, 305: 537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829, and in Traunecker et al., EMBO J., 10: 3655 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are not of particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure may facilitate the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach, the interface between a pair of antibody molecules may can be engineered to maximize the percentage of heterodimers which are recovered from recombinant cell culture. The preferred interface comprises at least a part of the $C_{H3}$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate may be coupled to avidin, the other to biotin. Such antibodies have, for example, been proposed to target immune system cells to unwanted cells (U.S. Pat. No. 4,676,980), and for treatment of HIV infection (WO 91/00360, WO 92/00373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies may be prepared using chemical linkage. Brennan et al., Science, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced may be used as agents for the selective immobilization of enzymes.

Recent progress has facilitated the direct recovery of Fab'-SH fragments from E. coli, which can be chemically coupled to form bispecific antibodies. Shalaby et al., J. Exp. Med., 175: 217-225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. See, e.g., Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See, Gruber et al., J. Immunol., 152:5368 (1994).

Antibodies with more than two valencies are contemplated. For example, trispecific antibodies can be prepared. See, e.g., Tutt et al. J. Immunol. 147: 60 (1991).

Multivalent Antibodies

A multivalent antibody may be internalized (and/or catabolized) faster than a bivalent antibody by a cell expressing an antigen to which the antibodies bind. The antibodies of the present disclosure may be multivalent antibodies (which are other than of the IgM class) with three or more antigen binding sites (e.g., tetravalent antibodies), which may be produced by recombinant expression of nucleic acid encoding the polypeptide chains of the antibody. The multivalent antibody may comprise a dimerization domain and three or more antigen binding sites. A preferred dimerization domain may comprise (or consist of) an Fc region or a hinge region. In this scenario, the antibody will comprise an Fc region and three or more antigen binding sites amino-terminal to the Fe region. A preferred multivalent antibody may comprise (or consist of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. A multivalent antibody may preferably further comprises at least two (and preferably four) light chain variable domain polypeptides. A multivalent antibody may, for instance, comprise from about two to about eight light chain variable domain polypeptides. The light chain variable domain polypeptides may comprise a light chain variable domain and, optionally, further comprise a CL domain.

Antibody Variants

In some embodiments, amino acid sequence modification(s) of the antibodies comprising an ultralong CDR3 as described herein are contemplated. For example, it may be desirable to improve the binding affinity and/or other biological properties of the antibody. Amino acid sequence variants including, for example, conservatively modified variants, of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) Science, 244: 1081-1085. Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g., for ADEPT) or a polypeptide which increases the serum half-life of the antibody.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fucose attached to an Fc region of the antibody have been described (see, e.g., US 2003/0157108, US 2004/0093621. Antibodies with a bisecting N-acetylglucosamine (GlcNAc) in the carbohydrate attached to an Fc region of the antibody have been described (see, e.g., WO 2003/011878, and U.S. Pat. No. 6,602,684). Antibodies with at least one galactose residue in the oligosaccharide attached to an Fc region of the antibody WO 1997/30087; see, also, WO 1998/58964 and WO 1999/22764 concerning antibodies with altered carbohydrate attached to the Fc region thereof). Antigen-binding molecules with modified glycosylation have been described (see, e.g., WO 99/54342, U.S. Pat. Nos. 6,602,684 and 7,517,670, and US 2004/0072290; see also, e.g., U.S. Pat. Nos. 7,214,775 and 7,682,610).

The preferred glycosylation variant herein comprises an Fc region, wherein a carbohydrate structure attached to the Fc region lacks fucose. Such variants have improved ADCC function. Optionally, the Fc region further comprises one or more amino acid substitutions therein which further improve ADCC, for example, substitutions at positions 298, 333, and/or 334 of the Fc region (Eu numbering of residues). Examples of publications related to "defucosylated" or "fucose-deficient" antibodies include: US 2003/0157108; WO 2000/61739; WO 2001/29246; US 2003/0115614 (now U.S. Pat. No. 6,946,292) US 2002/0164328 (now U.S. Pat. No. 7,064,191); US 2004/0093621; US 2004/0132140; US 2004/0110704; US 2004/0110282 (now U.S. Pat. No. 7,749, 753); US 2004/0109865; WO 2003/085119; WO 2003/ 084570; WO 2005/035586; WO 2005/035778; WO2005/ 053742; Okazaki et al. J. Mol. Biol. 336:1239-1249 (2004); Yamane-Ohnuki et al. Biotech. Bioeng. 87: 614 (2004). Examples of cell lines producing defucosylated antibodies include Lec13 CHO cells deficient in protein fucosylation (Ripka et al. Arch. Biochem. Biophys. 249:533-545 (1986); US Pat Appl No US 2003/0157108 A1, Presta, L; and WO 2004/056312 A1, Adams et al.), and knockout cell lines, such as alpha-1,6-fucosyltransferase gene, FUT8, knockout CHO cells (Yamane-Ohnuki et al. Biotech. Bioeng. 87: 614 (2004)).

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in Table 2 under the heading of "preferred substitutions". If such substitutions result in a change in biological activity, then more substantial changes, denominated "exemplary substitutions", or as further described below in reference to amino acid classes, may be introduced and the products screened.

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring amino acids are divided into groups based on common side-chain properties: (1) hydrophobic: norleucine, met, ala, val, leu, ile; (2) neutral hydrophilic: Cys, Ser, Thr, Asn, Gln; (3) acidic: asp, glu; (4) basic: his, lys, arg; (5) residues that influence chain orientation: gly, pro; and (6) aromatic: trp, tyr, phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the immunoglobulin polypeptides disclosed herein, thereby generating a Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions including that of a hinge cysteine.

In accordance with this description and the teachings of the art, it is contemplated that in some embodiments, an antibody used in methods disclosed herein may comprise one or more alterations as compared to the wild type counterpart antibody, e.g., in the Fc region. These antibodies would nonetheless retain substantially the same characteristics required for therapeutic utility as compared to their wild type counterpart. For example, it is thought that certain alterations can be made in the Fc region that would result in altered (e.g., either improved or diminished) C1q binding and/or Complement Dependent Cytotoxicity (CDC), e.g., as described in WO99/51642. See also Duncan & Winter Nature 322:738-40 (1988); U.S. Pat. No. 5,648,260; U.S. Pat. No. 5,624,821; and WO94/29351 concerning other examples of Fc region variants. WO00/42072 and WO 2004/056312 describe antibody variants with improved or diminished binding to FcRs. See, also, Shields et al. J. Biol. Chem. 9(2): 6591-6604 (2001). Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934 (Hinton et al.). These antibodies comprise an Fc reg on with one or more substitutions therein which improve binding of the Fc region to FcRn. Polypeptide variants with altered Fc region amino acid sequences and increased or decreased C1q binding capability are described in U.S. Pat. No. 6,194,551, WO99/51642. See, also, Idusogie et al. J. Immunol. 164:4178-4184 (2000).

In certain embodiments, the present disclosure contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'l Acad. Sci. USA 83:7059-7063 (1986)) and Hellstrom, I et al., Proc. Nat'l Acad. Sci. USA 82:1499-1502 (1985); U.S. Pat. No. 5,821, 337 (see, Bruggemann, M. et al., Exp. Med. 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. Proc. Nat'l Acad. Sci. USA 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., Immunol. Methods 202:163 (1996); Cragg, M. S. et al., Blood 101: 1045-1052 (2003); and Cragg, M. S, and M. J. Glennie, Blood 103:27382743 (2004)). FcRn binding and in vivo clearance/half life determinations can also be performed using methods known in the art (see, e.g., Petkova, S. B. et al., Int'l Immunol. 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., Biol. Chem. 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. Immunol. 164: 41784184 (2000).

Antibodies with increased half lives and improved binding to the neonatal Fc receptor (FcRn), which is responsible for the transfer of maternal IgGs to the fetus (Guyer et al., Immunol. 117:587 (1976) and Kim et al., Immunol. 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, Nature 322:738-40 (1988); U.S. Pat. No. 5,648,260; U.S. Pat. No. 5,624,821; and WO 94/29351 concerning other examples of Fc region variants.

Antibody Derivatives

The antibodies comprising an ultralong CDR3 as disclosed herein may be further modified to contain additional nonproteinaceous moieties that are known in the art and readily available. Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymers are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

Vectors, Host Cells and Recombinant Methods

For recombinant production of an antibody or fragment thereof as disclosed herein, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). In an exemplary embodiment, nucleic acid encoding an antibody comprising an ultralong CDR3, a variable region comprising an ultralong CDR3, or an ultralong CDR3, is isolated and inserted into a replicable vector for further cloning (amplification of the DNA) or for expression. Many vectors are available. The choice of vector depends in part on the host cell to be used. Generally, preferred host cells are of either prokaryotic or eukaryotic (generally mammalian) origin. It will be appreciated that constant regions of any isotype can be used for this purpose, including IgG, IgM, IgA, IgD, and IgE constant regions, and that such constant regions can be obtained from any human or animal species.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase and dihydrofolate reductase. Alternatively, high yield expression systems not involving gene amplification are also suitable, such as using a baculovirus vector in insect cells, with a nucleic acid sequence encoding a partially human ultralong CDR3 antibody chain under the direction of the polyhedrin promoter or other strong baculovirus promoters.

a. Generating Antibodies Using Prokaryotic or Eukaryotic Host Cells:

i. Vector Construction

Polynucleotide sequences encoding polypeptide components of the antibodies disclosed herein can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present disclosure. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence. Additionally, V regions comprising an ultralong CDR3 may optionally be fused to a C-region to produce an antibody comprising constant regions.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies have been described (see, e.g., U.S. Pat. No. 5,648,237).

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as E. coli LE392.

The expression vectors disclosed herein may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g., the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector disclosed herein.

Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include: an ara B promoter, a PhoA promoter, β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (e.g., Siebenlist et al. (1980) Cell 20: 269) using linkers or adaptors to supply any required restriction sites.

Suitable bacterial promoters are well known in the art and fully described in scientific literature such as Sambrook and Russell, supra, and Ausubel et al, supra. Bacterial expression systems for expressing antibody chains of the recombinant catalytic polypeptide are available in, e.g., E. coli, Bacillus sp., and Salmonella (Palva et al., Gene, 22:229-235 (1983); Mosbach et al., Nature, 302:543-545 (1983)).

In one aspect disclosed herein, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence should be one that is recognized and processed (e.g., cleaved by a signal peptidase) by the host cell. For prokaryotic host cells that do not recognize and process the signal sequences native to the heterologous polypeptides, the signal sequence is substituted by a prokaryotic signal sequence selected, for example PelB, OmpA, alkaline phosphatase, penicillinase, Ipp, or heat-stable enterotoxin II (STII) leaders, LamB, PhoE, and MBP. In one embodiment disclosed herein, the signal sequences used in both cistrons of the expression system are STII signal sequences or variants thereof.

In another aspect, the production of the immunoglobulins according to the disclosure can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the E. coli trxB-strains) provide cytoplasm conditions that are favorable for disulfide bond formation, thereby permitting proper folding and assembly of expressed protein subunits (see e.g., Proba and Pluckthun Gene, 159:203 (1995)).

Suitable host cells for cloning or expression of antibody-encoding vectors include prokaryotic or eukaryotic cells described herein. In one embodiment, the host cell is eukaryotic, e.g. a Chinese Hamster Ovary (CHO) cell, Human Embryonic Kidney (HEK) cell or lymphoid cell (e.g., YO, NSO, Sp20 cell). For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in E. coli.) After expression, the antibody may be isolated from the bacterial cell paste in a soluble fraction and can be further purified. In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gemgross, Nat. Biotech. 22: 1409-1414 (2004), and Li et al., Nat. Biotech. 24:210-215 (2006). Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E. coli, Serratia*, or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

Plant cell cultures can also be utilized as hosts. See, e.g. U.S. Pat. Nos. 5,959,177, 6,040,498, 6,420,548, 7,125, 978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., Gen VII'0l. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (V ERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TR1 cells, as described, e.g., in Mather et al., Annals NI'. Acad. Sci. 383:44-68 (1982); MRC 5 cells; and FS4 cells. Other useful mammalian host cell lines include Chinese hamster ovary (CHO) cells, including DHFR' CHO cells (Urlaub et al., Proc. Natl. Acad. Sci. USA 77:4216 (1980)); and myeloma cell lines such as YO, NSO and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody.

ii. Antibody Production

For recombinant production of a partially human ultralong CDR3 antibody, nucleic acid encoding an antibody comprising an ultralong CDR3 is inserted into one or more expression vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody). Host cells are transformed with such expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides disclosed herein are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector disclosed herein, protein expression is induced under conditions suitable for the activation of the promoter. For example, an ara B or phoA promoter may be used for controlling transcription of the polypeptides. A variety of inducers may be used, according to the vector construct employed, as is known in the art.

The expressed polypeptides of the present disclosure are secreted into and recovered from the periplasm of the host cells or transported into the culture media. Protein recovery from the periplasm typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins that are transported into the culture media may be isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

Antibody production may be conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (a preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 peptide of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides disclosed herein, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) may be used to co-transform the host prokaryotic cells. The chaperone proteins have been demonstrated to facilitate the proper folding and solubility of heterologous proteins produced in bacterial host cells. (see e.g., Chen et al. (1999) J Bio Chem 274:19601-19605; U.S. Pat. No. 6,083,715; U.S. Pat. No. 6,027,888; Bothmann and Pluckthun (2000) J. Biol. Chem. 275:17100-17105; Ramm and Pluckthun (2000) J. Biol. Chem. 275:17106-17113; Arie et al. (2001) Mol. Microbiol. 39:199-210).

To minimize proteolysis of expressed heterologous proteins (especially those that are proteolytically sensitive), certain host strains deficient for proteolytic enzymes can be used for the present disclosure. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some E. coli protease-deficient strains are available (see, e.g., Joly et al. (1998), supra; U.S. Pat. No. 5,264,365; U.S. Pat. No. 5,508,192; Hara et al., Microbial Drug Resistance, 2:63-72 (1996)).

E. coli strains deficient for proteolytic enzymes and transformed with plasmids overexpressing one or more chaperone proteins may be used as host cells in the expression systems disclosed herein.

In some cases, an antibody or fragment may not be biologically active upon isolation. Various methods for "refolding" or converting a polypeptide to its tertiary structure and generating disulfide linkages, can be used to restore biological activity. Such methods include exposing the solubilized polypeptide to a pH usually above 7 and in the presence of a particular concentration of a chaotrope. The selection of chaotrope is very similar to the choices used for inclusion body solubilization, but usually the chaotrope is used at a lower concentration and is not necessarily the same as chaotropes used for the solubilization. In most cases the refolding/oxidation solution will also contain a reducing agent or the reducing agent plus its oxidized form in a specific ratio to generate a particular redox potential allowing for disulfide shuffling to occur in the formation of the protein's cysteine bridge(s). Some of the commonly used redox couples include cysteine/cystamine, glutathione (GSH)/dithiobis GSH, cupric chloride, dithiothreitol (DTT)/dithiane DTT, and 2-mercaptoethanol(bME)/di-thio-b(ME). In many instances, a cosolvent may be used to increase the efficiency of the refolding, and common reagents used for this purpose include glycerol, polyethylene glycol of various molecular weights, arginine and the like.

Engineered Hybridomas

Hybridoma cells can be generated by fusing B cells producing a desired antibody with an immortalized cell line, usually a myeloma cell line, so that the resulting fusion cells will be an immortalized cell line that secrets a particular antibody. By the same principle, myeloma cells can be first transfected with a nucleic acid encoding a germline antibody V region and can be screened for the expression of the germline V region. Those myeloma cells with highest level of proteolytic light chain expression can be subsequently fused with B cells that produce an antibody with desired target protein specificity. The fusion cells will produce two types of antibodies: one is a heterologous antibody containing an endogenous antibody chain (either heavy or light) operably joined to the recombinant germline V region (either heavy or light), and the other is the same antibody that the parental B cells would secrete (e.g. both endogenous heavy and light chains). The operably joined heterologous heavy and light chains can be isolated by conventional methods such as chromatography and identification can be confirmed by target protein binding assays, assays identifying a unique tag of the germline polypeptide, or endopeptidase activity assays described in other sections of this disclosure. In some cases, where the heterologous antibody is the predominant type in quantity among the two types of antibodies, such isolation may not be needed. Hybridomas. Including bovine hybridomas, may be a source of bovine antibody gene sequences, including ultralong CDR3 sequences.

Transgenic Mammals

A nucleic acid sequence encoding a germline antibody polypeptide of the present disclosure can be introduced into a non-human mammal to generate a transgenic animal that expresses the germline antibody polypeptide. Unlike the transgenic animal models more commonly seen, the transgene expressed by the transgenic mammals of the present disclosure need not replace at least one allele of the endogenous coding sequence responsible for the variable regions of antibody chains following somatic recombination. Due to allelic exclusion, the presence of an exogenous, post-somatic rearrangement version of the germline V region DNA will inhibit the endogenous alleles of pre-somatic rearrangement V minigenes from undergoing somatic rearrangement and contributing to the makeup of antibody chains this mammal may produce. Thus, when exposed to a particular antigen, the mammal will generate heterologous antibodies comprising one endogenously rearranged antibody chain, and one transgenic gene which was rearranged a priori. Such heterologous antibodies are invaluable in research and in treating certain conditions in live subjects. On the other hand, a method that directs the integration of the transgene to the locus of an endogenous allele will fully serve the purpose of practicing the present disclosure as well.

The general methods of generating transgenic animals have been well established and frequently practiced. For reviews and protocols for generating transgenic animals and related methods for genetic manipulations, see, e.g., Mansour et al., Nature 336:348-352 (1988); Capecchi et al., Trends Genet. 5:70-76 (1989); Capecchi, Science 244:1288-1292 (1989); Capecchi et al., Current Communications in Molecular Biology, pp 45-52, Capecchi, M. R. (ed.), Cold Spring Harbor Press, Cold Spring Harbor, N.Y. (1989); Frohman et al., Cell 56: 145-147 (1989); Brinster et al., Proc. Natl. Acad. Sci. USA 82:4438-4442 (1985); Evans et. al., Nature 292:154-156 (1981); Bradley et al., Nature 309:255-258 (1984); Gossler et al., Proc. Natl. Acad. Sci. USA 83:9065-9069 (1986); Robertson et al., Nature 322: 445-448 (1986); Jaenisch Science 240:1468-1474 (1988); and Siedel, G. E., Jr., "Critical review of embryo transfer procedures with cattle" in Fertilization and Embryonic Development in Vitro, page 323, L. Mastroianni, Jr. and J. D. Biggers, ed., Plenum Press, New York, N.Y. (1981).

An exemplary transgenic animal of the present disclosure is mouse, whereas a number of other transgenic animals can also be produced using the same general method. These animals include, but are not limited to: rabbits, sheep, cattle, and pigs (Jaenisch Science 240:1468-1474 (1988); Hammer et al., J. Animal. Sci. 63:269 (1986); Hammer et al. Nature 315:680 (1985); Wagner et al., Theriogenology 21:29 (1984)).

Pharmaceutical Compositions

Antibodies comprising an ultralong CDR3, antibody fragments, nucleic acids, or vectors disclosed herein can be formulated in compositions, especially pharmaceutical compositions. Such compositions with antibodies comprising an ultralong CDR3 comprise a therapeutically or prophylactically effective amount of antibodies comprising an ultralong CDR3, antibody fragment, nucleic acid, or vector disclosed herein in admixture with a suitable carrier, e.g., a pharmaceutically acceptable agent. Typically, antibodies comprising an ultralong CDR3, antibody fragments, nucleic acids, or vectors disclosed herein are sufficiently purified for administration before formulation in a pharmaceutical composition.

Pharmaceutically acceptable salts, excipients, or vehicles for use in the present pharmaceutical compositions include carriers, excipients, diluents, antioxidants, preservatives, coloring, flavoring and diluting agents, emulsifying agents, suspending agents, solvents, fillers, bulking agents, buffers, delivery vehicles, tonicity agents, cosolvents, wetting agents, complexing agents, buffering agents, antimicrobials, and surfactants.

Neutral buffered saline or saline mixed with serum albumin are exemplary appropriate carriers. The pharmaceutical compositions may include antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics, or polyethylene glycol (PEG). Also by way of example, suitable tonicity enhancing agents include alkali metal halides (preferably sodium or potassium chloride), mannitol, sorbitol, and the like. Suitable preservatives include benzalkonium chloride, thimerosal, phenethyl alcohol, methylparaben, propylparaben, chlorhexidine, sorbic acid and the like. Hydrogen peroxide also may be used as preservative. Suitable cosolvents include glycerin, propylene glycol, and PEG. Suitable complexing agents include caffeine, polyvinylpyrrolidone, beta-cyclodextrin or hydroxy-propyl-beta-cyclodextrin. Suitable surfactants or wetting agents include sorbitan esters, polysorbates such as polysorbate 80, tromethamine, lecithin, cholesterol, tyloxapal, and the like. The buffers may be conventional buffers such as acetate, borate, citrate, phosphate, bicarbonate, or Tris-HCl. Acetate buffer may be about pH 4-5.5, and Tris buffer can be about pH 7-8.5. Additional pharmaceutical agents are set forth in Remington's Pharmaceutical Sciences, 18th Edition, A. R. Gennaro, ed., Mack Publishing Company, 1990.

The composition may be in liquid form or in a lyophilized or freeze-dried form and may include one or more lyoprotectants, excipients, surfactants, high molecular weight structural additives and/or bulking agents (see, for example, U.S. Pat. Nos. 6,685,940, 6,566,329, and 6,372,716). In one embodiment, a lyoprotectant is included, which is a non-reducing sugar such as sucrose, lactose or trehalose. The amount of lyoprotectant generally included is such that, upon reconstitution, the resulting formulation will be isotonic, although hypertonic or slightly hypotonic formulations also may be suitable. In addition, the amount of lyoprotectant should be sufficient to prevent an unacceptable amount of degradation and/or aggregation of the protein upon lyophilization. Exemplary lyoprotectant concentrations for sugars (e.g., sucrose, lactose, trehalose) in the pre-lyophilized formulation are from about 10 mM to about 400 mM. In another embodiment, a surfactant is included, such as for example, nonionic surfactants and ionic surfactants such as polysorbates (e.g., polysorbate 20, polysorbate 80); poloxamers (e.g., poloxamer 188); poly(ethylene glycol) phenyl ethers (e.g., Triton); sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl ofeyl-taurate; and the MONAQUAT™ series (Mona Industries, Inc., Paterson, N.J.), polyethyl glycol, polypropyl glycol, and copolymers of ethylene and propylene glycol (e.g., Pluronics, PF68 etc). Exemplary amounts of surfactant that may be present in the pre-lyophilized formulation are from about 0.001-0.5%. High molecular weight structural additives (e.g., fillers, binders) may include for example, acacia, albumin, alginic acid, calcium phosphate (dibasic), cellulose, carboxymethylcellulose, carboxymethylcellulose sodium, hydroxyethylcellulose, hydroxypropylcellulose, hydroxypropylmethylcellulose, microcrystalline cellulose, dextran, dextrin, dextrates, sucrose, tylose, pregelatinized starch, calcium sulfate, amylose, glycine, bentonite, maltose, sorbitol, ethylcellulose, disodium hydrogen phosphate, disodium phosphate, disodium pyrosulfite, polyvinyl alcohol, gelatin, glucose, guar gum, liquid glucose, compressible sugar, magnesium aluminum silicate, maltodextrin, polyethylene oxide, polymethacrylates, povidone, sodium alginate, tragacanth microcrystalline cellulose, starch, and zein. Exemplary concentrations of high molecular weight structural additives are from 0.1% to 10% by weight. In other embodiments, a bulking agent (e.g., mannitol, glycine) may be included.

Compositions may be suitable for parenteral administration. Exemplary compositions are suitable for injection or infusion into an animal by any route available to the skilled worker, such as intraarticular, subcutaneous, intravenous, intramuscular, intraperitoneal, intracerebral (intraparenchymal), intracerebroventricular, intramuscular, intraocular, intraarterial, or intralesional routes. A parenteral formulation typically will be a sterile, pyrogen-free, isotonic aqueous solution, optionally containing pharmaceutically acceptable preservatives.

Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringers' dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, anti-microbials, anti-oxidants, chelating agents, inert gases and the like. See generally, Remington's Pharmaceutical Science, 16th Ed., Mack Eds., 1980.

Pharmaceutical compositions described herein may be formulated for controlled or sustained delivery in a manner that provides local concentration of the product (e.g., bolus, depot effect) and/or increased stability or half-life in a particular local environment. The compositions can include the formulation of antibodies comprising an ultralong CDR3, antibody fragments, nucleic acids, or vectors disclosed herein with particulate preparations of polymeric compounds such as polylactic acid, polyglycolic acid, etc., as well as agents such as a biodegradable matrix, injectable microspheres, microcapsular particles, microcapsules, bioerodible particles beads, liposomes, and implantable delivery devices that provide for the controlled or sustained release of the active agent which then can be delivered as a depot injection. Techniques for formulating such sustained- or controlled-delivery means are known and a variety of polymers have been developed and used for the controlled release and delivery of drugs. Such polymers are typically biodegradable and biocompatible. Polymer hydrogels, including those formed by complexation of enantiomeric polymer or polypeptide segments, and hydrogels with temperature or pH sensitive properties, may be desirable for providing drug depot effect because of the mild and aqueous conditions involved in trapping bioactive protein agents (e.g., antibodies comprising an ultralong CDR3). See, for example, the description of controlled release porous polymeric microparticles for the delivery of pharmaceutical compositions in WO 93/15722.

Suitable materials for this purpose include polylactides (see, e.g., U.S. Pat. No. 3,773,919), polymers of poly-(a-hydroxycarboxylic acids), such as poly-D-(-)-3-hydroxybutyric acid (EP 133,988A), copolymers of L-glutamic acid and gamma ethyl-L-glutamate (Sidman et al., Biopolymers, 22: 547-556 (1983)), poly(2-hydroxyethyl-methacrylate) (Langer et al., J. Biomed. Mater. Res., 15: 167-277 (1981), and Langer, Chem. Tech., 12: 98-105 (1982)), ethylene vinyl acetate, or poly-D(-)-3-hydroxybutyric acid. Other biodegradable polymers include poly(lactones), poly(acetals), poly(orthoesters), and poly(orthocarbonates). Sustained-release compositions also may include liposomes, which can be prepared by any of several methods known in the art (see, e.g., Eppstein et al., Proc. Natl. Acad. Sci. USA, 82: 3688-92 (1985)). The carrier itself, or its degradation products, should be nontoxic in the target tissue and should not further aggravate the condition. This can be determined by routine screening in animal models of the target disorder or, if such models are unavailable, in normal animals.

Microencapsulation of recombinant proteins for sustained release has been performed successfully with human growth hormone (rhGH), interferon-(rhIFN-), interleukin-2, and MN rgp120. Johnson et al., Nat. Med., 2:795-799 (1996); Yasuda, Biomed. Ther., 27:1221-1223 (1993); Hora et al., Bio/Technology. 8:755-758 (1990); Cleland, "Design and Production of Single Immunization Vaccines Using Polylactide Polyglycolide Microsphere Systems," in Vaccine Design: The Subunit and Adjuvant Approach, Powell and Newman, eds, (Plenum Press: New York, 1995), pp. 439-462; WO 97/03692, WO 96/40072, WO 96/07399; and U.S. Pat. No. 5,654,010. The sustained-release formulations of these proteins were developed using poly-lactic-coglycolic acid (PLGA) polymer due to its biocompatibility and wide range of biodegradable properties. The degradation products of PLGA, lactic and glycolic acids can be cleared quickly within the human body. Moreover, the degradability of this polymer can be depending on its molecular weight and composition. Lewis, "Controlled release of bioactive agents from lactide/glycolide polymer," in: M. Chasin and R. Langer (Eds.), Biodegradable Polymers as Drug Delivery Systems (Marcel Dekker: New York, 1990), pp. 1-41. Additional examples of sustained release compositions include, for example, EP 58,481A, U.S. Pat. No. 3,887,699, EP 158,277A, Canadian Patent No. 1176565, U. Sidman et al., Biopolymers 22, 547 [1983], R. Langer et al., Chem. Tech. 12, 98 [1982], Sinha et al., J. Control. Release 90, 261 [2003], Zhu et al., Nat. Biotechnol. 18, 24 [2000], and Dai et al., Colloids Surf B Biointerfaces 41, 117 [2005].

Bioadhesive polymers are also contemplated for use in or with compositions of the present disclosure. Bioadhesives are synthetic and naturally occurring materials able to adhere to biological substrates for extended time periods. For example, Carbopol and polycarbophil are both synthetic cross-linked derivatives of poly(acrylic acid). Bioadhesive delivery systems based on naturally occurring substances include for example hyaluronic acid, also known as hyaluronan. Hyaluronic acid is a naturally occurring mucopolysaccharide consisting of residues of D-glucuronic and N-acetyl-D-glucosamine. Hyaluronic acid is found in the extracellular tissue matrix of vertebrates, including in connective tissues, as well as in synovial fluid and in the vitreous and aqueous humor of the eye. Esterified derivatives of hyaluronic acid have been used to produce microspheres for use in delivery that are biocompatible and biodegradable (see, for example, Cortivo et al., Biomaterials (1991) 12:727-730; EP 517,565; WO 96/29998; Illum et al., J. Controlled Rel. (1994) 29:133-141). Exemplary hyaluronic acid containing compositions of the present disclosure comprise a hyaluronic acid ester polymer in an amount of approximately 0.1% to about 40% (w/w) of an antibody comprising an ultralong CDR3 to hyaluronic acid polymer.

Both biodegradable and non-biodegradable polymeric matrices may be used to deliver compositions of the present disclosure, and such polymeric matrices may comprise natural or synthetic polymers. Biodegradable matrices are preferred. The period of time over which release occurs is based on selection of the polymer. Typically, release over a period ranging from between a few hours and three to twelve months is most desirable. Exemplary synthetic polymers which may be used to form the biodegradable delivery system include: polymers of lactic acid and glycolic acid, polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyanhydrides, polyurethanes and co-polymers thereof, poly(butic acid), poly(valeric acid), alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone. Exemplary natural polymers include alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The polymer optionally is in the form of a hydrogel (see, for example, WO 04/009664, WO 05/087201, Sawhney, et al., Macromolecules, 1993, 26, 581-587) that can absorb up to about 90% of its weight in water and further, optionally is cross-linked with multi-valent ions or other polymers.

Delivery systems also include non-polymer systems that are lipids including sterols such as cholesterol, cholesterol esters and fatty acids or neutral fats such as mono-di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the product is contained in a form within a matrix such as those described in U.S. Pat. Nos. 4,452,775, 4,675,189 and 5,736,152 and (b) diffusional systems in which a product permeates at a controlled rate from a polymer such as described in U.S. Pat. Nos. 3,854,480, 5,133,974 and 5,407,686. Liposomes containing the product may be prepared by methods known methods, such as for example (DE 3,218,121; Epstein et al., Proc. Natl. Acad. Sci. USA, 82: 3688-3692 (1985); Hwang et al., Proc. Natl. Acad. Sci. USA, 77: 4030-4034 (1980); EP 52,322; EP 36,676; EP 88,046; EP 143,949; EP 142,641; JP 83-118008; U.S. Pat. Nos. 4,485,045 and 4,544,545; and EP 102,324).

Alternatively or additionally, the compositions may be administered locally via implantation into the affected area of a membrane, sponge, or other appropriate material on to which an antibody comprising an ultralong CDR3, antibody fragment, nucleic acid, or vector disclosed herein has been absorbed or encapsulated. Where an implantation device is used, the device may be implanted into any suitable tissue or organ, and delivery of an antibody comprising an ultralong CDR3 antibody fragment, nucleic acid, or vector disclosed herein can be directly through the device via bolus, or via continuous administration, or via catheter using continuous infusion.

A pharmaceutical composition comprising an antibody comprising an ultralong CDR3, antibody fragment, nucleic acid, or vector disclosed herein may be formulated for inhalation, such as for example, as a dry powder. Inhalation solutions also may be formulated in a liquefied propellant for aerosol delivery. In yet another formulation, solutions may be nebulized. Additional pharmaceutical composition for pulmonary administration include, those described, for example, in WO 94/20069, which discloses pulmonary delivery of chemically modified proteins. For pulmonary delivery, the particle size should be suitable for delivery to the distal lung. For example, the particle size may be from 1 µm to 5 µm; however, larger particles may be used, for example, if each particle is fairly porous.

Certain formulations containing antibodies comprising an ultralong CDR3, antibody fragments, nucleic acids, or vectors disclosed herein may be administered orally. Formulations administered in this fashion may be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents may be included to facilitate absorption of a selective binding agent. Diluents, flavorings, low melting point waxes, vegetable oils, lubricants, suspending agents, tablet disintegrating agents, and binders also can be employed.

Another preparation may involve an effective quantity of an antibody comprising an ultralong CDR3, antibody fragment, nucleic acid, or vector disclosed herein in a mixture with non-toxic excipients which are suitable for the manufacture of tablets. By dissolving the tablets in sterile water, or another appropriate vehicle, solutions may be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Suitable and/or preferred pharmaceutical formulations may be determined in view of the present disclosure and general knowledge of formulation technology, depending upon the intended route of administration, delivery format, and desired dosage. Regardless of the manner of administration, an effective dose may be calculated according to patient body weight, body surface area, or organ size. Further refinement of the calculations for determining the appropriate dosage for treatment involving each of the formulations described herein are routinely made in the art and is within the ambit of tasks routinely performed in the art. Appropriate dosages may be ascertained through use of appropriate dose-response data.

In some embodiments, antibodies comprising an ultralong CDR3 or fragments thereof are provided with a modified Fc region where a naturally-occurring Fc region is modified to increase the half-life of the antibody or fragment in a biological environment, for example, the serum half-life or a half-life measured by an in vitro assay. Methods for altering the original form of a Fc region of an IgG also are described in U.S. Pat. No. 6,998,253.

In certain embodiments, it may be desirable to modify the antibody or fragment in order to increase its serum half-life, for example, adding molecules such as PEG or other water soluble polymers, including polysaccharide polymers, to antibody fragments to increase the half-life. This may also be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis) (see, International Publication No. WO96/32478). Salvage receptor binding epitope refers to an epitope of the Fc region of an IgG molecule (e.g., IgG1, IgG2, IgG3, or IgG4) that is responsible for increasing the in vivo serum half-life of the IgG molecule.

A salvage receptor binding epitope may include a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or VH region, or more than one such region, of the antibody. Alternatively, the epitope is taken from the CH2 domain of the Fc region and transferred to the $C_L$ region or $V_L$ region, or both, of the antibody fragment. See also WO 97/34631 and WO 96/32478 which describe Fc variants and their interaction with the salvage receptor.

Mutation of residues within Fc receptor binding sites may result in altered effector function, such as altered ADCC or CDC activity, or altered half-life. Potential mutations include insertion, deletion or substitution of one or more residues, including substitution with alanine, a conservative substitution, a non-conservative substitution, or replacement with a corresponding amino acid residue at the same position from a different IgG subclass (e.g., replacing an IgG1 residue with a corresponding IgG2 residue at that position). For example, it has been reported that mutating the serine at amino acid position 241 in IgG4 to proline (found at that position in IgG1 and IgG2) led to the production of a homogeneous antibody, as well as extending serum half-life and improving tissue distribution compared to the original chimeric IgG4. (Angal et al., Mol. Immunol. 30:105-8, 1993).

In some embodiments is a pharmaceutical composition comprising an antibody comprising an ultralong CDR3; and a pharmaceutically acceptable carrier. The antibody may comprise a therapeutic polypeptide, or derivative or variant thereof. The therapeutic polypeptide may be a non-antibody sequence. The therapeutic polypeptide, or derivative or variant thereof can be within the ultralong CDR3. In some instances, the therapeutic polypeptide is Moka1, Vm24, GLP-1, Exendin-4, human EPO, human FGF21, 550 peptide human GMCSF, human interferon-beta, human GCSF, bovine GCSF or derivative or variant thereof. Alternatively, the antibody is an immunoconjugate as described herein. The antibody can comprise one or more immunoglobulin domains. In some embodiments, the immunoglobulin domain is an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. In some instances, the immunoglobulin domain is from an engineered antibody or recombinant antibody. In other instances, the immunoglobulin domain is from a humanized, human engineered or fully human antibody. The mammalian antibody may be a bovine antibody. The mammalian antibody may be a human antibody. In other instances, the mammalian antibody is a murine antibody. The ultralong CDR3 can comprise at least a portion of a knob domain in the CDR3. The therapeutic polypeptide can be attached to the knob domain. Alternatively, or additionally, the ultralong CDR3 comprises at least a portion of a stalk domain in the CDR3. The therapeutic polypeptide may be attached to the stalk domain. In some instances, the antibody further comprises a linker. The linker can be within the ultralong CDR3. The linker can attach the therapeutic polypeptide to the immunoglobulin domain or fragment thereof. In other instances, the linker attaches the therapeutic polypeptide to the knob domain or stalk domain. In certain embodiments is a method of preventing or treating a disease in a subject in need thereof comprising administering this pharmaceutical composition to the subject. In some embodiments, the pharmaceutical composition comprising an immunoglobulin construct comprising a heavy chain polypeptide comprising a sequence selected from any one of SEQ ID NOS: 9-14 and the polypeptide sequence encoded by the DNA any one of SEQ ID NOS: 2-7; and a light chain polypeptide comprising a sequence selected from SEQ ID NO: 8 and a polypeptide sequence encoded by the DNA of SEQ ID NO: 1; and a pharmaceutically acceptable carrier. In certain embodiments is a method of preventing or treating a disease in a mammal in need thereof comprising administering this pharmaceutical composition to the mammal. In some embodiments, the disease is an infectious disease such as mastitis. In certain embodiments, the mammal in need is a dairy animal selected from a list comprising cow, camel, donkey, goat, horse, reindeer, sheep, water buffalo, moose and yak. In some embodiments, the mammal in need is bovine.

In some embodiments, the pharmaceutical compositions disclosed herein may be useful for providing prognostic or providing diagnostic information.

Kits/Articles of Manufacture

As an additional aspect, the present disclosure includes kits which comprise one or more compounds or compositions packaged in a manner which facilitates their use to practice methods of the present disclosure. In one embodiment, such a kit includes a compound or composition described herein (e.g., a composition comprising an antibody comprising an ultralong CDR3 alone or in combination with a second agent), packaged in a container with a label affixed to the container or a package insert that describes use of the compound or composition in practicing the method. Suitable containers include, for example, bottles, vials, syringes, etc. The containers may be formed from a variety of materials such as glass or plastic. The container may have a sterile access port (for example the container may be an intravenous solution bag or a vial having a stopper pierceable by a hypodermic injection needle). The article of manufacture may comprise (a) a first container with a composition contained therein, wherein the composition comprises an antibody comprising an ultralong CDR3 as disclosed herein; and (b) a second container with a composition contained therein, wherein the composition comprises a further therapeutic agent. The article of manufacture in this embodiment disclosed herein may further comprise a package insert indicating that the first and second compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes. Preferably, the compound or composition is packaged in a unit dosage form. The kit may further include a device suitable for administering the composition according to a specific route of administration or for practicing a screening assay. Preferably, the kit contains a label that describes use of the antibody comprising an ultralong CDR3 composition.

In certain embodiments, the composition comprising the antibody is formulated in accordance with routine procedures as a pharmaceutical composition adapted for intravenous administration to mammals, such as humans, bovines, felines, canines, and murines. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The amount of the composition described herein which will be effective in the treatment, inhibition and prevention of a disease or disorder associated with aberrant expression and/or activity of a Therapeutic protein can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses are extrapolated from dose-response curves derived from in vitro or animal model test systems.

The following are examples of the methods and compositions of the disclosure. It is understood that various other embodiments may be practiced, given the general description provided above.

Methods of Treatment

Further disclosed herein are methods of preventing or treating a disease or condition in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is oxyntomodulin, 550 peptide, Amgen1, Mamba1, parathyroid hormone, or derivative or variant thereof. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 can comprise at least a portion of a knob domain. The knob domain may comprise a conserved motif within the knob domain of an ultralong CDR3. For example, the knob domain may comprise a cysteine motif disclosed herein. The therapeutic polypeptide can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ (SEQ ID NO: 128) motif. The therapeutic polypeptide can be attached to the stalk domain. In some instances, the antibody, antibody fragment or immunoglobulin construct further comprises a linker. The linker can attach the therapeutic polypeptide to the immunoglobulin domain or fragment thereof. In other instances, the linker attaches the therapeutic polypeptide to the knob domain or stalk domain. In some instances, the disease or condition is an autoimmune disease, heteroimmune disease or condition, inflammatory disease, pathogenic infection, thromboembolic disorder, respiratory disease or condition, metabolic disease, central nervous system (CNS) disorder, bone disease or cancer. In other instances, the disease or condition is a blood disorder. In some instances, the disease or condition is obesity, diabetes, osteoporosis, anemia, or pain.

In some embodiments is a method of preventing or treating a disease or condition in a subject in need thereof comprising administering to the subject a composition comprising: an immunoglobulin construct comprising a heavy chain polypeptide comprising a sequence that is substantially similar to a sequence selected from SEQ ID NOS: 9-14; and a light chain polypeptide comprising the sequence that is substantially similar to a sequence of SEQ ID NO: 8. The heavy chain polypeptide sequence may share 50%, 60%, 70%, 80%, 85%, 90%, 95%, 97%, 99%, or more amino acid sequence identity to a heavy chain sequence provided by any one of SEQ ID NOS: 9-14. The light chain polypeptide sequence may share 50%, 60%, 70%, 80%, 85%, 90%, 95%, 97%, 99%, or more amino acid sequence identity to a light chain sequence provided by SEQ ID NO: 8. In some instances, the disease or condition is an autoimmune disease, heteroimmune disease or condition, inflammatory disease, pathogenic infection, thromboembolic disorder, respiratory disease or condition, metabolic disease, central nervous system (CNS) disorder, bone disease or cancer. In other instances, the disease or condition is a blood disorder. In some instances, the disease or condition is obesity, diabetes, osteoporosis, anemia, or pain.

In an embodiment is provided a method of preventing or treating a disease or condition in a subject in need thereof comprising administering to the subject a composition comprising: an immunoglobulin construct comprising a heavy chain polypeptide comprising a polypeptide sequence encoded by a DNA sequence that is substantially similar to a sequence selected from SEQ ID NOS: 2-7; and a light chain polypeptide comprising a polypeptide sequence encoded by a DNA sequence that is substantially similar to a sequence of SEQ ID NO: 1. The heavy chain nucleotide sequence may share 50%, 60%, 70%, 80%, 85%, 90%, 95%, 97%, 99%, or more homology to a heavy chain sequence provided by any one of SEQ ID NOS: 2-7. The light chain nucleotide sequence may share 50%, 60%, 70%, 80%, 85%, 90%, 95%, 97%, 99%, or more homology to a light chain sequence provided by SEQ ID NO: 1. In some instances, the disease or condition is an autoimmune disease, heteroimmune disease or condition, inflammatory disease, pathogenic infection, thromboembolic disorder, respiratory disease or condition, metabolic disease, central nervous system (CNS) disorder, bone disease or cancer. In other instances, the disease or condition is a blood disorder. In some instances, the disease or condition is obesity, diabetes, osteoporosis, anemia, or pain.

Disclosed herein in some embodiments is a method of preventing or treating an autoimmune disease in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is Moka1, VM-24 or beta-interferon or derivative or variant thereof. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The Moka1, VM-24, beta-interferon, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ (SEQ ID NO: 128) motif. The Moka1, VM-24, beta-interferon, or a derivative or variant thereof can be attached to the stalk domain. In some instances, the antibody, antibody fragment or immunoglobulin construct further comprises a linker. The linker can attach Moka1, VM-24, beta-interferon, or a derivative or variant thereof to the immunoglobulin domain or fragment thereof. In other instances, the linker attaches Moka1, VM-24, beta-interferon, or a derivative or variant thereof to the knob domain or stalk domain. In some instances, the autoimmune disease is a T-cell mediated autoimmune disease. T-cell mediated autoimmune diseases include, but are not limited to, multiple sclerosis, type-1 diabetes, and psoriasis. In other instances, the autoimmune disease lupus, Sjogren's syndrome, scleroderma, rheumatoid arthritis, dermatomyositis, Hasmimoto's thyroiditis, Addison's disease, celiac disease, Crohn's disease, pernicious anemia, pemphigus vulgaris, vitiligo, autoimmune hemolytic anemia, idiopathic thrombocytopenic purpura, myasthenia gravis, Ord's thyroiditis, Graves' disease, Guillain-Barre syndrome, acute disseminated encephalomyelitis, opsoclonus-myoclonus syndrome, ankylosing spondylitisis, antiphospholipid antibody syndrome, aplastic anemia, autoimmune hepatitis, Goodpasture's syndrome, Reiter's syndrome, Takayasu's arteritis, temporal arteritis, Wegener's granulomatosis, alopecia universalis, Behcet's disease, chronic fatigue, dysautonomia, endometriosis, interstitial cystitis, neuromyotonia, scleroderma, and vulvodynia. Lupus can include, but is not limited to, acute cutaneous lupus erythematosus, subacute cutaneous lupus erythematosus, chronic cutaneous lupus erythematosus, discoid lupus erythematosus, childhood discoid lupus erythematosus, generalized discoid lupus erythematosus, localized discoid lupus erythematosus, chilblain lupus erythematosus (hutchinson), lupus erythematosus-lichen planus overlap syndrome, lupus erythematosus panniculitis (lupus erythematosus *profundus*), tumid lupus erythematosus, verrucous lupus erythematosus (hypertrophic lupus erythematosus), complement deficiency syndromes, drug-induced lupus erythematosus, neonatal lupus erythematosus, and systemic lupus erythematosus.

Further disclosed herein is a method of preventing or treating a disease or condition which would benefit from the modulation of a potassium voltage-gated channel in a subject in need thereof comprising administering a composition comprising one or more antibodies comprising an ultralong CDR3 as disclosed herein to said subject. The composition can further comprise a pharmaceutically acceptable carrier. In some instances, the potassium voltage-gated channel is a KCNA3 or $K_v1.3$ channel. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is Moka1, VM-24, or derivative or variant thereof. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The Moka1, VM-24, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ (SEQ ID NO: 128) motif. The Moka1, VM-24, or a derivative or variant thereof can be attached to the stalk domain. In some instances, the antibody, antibody fragment or immunoglobulin construct further comprises a linker. The linker can attach Moka1, VM-24, or a derivative or variant thereof to the immunoglobulin domain or fragment thereof. In other instances, the linker attaches Moka1, VM-24, beta-interferon, or a derivative or variant thereof to the knob domain or stalk domain. In some instances, the disease or condition is an autoimmune disease. The autoimmune disease can be a T-cell mediated autoimmune disease. In some instances, modulating a potassium voltage-gated channel comprises inhibiting or blocking a potassium voltage-gated channel. In some instances, the disease or condition is episodic ataxia, seizure, or neuromyotonia.

Provided herein is a method of preventing or treating a metabolic disease or condition in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is GLP-1, Exendin-4, FGF21, oxyntomodulin or derivative or variant thereof. The GLP-1 may be a human GLP-1. In some instances, the FGF21 is a human FGF21. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The GLP-1, Exendin-4, FGF21, oxyntomodulin or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ (SEQ ID NO: 128) motif. The GLP-1, Exendin-4, FGF21, oxyntomodulin or a derivative or variant thereof can be attached to the stalk domain. In some instances, the antibody, antibody fragment or immunoglobulin construct further comprises a linker. The linker can attach GLP-1, Exendin-4, FGF21, oxyntomodulin, or a derivative or variant thereof to the immunoglobulin domain or fragment thereof. In other instances, the linker attaches GLP-1, Exendin-4, FGF21, oxyntomodulin, or a derivative or variant thereof to the knob domain or stalk domain. Metabolic diseases and/or conditions can include disorders of carbohydrate metabolism, amino acid metabolism, organic acid metabolism (organic acidurias), fatty acid oxidation and mitochondrial metabolism, porphyrin metabolism, purine or pyrimidine metabolism, steroid metabolism, mitochondrial function, peroxisomal function, urea cycle disorder, urea cycle defects or lysosomal storage disorders. In some instances, the metabolic disease or condition is diabetes. In other instances, the metabolic disese or condition is glycogen storage disease, phenylketonuria, maple syrup urine disease, glutaric acidemia type 1, Carbamoyl phosphate synthetase I deficiency, alcaptonuria, Medium-chain acyl-coenzyme A dehydrogenase deficiency (MCADD), acute intermittent *porphyria*, Lesch-Nyhan syndrome, lipoid congenital adrenal hyperplasia, congenital adrenal hyperplasia, Kearns-Sayre syndrome, Zellweger syndrome, Gaucher's disease, or Niemann Pick disease.

Provided herein is a method of preventing or treating a central nervous system (CNS) disorder in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is GLP-1, Exendin-4, or derivative or variant thereof. The GLP-1 may be a human GLP-1. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The GLP-1, Exendin-4, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ (SEQ ID NO: 128) motif. The GLP-1, Exendin-4, or a derivative or variant thereof can be attached to the stalk domain. In some instances, the antibody, antibody fragment or immunoglobulin construct further comprises a linker. The linker can attach GLP-1, Exendin-4, or a derivative or variant thereof to the immunoglobulin domain or fragment thereof. In other instances, the linker attaches GLP-1, Exendin-4, or a derivative or variant thereof to the knob domain or stalk domain. In some instances, the CNS disorder is Alzheimer's disease (AD). Additional CNS disorders include, but are not limited to, encephalitis, meningitis, tropical spastic paraparesis, arachnoid cysts, Huntington's disease, locked-in syndrome, Parkinson's disease, Tourette's, and multiple sclerosis.

Provided herein is a method of preventing or treating a disease or condition which benefits from a GLP-1R and/or glucagon receptor (GCGR) agonist in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is GLP-1, Exendin-4, oxyntomodulin, or derivative or variant thereof. The GLP-1 may be a human GLP-1. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The GLP-1, Exendin-4, oxyntomodulin, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ (SEQ ID NO: 128) motif. The GLP-1, Exendin-4, oxyntomodulin, or a derivative or variant thereof can be attached to the stalk domain. In some instances, the antibody, antibody fragment or immunoglobulin construct further comprises a linker. The linker can attach GLP-1, Exendin-4, oxyntomodulin, or a derivative or variant thereof to the immunoglobulin domain or fragment thereof. In other instances, the linker attaches GLP-1, Exendin-4, oxyntomodulin, or a derivative or variant thereof to the knob domain or stalk domain. The disease or condition can be a metabolic disease or disorder. In some instances, the disease or condition is diabetes. In other instances, the disease or condition is obesity. Additional diseases and/or conditions which benefit from a GLP-1R and/or GCGR agonist include, but are not limited to, dyslipidemia, cardiovascular and fatty liver diseases.

Provided herein is a method of preventing or treating a blood disorder in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is erythropoietin, GMCSF, or derivative or variant thereof. The erythropoietin may be a human erythropoietin. The GMCSF may be a human GMCSF. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The erythropoietin, GMCSF, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ (SEQ ID NO: 128) motif. The erythropoietin, GMCSF, or a derivative or variant thereof can be attached to the stalk domain. In some instances, the antibody, antibody fragment or immunoglobulin construct further comprises a linker. The linker can attach erythropoietin, GMCSF, or a derivative or variant thereof to the immunoglobulin domain or fragment thereof. In other instances, the linker attaches erythropoietin, GMCSF, or a derivative or variant thereof to the knob domain or stalk domain. In some instances, the blood disorder is anemia. Examples of anemia include, but are not limited to, hereditary xerocytosis, congenital dyserythropoietic anemia, Rh null disease, infectious mononucleosis related anemia, drugs-related anemia, aplastic anemia, microcytic anemia, macrocytic anemia, normocytic anemia, hemolytic anemia, poikilocytic anemia, spherocytic anemia, drepanocytic anemia, normochromic anemia, hyperchromic anemia, hypochromic anemia, macrocytic-normochromic anemia, microcytic-hypochromic anemia, normocytic-normochromic anemia, iron-deficiency anemia, pernicious anemia, folate-deficiency anemia, thalassemia, sideroblastic anemia, posthemorrhagic anemia, sickle cell anemia, chronic anemia, achrestic anemia, autoimmune haemolytic anemia, Cooley's anemia, drug-induced immune haemolytic anemia, erythroblastic anemia, hypoplastic anemia, Diamond-Blackfan anemia, Pearson's anemia, transient anemia, Fanconi's anemia, Lederer's anemia, myelpathic anemia, nutritional anemia, spur-cell anemia, Von Jaksh's anemia, sideroblatic anemia, sideropenic anemia, alpha thalassemia, beta thalassemia, hemoglobin h disease, acute acquired hemolytic anemia, warm autoimmune hemolytic anemia, cold autoimmune hemolytic anemia, primary cold autoimmune hemolytic anemia, secondary cold autoimmune hemolytic anemia, secondary autoimmune hemolytic anemia, primary autoimmune hemolytic anemia, x-linked sideroblastic anemia, pyridoxine-responsive anemia, nutritional sideroblastic anemia, pyridoxine deficiency-induced sideroblastic anemia, copper deficiency-induced sideroblastic anemia, cycloserine-induced sideroblastic anemia, chloramphenicol-induced sideroblastic anemia, ethanol-induced sideroblastic anemia, isoniazid-induced sideroblastic anemia, drug-induced sideroblastic anemia, toxin-induced sideroblastic anemia, microcytic hyperchromic anemia, macrocytic hyperchromic anemia, megalocytic-normochromic anemia, drug-induced immune hemolytic anemia, non-hereditary spherocytic anemia, inherited spherocytic anemia, and congenital spherocytic anemia. In other instances, the blood disorder is malaria. Alternatively, the blood disorder is lymphoma, leukemia, multiple myeloma, or myelodysplastic syndrome. In some instances, the blood disorder is neutropenia, Shwachmann-Daimond syndrome, Kostmann syndrome, chronic granulomatous disease, leukocyte adhesion deficiency, meyloperoxidase deficiency, or Chediak Higashi syndrome.

Provided herein is a method of preventing or treating a disease or disorder which benefits from stimulating or increasing white blood cell production in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is GMCSF, or derivative or variant thereof. The GMCSF may be a human GMCSF. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The GMCSF, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ (SEQ ID NO: 128) motif. The GMCSF, or a derivative or variant thereof can be attached to the stalk domain. In some instances, the antibody, antibody fragment or immunoglobulin construct further comprises a linker. The linker can attach GMCSF, or a derivative or variant thereof to the immunoglobulin domain or fragment thereof. In other instances, the linker attaches GMCSF, or a derivative or variant thereof to the knob domain or stalk domain. In some instances, the disease or disorder is neutropenia, Shwachmann-Daimond syndrome, Kostmann syndrome, chronic granulomatous disease, leukocyte adhesion deficiency, meyloperoxidase deficiency, or Chediak Higashi syndrome.

Provided herein is a method of preventing or treating a disease or disorder which benefits from stimulating or increasing red blood cell production in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is erythropoietin, or derivative or variant thereof. The erythropoietin may be a human erythropoietin. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The erythropoietin, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ (SEQ ID NO: 128) motif. The erythropoietin, or a derivative or variant thereof can be attached to the stalk domain. In some instances, the antibody, antibody fragment or immunoglobulin construct further comprises a linker. The linker can attach erythropoietin, or a derivative or variant thereof to the immunoglobulin domain or fragment thereof. In other instances, the linker attaches erythropoietin, or a derivative or variant thereof to the knob domain or stalk domain. In some instances, the disease or disorder is anemia.

Provided herein is a method of preventing or treating obesity in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is GLP-1, Exendin-4, FGF21, oxyntomodulin, or derivative or variant thereof. The GLP-1 may be a human GLP-1. In some instances, the FGF21 is a human FGF21. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The GLP-1, Exendin-4, FGF21, oxyntomodulin, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ (SEQ ID NO: 128) motif. The GLP-1, Exendin-4, FGF21, oxyntomodulin, or a derivative or variant thereof can be attached to the stalk domain. In some instances, the antibody, antibody fragment or immunoglobulin construct further comprises a linker. The linker can attach GLP-1, Exendin-4, FGF21, oxyntomodulin, or a derivative or variant thereof to the immunoglobulin domain or fragment thereof. In other instances, the linker attaches GLP-1, Exendin-4, FGF21, oxyntomodulin, or a derivative or variant thereof to the knob domain or stalk domain.

Provided herein is a method of preventing or treating a pain in a subject in need thereof comprising a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is protoxin2, 550 peptide, Amgen1, Mamba1 or derivative or variant thereof. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The protoxin2, 550 peptide, Amgen1, Mamba1 or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ (SEQ ID NO: 128) motif. The protoxin2, 550 peptide, Amgen1, Mamba1 or a derivative or variant thereof can be attached to the stalk domain. In some instances, the antibody, antibody fragment or immunoglobulin construct further comprises a linker. The linker can attach protoxin2, 550 peptide, Amgen1, Mamba1 or a derivative or variant thereof to the immunoglobulin domain or fragment thereof. In other instances, the linker attaches protoxin2, 550 peptide, Amgen1, Mamba1 or a derivative or variant thereof to the knob domain or stalk domain. In some instances, pain is chronic pain. Alternatively, pain is acute pain.

Provided herein is a method of preventing or treating a disease or condition which benefits from modulating a sodium ion channel in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is protoxin2, 550 peptide, Amgen1, or derivative or variant thereof. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The protoxin2, 550 peptide, Amgen1, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ (SEQ ID NO: 128) motif. The protoxin2, 550 peptide, Amgen1, or a derivative or variant thereof can be attached to the stalk domain. In some instances, the antibody, antibody fragment or immunoglobulin construct further comprises a linker. The linker can attach protoxin2, 550 peptide, Amgen1, or a derivative or variant thereof to the immunoglobulin domain or fragment thereof. In other instances, the linker attaches protoxin2, 550 peptide, Amgen1, or a derivative or variant thereof to the knob domain or stalk domain. In some instances, the sodium ion channel is a $Na_v$ channel. In some instances, the $Na_v$ channel is a $Na_v1.7$ channel. In some instances, modulating a sodium ion channel comprises inhibiting or blocking a sodium ion channel. In some instances, the disease or condition is Dravet Syndrome, generalized epilepsy with febrile seizures plus (GEFS+), paramyotonia congenital or erythromelalgia. In some instances, the disease or condition is pain.

Provided herein is a method of preventing or treating a disease or condition which benefits from modulating an acid sensing ion channel (ASIC) in a subject in need thereof comprising a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is protoxin2, Mamba1, or derivative or variant thereof. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The protoxin2, Mamba1, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ (SEQ ID NO: 128) motif. The protoxin2, Mamba1, or a derivative or variant thereof can be attached to the stalk domain. In some instances, the antibody, antibody fragment or immunoglobulin construct further comprises a linker. The linker can attach protoxin2, Mamba1, or a derivative or variant thereof to the immunoglobulin domain or fragment thereof. In other instances, the linker attaches protoxin2, Mamba1, or a derivative or variant thereof to the knob domain or stalk domain. In some instances, modulating an ASIC comprises inhibiting or blocking the ASIC. In some instances, the disease or condition is a central nervous system disorder. In other instances, the disease or condition is pain.

Provided herein is a method of preventing or treating a pathogenic infection in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is beta-interferon, or derivative or variant thereof. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The beta-interferon, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ (SEQ ID NO: 128) motif. The beta-interferon, or a derivative or variant thereof can be attached to the stalk domain. In some instances, the antibody, antibody fragment or immunoglobulin construct further comprises a linker. The linker can attach beta-interferon, or a derivative or variant thereof to the immunoglobulin domain or fragment thereof. In other instances, the linker attaches beta-interferon, or a derivative or variant thereof to the knob domain or stalk domain. In some instances, the pathogenic infection is a viral, bacterial, fungal, or parasitic infection. In some instances, the viral infection is a herpes virus.

Provided herein is a method of preventing or treating a cancer in a subject in need thereof comprising administering a composition comprising one or more antibodies comprising an ultralong CDR3 as disclosed herein to said subject. The composition can further comprise a pharmaceutically acceptable carrier. The subject may be a mammal. The mammal may be a human. Alternatively, the mammal is a bovine. The antibody may comprise a therapeutic polypeptide, or derivative or variant thereof. The therapeutic polypeptide can be encoded by a non-antibody sequence. The therapeutic polypeptide, or derivative or variant thereof can be attached to the immunoglobulin domain. The therapeutic polypeptide, or derivative or variant thereof may be within the ultralong CDR3. Alternatively, the therapeutic polypeptide, or derivative or variant thereof is conjugated to the ultralong CDR3. In some instances, the therapeutic polypeptide is beta-interferon, or derivative or variant thereof. The antibody may be an immunoconjugate as described herein. The antibody can comprise one or more immunoglobulin domains. The immunoglobulin domain may be an immunoglobulin A, an immunoglobulin D, an immunoglobulin E, an immunoglobulin G, or an immunoglobulin M. The immunoglobulin domain can be an immunoglobulin heavy chain region or fragment thereof. In some instances, the immunoglobulin domain is from a mammalian antibody. Alternatively, the immunoglobulin domain is from a chimeric antibody. The immunoglobulin domain may be from an engineered antibody or recombinant antibody. The immunoglobulin domain may be from a humanized, human engineered or fully human antibody. The mammalian antibody can be a bovine antibody. The mammalian antibody may be a human antibody. In other instances, the mammalian antibody is a murine antibody. The ultralong CDR3 may be 35 amino acids in length or more. The ultralong CDR3 may comprise at least 3 cysteine residues or more. The ultralong CDR3 may comprise one or more cysteine motifs. The ultralong CDR3 comprises at least a portion of a knob domain. The knob domain may comprise a conserved motif within the knob domain of an ultralong CDR3. For example, the knob domain may comprise a cysteine motif disclosed herein. The beta-interferon, or a derivative or variant thereof can be attached to the knob domain. Alternatively, or additionally, the ultralong CDR3 comprises at least a portion of a stalk domain. The stalk domain may comprise a conserved motif within the stalk domain of an ultralong CDR3. For example, the stalk domain may comprise a T(S/T)VHQ (SEQ ID NO: 128) motif. The beta-interferon, or a derivative or variant thereof can be attached to the stalk domain. In some instances, the antibody, antibody fragment or immunoglobulin construct further comprises a linker. The linker can attach beta-interferon, or a derivative or variant thereof to the immunoglobulin domain or fragment thereof. In other instances, the linker attaches beta-interferon, or a derivative or variant thereof to the knob domain or stalk domain. In some instances, the cancer is a hematological malignancy. The hematological malignancy can be a leukemia or lymphoma. In some instances, the hematological malignancy is a B-cell lymphoma, T-cell lymphoma, follicular lymphoma, marginal zone lymphoma, hairy cell leukemia, chronic myeloid leukemia, mantle cell lymphoma, nodular lymphoma, Burkitt's lymphoma, cutaneous T-cell lymphoma, chronic lymphocytic leukemia, or small lymphocytic leukemia.

Provided herein is a method of preventing or treating a bone disease in a subject in need thereof comprising administering a composition comprising one or more antibodies, antibody fragments, or immunoglobulin constructs described herein to said subject. In some instances, the subject is a mammal. In certain instances, the mammal is a human. Alternatively, the mammal is a bovine. In some instances, the one or more antibodies, antibody fragments, or immunoglobulin constructs comprise a parathyroid hormone. Alternatively, or additionally, the one or more antibodies, antibody fragments, or immunoglobulin constructs comprise at least a portion of a CDR3H. The portion of the CDR3H can be a stalk domain or knob domain in the CDR3H. In some instances, the one or more antibodies, antibody fragments, or immunoglobulin constructs further comprise a linker. The linker can attach the parathyroid hormone to the portion of the CDR3H. In some instances, the bone disease is osteoporosis. Additional bone diseases include, but are not limited to, low bone density, osteogenesis imperfecta, osteitis condensans ilii osteochondritis dissecans, osteochondroma (bone tumor), osteomalacia, osteomyelitis, osteopenia, osteopetrosis, osteosarcoma (bone tumor), osteonecrosis, osteoarthritis, osteitis pubis, and Paget's disease of bone.

Provided herein is a method of preventing or treating a disease in a mammal in need thereof comprising administering a pharmaceutical composition described herein to said mammal. In some embodiments, the disease is an infectious disease. In certain embodiments, the infectious disease is mastitis. In some embodiments, the infectious disease is a respiratory disease. In certain embodiments, the respiratory disease is bovine respiratory disease of shipping fever. In certain embodiments, the mammal in need is a dairy animal selected from a list comprising cow, camel, donkey, goat, horse, reindeer, sheep, water buffalo, moose and yak. In some embodiments, the mammal in need is bovine.

Provided are methods of treatment, inhibition and prevention by administration to a subject of an effective amount of an antibody or pharmaceutical composition described herein. The antibody may be substantially purified (e.g., substantially free from substances that limit its effect or produce undesired side-effects). The subject can be an animal, including but not limited to animals such as cows, pigs, sheep, goats, rabbits, horses, chickens, cats, dogs, mice, etc. The subject can be a mammal. In some instances, the subject is a human. Alternatively, the subject is a bovine.

Various delivery systems are known and can be used to administer an antibody formulation described herein, e.g., encapsulation in liposomes, microparticles, microcapsules, recombinant cells capable of expressing the compound, receptor-mediated endocytosis (see, e.g., Wu and Wu, J. Biol. Chem. 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, in certain embodiments, it is desirable to introduce the heteromultimer compositions described herein into the central nervous system by any suitable route, including intraventricular and intrathecal injection; intraventricular injection may be facilitated by an intraventricular catheter, for example, attached to a reservoir, such as an Ommaya reservoir.

In a specific embodiment, it is desirable to administer the antibody, or compositions described herein locally to the area in need of treatment; this may be achieved by, for example, and not by way of limitation, local infusion, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the antibody or pharmaceutical composition is delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the heteromultimers or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, e.g., the brain, thus requiring only a fraction of the systemic dose (see, e.g., Goodson, in Medical Applications of Controlled Release, supra, vol. 2, pp. 115-138 (1984)). Other controlled release systems are discussed in the review by Langer (Science 249:1527-1533 (1990)).

In a specific embodiment comprising a nucleic acid encoding an antibody decribed herein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

In certain embodiments, the half-life of an immunoglobulin construct described herein is greater than the half-life of the un-conjugated therapeutic peptide that is incorporated in the immunoglobulin construct. In some embodiments, the half-life of an immunoglobulin construct provided herein is greater than 4 hours when administered to a subject. In certain embodiments, the half-life of an immunoglobulin construct provided herein is greater than 4 hours, greater than 6 hours, greater than 12 hours, greater than 24 hours, greater than 36 hours, greater than 2 days, greater than 3 days, greater than 4 days, greater than 5 days, greater than 6 days, greater than 7 days, greater than 8 days, greater than 9 days, greater than 10 days, greater than 11 days, greater than 12 days, greater than 13 days, or greater than 14 days when administered to a subject. In some instances, the subject is a mammal. In some embodiments, the subject is a mouse or a bovine. In other instances, the subject is a human. In certain embodiments, a pharmaceutical composition comprising the immunoglobulin construct is administered to the subject once a day, every two days, every three days, every 4 days, every 7 days, every 10 days, every 14 days, every 21 days, every 28 days, every 2 months, or every three months.

EXAMPLES

The following specific and non-limiting examples are to be construed as merely illustrative, and do not limit the present disclosure in any way whatsoever. Without further elaboration, it is believed that one skilled in the art can, based on the description herein, utilize the present disclosure to its fullest extent. All publications cited herein are hereby incorporated by reference in their entirety.

Example 1. Constructing Vectors of BLV1H12-Oxyntomodulin Fusion Proteins for Expression in Mammalian Cells Gene encoding oxyntomodulin was synthesized by Genscript or IDT, and amplified by polymerase chain reaction (PCR). To optimize the folding and stability of fusion proteins, flexible linkers of (GGGGS) were added on both ends of oxyntomodulin fragments. Subsequently, PCR fragments of oxyntomodulin were grafted into the complementarity determining region 3 of the heavy chain (CDR3H) of BLV1H12 antibody by exploiting overlap extension PCR, to replace the 'knob' domain as shown in the crystal structure of BLV1H12. The expression vectors of BLV1H12-oxyntomodulin fusion proteins were generated by in-frame ligation of the amplified BLV1H12-oxyntomodulin fusion genes to the pFuse-hIgG1-Fc backbone vector (InvivoGen, CA). Similarly, the gene encoding the light chain of BLV1H12 antibody was cloned into the pFuse vector without hIgG1 Fc fragment. The obtained expression vectors were confirmed by sequencing.

Example 2. Expression and Purification of BLV1H12-Oxyntomodulin Fusion Antibodies BLV1H12-oxyntomodulin fusion antibodies were expressed through transient transfections of free style HEK 293 cells with vectors encoding BLV1H12-protoxin2 fusion heavy chain and the BLV1H12 light chain. Expressed BLV1H12-oxyntomodulin fusion antibodies were secreted into the culture medium and harvested at 48 hours and 96 hours after transfection. The BLV1H12-oxyntomodulin fusion proteins can be purified by Protein A/G chromatography (Thermo Fisher Scientific, IL), and analyzed by SDS-PAGE gel.

Example 3. Constructing Vectors of BLV1H12-550 Fusion Proteins for Expression in Mammalian Cells Gene encoding 550 was synthesized by Genscript or IDT, and amplified by polymerase chain reaction (PCR). To optimize the folding and stability of fusion proteins, flexible linkers of GGGGS were added on both ends of 550 fragments. Subsequently, PCR fragments of 550 were grafted into the complementarity determining region 3 of the heavy chain (CDR3H) of BLV1H12 antibody by exploiting overlap extension PCR, to replace the 'knob' domain as shown in the crystal structure of BLV1H12. The expression vectors of BLV1H12-550 fusion proteins were generated by in-frame ligation of the amplified BLV1H12-550 fusion genes to the pFuse-hIgG1-Fc backbone vector (InvivoGen, CA). Similarly, the gene encoding the light chain of BLV1H12 antibody was cloned into the pFuse vector without hIgG1 Fc fragment. The obtained expression vectors were confirmed by sequencing.

Example 4. Expression and Purification of BLV1H12-550 Fusion Antibodies

Figure 2:
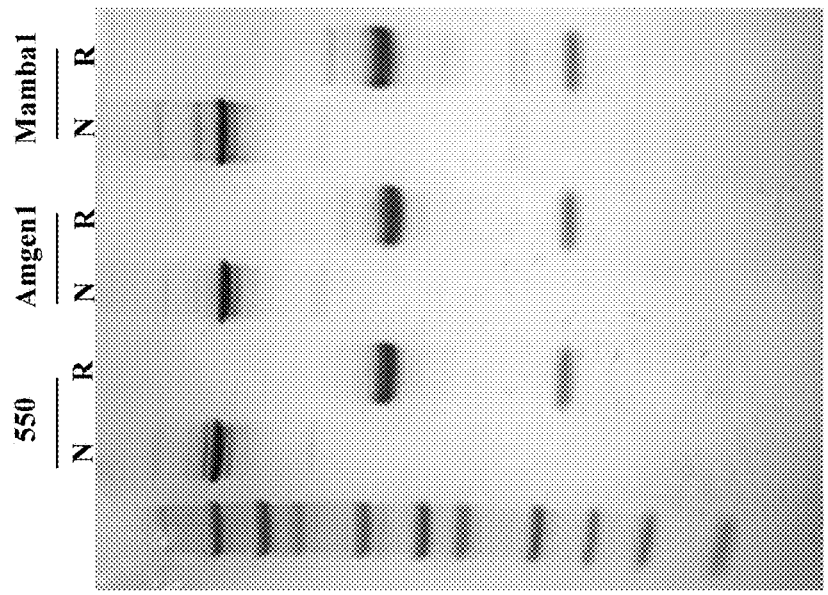
FIG. 2A-2B depict Western blots and SDS-PAGE of BLV1H12 fusion antibodies disclosed herein.
Figure 2:
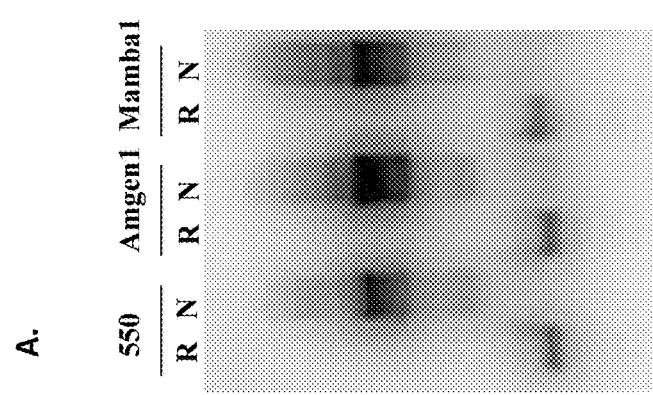

BLV1H12-550 fusion antibodies were expressed through transient transfections of free style HEK 293 cells with vectors encoding BLV1H12-fusion heavy chain and the BLV1H12 light chain. Expressed BLV1H12-550 fusion antibodies were secreted into the culture medium and harvested every 48 hours for twice after transfection. The BLV1H12-550 fusion antibodies were purified by Protein A/G chromatography (Thermo Fisher Scientific, IL), and analyzed by SDS PAGE gel. FIG. 2A shows the SDS PAGE of the 550 peptide. FIG. 2B shows the Western blot of the 550 peptide.

Example 5. Constructing Vectors of BLV1H12-Amgen1 Fusion Proteins for Expression in Mammalian Cells Gene encoding Amgen1 was synthesized by Genscript or IDT, and amplified by polymerase chain reaction (PCR). To optimize the folding and stability of fusion proteins, flexible linkers of GGGGS were added on both ends of Amgen1 fragments. Subsequently, PCR fragments of Amgen1 were grafted into the complementarity determining region 3 of the heavy chain (CDR3H) of BLV1H12 antibody by exploiting overlap extension PCR, to replace the 'knob' domain as shown in the crystal structure of BLV1H12. The expression vectors of BLV1H12-Amgen1 fusion proteins were generated by in-frame ligation of the amplified BLV1H12-Amgen1 fusion genes to the pFuse-hIgG1-Fc backbone vector (InvivoGen, CA). Similarly, the gene encoding the light chain of BLV1H12 antibody was cloned into the pFuse vector without hIgG1 Fc fragment. The obtained expression vectors were confirmed by sequencing.

Example 6. Expression and Purification of BLV1H12-Amgen1 Fusion Antibodies

BLV1H12-Amgen1 fusion antibodies were expressed through transient transfections of free style HEK 293 cells with vectors encoding BLV1H12-Amgen1 fusion heavy chain and the BLV1H12 light chain. Expressed BLV1H12-Amgen1 fusion antibodies were secreted into the culture medium and harvested at 48 hours and 96 hours after transfection. The BLV1H12-Amgen1 fusion antibodies were purified by Protein A/G chromatography (Thermo Fisher Scientific, IL), and analyzed by SDS-PAGE gel. FIG. 2A shows the SDS PAGE of Amgen1. FIG. 2B shows the Western blot of Amgen1.

Example 7. Constructing Vectors of BLV1H12-Mamba1 Fusion Proteins for Expression in Mammalian Cells Gene encoding Mamba1 was synthesized by Genscript or IDT, and amplified by polymerase chain reaction (PCR). To optimize the folding and stability of fusion proteins, flexible linkers of GGGGS were added on both ends of Mamba1 fragments. Subsequently, PCR fragments of Mamba1 were grafted into the complementarity determining region 3 of the heavy chain (CDR3H) of BLV1H12 antibody by exploiting overlap extension PCR, to replace the 'knob' domain as shown in the crystal structure of BLV1H12. The expression vectors of BLV1H12-Mamba1 fusion proteins were generated by in-frame ligation of the amplified BLV1H12-Mamba1 fusion genes to the pFuse-hIgG1-Fc backbone vector (InvivoGen, CA). Similarly, the gene encoding the light chain of BLV1H12 antibody was cloned into the pFuse vector without hIgG1 Fc fragment. The obtained expression vectors were confirmed by sequencing.

Example 8. Expression and Purification of BLV1H12-Mamba1 Fusion Antibodies

BLV1H12-Mamba1 fusion antibodies were expressed through transient transfections of free style HEK 293 cells with vectors encoding BLV1H12-Mamba1 fusion heavy chain and the BLV1H12 light chain. Expressed BLV1H12-Mamba1 fusion antibodies were secreted into the culture medium and harvested every 48 hours for twice after transfection. The BLV1H12-Mamba1 fusion antibodies were purified by Protein A/G chromatography (Thermo Fisher Scientific, IL), and analyzed by SDS-PAGE gel. FIG. 2A shows the SDS PAGE of Mamba1. FIG. 2B shows the Western blot of the Mamba1.

Example 9. Constructing Vectors of BLV1H12-Parathyroid Hormone Fusion Proteins for Expression in Mammalian Cells Gene encoding human parathyroid hormone (hPTH) was synthesized by Genscript or IDT, and amplified by polymerase chain reaction (PCR). To optimize the folding and stability of fusion proteins, flexible linkers of GGGGS were added on both ends of human parathyroid hormone (hPTH) fragments. Subsequently, PCR fragments of human parathyroid hormone (hPTH) were grafted into the complementarity determining region 3 of the heavy chain (CDR3H) of BLV1H12 antibody by exploiting overlap extension PCR, to replace the 'knob' domain as shown in the crystal structure of BLV1H12. The expression vectors of BLV1H12-hPTH fusion proteins were generated by in-frame ligation of the amplified BLV1H12-hPTH fusion genes to the pFuse-hIgG1-Fc backbone vector (InvivoGen, CA). Similarly, the gene encoding the light chain of BLV1H12 antibody was cloned into the pFuse vector without hIgG1 Fc fragment. The obtained expression vectors were confirmed by sequencing.

Example 10. Expression and Purification of BLV1H12-Parathyroid Fusion Antibodies BLV1H12-parathyroid (PTH) fusion antibodies are expressed through transient transfections of free style HEK 293 cells with vectors encoding BLV1H12-hPTH fusion heavy chain and the BLV1H12 light chain. Expressed BLV1H12-parathyroid (PTH) fusion antibodies are secreted into the culture medium and harvested every 48 hours for twice after transfection. The BLV1H12-parathyroid (PTH) fusion antibodies are purified by Protein A/G chromatography (Thermo Fisher Scientific, IL), and analyzed by SDS-PAGE gel.

Example 11. Constructing Vectors of BLV1H12-Therapeutic Polypeptide Fusion Proteins for Expression in Mammalian Cells Genes encoding various genes were synthesized by Genscript (NJ, USA) and amplified by polymerase chain reaction (PCR). To optimize the folding and stability of the immunoglobulin constructs, one or more flexible linkers of (GGGGS)n (n=0, 1) (SEQ ID NO: 129), GGGSGGGGS, and/or GGGGSGGGS were added on both ends of the gene fragment. Subsequently, PCR fragments of the genes with varied lengths of linkers were grafted into the complementarity determining region 3 of the heavy chain (CDR3H) of BLV1H12 antibody by exploiting overlap extension PCR, to replace at least a portion of the 'knob' domain as shown in the crystal structure of BLV1H12 (FIG. 1A). The expression vectors of BLV1H12-bGCSF fusion proteins were generated by in-frame ligation of the amplified BLV1H12-fusion genes to the pFuse-hIgG1-Fc backbone vector (InvivoGen, CA). Similarly, the gene encoding the light chain of BLV1H12 antibody was cloned into the pFuse vector without hIgG1 Fc fragment. The obtained expression vectors were confirmed by sequencing.

Nucleic acid sequences of the BLV1H12-fusion proteins are displayed in Table 1. Peptide sequences of the BLVH12-fusion proteins are displayed in Table 2. As shown in the tables, the bovine heavy chain sequence is in bold font; the human heavy chain sequence is highlighted with a dashed underline; the non-antibody sequence is in italicized font; the stalk domain is in bold font and underlined; the knob domain is in bold font and double underlined; the linker sequence is in italicized font and squiggly underlined.

TABLE 1

| Description | SEQ ID NO: | Sequence |
| --- | --- | --- |
| Light Chain | 1 | CAGGCCGTCCTGAACCAGCCAAGCAGCGTCTCCGGGTCTCTGGG GCAGCGGGTCTCAATCACCTGTAGCGGGTCTTCCTCCAATGTCGG CAACGGCTACGTGTCTTGGTATCAGCTGATCCCTGGCAGTGCCCC ACGAACCCTGATCTACGGCGACACATCCAGAGCTTCTGGGGTCC CCGATCGGTTCTCAGGGAGCAGATCCGGAAACACAGCTACTCTG |

TABLE 1-continued

| Description | SEQ ID NO: | Sequence |
|---|---|---|
| | | ACCATCAGCTCCCTGCAGGCTGAGGACGAAGCAGATTATTTCTG |
| | | CGCATCTGCCGAGGACTCTAGTTCAAATGCCGTGTTTGGAAGCG |
| | | GCACCACACTGACAGTCCTGGGGCAGCCCAAGAGTCCCCCTTCA |
| | | GTGACTCTGTTCCCACCCTCTACCGAGGAACTGAACGGAAACAA |
| | | GGCCACACTGGTGTGTCTGATCAGCGACTTTTACCCTGGATCCGT |
| | | CACTGTGGTCTGGAAGGCAGATGGCAGCACAATTACTAGGAACG |
| | | TGGAAACTACCCGCGCCTCCAAGCAGTCTAATAGTAAATACGCC |
| | | GCCAGCTCCTATCTGAGCCTGACCTCTAGTGATTGGAAGTCCAAA |
| | | GGGTCATATAGCTGCGAAGTGACCCATGAAGGCTCAACCGTGAC |
| | | TAAGACTGTGAAACCATCCGAGTGCTCC |
| Heavy Chain | 2 | CAGGTCCAGCTGAGAGAGAGCGGCCCTTCACTGGTCAAGCC |
| | | ATCCCAGACACTGAGCCTGACATGCACAGCAAGCGGGTTTTC |
| | | ACTGAGCGACAAGGCAGTGGGATGGGTCCGACAGGCACCAG |
| | | GAAAAGCCCTGGAATGGCTGGGCAGCATCGATACCGGCGGG |
| | | AACACAGGGTACAATCCCGGACTGAAGAGCAGACTGTCCATT |
| | | ACCAAGGACAACTCTAAAAGTCAGGTGTCACTGAGCGTGAGC |
| | | TCCGTCACCACAGAGGATAGTGCAACTTACTATTGCACCTCT |
| | | <u>GTGCACCAGGAAACTAAGAAATACCAGAGCTGTCCTGACGG</u> |
| | | <u>CTATCGGGAGAGATCTGATTGCAGTAATAGGCCAGCTTGTGG</u> |
| | | <u>CACATCCGACTGCTGTCGCGTGTCTGTCTTCGGGAACTGCCT</u> |
| | | <u>GACTACCCTGCCTGTGTCCTACTCTT</u>ATACCTACAATTATGAA |
| | | TGGCATGTGGATGTCTGGGGACAGGGCCTGCTGGTGACAGT |
| | | CTCTAGT |
| 550 | 3 | CAGGTCCAGCTGAGAGAGAGCGGCCCTTCACTGGTCAAGCC |
| | | ATCCCAGACACTGAGCCTGACATGCACAGCAAGCGGGTTTTC |
| | | ACTGAGCGACAAGGCAGTGGGATGGGTCCGACAGGCACCAG |
| | | GAAAAGCCCTGGAATGGCTGGGCAGCATCGATACCGGCGGG |
| | | AACACAGGGTACAATCCCGGACTGAAGAGCAGACTGTCCATT |
| | | ACCAAGGACAACTCTAAAAGTCAGGTGTCACTGAGCGTGAGC |
| | | TCCGTCACCACAGAGGATAGTGCAACTTACTATTGCACCTCT |
| | | <u>GTGCACCAGGAAACTAAGAAATACCAGAGC</u>*GGGGGTGGCGGA* |
| | | *AGCGAATGCATCGGTATGTTCAAATCTTGCGACCCGGAAAACGACAA* |
| | | *ATGCTGCAAAGGTCGTACCTGCTCTCGTAAACACCGTTGGTGCAAATA* |
| | | *CAAACTGGGCGGAGGTGGGAGT*<u>TCTTATACCTACAATTATGAAT</u> |
| | | <u>GG</u>CATGTGGATGTCTGGGGACAGGGCCTGCTGGTGACAGTC |
| | | TCTAGTGCTTCCACAACTGCACCAAAGGTGTACCCCCTGTCA |
| | | AGCTGCTGTGGGGACAAATCCTCTAGTACCGTGACACTGGGA |

TABLE 1-continued

| Description | SEQ ID NO: | Sequence |
|---|---|---|
| | | TGCCTGGTCTCAAGCTATATGCCCGAGCCTGTGACTGTCACC |
| | | TGGAACTCAGGAGCCCTGAAAAGCGGAGTGCACACCTTCCC |
| | | AGCTGTGCTGCAGTCCTCTGGCCTGTATAGCCTGAGTTCAAT |
| | | GGTGACAGTCCCCGGCAGTACTTCAGGGCAGACCTTCACCTG |
| | | TAATGTGGCCCATCCTGCCAGCTCCACCAAAGTGGACAAAGC |
| | | AGTGGAACCCAAATCTTGCGACAAAACTCACACATGCCCACCG |
| | | TGCCCAGCACCTGAACTCCTGGGGGGACCGTCAGTCTTCCTCTTC |
| | | CCCCCAAAACCCAAGGACACCCTCATGATCTCCCGGACCCCTGA |
| | | GGTCACATGCGTGGTGGTGGACGTGAGCCACGAAGACCCTGAGG |
| | | TCAAGTTCAACTGGTACGTGGACGGCGTGGAGGTGCATAATGCC |
| | | AAGACAAAGCCGCGGGAGGAGCAGTACAACAGCACGTACCGTG |
| | | TGGTCAGCGTCCTCACCGTCCTGCACCAGGACTGGCTGAATGGC |
| | | AAGGAGTACAAGTGCAAGGTCTCCAACAAAGCCCTCCCAGCCCC |
| | | CATCGAGAAAACCATCTCCAAAGCCAAGGGCAGCCCCGAGAA |
| | | CCACAGGTGTACACCCTGCCCCCATCCCGGGATGAGCTGACCAA |
| | | GAACCAGGTCAGCCTGACCTGCCTGGTCAAAGGCTTGTATCCCA |
| | | GCGACATCGCCGTGGAGTGGGAGAGCAATGGGCAGCCGGAGAA |
| | | CAACTACAAGACCACGCCTCCCGTGCTGGACTCCGACGGCTCCTT |
| | | CTTCCTCTACAGCAAGCTCACCGTGGACAAGAGCAGGTGGCAGC |
| | | AGGGGAACGTCTTCTCATGCTCCGTGATGCATGAGGCTCTGCAC |
| | | AACCACTACACGCAGAAGAGCCTCTCCCTGTCTCCGGGTAAA |
| Amgen1 | 4 | CAGGTCCAGCTGAGAGAGAGCGGCCCTTCACTGGTCAAGCC |
| | | ATCCCAGACACTGAGCCTGACATGCACAGCAAGCGGGTTTTC |
| | | ACTGAGCGACAAGGCAGTGGGATGGGTCCGACAGGCACCAG |
| | | GAAAAGCCCTGGAATGGCTGGGCAGCATCGATACCGGCGGG |
| | | AACACAGGGTACAATCCCGGACTGAAGAGCAGACTGTCCATT |
| | | ACCAAGGACAACTCTAAAAGTCAGGTGTCACTGAGCGTGAGC |
| | | TCCGTCACCACAGAGGATAGTGCAACTTACTATTGCACCTCT |
| | | GTGCACCAGGAAACTAAGAAATACCAGAGCGGGGGTGGCGGA |
| | | AGCGACTGCCTGGGTTCATGCGTAAATGCATCCCGGACAACGACAA |
| | | ATGCTGCCGTCCGAACCTGGTTTGCTCTCGTACCCACAAATGGTGCA |
| | | AATACGTTTTCGGCGGAGGTGGGAGTTCTTATACCTACAATTATG |
| | | AATGGCATGTGGATGTCTGGGGACAGGGCCTGCTGGTGACA |
| | | GTCTCTAGTGCTTCCACAACTGCACCAAAGGTGTACCCCCTG |
| | | TCAAGCTGCTGTGGGACAAATCCTCTAGTACCGTGACACTG |
| | | GGATGCCTGGTCTCAAGCTATATGCCCGAGCCTGTGACTGTC |
| | | ACCTGGAACTCAGGAGCCCTGAAAAGCGGAGTGCACACCTT |

TABLE 1-continued

| Description | SEQ ID NO: | Sequence |
|---|---|---|
| | | CCCAGCTGTGCTGCAGTCCTCTGGCCTGTATAGCCTGAGTTC |
| | | AATGGTGACAGTCCCCGGCAGTACTTCAGGGCAGACCTTCAC |
| | | CTGTAATGTGGCCCATCCTGCCAGCTCCACCAAAGTGGACAA |
| | | AGCAGTGGAACCCAAATCTTGCGACAAAACTCACACATGCCCA |
| | | CCGTGCCCAGCACCTGAACTCCTGGGGGACCGTCAGTCTTCCTC |
| | | TTCCCCCCAAAACCCAAGGACACCCTCATGATCTCCCGGACCCCT |
| | | GAGGTCACATGCGTGGTGGTGGACGTGAGCCACGAAGACCCTGA |
| | | GGTCAAGTTCAACTGGTACGTGGACGGCGTGGAGGTGCATAATG |
| | | CCAAGACAAAGCCGCGGGAGGAGCAGTACAACAGCACGTACCG |
| | | TGTGGTCAGCGTCCTCACCGTCCTGCACCAGGACTGGCTGAATG |
| | | GCAAGGAGTACAAGTGCAAGGTCTCCAACAAAGCCCTCCCAGCC |
| | | CCCATCGAGAAAACCATCTCCAAAGCCAAAGGGCAGCCCCGAGA |
| | | ACCACAGGTGTACACCCTGCCCCCATCCCGGGATGAGCTGACCA |
| | | AGAACCAGGTCAGCCTGACCTGCCTGGTCAAAGGCTTCTATCCC |
| | | AGCGACATCGCCGTGGAGTGGGAGAGCAATGGGCAGCCGGAGA |
| | | ACAACTACAAGACCACGCCTCCCGTGCTGGACTCCGACGGCTCC |
| | | TTCTTCCTCTACAGCAAGCTCACCGTGGACAAGAGCAGGTGGCA |
| | | GCAGGGGAACGTCTTCTCATGCTCCGTGATGCATGAGGCTCTGC |
| | | ACAACCACTACACGCAGAAGAGCCTCTCCCTGTCTCCGGGTAAA |
| Mamba1 | 5 | CAGGTCCAGCTGAGAGAGAGCGGCCCTTCACTGGTCAAGCC |
| | | ATCCCAGACACTGAGCCTGACATGCACAGCAAGCGGGTTTTC |
| | | ACTGAGCGACAAGGCAGTGGGATGGGTCCGACAGGCACCAG |
| | | GAAAAGCCCTGGAATGGCTGGGCAGCATCGATACCGGCGGG |
| | | AACACAGGGTACAATCCCGGACTGAAGAGCAGACTGTCCATT |
| | | ACCAAGGACAACTCTAAAAGTCAGGTGTCACTGAGCGTGAGC |
| | | TCCGTCACCACAGAGGATAGTGCAACTTACTATTGCACCTCT |
| | | GTGCACCAGGAAACTAAGAAATACCAGAGCGGGGGTGGCGGA |
| | | AGCCTGAAATGTTACCAACATGGTAAAGTTGTGACTTGTCATCGAGAT |
| | | ATGAAGTTTTGCTATCATAACACTGGCATGCCTTTTCGAAATCTCAAGC |
| | | TCATCCTACAGGGATGTTCTTCTTCGTGCAGTGAAACAGAAAACAATA |
| | | AGTGTTGCTCAACAGACAGATGCAACAAAGGCGGAGGTGGGAGTTC |
| | | TTATACCTACAATTATGAATGGCATGTGGATGTCTGGGGACA |
| | | GGGCCTGCTGGTGACAGTCTCTAGTGCTTCCACAACTGCACC |
| | | AAAGGTGTACCCCCTGTCAAGCTGCTGTGGGGACAAATCCTC |
| | | TAGTACCGTGACACTGGGATGCCTGGTCTCAAGCTATATGCC |
| | | CGAGCCTGTGACTGTCACCTGGAACTCAGGAGCCCTGAAAA |

TABLE 1-continued

| Description | SEQ ID NO: | Sequence |
|---|---|---|
| | | GCGGAGTGCACACCTTCCCAGCTGTGCTGCAGTCCTCTGGCC |
| | | TGTATAGCCTGAGTTCAATGGTGACAGTCCCCGGCAGTACTT |
| | | CAGGGCAGACCTTCACCTGTAATGTGGCCCATCCTGCCAGCT |
| | | CCACCAAAGTGGACAAAGCAGTGGAACCCAAATCTTGC<u>GACA</u> |
| | | <u>AAACTCACACATGCCCACCGTGCCCAGCACCTGAACTCCTGGGG</u> |
| | | <u>GGACCGTCAGTCTTCCTCTTCCCCCCAAAACCCAAGGACACCCTC</u> |
| | | <u>ATGATCTCCCGGACCCCTGAGGTCACATGCGTGGTGGTGGACGT</u> |
| | | <u>GAGCCACGAACACCCTGAGGTCAAGTTCAACTGGTACGTGGACG</u> |
| | | <u>GCGTGGAGGTGCATAATGCCAAGACAAAGCCGCGGGAGGAGCA</u> |
| | | <u>GTACAACAGCACGTACCGTGTGGTCAGCGTCCTCACCGTCCTGC</u> |
| | | <u>ACCAGGACTGGCTGAATGGCAAGGAGTCACCGTGCAAGGTCTCC</u> |
| | | <u>AACAAAGCCCTCCCAGCCCCCATCGAGAAAACCATCTCCAAAGC</u> |
| | | <u>CAAAGGGCAGCCCCGAGAACCACAGGTGTACACCCTGCCCCCAT</u> |
| | | <u>CCCGGGATGAGCTGACCAAGAACCAGGTCAGCCTGACCTGCCTG</u> |
| | | <u>GTCAAAGGCTTCTATCCCAGCGACATCGCCGTGGAGTGGGAGAG</u> |
| | | <u>CAATGGGCAGCCGGAGAACAACTACAAGACCACGCCTCCCGTGC</u> |
| | | <u>TGGACTCCGACGGCTCCTTCTTCCTCTACAGCAAGCTCACCGTGG</u> |
| | | <u>ACAAGAGCAGGTGGCAGCAGGGGAACGTCTTCTCATGCTCCGTG</u> |
| | | <u>ATGCATGAGGCTCTGCACAACCACTACACGCAGAAGAGCCTCTC</u> |
| | | <u>CCTGTCTCCGGGTAAA</u> |
| oxynto-modulin | 6 | CAGGTCCAGCTGAGAGAGAGCGGCCCTTCACTGGTCAAGCC |
| | | ATCCCAGACACTGAGCCTGACATGCACAGCAAGCGGGTTTTC |
| | | ACTGAGCGACAAGGCAGTGGGATGGGTCCGACAGGCACCAG |
| | | GAAAAGCCCTGGAATGGCTGGGCAGCATCGATACCGGCGGG |
| | | AACACAGGGTACAATCCCGGACTGAAGAGCAGACTGTCCATT |
| | | ACCAAGGACAACTCTAAAAGTCAGGTGTCACTGAGCGTGAGC |
| | | TCCGTCACCACAGAGGATAGTGCAACTTACTATTGCACCTCT |
| | | <u>GTGCACCAGGAAACTAAGAAATACCAGAGC</u>*GGGGGTGGCGGA* |
| | | *AGCCACTCTCAGGGTACCTTCACCTCTGACTACTCTAAATACCTGGAC* |
| | | *TCTCGTCGTGCTCAGGACTTCGTTCAGTGGCTGATGAACACCAAACG* |
| | | *TAACCGTAACAACATCGCTGGCGGAGGTGGGAGT*TCTTATACCTAC |
| | | AATTATGAATGGCATGTGGATGTCTGGGGACAGGGCCTGCT |
| | | GGTGACAGTCTCTAGTGCTTCCACAACTGCACCAAAGGTGTA |
| | | CCCCCTGTCAAGCTGCTGTGGGGACAAATCCTCTAGTACCGT |
| | | GACACTGGGATGCCTGGTCTCAAGCTATATGCCCGAGCCTGT |
| | | GACTGTCACCTGGAACTCAGGAGCCCTGAAAAGCGGAGTGC |
| | | ACACCTTCCCAGCTGTGCTGCAGTCCTCTGGCCTGTATAGCC |

TABLE 1-continued

| Description | SEQ ID NO: | Sequence |
|---|---|---|
| | | TGAGTTCAATGGTGACAGTCCCCGGCAGTACTTCAGGGCAGA |
| | | CCTTCACCTGTAATGTGGCCCATCCTGCCAGCTCCACCAAAG |
| | | TGGACAAAGCAGTGGAACCCAAATCTTGCGACAAAACTCACA |
| | | CATGCCCACCGTGCCCAGCACCTGAACTCCTGGGGGACCGTCA |
| | | GTCTTCCTCTTCCCCCCAAAACCCAAGGACACCCTCATGATCTCC |
| | | CGGACCCCTGAGGTCACATGCGTGGTGGTGGACGTGAGCCACGA |
| | | AGACCCTGAGGTCAAGTTCAACTGGTACGTGGACGGCGTGGAGG |
| | | TGCATAATGCCAAGACAAAGCCGCGGGAGGAGCAGTACAACAG |
| | | CACGTACCGTGTGGTCAGCGTCCTCACCGTCCTGCACCAGGACTG |
| | | GCTGAATGGCAAGGAGTACAAGTGCAAGGTCTCCAACAAAGCCC |
| | | TCCCAGCCCCCATCGAGAAAACCATCTCCAAAGCCAAAGGGCAG |
| | | CCCCGAGAACCACAGGTGTACACCCTGCCCCCATCCCGGGATGA |
| | | GCTGACCAAGAACCAGGTCAGCCTGACCTGCCTGGTCAAAGGCT |
| | | TCTATCCCAGCGACATCGCCGTGGAGTGGGAGAGCAATGGGCAG |
| | | CCGGAGAACAACTACAAGACCACGCCTCCCGTGCTGGACTCCGA |
| | | CGGCTCCTTCTTCCTCTACAGCAAGCTCACCGTGGACAAGAGCA |
| | | GGTGGCAGCAGGGGAACGTCTTCTCATGCTCCGTGATGCATGAG |
| | | GCTCTGCACAACCACTACACGCAGAAGAGCCTCTCCCTGTCTCCG |
| | | GGTAAA |
| Parathyroid (PTH) | 7 | CAGGTCCAGCTGAGAGAGAGCGGCCCTTCACTGGTCAAGCC |
| | | ATCCCAGACACTGAGCCTGACATGCACAGCAAGCGGGTTTTC |
| | | ACTGAGCGACAAGGCAGTGGGATGGGTCCGACAGGCACCAG |
| | | GAAAAGCCCTGGAATGGCTGGGCAGCATCGATACCGGCGGG |
| | | AACACAGGGTACAATCCCGGACTGAAGAGCAGACTGTCCATT |
| | | ACCAAGGACAACTCTAAAAGTCAGGTGTCACTGAGCGTGAGC |
| | | TCCGTCACCACAGAGGATAGTGCAACTTACTATTGCACCTCT |
| | | GTGCACCAGGAAACTAAGAAATACCAGAGCGGGGGTGGCGGA |
| | | AGCTCTGTGAGTGAAATACAGCTTATGCATAACCTGGGAAAACATCTG |
| | | AACTCGATGGAGAGAGTAGAATGGCTGCGTAAGAAGCTGCAGGATGT |
| | | GCACAATTTTGTTGCCCTTGGAGCTCCTCTAGCTCCCAGAGATGCTG |
| | | GTTCCCAGAGGCCCCGAAAAAAGGAAGACAATGTCTTGGTTGAGAGC |
| | | CATGAAAAAGTCTTGGAGAGGCAGACAAAGCTGATGTGAATGTATTA |
| | | ACTAAAGCTAAATCCCAGGGCGGAGGTGGGAGTTCTTATACCTAC |
| | | AATTATGAATGGCATGTGGATGTCTGGGGACAGGGCCTGCT |
| | | GGTGACAGTCTCTAGTGCTTCCACAACTGCACCAAAGGTGTA |
| | | CCCCCTGTCAAGCTGCTGTGGGGACAAATCCTCTAGTACCGT |

TABLE 1-continued

| Description | SEQ ID NO: | Sequence |
|---|---|---|
| | | GACACTGGGATGCCTGGTCTCAAGCTATATGCCCGAGCCTGT |
| | | GACTGTCACCTGGAACTCAGGAGCCCTGAAAAGCGGAGTGC |
| | | ACACCTTCCCAGCTGTGCTGCAGTCCTCTGGCCTGTATAGCC |
| | | TGAGTTCAATGGTGACAGTCCCCGGCAGTACTTCAGGGCAGA |
| | | CCTTCACCTGTAATGTGGCCCATCCTGCCAGCTCCACCAAAG |
| | | TGGACAAAGCAGTGGAACCCAAATCTTGC<u>GACAAAACTCACA</u> |
| | | <u>CATGCCCACCGTGCCCAGCACCTGAACTCCTGGGGGACCGTCA</u> |
| | | <u>GTCTTCCTCTTCCCCCCAAAACCCAAGGACACCCTCATGATCTCC</u> |
| | | <u>CGGACCCCTGAGGTCACATGCGTGGTGGTGGACGTGAGCCACGA</u> |
| | | <u>AGACCCTGAGGTCAAGTTCAACTGGTACGTGGACGGCGTGGAGG</u> |
| | | <u>TGCATAATGCCAAGACAAAGCCGCGGGAGGAGCAGTACAACAG</u> |
| | | <u>CACGTACCGTGTGGTCAGCGTCCTCACCGTCCTGCACCAGGACTG</u> |
| | | <u>GCTGAATGGCAAGGAGTACAAGTGCAAGGTCTCCAACAAAGCCC</u> |
| | | <u>TCCCAGCCCCCATCGAGAAAACCATCTCCAAAGCCAAAGGGCAG</u> |
| | | <u>CCCCGAGAACCACAGGTGTACACCCTGCCCCCATCCCGGGATGA</u> |
| | | <u>GCTGACCAAGAACCAGGTCAGCCTGACCTGCCTGGTCAAAGGCT</u> |
| | | <u>TCTATCCCAGCGACATCGCCGTGGAGTGGGAGAGCAATGGGCAG</u> |
| | | <u>CCGGAGAACAACTACAAGACCACGCCTCCCGTGCTGGACTCCGA</u> |
| | | <u>CGGCTCCTTCTTCCTCTACAGCAAGCTCACCGTGGACAAGAGCA</u> |
| | | <u>GGTGGCAGCAGGGGAACGTCTTCTCATGCTCCGTGATGCATGAG</u> |
| | | <u>GCTCTGCACAACCACTACACGCAGAAGAGCCTCTCCCTGTCTCCG</u> |
| | | <u>GGTAAA</u> |

For SEQ ID NOS: 2-7
bovine heavy chain sequence = bold
human heavy chain sequence = <u>dashed underline</u>
non-antibody sequence = *italic*
Stalk = <u>bold, underline</u>;
knob = <u>bold, double underline</u>;
linker = *<u>italic, squiggly underline</u>*

TABLE 2

| Description | SEQ ID NO: | Sequence |
|---|---|---|
| Light Chain | 8 | QAVLNQPSSVSGSLGQRVSITCSGSSSNVGNGYVSWYQLIPGSAP RTLIYGDTSRASGVPDRFSGSRSGNTATLTISSLQAEDEADYFCA SAEDSSSNAVFGSGTTLTVLGQPKSPPSVTLFPPSTEELNGNKAT LVCLISDFYPGSVTVVWKADGSTITRNVETTRASKQSNSKYAAS SYLSLTSSDWKSKGSYSCEVTHEGSTVTKTVKPSECS |

TABLE 2-continued

| Description | SEQ ID NO: | Sequence |
|---|---|---|
| Heavy Chain-no insert | 9 | QVQLRESGPSLVKPSQTLSLTCTASGFSLSDKAVGWVRQAPG KALEWLGSIDTGGNTGYNPGLKSRLSITKDNSKSQVSLSVSS VTTEDSATYYCTSVHQETKKYQ*SCPDGYRERSDCSNRPACGTS DCCRVSVFGNCLTTLPVSYS*YTYNYEWHVDVWGQGLLVTVSS |
| 550 | 10 | QVQLRESGPSLVKPSQTLSLTCTASGFSLSDKAVGWVRQAPG KALEWLGSIDTGGNTGYNPGLKSRLSITKDNSKSQVSLSVSS VTTEDSATYYCTSVHQETKKYQSGGGGSECIGMFKSCDPENDK CCKGRTCSRKHRWCKYKLGGGGSSYTYNYEWHVDVWGQGLL VTVSSASTTAPKVYPLSSCCGDKSSSTVTLGCLVSSYMPEPVT VTWNSGALKSGVHTFPAVLQSSGLYSLSSMVTVPGSTSGQTF TCNVAHPASSTKVDKAVEPKSCDKTHTCPPCPAPELLGGPSVF LFPPKPKDTLMISRTPEVTCVVVDVSHEDPEVKFNWYVDGVEV HNAKTKPREEQYNSTYRVVSVLTVLHQDWLNGKEYKCKVSNK ALPAPIEKTISKAKGQPREPQVYTLPPSRDELTKNQVSLTCLVKG FYPSDIAVEWESNGQPENNYKTTPPVLDSDGSFFLYSKLTVDKS RWQQGNVFSCSVMHEALHNHYTQKSLSLSPGK |
| Amgen1 | 11 | QVQLRESGPSLVKPSQTLSLTCTASGFSLSDKAVGWVRQAPG KALEWLGSIDTGGNTGYNPGLKSRLSITKDNSKSQVSLSVSS VTTEDSATYYCTSVHQETKKYQSGGGGSDCLGFMRKCIPDND KCCRPNLVCSRTHKWCKYVFGGGGSSYTYNYEWHVDVWGQGLL LVTVSSASTTAPKVYPLSSCCGDKSSSTVTLGCLVSSYMPEPV TVTWNSGALKSGVHTFPAVLQSSGLYSLSSMVTVPGSTSGQT FTCNVAHPASSTKVDKAVEPKSCDKTHTCPPCPAPELLGGPSV FLFPPKPKDTLMISRTPEVTCVVVDVSHEDPEVKFNWYVDGVEV HNAKTKPREEQYNSTYRVVSVLTVLHQDWLNGKEYKCKVSNK ALPAPIEKTISKAKGQPREPQVYTLPPSRDELTKNQVSLTCLVKG FYPSDIAVEWESNGQPENNYKTTPPVLDSDGSFFLYSKLTVDKS RWQQGNVFSCSVMHEALHNHYTQKSLSLSPGK |
| Mamba1 | 12 | QVQLRESGPSLVKPSQTLSLTCTASGFSLSDKAVGWVRQAPG KALEWLGSIDTGGNTGYNPGLKSRLSITKDNSKSQVSLSVSS VTTEDSATYYCTSVHQETKKYQSGGGGSLKCYQHGKVVTCHR DMKFCYHNTGMPFRNLKILQGCSSSCSETENNKCCSTDRCNKGG GGSSYTYNYEWHVDVWGQGLLVTVSSASTTAPKVYPLSSCC GDKSSSTVTLGCLVSSYMPEPVTVTWNSGALKSGVHTFPAVL QSSGLYSLSSMVTVPGSTSGQTFTCNVAHPASSTKVDKAVEP KSCDKTHTCPPCPAPELLGGPSVFLFPPKPKDTLMISRTPEVTCV |

TABLE 2-continued

| Description | SEQ ID NO: | Sequence |
|---|---|---|
| | | VVDVSHEDPEVKFNWYVDGVEVHNAKTKPREEQYNSTYRVVS |
| | | VLTVLHQDWLNGKEYKCKVSNKALPAPIEKTISKAKGPREPQ |
| | | VYTLPPSRDELTKNQVSLTCLVKGFYPSDIAVEWESNGQPENNY |
| | | KTTPPVLDSDGSFFLYSKLTVDKSRWQQGNVFSCSVMHEALHN |
| | | HYTQKSLSLSPGK |
| oxyntomodulin | 13 | QVQLRESGPSLVKPSQTLSLTCTASGFSLSDKAVGWVRQAPG |
| | | KALEWLGSIDTGGNTGYNPGLKSRLSITKDNSKSQVSLSVSS |
| | | VTTEDSATYYCTSVHQETKKYQSGGGGSHSQGTFTSKYSKYLDS |
| | | RRAQDFVQWLMNTKRNRNNIAGGGGSSYTYNYEWHVDVWGQG |
| | | LLVTVSSASTTAPKVYPLSSCCGDKSSSTVTLGCLVSSYMPEP |
| | | VTVTWNSGALKSGVHTFPAVLQSSGLYSLSSMVTVPGSTSGQ |
| | | TFTCNVAHPASSTKVDKAVEPKSCDKTHTCPPCPAPELLGGPS |
| | | VFLFPPKPKDTLMISRTPEVTCVVVDVSHEDPEVKFNWYVDGVE |
| | | VHNAKTKPREEQYNSTYRVVSVLTVLHQDWLNGKEYKCKVSN |
| | | KALPAPIEKTISKAKGQPREPQVYTLPPSRDELTKNQVSLTCLVK |
| | | GFYPSDIAVEWESNGQPENNYKTTPPVLDSDGSFFLYSKLTVDK |
| | | SRWQQGNVFSCSVMHEALHNHYTQKSLSLSPGK |
| Parathyroid (PTH) | 14 | QVQLRESGPSLVKPSQTLSLTCTASGFSLSDKAVGWVRQAPG |
| | | KALEWLGSIDTGGNTGYNPGLKSRLSITKDNSKSQVSLSVSS |
| | | VTTEDSATYYCTSVHQETKKYQSGGGGSSVSEIQLMHNLGKHL |
| | | NSMERVEWLRKKLQDVHNFVALGAPLAPRDAGSQRPRKKEDNVLV |
| | | ESHEKSLGEADKADVNVLTKAKSQGGGGSSYTYNYEWHVDVWG |
| | | QGLLVTVSSASTTAPKVYPLSSCCGDKSSSTVTLGCLVSSYMP |
| | | EPVTVTWNSGALKSGVHTFPAVLQSSGLYSLSSMVTVPGSTS |
| | | GQTFTCNVAHPASSTKVDKAVEPKSCDKTHTCPPCPAPELLGG |
| | | PSVFLFPPKPKDTLMISRTPEVTCVVVDVSHEDPEVKFNWYVDG |
| | | VEVHNAKTKPREEQYNSTYRVVSVLTVLHQDWLNGKEYKCKV |
| | | SNKALPAPIEKTISKAKGQPREPQVYTLPPSRDELTKNQVSLTCL |
| | | VKGFYPSDIAVEWESNGQPENNYKTTPPVLDSDGSFFLYSKLTV |
| | | DKSRWQQGNVFSCSVMHEALHNHYTQKSLSLSPGK |

For SEQ ID NOs: 9-14
bovine heavy chain sequence = bold
human heavy chain sequence = dashed underline
non-antibody sequence = *italic*
Stalk = bold, underline;
knob = bold, double underline;
linker = *italic, squiggly underline*

Example 12. Expression and Purification of BLV1H12-Therapeutic Polypeptide Fusion Antibodies BLV1H12-therapeutic polypeptide fusion antibodies can be expressed through transient transfections of free style HEK 293 cells with vectors encoding BLV1H12-fusion protein heavy chain and the BLV1H12 light chain. Expressed BLV1H12-protein fusion antibodies are secreted into the culture medium and harvested at 48 hours and 96 hours after transfection. The BLV1H12-therapeutic polypeptide fusion antibodies are purified by Protein A/G chromatography (Thermo Fisher Scientific, IL), and analyzed by SDS-PAGE gel. BLV1H12-therapeutic polypeptide fusion antibodies comprising a cleavage site can be further treated with protease to release the N-terminus and/or C-terminus of the fused therapeutic polypeptides. After treatment, BLV1H12-therapeutic polypeptide fusion antibody can be re-purified by Protein A/G affinity column to remove protease and analyzed by SDS-PAGE gel.

DEFINITIONS

An "ultralong CDR3" or an "ultralong CDR3 sequence", used interchangeably herein, comprises a CDR3 or CDR3 sequence that is not derived from a human antibody sequence. An ultralong CDR3 may be 35 amino acids in length or longer, for example, 40 amino acids in length or longer, 45 amino acids in length or longer, 50 amino acids in length or longer, 55 amino acids in length or longer, or 60 amino acids in length or longer. The length of the ultralong CDR3 may include a non-antibody sequence. An ultralong CDR3 may comprise at least a portion of a knob domain and/or knob domain. An ultralong CDR3 may comprise a non-antibody sequence, including, for example, a cytokine, chemokine, growth factor or hormone sequence. Preferably, the ultralong CDR3 is a heavy chain CDR3 (CDR-H3 or CDRH3). Preferably, the ultralong CDR3 is a sequence derived from or based on a ruminant (e.g., bovine) sequence. An ultralong CDR3 may comprise at least 3 or more cysteine residues, for example, 4 or more cysteine residues, 6 or more cysteine residues, or 8 or more cysteine residues. An ultralong CDR3 may comprise one or more cysteine motifs. Such a sequence may be derived from or based on a bovine germline For example, the ultralong CDR3 may comprise a sequence that aligns to 5, 10, 15, 20, 25, 30, 35, 40, 45, 50, 55, 60 or more amino acids to a sequence derived from or based SEQ ID NOS: 9-14. In another embodiment, an ultralong CDR3 may comprise a sequence that comprises 5 or more consecutive amino acids to a sequence derived from or based SEQ ID NOS: 9-14. For example, the ultralong CDR3 may comprise a sequence that comprises 5, 10, 15, 20, 25, 30, 35, 40, 45, 50, 55, 60 or more consecutive amino acids to a sequence derived from or based SEQ ID NOS: 9-14. In another embodiment, an ultralong CDR3 may comprise a sequence that is about 50% or more homologous to a sequence derived from or based on a knob domain sequence. For example, the ultralong CDR3 may comprise a sequence that is about 60%, 70%, 80%, 85%, 90%, 95%, 97% or more homologous to a sequence derived from or based on a knob domain sequence. In another embodiment, an ultralong CDR3 may comprise a sequence that aligns to 5 or more amino acids to a sequence derived from or based a knob domain sequence. For example, the ultralong CDR3 may comprise a sequence that aligns to 5, 10, 15, 20, 25, 30, 35, 40, 45, 50, 55, 60 or more amino acids to a sequence derived from or based a knob domain sequence In another embodiment, an ultralong CDR3 may comprise a sequence that comprises 5 or more consecutive amino acids to a sequence derived from or based a knob domain sequence For example, the ultralong CDR3 may comprise a sequence that comprises 5, 10, 15, 20, 25, 30, 35, 40, 45, 50, 55, 60 or more consecutive amino acids to a sequence derived from or based a knob domain sequence. In another embodiment, an ultralong CDR3 may comprise a sequence that is about 50% or more homologous to a sequence derived from or based on a knob domain sequence. For example, the ultralong CDR3 may comprise a sequence that is about 60%, 70%, 80%, 85%, 90%, 95%, 97% or more homologous to a sequence derived from or based on a knob domain sequence. In another embodiment, an ultralong CDR3 may comprise a sequence that aligns to 5 or more amino acids to a sequence derived from or based a knob domain sequence For example, the ultralong CDR3 may comprise a sequence that aligns to 5, 10, 15, 20, 25, 30, 35, 40, 45, 50, 55, 60 or more amino acids to a sequence derived from or based a knob domain sequence In another embodiment, an ultralong CDR3 may comprise a sequence that comprises 5 or more consecutive amino acids to a sequence derived from or based a stalk domain sequence For example, the ultralong CDR3 may comprise a sequence that comprises 5, 10, 15, 20, 25, 30, 35, 40, 45, 50, 55, 60 or more consecutive amino acids to a sequence derived from or based a stalk domain sequence. The antibodies disclosed herein may comprise at least a portion of an ultralong CDR3 derived from or based on a sequence of any of the ultralong CDR3s disclosed herein. The sequence of the ultralong CDR3 or a portion thereof may be modified or altered to contain one or more non-bovine antibody-based nucleotides and/or amino acids. The modifications and/or alterations in the sequence of the ultralong CDR3 or portion thereof may improve one or more features of the expressed antibody. For example, the modifications and/or alterations may improve expression, folding, half-life, activity and/or solubility of the antibody.

An "isolated" biological molecule, such as the various polypeptides, polynucleotides, and antibodies disclosed herein, may refer to a biological molecule that has been identified and separated and/or recovered from at least one component of its natural environment.

"Antagonist" may refer to any molecule that partially or fully blocks, inhibits, or neutralizes an activity (e.g., biological activity) of a polypeptide. Also encompassed by "antagonist" are molecules that fully or partially inhibit the transcription or translation of mRNA encoding the polypeptide. Suitable antagonist molecules include, e.g., antagonist antibodies or antibody fragments; fragments or amino acid sequence variants of a native polypeptide; peptides; antisense oligonucleotides; small organic molecules; and nucleic acids that encode polypeptide antagonists or antagonist antibodies. Reference to "an" antagonist encompasses a single antagonist or a combination of two or more different antagonists.

"Agonist" may refer to any molecule that partially or fully mimics a biological activity of a polypeptide. Also encompassed by "agonist" are molecules that stimulate the transcription or translation of mRNA encoding the polypeptide. Suitable agonist molecules include, e.g., agonist antibodies or antibody fragments; a native polypeptide; fragments or amino acid sequence variants of a native polypeptide; peptides; antisense oligonucleotides; small organic molecules; and nucleic acids that encode polypeptides agonists or antibodies. Reference to "an" agonist encompasses a single agonist or a combination of two or more different agonists.

An "isolated" antibody may refer to one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody (e.g., as determined by the Lowry method), and preferably to more than 99% by weight, (2) to a degree sufficient to obtain at least 15 residues of N-terminal or internal amino acid sequence (e.g., by use of a spinning cup sequenator), or (3) to homogeneity by SDS-PAGE under reducing or nonreducing conditions (e.g., using Coomassie™ blue or, preferably, silver stain). Isolated antibody includes the antibody in situ within recombinant cells since at least one component of the antibody's natural environment will not be present. Similarly, isolated antibody includes the antibody in medium around recombinant cells. An isolated antibody may be prepared by at least one purification step.

An "isolated" nucleic acid molecule may refer to a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that express an antibody where, for example, the nucleic acid molecule is in a chromosomal location different from that of natural cells.

Variable domain residue numbering as in Kabat or amino acid position numbering as in Kabat, and variations thereof, may refer to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (e.g., residue 52a according to Kabat) after residue 52 of H2 and inserted residues (e.g., residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence.

"Substantially similar," or "substantially the same", may refer to a sufficiently high degree of similarity between two numeric values (generally one associated with an antibody disclosed herein and the other associated with a reference/comparator antibody) such that one of skill in the art would consider the difference between the two values to be of little or no biological and/or statistical significance within the context of the biological characteristic measured by said values (e.g., Kd values). The difference between said two values is preferably less than about 50%, preferably less than about 40%, preferably less than about 30%, preferably less than about 20%, preferably less than about 10% as a function of the value for the reference/comparator antibody.

"Binding affinity" may refer to the strength of the sum total of noncovalent interactions between a single binding site of a molecule (e.g., an antibody) and its binding partner (e.g., an antigen). Unless indicated otherwise, "binding affinity" may refer to intrinsic binding affinity which reflects a 1:1 interaction between members of a binding pair (e.g., antibody and antigen). The affinity of a molecule X for its partner Y can generally be represented by the dissociation constant. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure.

An "on-rate" or "rate of association" or "association rate" or "$k_{on}$" may be determined with a surface plasmon resonance technique such as Biacore (e.g., Biacore A100, Biacore™-2000, Biacore™-3000, Biacore, Inc., Piscataway, N.J.) carboxymethylated dextran biosensor chips (CM5, Biacore Inc.) and according to the supplier's instructions.

"Vector" may refer to a nucleic acid molecule capable of transporting another nucleic acid to which it has been linked. One type of vector is a "plasmid", which may refer to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. Accordingly, "plasmid" and "vector" may, at times, be used interchangeably as the plasmid is a commonly used form of vector.

"Gene" may refer to a nucleic acid (e.g., DNA) sequence that comprises coding sequences necessary for the production of a polypeptide, precursor, or RNA (e.g., mRNA, rRNA, tRNA). The polypeptide may be encoded by a full length coding sequence or by any portion of the coding sequence so long as the desired activity or functional properties (e.g., enzymatic activity, ligand binding, signal transduction, immunogenicity, etc.) of the full-length or fragment are retained. The term may also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" may encompass both cDNA and genomic forms of a gene. A genomic form or clone of a gene may contain the coding region interrupted with non-coding sequences termed "introns" or "intervening regions" or "intervening sequences." Introns may be segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. In addition to containing introns, genomic forms of a gene can also include sequences located on both the 5' and 3' end of the sequences that are present on the RNA transcript. These sequences may be referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region can contain sequences that direct the termination of transcription, post transcriptional cleavage and polyadenylation.

"Polynucleotide," or "nucleic acid," as used interchangeably herein, may refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide" may refer to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

"Stringent hybridization conditions" refer to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions may be selected to be about 5-10° C. lower than the thermal melting point (Tm) for the specific sequence at a defined ionic strength pH. The Tm may be the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

"Recombinant" when used with reference to a cell, nucleic acid, protein, antibody or vector indicates that the cell, nucleic acid, protein or vector has been modified by the introduction of a heterologous nucleic acid or protein, the alteration of a native nucleic acid or protein, or that the cell is derived from a cell so modified. For example, recombinant cells express genes that are not found within the native (non-recombinant) form of the cell or express native genes that are overexpressed or otherwise abnormally expressed such as, for example, expressed as non-naturally occurring fragments or splice variants. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, may be both considered recombinant for the purposes of this disclosure. It is understood that once a recombinant nucleic acid is made and introduced into a host cell or organism, it may replicate non-recombinantly, e.g., using the in vivo cellular machinery of the host cell rather than in vitro manipulations; however, such nucleic acids, once produced recombinantly, although subsequently replicated non-recombinantly, may be still considered recombinant for the purposes disclosed herein. Similarly, a "recombinant protein" may be a protein made using recombinant techniques, e.g., through the expression of a recombinant nucleic acid as depicted herein.

"Percent (%) amino acid sequence identity" with respect to a peptide or polypeptide sequence may refer to the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MegAlign (DNASTAR) software. Those skilled in the art can determine appropriate parameters for measuring alignment, including any algorithms needed to achieve maximal alignment over the full length of the sequences being compared.

The terms "polypeptide," "peptide," "protein," and "protein fragment" may be used interchangeably to refer to a polymer of amino acid residues. The terms may apply to amino acid polymers in which one or more amino acid residue is an artificial chemical mimetic of a corresponding naturally occurring amino acid, as well as to naturally occurring amino acid polymers and non-naturally occurring amino acid polymers.

"Amino acid" may refer to naturally occurring and synthetic amino acids, as well as amino acid analogs and amino acid mimetics that function similarly to the naturally occurring amino acids. Naturally occurring amino acids may be those encoded by the genetic code, as well as those amino acids that are later modified, e.g., hydroxyproline, gamma-carboxyglutamate, and O-phosphoserine. Amino acid analogs may refer to compounds that have the same basic chemical structure as a naturally occurring amino acid, e.g., an alpha carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but retain the same basic chemical structure as a naturally occurring amino acid. Amino acid mimetics may refer to chemical compounds that have a structure that is different from the general chemical structure of an amino acid, but that functions similarly to a naturally occurring amino acid.

"Conservatively modified variants" may apply to both amino acid and nucleic acid sequences. "Amino acid variants" may refer to amino acid sequences. With respect to particular nucleic acid sequences, conservatively modified variants may refer to those nucleic acids which encode identical or essentially identical amino acid sequences, or where the nucleic acid does not encode an amino acid sequence, to essentially identical or associated (e.g., naturally contiguous) sequences. Because of the degeneracy of the genetic code, a large number of functionally identical nucleic acids may encode most proteins. For instance, the codons GCA, GCC, GCG and GCU all encode the amino acid alanine. Thus, at every position where an alanine is specified by a codon, the codon may be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a nucleic acid which encodes a polypeptide is implicit in a described sequence with respect to the expression product, but not with respect to actual probe sequences. As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" including where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles disclosed herein. Typically conservative substitutions include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

"Antibodies" (Abs) and "immunoglobulins" (Igs) may be glycoproteins having similar structural characteristics. While antibodies may exhibit binding specificity to a specific antigen, immunoglobulins may include both antibodies and other antibody-like molecules which generally lack antigen specificity. Polypeptides of the latter kind are, for example, produced at low levels by the lymph system and at increased levels by myelomas.

"Antibody", "immunoglobulin" and "immunoglobulin construct" are used interchangeably in the broadest sense and include monoclonal antibodies (e.g., full length or intact monoclonal antibodies), polyclonal antibodies, multivalent antibodies, multi specific antibodies (e.g., bispecific antibodies so long as they exhibit the desired biological activity) and may also include certain antibody fragments (as described in greater detail herein). The term "antibody" can refer to a full length antibody or a portion thereof. An antibody can refer to a peptide comprising at least one antibody sequence. The antibody sequence can comprise 5 or more amino acids of an antibody sequence. For example the antibody sequence can comprise 6, 7, 8, 9, 10, 11, 12, 13, 14, 15, 16, 17, 18, 19, 20 or more amino acids of an antibody sequence. The 5 or more amino acids may be consecutive amino acids of an antibody sequence. Alternatively, the 5 or more amino acids are non-consecutive amino acids of an antibody sequence. For example, the 5 or more amino acids may comprise a conserved motif within the antibody sequence. For example, the 5 or more amino acids may comprise a conserved motif within an ultralong CDR3 sequence. An antibody can be human, humanized, fully human and/or affinity matured. An antibody can be a chimeric antibody. An antibody can be a recombinant, engineered, or synthetic antibody. An antibody may be a bovine, bovine engineered, fully bovine and/or affinity matured. The bovine engineered antibody may comprise one or more nucleotides or peptides derived from a bovine antibody sequence. A fully bovine antibody may comprise replacing one or more nucleotides or peptides from a non-bovine antibody sequence with one or more nucleotides or peptides based on a bovine antibody sequence. An antibody may refer to immunoglobulins and immunoglobulin portions, whether natural or partially or wholly synthetic, such as recombinantly produced, including any portion thereof containing at least a portion of the variable region of the immunoglobulin molecule that is sufficient to form an antigen binding site. Hence, an antibody or portion thereof includes any protein having a binding domain that is homologous or substantially homologous to an immunoglobulin antigen binding site. For example, an antibody may refer to an antibody that contains two heavy chains (which can be denoted H and H') and two light chains (which can be denoted L and L'), where each heavy chain can be a full-length immunoglobulin heavy chain or a portion thereof sufficient to form an antigen binding site (e.g. heavy chains include, but are not limited to, VH, chains VH-CH1 chains and VH-CH1-CH2-CH3 chains), and each light chain can be a full-length light chain or a thereof sufficient to form an antigen binding site (e.g. light chains include, but are not limited to, VL chains and VL-CL chains). Each heavy chain (H and H') pairs with one light chain (L and L', respectively). Typically, antibodies minimally include all or at least a portion of the variable heavy (VH) chain and/or the variable light (VL) chain. The antibody also can include all or a portion of the constant region. For example, a full-length antibody is an antibody having two full-length heavy chains (e.g. VH-CH1-CH2-CH3 or VH-CH1-CH2-CH3-CH4) and two full-length light chains (VL-CL) and hinge regions, such as antibodies produced by antibody secreting B cells and antibodies with the same domains that are produced synthetically. Additionally, an "antibody" may refer to a protein of the immunoglobulin family or a polypeptide comprising fragments of an immunoglobulin that is capable of noncovalently, reversibly, and in a specific manner binding a corresponding antigen. An exemplary antibody structural unit comprises a tetramer. Each tetramer is composed of two identical pairs of polypeptide chains, each pair having one "light" (about 25 kD) and one "heavy" chain (about 50-70 kD), connected through a disulfide bond. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. The N-terminus of each chain defines a variable region of about 100 to 110 or more amino acids primarily responsible for antigen recognition. The terms variable light chain (VL) and variable heavy chain (VH) refer to these regions of light and heavy chains respectively. In some instances, the antibodies provided herein comprise at least one immunoglobulin domain from an avian antibody, reptilian antibody, amphibian antibody, insect antibody, or chimeric combinations thereof. The antibodies can comprise at least one immunoglobulin domain from a chimeric antibody. The chimeric antibody can be derived from two or more different species (e.g., mouse and human, bovine and human). The antibodies can comprise at least one immunoglobulin domain from an engineered, recombinant or synthetic antibody. In some instances, engineered, recombinant or synthetic antibodies are created using antibody genes made in a laboratory or taken from cells. The antibody genes can be derived from one or more mammals. For example, the antibody genes are derived from a human. The antibody genes may be derived from a bovine. Alternatively, or additionally, the antibodies disclosed herein comprise at least one immunoglobulin domain from a humanized, human engineered or fully human antibody. The antibody may comprise antibody sequences from two or more different antibodies. The two or more different antibodies may be from the same species. For example, the specie may be a bovine specie, human specie, or murine specie. The two or more different antibodies may be from the same type of animal. For example the two or more different antibodies may be from a cow. The two or more different antibodies may be from a human. Alternatively, the two or more different antibodies are from different species. For example, the two or more different antibodies are from a human specie and bovine specie. In another example, the two or more diffent antibodies are from a bovine specie and a non-bovine specie. In another example, the two or more different antibodies are from a human specie and a non-human specie. The two or more different antibodies may be from different animals. For example, the two different animals are a human and a cow. The different animals may be from the same specie. For example, the different animals may be a cow and a water buffalo.

"Variable" may refer to the fact that certain portions of the variable domains (also referred to as variable regions) differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions (HVRs) both in the light-chain and the heavy-chain variable domains. CDRs include those specified as Kabat, Chothia, and IMGT as shown herein within the variable region sequences. The more highly conserved portions of variable domains are called the framework (FR). The variable domains of native heavy and light chains each may comprise four FR regions, largely adopting a β-sheet configuration, connected by three CDRs, which form loops connecting, and in some cases forming part of, the β-sheet structure. The CDRs in each chain may be held together in close proximity by the FR regions and, with the CDRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

"Fv" may refer to an antibody fragment which contains an antigen-recognition and antigen-binding site. In a two-chain Fv species, this region consists of a dimer of one heavy and one light chain variable domain in non-covalent association. In a single chain Fv (scFv) species, one heavy chain and one light chain variable domain can be covalently linked by a flexible peptide linker such that the light and heavy chains can associate in a "dimeric" structure analogous to that in a two-chain Fv (scFv) species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CHl) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG$_1$, IgG$_2$, IgG$_3$, IgG$_4$ IgA$_1$, and IgA$_2$. The heavy-chain constant domains that correspond to the different classes of immunoglobulins are called α, δ, ε, γ, and μ, respectively. The subunit structures and three-dimensional configurations of different classes of immunoglobulins are well known.

"Antibody fragments" may comprise only a portion of an intact antibody, wherein the portion preferably retains at least one, preferably most or all, of the functions normally associated with that portion when present in an intact antibody. Examples of antibody fragments include Fab, Fab', F(ab')2, single-chain Fvs (scFv), Fv, dsFv, diabody (e.g., (ds Fv)$_2$), Fd and Fd' fragments Fab fragments, Fd fragments, scFv fragments, linear antibodies, single-chain antibody molecules, minibodies, flex minibodies, bispecific fragments, and multispecific antibodies formed from antibody fragments (see, for example, Methods in Molecular Biology, Vol 207: Recombinant Antibodies for Cancer Therapy Methods and Protocols (2003); Chapter 1; p 3-25, Kipriyanov). Other known fragments include, but are not limited to, scFab fragments (Hust et al., BMC Biotechnology (2007), 7:14). In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For example, such an antibody fragment may comprise on antigen binding arm linked to an Fc sequence capable of conferring in vivo stability to the fragment. For another example, an antibody fragment or antibody portion may refer to any portion of a full-length antibody that is less than full length but contains at least a portion of the variable region of the antibody sufficient to form an antigen binding site (e.g. one or more CDRs) and thus retains the a binding specificity and/or an activity of the full-length antibody; antibody fragments include antibody derivatives produced by enzymatic treatment of full-length antibodies, as well as synthetically, e.g. recombinantly produced derivatives.

A "dsFv" may refer to an Fv with an engineered intermolecular disulfide bond, which stabilizes the VH-VL pair.

A "Fd fragment" may refer to a fragment of an antibody containing a variable domain (VH) and one constant region domain (CH1) of an antibody heavy chain.

A "Fab fragment" may refer to an antibody fragment that contains the portion of the full-length antibody that would results from digestion of a full-length immunoglobulin with papain, or a fragment having the same structure that is produced synthetically, e.g. recombinantly. A Fab fragment contains a light chain (containing a VL and CL portion) and another chain containing a variable domain of a heavy chain (VH) and one constant region domain portion of the heavy chain (CH1); it can be recombinantly produced.

A "F(ab')2 fragment" may refer to an antibody fragment that results from digestion of an immunoglobulin with pepsin at pH 4.0-4.5, or a synthetically, e.g. recombinantly, produced antibody having the same structure. The F(ab')2 fragment contains two Fab fragments but where each heavy chain portion contains an additional few amino acids, including cysteine residues that form disulfide linkages joining the two fragments; it can be recombinantly produced.

A "Fab' fragment" may refer to a fragment containing one half (one heavy chain and one light chain) of the F(ab')2 fragment.

A "Fd' fragment" may refer to a fragment of an antibody containing one heavy chain portion of a F(ab')2 fragment.

A "Fv' fragment" may refer to a fragment containing only the VH and VL domains of an antibody molecule.

A "scFv fragment" may refer to an antibody fragment that contains a variable light chain (VL) and variable heavy chain (VH), covalently connected by a polypeptide linker in any order. The linker is of a length such that the two variable domains are bridged without substantial interference. Exemplary linkers are (Gly-Ser)n residues with some Glu or Lys residues dispersed throughout to increase solubility.

Diabodies are dimeric scFv; diabodies typically have shorter peptide linkers than scFvs, and they preferentially dimerize.

"HsFv" may refer to antibody fragments in which the constant domains normally present in a Fab fragment have been substituted with a heterodimeric coiled-coil domain (see, e.g., Arndt et al. (2001) J Mol Biol. 7:312:221-228).

"Hypervariable region", "HVR", or "HV", as well as "complementary determining region" or "CDR", may refer to the regions of an antibody variable domain which are hypervariable in sequence and/or form structurally defined loops. Generally, antibodies comprise six hypervariable or CDR regions; three in the VH (H1, H2, H3), and three in the VL (L1, L2, L3). A number of hypervariable region or CDR delineations are in use and are encompassed herein. The Kabat Complementarity Determining Regions (Kabat CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk, J. Mol. Biol. 196:901-917 (1987)). The AbM hypervariable regions represent a compromise between the Kabat CDRs and Chothia structural loops, (Chothia "CDRs") and are used by Oxford Molecular's AbM antibody modeling software. The "contact" hypervariable regions are based on an analysis of the available complex crystal structures. The residues from each of these hypervariable regions are noted below. (See also, for example, FIG. 1 and bold, italicized text for Kabat CDRs and underlined text for Chothia CDRs for 12.3 ICI antibody).

| Loop | Kabat | AbM | Chothia | Contact |
|------|-------|-----|---------|---------|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
| | | (Kabat Numbering) | | |
| H1 | H31-H35 | H26-H35 | H26-H32 | H30-H35 |
| | | (Chothia Numbering) | | |
| H2 | H50-H65 | H50-H58 | H53-H55 | H47-H58 |
| H3 | H95-H102 | H95-H102 | H96-H101 | H93-H101 |

IMGT refers to the international ImMunoGeneTics Information System, as described by Lefrace et al., Nucl. Acids, Res. 37; D1006-D1012 (2009), including for example, IMGT designated CDRs for antibodies (see also, for example, FIG. 1 and bracketed text for 12.3 1C1 antibody).

Hypervariable regions may comprise "extended hypervariable regions" as follows: 24-36 or 24-34 (L1), 46-56 or 50-56 (L2) and 89-97 (L3) in the VL and 26-35 (H1), 50-65 or 49-65 (H2) and 93-102, 94-102 or 95-102 (H3) in the VH. The variable domain residues are numbered according to Kabat et al., Supra for each of these definitions.

"Framework" or "FR" residues are those variable domain residues other than the hypervariable region residues as herein defined. "Framework regions" (FRs) may be the domains within the antibody variable region domains comprising framework residues that are located within the beta sheets; the FR regions are comparatively more conserved, in terms of their amino acid sequences, than the hypervariable regions.

"Monoclonal antibody" may refer to an antibody from a population of substantially homogeneous antibodies, that is, for example, the individual antibodies comprising the population are identical and/or bind the same epitope(s), except for possible variants that may arise during production of the monoclonal antibody, such variants generally being present in minor amounts. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones. It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this disclosure. In contrast to polyclonal antibody preparations which typically include different antibodies directed against different determinants (e.g., epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" may indicates the character of the antibody as being obtained from a substantially homogeneous population of antibodies, and is not to be construed as requiring production of the antibody by any particular method. For example, the monoclonal antibodies to be used in accordance with the present disclosure may be made by a variety of techniques, including, for example, the hybridoma method (e.g., Kohler et al., Nature, 256:495 (1975); Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681, (Elsevier, N.Y., 1981)), recombinant DNA methods (see, e.g., U.S. Pat. No. 4,816,567), phage display technologies (see, e.g., Clackson et al., Nature, 352:624-628 (1991); Marks et al., J. Mol. Biol., 222:581-597 (1991); Sidhu et al., J. Mol. Biol. 338(2):299-310 (2004); Lee et al., J. Mol. Biol. 340(5):1073-1093 (2004); Fellouse, Proc. Nat. Acad. Sci. USA 101(34):12467-12472 (2004); and Lee et al. J. Immunol. Methods 284(1-2):119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806; 5,569,825; 5,591,669; 5,545,807; WO 1997/17852; U.S. Pat. Nos. 5,545,807; 5,545,806; 5,569,825; 5,625,126; 5,633,425; and 5,661,016; Marks et al., Bio/Technology, 10: 779-783 (1992); Lonberg et al., Nature, 368: 856-859 (1994); Morrison, Nature, 368: 812-813 (1994); Fishwild et al., Nature Biotechnology, 14: 845-851 (1996); Neuberger, Nature Biotechnology, 14: 826 (1996); and Lonberg and Huszar, Intern. Rev. Immunol., 13: 65-93 (1995)).

"Humanized" or "Human engineered" forms of non-human (e.g., murine, bovine) antibodies are chimeric antibodies that contain amino acids represented in human immunoglobulin sequences, including, for example, wherein minimal sequence is derived from non-human immunoglobulin. For example, humanized antibodies may be human antibodies in which some hypervariable region residues and possibly some FR residues are substituted by residues from analogous sites in non-human (e.g., rodent) antibodies. Alternatively, humanized or human engineered antibodies may be non-human (e.g., rodent) antibodies in which some residues are substituted by residues from analogous sites in human antibodies (see, e.g., U.S. Pat. No. 5,766,886). Humanized antibodies include human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody, including, for example non-antibody sequences such as a chemokine, growth factor, peptide, cytokine, cell surface protein, serum protein, toxin, extracellular matrix protein, clotting factor, or secreted protein sequence. These modifications may be made to further refine antibody performance. Humanized antibodies include human engineered antibodies, for example, as described by U.S. Pat. No. 5,766,886, including methods for preparing modified antibody variable domains. A humanized antibody may comprise substantially all of at least one, and typically two, variable domains, in which all or substantially all of the hypervariable loops correspond to those of a non-human immunoglobulin and all or substantially all of the FRs are those of a human immunoglobulin sequence. A humanized antibody optionally may also comprise at least a portion of an immunoglobulin constant region (Fc), typically that of a human immunoglobulin. For further details, see Jones et al., Nature 321:522-525 (1986); Riechmann et al., Nature 332: 323-329 (1988); and Presta, Curr. Op. Struct. Biol. 2:593-596 (1992). See also the following review articles and references cited therein: Vaswani and Hamilton, Ann. Allergy, Asthma & Immunol. 1: 105-115 (1998); Harris, Biochem. Soc. Transactions 23:1035-1038 (1995); Hurle and Gross, Curr. Op. Biotech. 5:428-433 (1994).

"Hybrid antibodies" may refer to immunoglobulin molecules in which pairs of heavy and light chains from antibodies with different antigenic determinant regions are assembled together so that two different epitopes or two different antigens can be recognized and bound by the resulting tetramer.

"Chimeric" antibodies (immunoglobulins) may have a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see e.g., Morrison et al., Proc. Natl. Acad. Sci. USA 81:6851-6855 (1984)). Humanized antibody may refer to a subset of chimeric antibodies.

"Single-chain Fv" or "scFv" antibody fragments may comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see e.g., Pluckthun, in The Pharmacology of Monoclonal Antibodies, vol. 113, Rosenburg and Moore eds., Springer-Verlag, New York, pp. 269-315 (1994).

An "antigen" may refer to a predetermined antigen to which an antibody can selectively bind. The target antigen may be polypeptide, carbohydrate, nucleic acid, lipid, hapten or other naturally occurring or synthetic compound. Preferably, the target antigen is a polypeptide.

"Epitope" or "antigenic determinant", used interchangeably herein, may refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation. Antibodies may bind to the same or a different epitope on an antigen. Antibodies may be characterized in different epitope bins. Whether an antibody binds to the same or different epitope as another antibody (e.g., a reference antibody or benchmark antibody) may be determined by competition between antibodies in assays (e.g., competitive binding assays).

Competition between antibodies may be determined by an assay in which the immunoglobulin under test inhibits specific binding of a reference antibody to a common antigen. Numerous types of competitive binding assays are known, for example: solid phase direct or indirect radioimmunoassay (MA), solid phase direct or indirect enzyme immunoassay or enzyme-linked immunosorbent assay (EIA or ELISA), sandwich competition assay including an ELISA assay (see Stahli et al., Methods in Enzymology 9:242-253 (1983)); solid phase direct biotin-avidin EIA (see Kirkland et al., J. Immunol. 137:3614-3619 (1986)); solid phase direct labeled assay, solid phase direct labeled sandwich assay (see Harlow and Lane, "Antibodies, A Laboratory Manual," Cold Spring Harbor Press (1988)); solid phase direct label MA using I-125 label (see Morel et al., Molec. Immunol. 25(1): 7-15 (1988)); solid phase direct biotin-avidin EIA (Cheung et al., Virology 176:546-552 (1990)); and direct labeled MA (Moldenhauer et al., Scand. J. Immunol., 32:77-82 (1990)). Competition binding assays may be performed using Surface Plasmon Resonance (SPR), for example, with a Biacore® instrument for kinetic analysis of binding interactions. In such an assay, an antibody comprising an ultralong CDR3 of unknown epitope specificity may be evaluated for its ability to compete for binding against a comparator antibody (e.g., a BA1 or BA2 antibody as described herein). An assay may involve the use of purified antigen bound to a solid surface or cells bearing either of these, an unlabeled test immunoglobulin and a labeled reference immunoglobulin. Competitive inhibition may be measured by determining the amount of label bound to the solid surface or cells in the presence of the test immunoglobulin. Usually the test immunoglobulin is present in excess. An assay (competing antibodies) may include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50%, or at least about 70%, or at least about 80%, or at least about 90%, or at least about 95%, or at least about 99% or about 100% for a competitor antibody.

That an antibody "selectively binds" or "specifically binds" may mean that the antibody reacts or associates more frequently, more rapidly, with greater duration, with greater affinity, or with some combination of the above to an antigen or an epitope than with alternative substances, including unrelated proteins. "Selectively binds" or "specifically binds" may mean, for example, that an antibody binds to a protein with a $K_D$ of at least about 0.1 mM, or at least about 1 µM or at least about 0.1 µM or better, or at least about 0.01 µM or better. Because of the sequence identity between homologous proteins in different species, specific binding can include an antibody that recognizes a given antigen in more than one species.

"Non-specific binding" and "background binding" when used in reference to the interaction of an antibody and a protein or peptide may refer to an interaction that is not dependent on the presence of a particular structure (e.g., the antibody is binding to proteins in general rather that a particular structure such as an epitope).

"Diabodies" may refer to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et. al., Proc. Natl. Acad. Sci. USA, 90:6444-6448 (1993).

A "human antibody" may refer to one which possesses an amino acid sequence which corresponds to that of an antibody produced by a human and/or has been made using any of the techniques for making human antibodies as disclosed herein.

An "affinity matured" antibody may refer to one with one or more alterations in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al., Bio/Technology 10:779-783 (1992) describes affinity maturation by VH and VL domain shuffling. Random mutagenesis of CDR and/or framework residues is described by: Barbas et al., Proc Nat. Acad. Sci. USA 91:3809-3813 (1994); Schier et al., Gene 169:147-155 (1995); Yelton et al., J. Immunol. 155:1994-2004 (1995); Jackson et al., J. Immunol. 154(7): 3310-9 (1995); and Hawkins et al., J. Mol. Biol. 226:889-896 (1992).

Antibody "effector functions" may refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g. B cell receptor); and B cell activation.

"Antibody-dependent cell-mediated cytotoxicity" or "ADCC" may refer to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and may be required for such killing. The primary cells for mediating ADCC, NK cells, express FcγRIII only, whereas monocytes express FcγRT, FcγRII and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. Proc. Natl. Acad. Sci. USA 95:652-656 (1998).

"Effector cells" may be leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g., from blood.

"Fc receptor" or "FcR" may describe a receptor that binds to the Fc region of an antibody. The preferred FcR is a native sequence human FcR. Moreover, a preferred FcR may be one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)) and regulates homeostasis of immunoglobulins. For example, antibody variants with improved or diminished binding to FcRs have been described (see, e.g., Shields et al. J. Biol. Chem. 9(2): 6591-6604 (2001)).

Methods of measuring binding to FcRn are known (see, e.g., Ghetie 1997, Hinton 2004). Binding to human FcRn in vivo and serum half life of human FcRn high affinity binding polypeptides can be assayed, e.g., in transgenic mice or transfected human cell lines expressing human FcRn, or in primates administered with the Fc variant polypeptides.

"Complement dependent cytotoxicity" or "CDC" may refer to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, for example, as described in Gazzano-Santoro et al., J. Immunol. Methods 202:163 (1996), may be performed.

Polypeptide variants with altered Fc region amino acid sequences and increased or decreased C1q binding capability have been described (e.g., see, also, Idusogie et al. J. Immunol. 164: 4178-4184 (2000)).

"Fc region-comprising polypeptide" may refer to a polypeptide, such as an antibody or immunoadhesin (see definitions below), which comprises an Fc region. The C-terminal lysine (residue 447 according to the EU numbering system) of the Fc region may be removed, for example, during purification of the polypeptide or by recombinant engineering the nucleic acid encoding the polypeptide.

"Blocking" antibody or an "antagonist" antibody may refer to one which inhibits or reduces biological activity of the antigen it binds. Preferred blocking antibodies or antagonist antibodies substantially or completely inhibit the biological activity of the antigen.

"Agonist" antibody may refer to an antibody which mimics (e.g., partially or fully) at least one of the functional activities of a polypeptide of interest.

"Acceptor human framework" may refer to a framework comprising the amino acid sequence of a VL or VH framework derived from a human immunoglobulin framework, or from a human consensus framework. An acceptor human framework "derived from" a human immunoglobulin framework or human consensus framework may comprise the same amino acid sequence thereof, or may contain pre-existing amino acid sequence changes. Where pre-existing amino acid changes are present, preferably no more than 5 and preferably 4 or less, or 3 or less, pre-existing amino acid changes are present.

A "human consensus framework" may refer to a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

"Disorder" or "disease" may refer to any condition that would benefit from treatment with a substance/molecule (e.g., an antibody comprising an ultralong CDR3 as disclosed herein) or method disclosed herein. This includes chronic and acute disorders or diseases including those pathological conditions which predispose the mammal to the disorder in question.

"Treatment" may refer to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies disclosed herein are used to delay development of a disease or disorder.

"Individual" (e.g., a "subject") may refer to a vertebrate, preferably a mammal, more preferably a human. Mammals include, but are not limited to, farm animals (such as cows), sport animals, pets (such as cats, dogs and horses), primates, mice and rats.

"Mammal" for purposes of treatment may refer to any animal classified as a mammal, including humans, rodents (e.g., mice and rats), and monkeys; domestic and farm animals; and zoo, sports, laboratory, or pet animals, such as dogs, cats, cattle, horses, sheep, pigs, goats, rabbits, etc. In some embodiments, the mammal is selected from a human, rodent, or monkey.

"Pharmaceutically acceptable" may refer to approved or approvable by a regulatory agency of the Federal or a state government or listed in the U.S. Pharmacopeia or other generally recognized pharmacopeia for use in animals, including humans.

"Pharmaceutically acceptable salt" may refer to a salt of a compound that is pharmaceutically acceptable and that possesses the desired pharmacological activity of the parent compound.

"Pharmaceutically acceptable excipient, carrier or adjuvant" may refer to an excipient, carrier or adjuvant that can be administered to a subject, together with at least one antibody of the present disclosure, and which does not destroy the pharmacological activity thereof and is nontoxic when administered in doses sufficient to deliver a therapeutic amount of the compound.

"Pharmaceutically acceptable vehicle" may refer to a diluent, adjuvant, excipient, or carrier with which at least one antibody of the present disclosure is administered.

"Providing a prognosis", "prognostic information", or "predictive information" refer to providing information, including for example the presence of cancer cells in a subject's tumor, regarding the impact of the presence of cancer (e.g., as determined by the diagnostic methods of the present disclosure) on a subject's future health (e.g., expected morbidity or mortality, the likelihood of getting cancer, and the risk of metastasis).

Terms such as "treating" or "treatment" or "to treat" or "alleviating" or "to alleviate" may refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder. Thus, those in need of treatment may include those already with the disorder; those prone to have the disorder; and those in whom the disorder is to be prevented.

"Providing a diagnosis" or "diagnostic information" may refer to any information, including for example the presence of cancer cells, that is useful in determining whether a patient has a disease or condition and/or in classifying the disease or condition into a phenotypic category or any category having significance with regards to the prognosis of or likely response to treatment (either treatment in general or any particular treatment) of the disease or condition. Similarly, diagnosis may refer to providing any type of diagnostic information, including, but not limited to, whether a subject is likely to have a condition (such as a tumor), whether a subject's tumor comprises cancer stem cells, information related to the nature or classification of a tumor as for example a high risk tumor or a low risk tumor, information related to prognosis and/or information useful in selecting an appropriate treatment. Selection of treatment can include the choice of a particular chemotherapeutic agent or other treatment modality such as surgery or radiation or a choice about whether to withhold or deliver therapy.

A "human consensus framework" may refer to a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

An "acceptor human framework" for the purposes herein may refer to a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Antigen-binding site" may refer to the interface formed by one or more complementary determining regions. An antibody molecule has two antigen combining sites, each containing portions of a heavy chain variable region and portions of a light chain variable region. The antigen combining sites can contain other portions of the variable region domains in addition to the CDRs.

An "antibody light chain" or an "antibody heavy chain" may refer to a polypeptide comprising the VL or VH, respectively. The VL is encoded by the minigenes V (variable) and J (junctional), and the VH by minigenes V, D (diversity), and J. Each of VL or VH includes the CDRs as well as the framework regions. In this application, antibody light chains and/or antibody heavy chains may, from time to time, be collectively referred to as "antibody chains." These terms encompass antibody chains containing mutations that do not disrupt the basic structure of VL or VH, as one skilled in the art will readily recognize.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide bonded. From N- to C-terminus, each heavy chain has a variable region (V H), also called a variable heavy domain or a heavy chain variable domain, followed by three constant domains (CH1, CH2, and CH3). Similarly, from N- to C-terminus, each light chain has a variable region (V L), also called a variable light domain or a light chain variable domain, followed by a constant light (CL) domain. The light chain of an antibody may be assigned to one of two types, called kappa (K) and lambda (K), based on the amino acid sequence of its constant domain.

"Combinatorial library" may refer to collections of compounds formed by reacting different combinations of interchangeable chemical "building blocks" to produce a collection of compounds based on permutations of the building blocks. For an antibody combinatorial library, the building blocks are the component V, D and J regions (or modified forms thereof) from which antibodies are formed. For purposes herein, the terms "library" or "collection" are used interchangeably.

A "combinatorial antibody library" may refer to a collection of antibodies (or portions thereof, such as Fabs), where the antibodies are encoded by nucleic acid molecules produced by the combination of V, D and J gene segments, particularly human V, D and J germline segments. The combinatorial libraries herein typically contain at least 50 different antibody (or antibody portions or fragment) members, typically at or about 50, 100, 500, 103, 1×103, 2×103, 3×103, 4×103, 5×103, 6×103, 7×103, 8×103, 9×103, 1×104, 2×104, 3×104, 4×104, 5×104, 6×104, 7×104, 8×104, 9×104, 1×105, 2×105, 3×105, 4×105, 5×105, 6×105, 7×105, 8×105, 9×105, 106, 107, 108, 109, 1010, or more different members. The resulting libraries or collections of antibodies or portions thereof, can be screened for binding to a target protein or modulation of a functional activity.

A "human combinatorial antibody library" may refer to a collection of antibodies or portions thereof, whereby each member contains a VL and VH chains or a sufficient portion thereof to form an antigen binding site encoded by nucleic acid containing human germline segments produced as described herein.

A "variable germline segment" may refer to V, D and J groups, subgroups, genes or alleles thereof. Gene segment sequences are accessible from known database (e.g., National Center for Biotechnology Information (NCBI), the international ImMunoGeneTics information System® (IMGT), the Kabat database and the Tomlinson's VBase database (Lefranc (2003) Nucleic Acids Res., 31:307-310; Martin et al., Bioinformatics Tools for Antibody Engineering in Handbook of Therapeutic Antibodies, Wiley-VCH (2007), pp. 104-107). Tables 3-5 list exemplary human variable germline segments. Sequences of exemplary VH, DH, JH, Vκ, Jκ, Vλ and or Jλ, germline segments are set forth in SEQ ID NOS: 10-451 and 868. For purposes herein, a germline segment includes modified sequences thereof, that are modified in accord with the rules of sequence compilation provided herein to permit practice of the method. For example, germline gene segments include those that contain one amino acid deletion or insertion at the 5' or 3' end compared to any of the sequences of nucleotides set forth in SEQ ID NOS:10-451, 868.

"Compilation," "compile," "combine," "combination," "rearrange," "rearrangement," or other similar terms or grammatical variations thereof may refer to the process by which germline segments are ordered or assembled into nucleic acid sequences representing genes. For example, variable heavy chain germline segments are assembled such that the VH segment is 5' to the DH segment which is 5' to the JH segment, thereby resulting in a nucleic acid sequence encoding a VH chain. Variable light chain germline segments are assembled such that the VL segment is 5' to the JL segment, thereby resulting in a nucleic acid sequence encoding a VL chain. A constant gene segment or segments also can be assembled onto the 3' end of a nucleic acid encoding a VH or VL chain.

"Linked," or "linkage" or other grammatical variations thereof with reference to germline segments may refer to the joining of germline segments. Linkage can be direct or indirect. Germline segments can be linked directly without additional nucleotides between segments, or additional nucleotides can be added to render the entire segment in-frame, or nucleotides can be deleted to render the resulting segment in-frame. It is understood that the choice of linker nucleotides is made such that the resulting nucleic acid molecule is in-frame and encodes a functional and productive antibody.

"In-frame" or "linked in-frame" with reference to linkage of human germline segments may mean that there are insertions and/or deletions in the nucleotide germline segments at the joined junctions to render the resulting nucleic acid molecule in-frame with the 5' start codon (ATG), thereby producing a "productive" or functional full-length polypeptide. The choice of nucleotides inserted or deleted from germline segments, particularly at joints joining various VD, DJ and VJ segments, is in accord with the rules provided in the method herein for V(D)J joint generation. For example, germline segments are assembled such that the VH segment is 5' to the DH segment which is 5' to the JH segment. At the junction joining the VH and the DH and at the junction joining the DH and JH segments, nucleotides can be inserted or deleted from the individual VH, DH or JH segments, such that the resulting nucleic acid molecule containing the joined VDJ segments are in-frame with the 5' start codon (ATG).

A "reading frame" may refer to a contiguous and non-overlapping set of three-nucleotide codons in DNA or RNA. Because three codons encode one amino acid, there exist three possible reading frames for given nucleotide sequence, reading frames 1, 2 or 3. For example, the sequence ACTG-GTCA will be ACT GGT CA for reading frame 1, A CTG GTC A for reading frame 2 and AC TGG TCA for reading frame 3. Generally for practice of the method described herein, nucleic acid sequences are combined so that the V sequence has reading frame 1.

A "stop codon" may refer to a three-nucleotide sequence that signals a halt in protein synthesis during translation, or any sequence encoding that sequence (e.g. a DNA sequence encoding an RNA stop codon sequence), including the amber stop codon (UAG or TAG)), the ochre stop codon (UAA or TAA)) and the opal stop codon (UGA or TGA)). It is not necessary that the stop codon signal termination of translation in every cell or in every organism. For example, in suppressor strain host cells, such as amber suppressor strains and partial amber suppressor strains, translation proceeds through one or more stop codon (e.g. the amber stop codon for an amber suppressor strain), at least some of the time.

A "variable heavy" (VH) chain or a "variable light" (VL) chain (also termed VH domain or VL domain) may refer to the polypeptide chains that make up the variable domain of an antibody. For purposes herein, heavy chain germline segments are designated as VH, DH and JH, and compilation thereof results in a nucleic acid encoding a VH chain. Light chain germline segments are designated as VL or JL, and include kappa and lambda light chains (Vκ and Jκ; Vλ and Jλ) and compilation thereof results in a nucleic acid encoding a VL chain. It is understood that a light chain is either a kappa or lambda light chain, but does not include a kappa/lambda combination by virtue of compilation of a Vκ and JX.

A "degenerate codon" may refer to three-nucleotide codon that specifies the same amino acid as a codon in a parent nucleotide sequence. One of skill in the art is familiar with degeneracy of the genetic code and can identify degenerate codons.

"Diversity" with respect to members in a collection may refer to the number of unique members in a collection. Hence, diversity may refer to the number of different amino acid sequences or nucleic acid sequences, respectively, among the analogous polypeptide members of that collection. For example, a collection of polynucleotides having a diversity of 104 contains 104 different nucleic acid sequences among the analogous polynucleotide members. In one example, the provided collections of polynucleotides and/or polypeptides have diversities of at least at or about $10^2$, $10^3$, $10^4$, $10^5$, $10^6$, $10^7$, $10^8$, $10^9$, $10^{10}$ or more.

"Sequence diversity" may refer to a representation of nucleic acid sequence similarity and is determined using sequence alignments, diversity scores, and/or sequence clustering. Any two sequences can be aligned by laying the sequences side-by-side and analyzing differences within nucleotides at every position along the length of the sequences. Sequence alignment can be assessed in silico using Basic Local Alignment Search Tool (BLAST), an NCBI tool for comparing nucleic acid and/or protein sequences. The use of BLAST for sequence alignment is well known to one of skill in the art. The Blast search algorithm compares two sequences and calculates the statistical significance of each match (a Blast score). Sequences that are most similar to each other will have a high Blast score, whereas sequences that are most varied will have a low Blast score.

A "polypeptide domain" may refer to a part of a polypeptide (a sequence of three or more, generally 5 or 7 or more amino acids) that is a structurally and/or functionally distinguishable or definable. Exemplary of a polypeptide domain is a part of the polypeptide that can form an independently folded structure within a polypeptide made up of one or more structural motifs (e.g. combinations of alpha helices and/or beta strands connected by loop regions) and/or that is recognized by a particular functional activity, such as enzymatic activity or antigen binding. A polypeptide can have one, typically more than one, distinct domains. For example, the polypeptide can have one or more structural domains and one or more functional domains. A single polypeptide domain can be distinguished based on structure and function. A domain can encompass a contiguous linear sequence of amino acids. Alternatively, a domain can encompass a plurality of non-contiguous amino acid portions, which are non-contiguous along the linear sequence of amino acids of the polypeptide. Typically, a polypeptide contains a plurality of domains. For example, each heavy chain and each light chain of an antibody molecule contains a plurality of immunoglobulin (Ig) domains, each about 110 amino acids in length.

An "Ig domain" may refer to a domain, recognized as such by those in the art, that is distinguished by a structure, called the Immunoglobulin (Ig) fold, which contains two beta-pleated sheets, each containing anti-parallel beta strands of amino acids connected by loops. The two beta sheets in the Ig fold are sandwiched together by hydrophobic interactions and a conserved intra-chain disulfide bond. Individual immunoglobulin domains within an antibody chain further can be distinguished based on function. For example, a light chain contains one variable region domain (VL) and one constant region domain (CL), while a heavy chain contains one variable region domain (VH) and three or four constant region domains (CH). Each VL, CL, VH, and CH domain is an example of an immunoglobulin domain.

A "variable domain" with reference to an antibody may refer to a specific Ig domain of an antibody heavy or light chain that contains a sequence of amino acids that varies among different antibodies. Each light chain and each heavy chain has one variable region domain (VL, and, VH). The variable domains provide antigen specificity, and thus are responsible for antigen recognition. Each variable region contains CDRs that are part of the antigen binding site domain and framework regions (FRs).

A "constant region domain" may refer to a domain in an antibody heavy or light chain that contains a sequence of amino acids that is comparatively more conserved among antibodies than the variable region domain. Each light chain has a single light chain constant region (CL) domain and each heavy chain contains one or more heavy chain constant region (CH) domains, which include, CH1, CH2, CH3 and CH4. Full-length IgA, IgD and IgG isotypes contain CH1, CH2 CH3 and a hinge region, while IgE and IgM contain CH1, CH2 CH3 and CH4. CH1 and CL domains extend the Fab arm of the antibody molecule, thus contributing to the interaction with antigen and rotation of the antibody arms. Antibody constant regions can serve effector functions, such as, but not limited to, clearance of antigens, pathogens and toxins to which the antibody specifically binds, e.g. through interactions with various cells, biomolecules and tissues.

A "peptide mimetic" may refer to a peptide that mimics the activity of a polypeptide. For example, an erythropoietin (EPO) peptide mimetic is a peptide that mimics the activity of Epo, such as for binding and activation of the EPO receptor.

An "address" may refer to a unique identifier for each locus in a collection whereby an addressed member (e.g. an antibody) can be identified. An addressed moiety is one that can be identified by virtue of its locus or location. Addressing can be effected by position on a surface, such as a well of a microplate. For example, an address for a protein in a microwell plate that is F9 means that the protein is located in row F, column 9 of the microwell plate. Addressing also can be effected by other identifiers, such as a tag encoded with a bar code or other symbology, a chemical tag, an electronic, such RF tag, a color-coded tag or other such identifier.

An "array" may refer to a collection of elements, such as antibodies, containing three or more members.

A "spatial array" may refer to an array where members are separated or occupy a distinct space in an array. Hence, spatial arrays are a type of addressable array. Examples of spatial arrays include microtiter plates where each well of a plate is an address in the array. Spatial arrays include any arrangement wherein a plurality of different molecules, e.g., polypeptides, are held, presented, positioned, situated, or supported. Arrays can include microtiter plates, such as 48-well, 96-well, 144-well, 192-well, 240-well, 288-well, 336-well, 384-well, 432-well, 480-well, 576-well, 672-well, 768-well, 864-well, 960-well, 1056-well, 1152-well, 1248-well, 1344-well, 1440-well, or 1536-well plates, tubes, slides, chips, flasks, or any other suitable laboratory apparatus. Furthermore, arrays can also include a plurality of sub-arrays. A plurality of sub-arrays encompasses an array where more than one arrangement is used to position the polypeptides. For example, multiple 96-well plates could constitute a plurality of sub-arrays and a single array.

An "addressable library" or "spatially addressed library" may refer to a collection of molecules such as nucleic acid molecules or protein agents, such as antibodies, in which each member of the collection is identifiable by virtue of its address.

An "addressable array" may refer to one in which the members of the array are identifiable by their address, the position in a spatial array, such as a well of a microtiter plate, or on a solid phase support, or by virtue of an identifiable or detectable label, such as by color, fluorescence, electronic signal (i.e. RF, microwave or other frequency that does not substantially alter the interaction of the molecules of interest), bar code or other symbology, chemical or other such label. Hence, in general the members of the array are located at identifiable loci on the surface of a solid phase or directly or indirectly linked to or otherwise associated with the identifiable label, such as affixed to a microsphere or other particulate support (herein referred to as beads) and suspended in solution or spread out on a surface.

"An addressable combinatorial antibody library" may refer to a collection of antibodies in which member antibodies are identifiable and all antibodies with the same identifier, such as position in a spatial array or on a solid support, or a chemical or RF tag, bind to the same antigen, and generally are substantially the same in amino acid sequence. For purposes herein, reference to an "addressable arrayed combinatorial antibody library" means that the antibody members are addressed in an array.

"In silico" may refer to research and experiments performed using a computer. In silico methods include, but are not limited to, molecular modeling studies, biomolecular docking experiments, and virtual representations of molecular structures and/or processes, such as molecular interactions. For purposes herein, the antibody members of a library can be designed using a computer program that selects component V, D and J germline segments from among those input into the computer and joins them in-frame to output a list of nucleic acid molecules for synthesis. Thus, the recombination of the components of the antibodies in the collections or libraries provided herein, can be performed in silico by combining the nucleotide sequences of each building block in accord with software that contains rules for doing so. The process could be performed manually without a computer, but the computer provides the convenience of speed.

A "database" may refer to a collection of data items. For purposes herein, reference to a database is typically with reference to antibody databases, which provide a collection of sequence and structure information for antibody genes and sequences. Exemplary antibody databases include, but are not limited to, IMGT®, the international ImMunoGeneTics information system (imgt.cines.fr; see e.g., Lefranc et al. (2008) Briefings in Bioinformatics, 9:263-275), National Center for Biotechnology Information (NCBI), the Kabat database and the Tomlinson's VBase database (Lefranc (2003) Nucleic Acids Res., 31:307-310; Martin et al., Bioinformatics Tools for Antibody Engineering in Handbook of Therapeutic Antibodies, Wiley-VCH (2007), pp. 104-107). A database also can be created by a user to include any desired sequences. The database can be created such that the sequences are inputted in a desired format (e.g., in a particular reading frame; lacking stop codons; lacking signal sequences). The database also can be created to include sequences in addition to antibody sequences.

"Screening" may refer to identification or selection of an antibody or portion thereof from a collection or library of antibodies and/or portions thereof, based on determination of the activity or property of an antibody or portion thereof. Screening can be performed in any of a variety of ways, including, for example, by assays assessing direct binding (e.g. binding affinity) of the antibody to a target protein or by functional assays assessing modulation of an activity of a target protein.

"Activity towards a target protein" may refer to binding specificity and/or modulation of a functional activity of a target protein, or other measurements that reflects the activity of an antibody or portion thereof towards a target protein.

A "target protein" or "protein target" may refer to candidate proteins or peptides that are specifically recognized by an antibody or portion thereof and/or whose activity is modulated by an antibody or portion thereof. Modulating the activity can comprise increasing, decreasing, stimulating, or preventing the activity or expression of the target protein. A target protein includes any peptide or protein that contains an epitope for antibody recognition. Target proteins include proteins involved in the etiology of a disease or disorder by virtue of expression or activity. Exemplary target proteins are described herein. In some instances, the target protein is a transmembrane protein target. Transmembrane protein targets include, but are not limited to, GPCRs, ion channels, transporters, and cell surface receptors. Ion channels may be potassium ion channels, sodium ion channels, calcium ion channels, and voltage gated channels. In some instances, the antibodies disclosed herein modulate a Kv1.3 ion channel, Nav1.7 ion channel, or acid sensing ion channel (ASIC). The antibodies disclosed herein may modulate cell surface receptors such as GLP1R, GCGR, EPO receptor, FGFR, FGF21R, CSFR, GMCSFR, and GCSFR. Additional target proteins include, but are not limited to, cytokines, kinases, interferons, hormones, and growth factors. The target proteins can be from a mammal or non-mammal. The target proteins can be from a human. Alternatively, the target proteins are from a bovine.

"Hit" may refer to an antibody or portion thereof identified, recognized or selected as having an activity in a screening assay.

"Iterative" with respect to screening means that the screening is repeated a plurality of times, such as 2, 3, 4, 5 or more times, until a "Hit" is identified whose activity is optimized or improved compared to prior iterations.

"High-throughput" may refer to a large-scale method or process that permits manipulation of large numbers of molecules or compounds, generally tens to hundreds to thousands of compounds. For example, methods of purification and screening can be rendered high-throughput. High-throughput methods can be performed manually. Generally, however, high-throughput methods involve automation, robotics or software.

Basic Local Alignment Search Tool (BLAST) is a search algorithm developed by Altschul et al. (1990) to separately search protein or DNA databases, for example, based on sequence identity. For example, blastn is a program that compares a nucleotide query sequence against a nucleotide sequence database (e.g. GenBank). BlastP is a program that compares an amino acid query sequence against a protein sequence database.

A BLAST bit score is a value calculated from the number of gaps and substitutions associated with each aligned sequence. The higher the score, the more significant the alignment.

A "human protein" may refer to a protein encoded by a nucleic acid molecule, such as DNA, present in the genome of a human, including all allelic variants and conservative variations thereof. A variant or modification of a protein is a human protein if the modification is based on the wildtype or prominent sequence of a human protein.

"Naturally occurring amino acids" refer to the 20 L-amino acids that occur in polypeptides. The residues are those 20 α-amino acids found in nature which are incorporated into protein by the specific recognition of the charged tRNA molecule with its cognate mRNA codon in humans.

"Non-naturally occurring amino acids" refer to amino acids that are not genetically encoded. For example, a non-natural amino acid is an organic compound that has a structure similar to a natural amino acid but has been modified structurally to mimic the structure and reactivity of a natural amino acid. Non-naturally occurring amino acids thus include, for example, amino acids or analogs of amino acids other than the 20 naturally-occurring amino acids and include, but are not limited to, the D-isostereomers of amino acids. Exemplary non-natural amino acids are known to those of skill in the art.

"Nucleic acids" include DNA, RNA and analogs thereof, including peptide nucleic acids (PNA) and mixtures thereof. Nucleic acids can be single or double-stranded. When referring to probes or primers, which are optionally labeled, such as with a detectable label, such as a fluorescent or radiolabel, single-stranded molecules are contemplated. Such molecules are typically of a length such that their target is statistically unique or of low copy number (typically less than 5, generally less than 3) for probing or priming a library. Generally a probe or primer contains at least 14, 16 or 30 contiguous nucleotides of sequence complementary to or identical to a gene of interest. Probes and primers can be 10, 20, 30, 50, 100 or more nucleic acids long.

A "peptide" may refer to a polypeptide that is from 2 to 40 amino acids in length.

The amino acids which occur in the various sequences of amino acids provided herein are identified according to their known, three-letter or one-letter abbreviations (Table 1). The nucleotides which occur in the various nucleic acid fragments are designated with the standard single-letter designations used routinely in the art.

An "amino acid" is an organic compound containing an amino group and a carboxylic acid group. A polypeptide contains two or more amino acids. For purposes herein, amino acids include the twenty naturally-occurring amino acids, non-natural amino acids and amino acid analogs (i.e., amino acids wherein the α-carbon has a side chain).

"Amino acid residue" may refer to an amino acid formed upon chemical digestion (hydrolysis) of a polypeptide at its peptide linkages. The amino acid residues described herein are presumed to be in the "L" isomeric form. Residues in the "D" isomeric form, which are so designated, can be substituted for any L-amino acid residue as long as the desired functional property is retained by the polypeptide. NH2 may refer to the free amino group present at the amino terminus of a polypeptide. COOH may refer to the free carboxy group present at the carboxyl terminus of a polypeptide. In keeping with standard polypeptide nomenclature described in J. Biol. Chem., 243: 3552-3559 (1969), and adopted 37 C.F.R. §§1.821-1.822, abbreviations for amino acid residues are shown below:

| SYMBOL | | |
|---|---|---|
| 1-Letter | 3-Letter | AMINO ACID |
| Y | Tyr | Tyrosine |
| G | Gly | Glycine |
| F | Phe | Phenylalanine |
| M | Met | Methionine |
| A | Ala | Alanine |
| S | Ser | Serine |
| I | Ile | Isoleucine |
| L | Leu | Leucine |
| T | Thr | Threonine |
| V | Val | Valine |
| P | Pro | Proline |
| K | Lys | Lysine |
| H | His | Histidine |
| Q | Gln | Glutamine |
| E | Glu | Glutamic acid |
| Z | Glx | Glu and/or Gln |
| W | Trp | Tryptophan |
| R | Arg | Arginine |
| D | Asp | Aspartic acid |
| N | Asn | Asparagine |
| B | Asx | Asn and/or Asp |
| C | Cys | Cysteine |
| X | Xaa | Unknown or other |

It should be noted that all amino acid residue sequences represented herein by formulae have a left to right orientation in the conventional direction of amino-terminus to carboxyl-terminus. In addition, the phrase "amino acid residue" is broadly defined to include the amino acids listed in the Table of Correspondence (Table 1) and modified and unusual amino acids, such as those referred to in 37 C.F.R. §§1.821-1.822, and incorporated herein by reference. Furthermore, it should be noted that a dash at the beginning or end of an amino acid residue sequence indicates a peptide bond to a further sequence of one or more amino acid residues, to an amino-terminal group such as NH2 or to a carboxyl-terminal group such as COOH. The abbreviations for any protective groups, amino acids and other compounds, are, unless indicated otherwise, in accord with their common usage, recognized abbreviations, or the IUPAC-IUB Commission on Biochemical Nomenclature (see, (1972) Biochem. 11:1726). Each naturally occurring L-amino acid is identified by the standard three letter code (or single letter code) or the standard three letter code (or single letter code) with the prefix "L-"; the prefix "D-" indicates that the stereoisomeric form of the amino acid is D.

An "immunoconjugate" may refer to an antibody conjugated to one or more heterologous molecule(s), including but not limited to a cytotoxic agent, non-antibody peptide or therapeutic polypeptide. An immunoconjugate may include non-antibody sequences. The non-antibody sequence can be conjugated to the antibody. Alternatively, the non-antibody sequence can be within the antibody sequence.

A "non-antibody peptide" may refer to a peptide encoded by a non-antibody antibody sequence. For example, a non-antibody peptide may be a hormone, a lymphokine, an interleukin, a chemokines, a cytokine or a peptide toxin.

As used herein, the terms "therapeutic polypeptide," "therapeutic peptides," and therapeutic immunoglobulin construct" mean one or more peptides having demonstrated or potential use in treating, preventing, or ameliorating one or more diseases, disorders, or conditions in a subject in need thereof, as well as related peptides. Therapeutic peptides include peptides found to have use in treating, preventing, or ameliorating one or more diseases, disorders, or conditions after the time of filing of this application. Related peptides include fragments of therapeutic peptides, therapeutic peptide variants, and therapeutic peptide derivatives that retain some or all of the therapeutic activities of the therapeutic peptide. As will be known to one of skill in the art, as a general principle, modifications may be made to peptides that do not alter, or only partially abrogate, the properties and activities of those peptides. In some instances, modifications result in an increase in therapeutic activities. The terms "therapeutic polypeptide" or "therapeutic peptides" encompass modifications to the therapeutic peptides defined and/or disclosed herein. In certain embodiments, the therapeutic polypeptide is selected from a hormone, a lymphokine, an interleukin, a chemokines, a cytokine, a peptide toxin, and combinations thereof. Therapeutic polypeptides can be peptides encoded by non-antibody sequences.

A derivative or a variant of a polypeptide is said to share "homology" or be "homologous" with the peptide if the amino acid sequences of the derivative or variant has at least 50% identity with the original peptide. In certain embodiments, the derivative or variant is at least 75% the same as that of either the peptide or a fragment of the peptide having the same number of amino acid residues as the derivative. In certain embodiments, the derivative or variant is at least 85% the same as that of either the peptide or a fragment of the peptide having the same number of amino acid residues as the derivative. In certain embodiments, the amino acid sequence of the derivative is at least 90% the same as the peptide or a fragment of the peptide having the same number of amino acid residues as the derivative. In some embodiments, the amino acid sequence of the derivative is at least 95% the same as the peptide or a fragment of the peptide having the same number of amino acid residues as the derivative. In certain embodiments, the derivative or variant is at least 99% the same as that of either the peptide or a fragment of the peptide having the same number of amino acid residues as the derivative.

TABLE 3

| Description | SEQ ID NO: | Sequence |
|---|---|---|
| Linker1 | 15 | GGGSGGGGS |
| Linker2 | 16 | GGGGSGGGS |
| Linker3 | 17 | (GGGGS)n |

TABLE 4

| Description | SEQ ID NO: | Sequence |
|---|---|---|
| Stalk1A | 18 | TSVHQETKKYQ |
| Stalk1B | 19 | VHQETKKYQ |
| Stalk1C | 20 | TTVHQ |
| Stalk1D | 21 | TSVHQ |

TABLE 4-continued

| Description | SEQ ID NO: | Sequence |
|---|---|---|
| Stalk1E | 22 | VHQ |
| Stalk1F | 23 | KKQ |
| Stalk1G | 24 | VYQ |
| Stalk1H | 25 | CTTVHQX$_n$ |
| Stalk1I | 26 | CTSVHQX$_n$ |
| Stalk1J | 27 | CX$^1$X$^2$X$^3$X$^4$Q |
| Stalk1K | 28 | X$^1$X$^2$VHQ |
| Stalk1L | 29 | CX$^1$X$^2$VHQ |
| Stalk1M | 30 | X$^1$X$^2$VX$^3$Q |
| Stalk1N | 31 | CX$^1$X$^2$VX$^3$Q |
| Stalk1O | 32 | X$^1$X$^2$KKQ |
| Stalk1P | 33 | CX$^1$X$^2$KKQ |
| Stalk2A | 34 | YTYNYEW |
| Stalk2B | 35 | YTYNYE |
| Stalk2C | 36 | YLYTYEH |
| Stalk2D | 37 | YLYTYE |
| Stalk2E | 38 | YX$^1$YX$^2$ |
| Stalk2F | 39 | YX$^1$YX$^2$ Y |
| Stalk2G | 40 | YX$^1$YX$^2$ YX$^3$ |
| Stalk2H | 41 | YX$^1$YX$^2$ YX$^3$X$^4$ |
| Stalk2I | 42 | YEX |
| Stalk2J | 43 | YDX |
| Stalk2K | 44 | XYE |
| Stalk2L | 45 | XYD |
| Stalk2M | 46 | Y(E/D)X$^1$X$_n$W |
| Stalk2N | 47 | Y(E/D)X$^1$X$^2$X$^3$X$^4$X$^5$W |

TABLE 5

| SEQ ID NO: | Sequence |
|---|---|
| 48 | CX$_{10}$CX$_5$CX$_5$CXCX$_7$C |
| 49 | CX$_{10}$CX$_6$CX$_5$CXCX$_{15}$C |
| 50 | CX$_{11}$CXCX$_5$C |
| 51 | CX$_{11}$CX$_5$CX$_5$CXCX$_7$C |
| 52 | CX$_{10}$CX$_6$CX$_5$CXCX$_{13}$C |
| 53 | CX$_{10}$CX$_5$CXCX$_4$CX$_8$C |
| 54 | CX$_{10}$CX$_6$CX$_6$CXCX$_7$C |
| 55 | CX$_{10}$CX$_4$CX$_7$CXCX$_8$C |
| 56 | CX$_{10}$CX$_4$CX$_7$CXCX$_7$C |

TABLE 5-continued

| SEQ ID NO: | Sequence |
|---|---|
| 57 | $CX_{13}CX_8CX_8C$ |
| 58 | $CX_{10}CX_6CX_5CXCX_7C$ |
| 59 | $CX_{10}CX_5CX_5C$ |
| 60 | $CX_{10}CX_5CX_6CXCX_7C$ |
| 61 | $CX_{10}CX_6CX_5CX_7CX_9C$ |
| 62 | $CX_9CX_7CX_5CXCX_7C$ |
| 63 | $CX_{10}CX_6CX_5CXCX_9C$ |
| 64 | $CX_{10}CXCX_4CX_5CX_{11}C$ |
| 65 | $CX_7CX_3CX_6CX_5CXCX_5CX_{10}C$ |
| 66 | $CX_{10}CXCX_4CX_5CXCX_2CX_3C$ |
| 67 | $CX_{16}CX_5CXC$ |
| 68 | $CX_6CX_4CXCX_4CX_5C$ |
| 69 | $CX_{11}CX_4CX_5CX_6CX_3C$ |
| 70 | $CX_8CX_2CX_6CX_5C$ |
| 71 | $CX_{10}CX_5CX_5CXCX_{10}C$ |
| 72 | $CX_{10}CXCX_6CX_4CXC$ |
| 73 | $CX_{10}CX_5CX_5CXCX_2C$ |
| 74 | $CX_{14}CX_2CX_3CXCXC$ |
| 75 | $CX_{15}CX_5CXC$ |
| 76 | $CX_4CX_6CX_9CX_2CX_{11}C$ |
| 77 | $CX_6CX_4CX_5CX_5CX_{12}C$ |
| 78 | $CX_7CX_3CXCXCX_4CX_5CX_9C$ |
| 79 | $CX_{10}CX_6CX_5C$ |
| 80 | $CX_7CX_3CX_5CX_5CX_9C$ |
| 81 | $CX_7CX_5CXCX_2C$ |
| 82 | $CX_{10}CXCX_6C$ |
| 83 | $CX_{10}CX_3CX_3CX_5CX_7CXCX_6C$ |
| 84 | $CX_{10}CX_4CX_5CX_{12}CX_2C$ |
| 85 | $CX_{12}CX_4CX_5CXCXCX_9CX_3C$ |
| 86 | $CX_{12}CX_4CX_5CX_{12}CX_2C$ |
| 87 | $CX_{10}CX_6CX_5CXCX_{11}C$ |
| 88 | $CX_{16}CX_5CXCXCX_{14}C$ |
| 89 | $CX_{10}CX_5CXCX_8CX_6C$ |
| 90 | $CX_{12}CX_4CX_5CXXX_2C$ |
| 91 | $CX_{12}CX_5CX_5CXCX_8C$ |
| 92 | $CX_{10}CX_6CX_5CXCX_4CXCX_9C$ |
| 93 | $CX_{11}CX_4CX_5CXXX_2C$ |
| 94 | $CX_{10}CX_6CX_5CX_8CX_2C$ |
| 95 | $CX_{10}CX_6CX_5CXCX_8C$ |
| 96 | $CX_{10}CX_6CX_5CXCX_3CX_8CX_2C$ |
| 97 | $CX_{10}CX_6CX_5CXCX_2CX_6CX_5C$ |
| 98 | $CX_{10}CX_6CX_5CX_3CX_8C$ |
| 99 | $CX_7CX_6CX_3CX_3CX_9C$ |
| 100 | $CX_9CX_8CX_5CX_6CX_5C$ |
| 101 | $CX_{10}CX_2CX_2CX_7CXCX_{11}CX_5C$ |
| 102 | $CX_{10}CX_6CX_5CXCX_2CX_8CX_4C$ |

What is claimed is:

1. An antibody fusion comprising:
   (a) a first antibody sequence;
   (b) at least a portion of an ultralong complementarity determining region 3 (CDR3), wherein the portion of the ultralong CDR3 is 15 amino acids to 61 amino acids long; and
   (c) a non-antibody sequence, wherein the non-antibody sequence is selected from a polypeptide selected from a group consisting of a Mamba1, a oxyntomodulin, a 550 peptide, an Amgen 1, and a parathyroid hormone;
   wherein the portion of the ultralong CDR3 is fused or inserted into a hypervariable region of the first antibody sequence, and wherein the non-antibody sequence is fused or inserted into the portion of the ultralong CDR3.

2. The antibody fusion of claim 1, wherein the first antibody sequence is selected from a bovine antibody, a human antibody, a human engineered antibody, a humanized antibody, and a chimeric antibody.

3. The antibody fusion of claim 1, wherein the ultralong CDR3 is selected from a BLV1H12 ultralong CDR3, BLV5B8 ultralong CDR3, or BF1H1 ultralong CDR3.

4. The antibody fusion of claim 1, wherein the first antibody sequence comprises a heavy chain sequence.

5. The antibody fusion of claim 1, wherein the first antibody sequence comprises an amino acid sequence that is at least 90% homologous to SEQ ID NO: 9 or is encoded by a nucleotide sequence that is at least 90% homologous to SEQ ID NO: 2.

6. The antibody fusion of claim 1, wherein the ultralong CDR3 is selected from a bovine ultralong CDR3, a camelid ultralong CDR3, and a shark ultralong CDR3.

7. The antibody fusion of claim 1, wherein the ultralong CDR3 is a bovine ultralong CDR3.

8. The antibody fusion of claim 1, wherein the antibody fusion comprises an amino acid sequence that is at least 90% homologous to SEQ ID NOs: 10-14 or is encoded by a nucleotide sequence that is at least 90% homologous to SEQ ID NOs: 3-7.

9. The antibody fusion of claim 1, further comprising a second antibody sequence.

10. The antibody fusion of claim 9, wherein the second antibody sequence comprises an amino acid sequence that is at least 90% homologous to SEQ ID NO: 8 or is encoded by a nucleotide sequence that is at least 90% homologous to SEQ ID NO: 1.

11. The antibody fusion of claim 1, further comprising a first linker sequence.

12. The antibody fusion of claim 11, further comprising a second linker sequence.

13. The antibody fusion of claim 12, wherein the first linker sequence attaches the non-antibody sequence to the first antibody sequence, the second linker sequence attaches the non-antibody sequence to the first antibody sequence, or both the first and second linker sequences attach the non-antibody sequence to the first antibody sequence.

14. The antibody fusion of claim 12, wherein the first linker sequence comprises a sequence selected from SEQ ID NOs: 15-17, 103, and 129, the second linker sequence comprises a sequence selected from SEQ ID NOs: 15-17, 103, and 129, or both the first and second linker sequences each independently comprise a sequence selected from SEQ ID NOs: 15-17, 103, and 129.

15. The antibody fusion of claim 1, further comprising one or more proteolytic cleavage sites.

16. The antibody fusion of claim 15, wherein the one or more proteolytic cleavage sites comprises SEQ ID NO: 104.

17. A vector comprising a polynucleotide comprising a sequence that is at least 90% homologous to SEQ ID NOs: 3-7 or a sequence that encodes for an amino acid that is at least 90% homologous to SEQ ID NOs: 10-14.

18. A host cell comprising a polynucleotide comprising a sequence that is at least 90% homologous to SEQ ID NOs: 3-7 or expressing an amino acid that is at least 90% homologous to SEQ ID NOs: 10-14.

19. A method of producing an antibody fusion, the method comprising culturing the host cell of claim 18 under conditions wherein the host cell expresses the polynucleotide comprising the sequence that is at least 90% homologous to SEQ ID NOs: 3-7 or the host cell produces the amino acid that is at least 90% homologous to SEQ ID NOs: 10-14.

* * * * *

UNITED STATES PATENT AND TRADEMARK OFFICE
CERTIFICATE OF CORRECTION

PATENT NO. : 9,644,021 B2  
APPLICATION NO. : 14/152441  
DATED : May 9, 2017  
INVENTOR(S) : Feng Wang et al.

Page 1 of 1

It is certified that error appears in the above-identified patent and that said Letters Patent is hereby corrected as shown below:

In the Claims

Claim 1, Column 241, Line 26, "is selected from a polypeptide" should read --is a polypeptide--.

Claim 18, Column 242, Line 51, "expressing an amino acid that" should read --expressing an amino acid sequence that--.

Claim 19, Column 242, Line 57, "produces the amino acid" should read --produces the amino acid sequence--.

Signed and Sealed this  
Twenty-ninth Day of May, 2018

Andrei Iancu  
*Director of the United States Patent and Trademark Office*

UNITED STATES PATENT AND TRADEMARK OFFICE
CERTIFICATE OF CORRECTION

| | | |
|---|---|---|
| PATENT NO. | : 9,644,021 B2 | Page 1 of 1 |
| APPLICATION NO. | : 14/152441 | |
| DATED | : May 9, 2017 | |
| INVENTOR(S) | : Wang et al. | |

It is certified that error appears in the above-identified patent and that said Letters Patent is hereby corrected as shown below:

In the Specification

Column 1, Line 10, insert the paragraph below:
-- STATEMENT OF GOVERNMENT LICENSE RIGHTS
This invention was made with government support under grant number GM062159 awarded by The National Institutes of Health. The government has certain rights in the invention. --

Signed and Sealed this
Eighth Day of June, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 129

<210> SEQ ID NO 1
<211> LENGTH: 648
<212> TYPE: DNA
<213> ORGANISM: Bos sp.

<400> SEQUENCE: 1

```
caggccgtcc tgaaccagcc aagcagcgtc tccgggtctc tggggcagcg ggtctcaatc      60
acctgtagcg gtcttcctc caatgtcggc aacggctacg tgtcttggta tcagctgatc     120
cctggcagtg ccccacgaac cctgatctac ggcgacacat ccagagcttc tggggtcccc     180
gatcggttct cagggagcag atccggaaac acagctactc tgaccatcag ctccctgcag     240
gctgaggacg aagcagatta tttctgcgca tctgccgagg actctagttc aaatgccgtg     300
tttggaagcg gcaccacact gacagtcctg ggcagccca agagtccccc ttcagtgact     360
ctgttcccac cctctaccga ggaactgaac ggaaacaagg ccacactggt gtgtctgatc     420
agcgactttt accctgatc cgtcactgtg gtctggaagg cagatggcag cacaattact     480
```

```
aggaacgtgg aaactacccg cgcctccaag cagtctaata gtaaatacgc cgccagctcc    540
tatctgagcc tgacctctag tgattggaag tccaaagggt catatagctg cgaagtgacc    600
catgaaggct caaccgtgac taagactgtg aaaccatccg agtgctcc                 648
```

<210> SEQ ID NO 2
<211> LENGTH: 507
<212> TYPE: DNA
<213> ORGANISM: Bos sp.

<400> SEQUENCE: 2

```
caggtccagc tgagagagag cggcccttca ctggtcaagc catcccagac actgagcctg     60
acatgcacag caagcgggtt ttcactgagc gacaaggcag tgggatgggt ccgacaggca    120
ccaggaaaag ccctggaatg gctgggcagc atcgataccg gcgggaacac agggtacaat    180
cccggactga agagcagact gtccattacc aaggacaact ctaaaagtca ggtgtcactg    240
agcgtgagct ccgtcaccac agaggatagt gcaacttact attgcacctc tgtgcaccag    300
gaaactaaga ataccagag ctgtcctgac ggctatcggg agagatctga ttgcagtaat    360
aggccagctt gtggcacatc cgactgctgt cgcgtgtctg tcttcgggaa ctgcctgact    420
accctgcctg tgtcctactc ttatacctac aattatgaat ggcatgtgga tgtctgggga    480
cagggcctgc tggtgacagt ctctagt                                        507
```

<210> SEQ ID NO 3
<211> LENGTH: 1506
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
caggtccagc tgagagagag cggcccttca ctggtcaagc catcccagac actgagcctg     60
acatgcacag caagcgggtt ttcactgagc gacaaggcag tgggatgggt ccgacaggca    120
ccaggaaaag ccctggaatg gctgggcagc atcgataccg gcgggaacac agggtacaat    180
cccggactga agagcagact gtccattacc aaggacaact ctaaaagtca ggtgtcactg    240
agcgtgagct ccgtcaccac agaggatagt gcaacttact attgcacctc tgtgcaccag    300
gaaactaaga ataccagag cggggtggc ggaagcgaat gcatcggtat gttcaaatct    360
tgcgacccgg aaaacgacaa atgctgcaaa ggtcgtacct gctctcgtaa acaccgttgg    420
tgcaaataca aactgggcgg aagtgggagt tcttatacct acaattatga atggcatgtg    480
gatgtctggg gacagggcct gctggtgaca gtctctagtg cttccacaac tgcaccaaag    540
gtgtaccccc tgtcaagctg ctgtgggac aaatcctcta gtaccgtgac actgggatgc    600
ctggtctcaa gctatatgcc cgagcctgtg actgtcacct ggaactcagg agccctgaaa    660
agcggagtgc acaccttccc agctgtgctg cagtcctctg gcctgtatag cctgagttca    720
atggtgacag tccccggcag tacttcaggg cagaccttca cctgtaatgt ggcccatcct    780
gccagctcca ccaaagtgga caaagcagtg aacccaaat cttgcgacaa aactcacaca    840
tgcccaccgt gcccagcacc tgaactcctg ggggaccgt cagtcttcct cttccccca    900 aaacccaagg acaccctcat gatctcccgg acccctgagg tcacatgcgt ggtggtggac    960
gtgagccacg aagaccctga ggtcaagttc aactggtacg tggacggcgt ggaggtgcat   1020
aatgccaaga caaagccgcg ggaggagcag tacaacagca cgtaccgtgt ggtcagcgtc   1080
```

```
ctcaccgtcc tgcaccagga ctggctgaat ggcaaggagt acaagtgcaa ggtctccaac    1140
aaagccctcc cagcccccat cgagaaaacc atctccaaag ccaaagggca gccccgagaa    1200
ccacaggtgt acaccctgcc cccatcccgg gatgagctga ccaagaacca ggtcagcctg    1260
acctgcctgg tcaaaggctt ctatcccagc gacatcgccg tggagtggga gagcaatggg    1320
cagccggaga caactacaa gaccacgcct cccgtgctgg actccgacgg ctccttcttc    1380
ctctacagca agctcaccgt ggacaagagc aggtggcagc aggggaacgt cttctcatgc    1440
tccgtgatgc atgaggctct gcacaaccac tacacgcaga agagcctctc cctgtctccg    1500
ggtaaa                                                               1506
```

```
<210> SEQ ID NO 4
<211> LENGTH: 1509
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
caggtccagc tgagagagag cggcccttca ctggtcaagc catcccagac actgagcctg     60
acatgcacag caagcgggtt ttcactgagc gacaaggcag tgggatgggt ccgacaggca    120
ccaggaaaag ccctggaatg gctgggcagc atcgataccg gcgggaacac agggtacaat    180
cccggactga agagcagact gtccattacc aaggacaact ctaaaagtca ggtgtcactg    240
agcgtgagct ccgtcaccac agaggatagt gcaacttact attgcacctc tgtgcaccag    300
gaaactaaga ataccagag cggggtggc ggaagcgact gcctgggttt catgcgtaaa    360
tgcatcccgg acaacgacaa atgctgccgt ccgaacctgg tttgctctcg tacccacaaa    420
tggtgcaaat acgttttcgg cggaggtggg agttcttata cctacaatta tgaatggcat    480
gtggatgtct ggggacaggg cctgctggtg acagtctcta gtgcttccac aactgcacca    540
aaggtgtacc ccctgtcaag ctgctgtggg acaaatcct ctagtaccgt gacactggga    600
tgcctggtct caagctatat gcccgagcct gtgactgtca cctggaactc aggagccctg    660
aaaagcggag tgcacacctt cccagctgtg ctgcagtcct ctggcctgta tagcctgagt    720
tcaatggtga cagtccccgg cagtacttca gggcagacct tcacctgtaa tgtggcccat    780
cctgccagct ccaccaaagt ggacaaagca gtggaaccca atcttgcga caaaactcac    840 acatgcccac cgtgcccagc acctgaactc ctggggggac cgtcagtctt cctcttcccc    900
ccaaaaccca aggacaccct catgatctcc cggacccctg aggtcacatg cgtggtggtg    960
gacgtgagcc acgaagaccc tgaggtcaag ttcaactggt acgtggacgg cgtggaggtg   1020
cataatgcca agacaaagcc gcgggaggag cagtacaaca gcacgtaccg tgtggtcagc   1080
gtcctcaccg tcctgcacca ggactggctg aatggcaagg agtacaagtg caaggtctcc   1140
aacaaagccc tccagccccc atcgagaaa accatctcca aagccaaagg gcagccccga   1200
gaaccacagg tgtacaccct gcccccatcc cgggatgagc tgaccaagaa ccaggtcagc   1260
ctgacctgcc tggtcaaagg cttctatccc agcgacatcg ccgtggagtg ggagagcaat   1320
gggcagccgg agaacaacta caagaccacg cctcccgtgc tggactccga cggctccttc   1380
ttcctctaca gcaagctcac cgtggacaag agcaggtggc agcaggggaa cgtcttctca   1440
tgctccgtga tgcatgaggc tctgcacaac cactacacgc agaagagcct ctccctgtct   1500
ccgggtaaa                                                           1509
```

<210> SEQ ID NO 5
<211> LENGTH: 1578
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

```
caggtccagc tgagagagag cggcccttca ctggtcaagc catcccagac actgagcctg      60
acatgcacag caagcgggtt ttcactgagc gacaaggcag tgggatgggt ccgacaggca     120
ccaggaaaag ccctggaatg gctgggcagc atcgataccg gcgggaacac agggtacaat     180
cccggactga agagcagact gtccattacc aaggacaact ctaaaagtca ggtgtcactg     240
agcgtgagct ccgtcaccac agaggatagt gcaacttact attgcaccct tgtgcaccag     300
gaaactaaga ataccagag cggggtggc ggaagcctga atgttacca acatggtaaa       360
gttgtgactt gtcatcgaga tatgaagttt tgctatcata cactggcat gccttttcga      420
aatctcaagc tcatcctaca gggatgttct tcttcgtgca gtgaaacaga aacaataag      480
tgttgctcaa cagacagatg caacaaaggc ggaggtggga gttcttatac ctacaattat     540
gaatggcatg tggatgtctg gggacagggc ctgctggtga cagtctctag tgcttccaca     600
actgcaccaa aggtgtaccc cctgtcaagc tgctgtgggg acaaatcctc tagtaccgtg     660
acactgggat gcctggtctc aagctatatg cccgagcctg tgactgtcac ctggaactca     720
ggagccctga aaagcggagt gcacaccttc ccagctgtgc tgcagtcctc tggcctgtat     780
agcctgagtt caatggtgac agtccccggc agtacttcag ggcagacctt cacctgtaat     840
gtggcccatc ctgccagctc caccaaagtg gacaaagcag tggaacccaa atcttgcgac     900
aaaactcaca catgcccacc gtgcccagca cctgaactcc tggggggacc gtcagtcttc     960
ctcttccccc caaaacccaa ggacaccctc atgatctccc ggacccctga ggtcacatgc    1020
gtggtggtgg acgtgagcca cgaagaccct gaggtcaagt tcaactggta cgtggacggc    1080
gtggaggtgc ataatgccaa gacaaagccg cgggaggagc agtacaacag cacgtaccgt    1140
gtggtcagcg tcctcaccgt cctgcaccag gactggctga atggcaagga gtacaagtgc    1200
aaggtctcca acaaagccct cccagccccc atcgagaaaa ccatctccaa agccaaaggg    1260
cagccccgag aaccacaggt gtacaccctg cccccatccc gggatgagct gaccaagaac    1320
caggtcagcc tgacctgcct ggtcaaaggc ttctatccca gcgacatcgc cgtggagtgg    1380
gagagcaatg ggcagccgga gaacaactac aagaccacgc ctcccgtgct ggactccgac    1440
ggctccttct tcctctacag caagctcacc gtggacaaga gcaggtggca gcagggaaac    1500
gtcttctcat gctccgtgat gcatgaggct ctgcacaacc actacacgca gaagagcctc    1560
tccctgtctc cgggtaaa                                                  1578
```

<210> SEQ ID NO 6
<211> LENGTH: 1518
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
caggtccagc tgagagagag cggcccttca ctggtcaagc catcccagac actgagcctg      60
acatgcacag caagcgggtt ttcactgagc gacaaggcag tgggatgggt ccgacaggca     120
```

```
ccaggaaaag ccctggaatg gctgggcagc atcgataccg gcgggaacac agggtacaat     180
cccggactga agagcagact gtccattacc aaggacaact ctaaaagtca ggtgtcactg     240
agcgtgagct ccgtcaccac agaggatagt gcaacttact attgcacctc tgtgcaccag     300
gaaactaaga aataccagag cggggtggc ggaagccact ctcagggtac cttcacctct      360
gactactcta aatacctgga ctctcgtcgt gctcaggact tcgttcagtg gctgatgaac     420
accaaacgta accgtaacaa catcgctggc ggaggtggga gttcttatac ctacaattat     480
gaatggcatg tggatgtctg gggacagggc ctgctggtga cagtctctag tgcttccaca     540
actgcaccaa aggtgtaccc cctgtcaagc tgctgtgggg acaaatcctc tagtaccgtg     600
acactgggat gcctggtctc aagctatatg cccgagcctg tgactgtcac ctggaactca     660
ggagccctga aaagcggagt gcacaccttc ccagctgtgc tgcagtcctc tggcctgtat     720
agcctgagtt caatggtgac agtccccggc agtacttcag ggcagacctt cacctgtaat     780
gtggcccatc ctgccagctc caccaaagtg acaaagcag tggaacccaa atcttgcgac      840
aaaactcaca catgcccacc gtgcccagca cctgaactcc tggggggacc gtcagtcttc     900
ctcttccccc caaaacccaa ggacaccctc atgatctccc ggacccctga ggtcacatgc     960
gtggtggtgg acgtgagcca cgaagaccct gaggtcaagt tcaactggta cgtggacggc    1020
gtggaggtgc ataatgccaa gacaaagccg cgggaggagc agtacaacag cacgtaccgt    1080
gtggtcagcg tcctcaccgt cctgcaccag gactggctga atggcaagga gtacaagtgc    1140
aaggtctcca acaaagccct cccagccccc atcgagaaaa ccatctccaa agccaaaggg    1200
cagccccgag aaccacaggt gtacaccctg cccccatccc gggatgagct gaccaagaac    1260
caggtcagcc tgacctgcct ggtcaaaggc ttctatccca gcgacatcgc cgtggagtgg    1320
gagagcaatg ggcagccgga gaacaactac aagaccacgc ctcccgtgct ggactccgac    1380
ggctccttct cctctacag caagctcacc gtggacaaga gcaggtggca gcaggggaac    1440
gtcttctcat gctccgtgat gcatgaggct ctgcacaacc actacacgca gaagagcctc    1500
tccctgtctc cgggtaaa                                                  1518

<210> SEQ ID NO 7
<211> LENGTH: 1659
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
caggtccagc tgagagagag cggcccttca ctggtcaagc catcccagac actgagcctg      60
acatgcacag caagcgggtt ttcactgagc gacaaggcag tgggatgggt ccgacaggca     120
ccaggaaaag ccctggaatg gctgggcagc atcgataccg gcgggaacac agggtacaat     180
cccggactga agagcagact gtccattacc aaggacaact ctaaaagtca ggtgtcactg     240
agcgtgagct ccgtcaccac agaggatagt gcaacttact attgcacctc tgtgcaccag     300
gaaactaaga aataccagag cggggtggc ggaagctctg tgagtgaaat acagcttatg      360
cataacctgg gaaaacatct gaactcgatg gagagagtag aatggctgcg taagaagctg     420
caggatgtgc acaatttgt tgcccttgga gctcctctag ctcccagaga tgctggttcc     480
cagaggcccc gaaaaaggaa agacaatgtc ttggttgaga gccatgaaaa aagtcttgga     540
gaggcagaca aagctgatgt gaatgtatta actaaagcta aatcccaggg cggaggtggg     600
```

```
agttcttata cctacaatta tgaatggcat gtggatgtct ggggacaggg cctgctggtg        660
acagtctcta gtgcttccac aactgcacca aaggtgtacc ccctgtcaag ctgctgtggg        720
gacaaatcct ctagtaccgt gacactggga tgcctggtct caagctatat gcccgagcct        780
gtgactgtca cctggaactc aggagccctg aaaagcggag tgcacacctt cccagctgtg        840
ctgcagtcct ctggcctgta tagcctgagt tcaatggtga cagtccccgg cagtacttca        900
gggcagacct tcacctgtaa tgtggcccat cctgccagct ccaccaaagt ggacaaagca        960
gtggaaccca atcttgcga caaaactcac acatgcccac cgtgcccagc acctgaactc       1020 ctgggggac cgtcagtctt cctcttcccc ccaaaaccca aggacaccct catgatctcc       1080
cggacccctg aggtcacatg cgtggtggtg gacgtgagcc acgaagaccc tgaggtcaag       1140
ttcaactggt acgtggacgg cgtggaggtg cataatgcca agacaaagcc gcgggaggag       1200
cagtacaaca gcacgtaccg tgtggtcagc gtcctcaccg tcctgcacca ggactggctg       1260
aatggcaagg agtacaagtg caaggtctcc aacaaagccc tcccagcccc catcgagaaa       1320
accatctcca agccaaagg gcagccccga gaaccacagg tgtacaccct gcccccatcc        1380
cgggatgagc tgaccaagaa ccaggtcagc ctgacctgcc tggtcaaagg cttctatccc       1440
agcgacatcg ccgtggagtg ggagagcaat gggcagccgg agaacaacta caagaccacg       1500
cctcccgtgc tggactccga cggctccttc ttcctctaca gcaagctcac cgtggacaag       1560
agcaggtggc agcaggggaa cgtcttctca tgctccgtga tgcatgaggc tctgcacaac       1620
cactacacgc agaagagcct ctccctgtct ccgggtaaa                              1659
```

<210> SEQ ID NO 8
<211> LENGTH: 216
<212> TYPE: PRT
<213> ORGANISM: Bos sp.

<400> SEQUENCE: 8

```
Gln Ala Val Leu Asn Gln Pro Ser Ser Val Ser Gly Ser Leu Gly Gln
1               5                   10                  15

Arg Val Ser Ile Thr Cys Ser Gly Ser Ser Ser Asn Val Gly Asn Gly
            20                  25                  30

Tyr Val Ser Trp Tyr Gln Leu Ile Pro Gly Ser Ala Pro Arg Thr Leu
        35                  40                  45

Ile Tyr Gly Asp Thr Ser Arg Ala Ser Gly Val Pro Asp Arg Phe Ser
    50                  55                  60

Gly Ser Arg Ser Gly Asn Thr Ala Thr Leu Thr Ile Ser Ser Leu Gln
65                  70                  75                  80

Ala Glu Asp Glu Ala Asp Tyr Phe Cys Ala Ser Ala Glu Asp Ser Ser
                85                  90                  95

Ser Asn Ala Val Phe Gly Ser Gly Thr Thr Leu Thr Val Leu Gly Gln
            100                 105                 110

Pro Lys Ser Pro Pro Ser Val Thr Leu Phe Pro Pro Ser Thr Glu Glu
        115                 120                 125

Leu Asn Gly Asn Lys Ala Thr Leu Val Cys Leu Ile Ser Asp Phe Tyr
    130                 135                 140

Pro Gly Ser Val Thr Val Val Trp Lys Ala Asp Gly Ser Thr Ile Thr
145                 150                 155                 160

Arg Asn Val Glu Thr Thr Arg Ala Ser Lys Gln Ser Asn Ser Lys Tyr
                165                 170                 175

Ala Ala Ser Ser Tyr Leu Ser Leu Thr Ser Ser Asp Trp Lys Ser Lys
```

```
                    180                 185                 190
Gly Ser Tyr Ser Cys Glu Val Thr His Glu Gly Ser Thr Val Thr Lys
            195                 200                 205

Thr Val Lys Pro Ser Glu Cys Ser
        210                 215

<210> SEQ ID NO 9
<211> LENGTH: 169
<212> TYPE: PRT
<213> ORGANISM: Bos sp.

<400> SEQUENCE: 9

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Ser Val His Gln Glu Thr Lys Lys Tyr Gln Ser Cys Pro Asp Gly Tyr
            100                 105                 110

Arg Glu Arg Ser Asp Cys Ser Asn Arg Pro Ala Cys Gly Thr Ser Asp
        115                 120                 125

Cys Cys Arg Val Ser Val Phe Gly Asn Cys Leu Thr Thr Leu Pro Val
    130                 135                 140

Ser Tyr Ser Tyr Thr Tyr Asn Tyr Glu Trp His Val Asp Val Trp Gly
145                 150                 155                 160

Gln Gly Leu Leu Val Thr Val Ser Ser
                165

<210> SEQ ID NO 10
<211> LENGTH: 502
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Ser Val His Gln Glu Thr Lys Lys Tyr Gln Ser Gly Gly Gly Gly Ser
```

```
            100                 105                 110
    Glu Cys Ile Gly Met Phe Lys Ser Cys Asp Pro Glu Asn Asp Lys Cys
            115                 120                 125

Cys Lys Gly Arg Thr Cys Ser Arg Lys His Arg Trp Cys Lys Tyr Lys
            130                 135                 140

Leu Gly Gly Gly Ser Ser Tyr Thr Tyr Asn Tyr Glu Trp His Val
    145                 150                 155                 160

Asp Val Trp Gly Gln Gly Leu Leu Val Thr Val Ser Ser Ala Ser Thr
                        165                 170                 175

Thr Ala Pro Lys Val Tyr Pro Leu Ser Ser Cys Cys Gly Asp Lys Ser
                180                 185                 190

Ser Ser Thr Val Thr Leu Gly Cys Leu Val Ser Ser Tyr Met Pro Glu
                195                 200                 205

Pro Val Thr Val Thr Trp Asn Ser Gly Ala Leu Lys Ser Gly Val His
            210                 215                 220

Thr Phe Pro Ala Val Leu Gln Ser Ser Gly Leu Tyr Ser Leu Ser Ser
    225                 230                 235                 240

Met Val Thr Val Pro Gly Ser Thr Ser Gly Gln Thr Phe Thr Cys Asn
                        245                 250                 255

Val Ala His Pro Ala Ser Ser Thr Lys Val Asp Lys Ala Val Glu Pro
                260                 265                 270

Lys Ser Cys Asp Lys Thr His Thr Cys Pro Pro Cys Pro Ala Pro Glu
                275                 280                 285

Leu Leu Gly Gly Pro Ser Val Phe Leu Phe Pro Pro Lys Pro Lys Asp
            290                 295                 300

Thr Leu Met Ile Ser Arg Thr Pro Glu Val Thr Cys Val Val Val Asp
    305                 310                 315                 320

Val Ser His Glu Asp Pro Glu Val Lys Phe Asn Trp Tyr Val Asp Gly
                        325                 330                 335

Val Glu Val His Asn Ala Lys Thr Lys Pro Arg Glu Glu Gln Tyr Asn
                340                 345                 350

Ser Thr Tyr Arg Val Val Ser Val Leu Thr Val Leu His Gln Asp Trp
                355                 360                 365

Leu Asn Gly Lys Glu Tyr Lys Cys Lys Val Ser Asn Lys Ala Leu Pro
            370                 375                 380

Ala Pro Ile Glu Lys Thr Ile Ser Lys Ala Lys Gly Gln Pro Arg Glu
    385                 390                 395                 400

Pro Gln Val Tyr Thr Leu Pro Pro Ser Arg Asp Glu Leu Thr Lys Asn
                        405                 410                 415

Gln Val Ser Leu Thr Cys Leu Val Lys Gly Phe Tyr Pro Ser Asp Ile
                420                 425                 430

Ala Val Glu Trp Glu Ser Asn Gly Gln Pro Glu Asn Asn Tyr Lys Thr
                435                 440                 445

Thr Pro Pro Val Leu Asp Ser Asp Gly Ser Phe Phe Leu Tyr Ser Lys
            450                 455                 460

Leu Thr Val Asp Lys Ser Arg Trp Gln Gln Gly Asn Val Phe Ser Cys
    465                 470                 475                 480

Ser Val Met His Glu Ala Leu His Asn His Tyr Thr Gln Lys Ser Leu
                        485                 490                 495

Ser Leu Ser Pro Gly Lys
                500

<210> SEQ ID NO 11
```

<211> LENGTH: 503
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Ser Val His Gln Glu Thr Lys Lys Tyr Gln Ser Gly Gly Gly Ser
            100                 105                 110

Asp Cys Leu Gly Phe Met Arg Lys Cys Ile Pro Asp Asn Asp Lys Cys
        115                 120                 125

Cys Arg Pro Asn Leu Val Cys Ser Arg Thr His Lys Trp Cys Lys Tyr
    130                 135                 140

Val Phe Gly Gly Gly Ser Ser Tyr Thr Tyr Asn Tyr Glu Trp His
145                 150                 155                 160

Val Asp Val Trp Gly Gln Gly Leu Leu Val Thr Val Ser Ser Ala Ser
                165                 170                 175

Thr Thr Ala Pro Lys Val Tyr Pro Leu Ser Ser Cys Cys Gly Asp Lys
            180                 185                 190

Ser Ser Ser Thr Val Thr Leu Gly Cys Leu Val Ser Ser Tyr Met Pro
        195                 200                 205

Glu Pro Val Thr Val Thr Trp Asn Ser Gly Ala Leu Lys Ser Gly Val
    210                 215                 220

His Thr Phe Pro Ala Val Leu Gln Ser Ser Gly Leu Tyr Ser Leu Ser
225                 230                 235                 240

Ser Met Val Thr Val Pro Gly Ser Thr Ser Gly Gln Thr Phe Thr Cys
                245                 250                 255

Asn Val Ala His Pro Ala Ser Ser Thr Lys Val Asp Lys Ala Val Glu
            260                 265                 270

Pro Lys Ser Cys Asp Lys Thr His Thr Cys Pro Pro Cys Pro Ala Pro
        275                 280                 285

Glu Leu Leu Gly Gly Pro Ser Val Phe Leu Phe Pro Pro Lys Pro Lys
    290                 295                 300

Asp Thr Leu Met Ile Ser Arg Thr Pro Glu Val Thr Cys Val Val Val
305                 310                 315                 320

Asp Val Ser His Glu Asp Pro Glu Val Lys Phe Asn Trp Tyr Val Asp
                325                 330                 335

Gly Val Glu Val His Asn Ala Lys Thr Lys Pro Arg Glu Glu Gln Tyr
            340                 345                 350

Asn Ser Thr Tyr Arg Val Val Ser Val Leu Thr Val Leu His Gln Asp
        355                 360                 365

Trp Leu Asn Gly Lys Glu Tyr Lys Cys Lys Val Ser Asn Lys Ala Leu

-continued

```
            370                 375                 380
Pro Ala Pro Ile Glu Lys Thr Ile Ser Lys Ala Lys Gly Gln Pro Arg
385                 390                 395                 400

Glu Pro Gln Val Tyr Thr Leu Pro Pro Ser Arg Asp Glu Leu Thr Lys
                405                 410                 415

Asn Gln Val Ser Leu Thr Cys Leu Val Lys Gly Phe Tyr Pro Ser Asp
            420                 425                 430

Ile Ala Val Glu Trp Glu Ser Asn Gly Gln Pro Glu Asn Asn Tyr Lys
        435                 440                 445

Thr Thr Pro Pro Val Leu Asp Ser Asp Gly Ser Phe Phe Leu Tyr Ser
    450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
                485                 490                 495

Leu Ser Leu Ser Pro Gly Lys
                500
```

<210> SEQ ID NO 12
<211> LENGTH: 526
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

```
Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Ser Val His Gln Glu Thr Lys Lys Tyr Gln Ser Gly Gly Gly Gly Ser
            100                 105                 110

Leu Lys Cys Tyr Gln His Gly Lys Val Val Thr Cys His Arg Asp Met
        115                 120                 125

Lys Phe Cys Tyr His Asn Thr Gly Met Pro Phe Arg Asn Leu Lys Leu
    130                 135                 140

Ile Leu Gln Gly Cys Ser Ser Ser Cys Ser Glu Thr Glu Asn Asn Lys
145                 150                 155                 160

Cys Cys Ser Thr Asp Arg Cys Asn Lys Gly Gly Gly Ser Ser Tyr
                165                 170                 175

Thr Tyr Asn Tyr Glu Trp His Val Asp Val Trp Gly Gln Gly Leu Leu
            180                 185                 190

Val Thr Val Ser Ser Ala Ser Thr Thr Ala Pro Lys Val Tyr Pro Leu
        195                 200                 205

Ser Ser Cys Cys Gly Asp Lys Ser Ser Ser Thr Val Thr Leu Gly Cys
    210                 215                 220
```

```
Leu Val Ser Ser Tyr Met Pro Glu Pro Val Thr Val Thr Trp Asn Ser
225                 230                 235                 240

Gly Ala Leu Lys Ser Gly Val His Thr Phe Pro Ala Val Leu Gln Ser
            245                 250                 255

Ser Gly Leu Tyr Ser Leu Ser Ser Met Val Thr Val Pro Gly Ser Thr
        260                 265                 270

Ser Gly Gln Thr Phe Thr Cys Asn Val Ala His Pro Ala Ser Ser Thr
    275                 280                 285

Lys Val Asp Lys Ala Val Glu Pro Lys Ser Cys Asp Lys Thr His Thr
290                 295                 300

Cys Pro Pro Cys Pro Ala Pro Glu Leu Leu Gly Gly Pro Ser Val Phe
305                 310                 315                 320

Leu Phe Pro Pro Lys Pro Lys Asp Thr Leu Met Ile Ser Arg Thr Pro
            325                 330                 335

Glu Val Thr Cys Val Val Val Asp Val Ser His Glu Asp Pro Glu Val
        340                 345                 350

Lys Phe Asn Trp Tyr Val Asp Gly Val Glu Val His Asn Ala Lys Thr
    355                 360                 365

Lys Pro Arg Glu Glu Gln Tyr Asn Ser Thr Tyr Arg Val Val Ser Val
370                 375                 380

Leu Thr Val Leu His Gln Asp Trp Leu Asn Gly Lys Glu Tyr Lys Cys
385                 390                 395                 400

Lys Val Ser Asn Lys Ala Leu Pro Ala Pro Ile Glu Lys Thr Ile Ser
            405                 410                 415

Lys Ala Lys Gly Gln Pro Arg Glu Pro Gln Val Tyr Thr Leu Pro Pro
        420                 425                 430

Ser Arg Asp Glu Leu Thr Lys Asn Gln Val Ser Leu Thr Cys Leu Val
    435                 440                 445

Lys Gly Phe Tyr Pro Ser Asp Ile Ala Val Glu Trp Glu Ser Asn Gly
450                 455                 460

Gln Pro Glu Asn Asn Tyr Lys Thr Thr Pro Pro Val Leu Asp Ser Asp
465                 470                 475                 480

Gly Ser Phe Phe Leu Tyr Ser Lys Leu Thr Val Asp Lys Ser Arg Trp
            485                 490                 495

Gln Gln Gly Asn Val Phe Ser Cys Ser Val Met His Glu Ala Leu His
        500                 505                 510

Asn His Tyr Thr Gln Lys Ser Leu Ser Leu Ser Pro Gly Lys
    515                 520                 525

<210> SEQ ID NO 13
<211> LENGTH: 506
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60
```

```
Ser Arg Leu Ser Ile Thr Lys Asp Asn Ser Lys Ser Gln Val Ser Leu
 65                  70                  75                  80

Ser Val Ser Ser Val Thr Thr Glu Asp Ser Ala Thr Tyr Tyr Cys Thr
                 85                  90                  95

Ser Val His Gln Glu Thr Lys Lys Tyr Gln Ser Gly Gly Gly Gly Ser
            100                 105                 110

His Ser Gln Gly Thr Phe Thr Ser Asp Tyr Ser Lys Tyr Leu Asp Ser
        115                 120                 125

Arg Arg Ala Gln Asp Phe Val Gln Trp Leu Met Asn Thr Lys Arg Asn
130                 135                 140

Arg Asn Asn Ile Ala Gly Gly Gly Ser Ser Tyr Thr Tyr Asn Tyr
145                 150                 155                 160

Glu Trp His Val Asp Val Trp Gly Gln Gly Leu Leu Val Thr Val Ser
                165                 170                 175

Ser Ala Ser Thr Thr Ala Pro Lys Val Tyr Pro Leu Ser Ser Cys Cys
            180                 185                 190

Gly Asp Lys Ser Ser Ser Thr Val Thr Leu Gly Cys Leu Val Ser Ser
            195                 200                 205

Tyr Met Pro Glu Pro Val Thr Val Thr Trp Asn Ser Gly Ala Leu Lys
210                 215                 220

Ser Gly Val His Thr Phe Pro Ala Val Leu Gln Ser Ser Gly Leu Tyr
225                 230                 235                 240

Ser Leu Ser Ser Met Val Thr Val Pro Gly Ser Thr Ser Gly Gln Thr
                245                 250                 255

Phe Thr Cys Asn Val Ala His Pro Ala Ser Ser Thr Lys Val Asp Lys
            260                 265                 270

Ala Val Glu Pro Lys Ser Cys Asp Lys Thr His Thr Cys Pro Pro Cys
            275                 280                 285

Pro Ala Pro Glu Leu Leu Gly Gly Pro Ser Val Phe Leu Phe Pro Pro
        290                 295                 300

Lys Pro Lys Asp Thr Leu Met Ile Ser Arg Thr Pro Glu Val Thr Cys
305                 310                 315                 320

Val Val Val Asp Val Ser His Glu Asp Pro Glu Val Lys Phe Asn Trp
                325                 330                 335

Tyr Val Asp Gly Val Glu Val His Asn Ala Lys Thr Lys Pro Arg Glu
            340                 345                 350

Glu Gln Tyr Asn Ser Thr Tyr Arg Val Val Ser Val Leu Thr Val Leu
        355                 360                 365

His Gln Asp Trp Leu Asn Gly Lys Glu Tyr Lys Cys Lys Val Ser Asn
        370                 375                 380

Lys Ala Leu Pro Ala Pro Ile Glu Lys Thr Ile Ser Lys Ala Lys Gly
385                 390                 395                 400

Gln Pro Arg Glu Pro Gln Val Tyr Thr Leu Pro Pro Ser Arg Asp Glu
                405                 410                 415

Leu Thr Lys Asn Gln Val Ser Leu Thr Cys Leu Val Lys Gly Phe Tyr
            420                 425                 430

Pro Ser Asp Ile Ala Val Glu Trp Glu Ser Asn Gly Gln Pro Glu Asn
            435                 440                 445

Asn Tyr Lys Thr Thr Pro Pro Val Leu Asp Ser Asp Gly Ser Phe Phe
        450                 455                 460

Leu Tyr Ser Lys Leu Thr Val Asp Lys Ser Arg Trp Gln Gln Gly Asn
465                 470                 475                 480
```

-continued

Val Phe Ser Cys Ser Val Met His Glu Ala Leu His Asn His Tyr Thr
                485                 490                 495

Gln Lys Ser Leu Ser Leu Ser Pro Gly Lys
        500                 505

<210> SEQ ID NO 14
<211> LENGTH: 553
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Arg Glu Ser Gly Pro Ser Leu Val Lys Pro Ser Gln
1               5                   10                  15

Thr Leu Ser Leu Thr Cys Thr Ala Ser Gly Phe Ser Leu Ser Asp Lys
            20                  25                  30

Ala Val Gly Trp Val Arg Gln Ala Pro Gly Lys Ala Leu Glu Trp Leu
        35                  40                  45

Gly Ser Ile Asp Thr Gly Gly Asn Thr Gly Tyr Asn Pro Gly Leu Lys
    50                  55                  60

Ser Arg Leu Ser Ile Thr Lys Asp Asn Ser Lys Ser Gln Val Ser Leu
65                  70                  75                  80

Ser Val Ser Ser Val Thr Thr Glu Asp Ser Ala Thr Tyr Tyr Cys Thr
                85                  90                  95

Ser Val His Gln Glu Thr Lys Lys Tyr Gln Ser Gly Gly Gly Gly Ser
            100                 105                 110

Ser Val Ser Glu Ile Gln Leu Met His Asn Leu Gly Lys His Leu Asn
        115                 120                 125

Ser Met Glu Arg Val Glu Trp Leu Arg Lys Lys Leu Gln Asp Val His
    130                 135                 140

Asn Phe Val Ala Leu Gly Ala Pro Leu Ala Pro Arg Asp Ala Gly Ser
145                 150                 155                 160

Gln Arg Pro Arg Lys Lys Glu Asp Asn Val Leu Val Glu Ser His Glu
                165                 170                 175

Lys Ser Leu Gly Glu Ala Asp Lys Ala Asp Val Asn Val Leu Thr Lys
            180                 185                 190

Ala Lys Ser Gln Gly Gly Gly Ser Ser Tyr Thr Tyr Asn Tyr Glu
        195                 200                 205

Trp His Val Asp Val Trp Gly Gln Gly Leu Leu Val Thr Val Ser Ser
    210                 215                 220

Ala Ser Thr Thr Ala Pro Lys Val Tyr Pro Leu Ser Ser Cys Cys Gly
225                 230                 235                 240

Asp Lys Ser Ser Ser Thr Val Thr Leu Gly Cys Leu Val Ser Ser Tyr
                245                 250                 255

Met Pro Glu Pro Val Thr Val Thr Trp Asn Ser Gly Ala Leu Lys Ser
            260                 265                 270

Gly Val His Thr Phe Pro Ala Val Leu Gln Ser Ser Gly Leu Tyr Ser
        275                 280                 285

Leu Ser Ser Met Val Thr Val Pro Gly Ser Thr Ser Gly Gln Thr Phe
    290                 295                 300

Thr Cys Asn Val Ala His Pro Ala Ser Ser Thr Lys Val Asp Lys Ala
305                 310                 315                 320

Val Glu Pro Lys Ser Cys Asp Lys Thr His Thr Cys Pro Pro Cys Pro
                325                 330                 335

```
Ala Pro Glu Leu Leu Gly Gly Pro Ser Val Phe Leu Phe Pro Pro Lys
            340                 345                 350

Pro Lys Asp Thr Leu Met Ile Ser Arg Thr Pro Glu Val Thr Cys Val
        355                 360                 365

Val Val Asp Val Ser His Glu Asp Pro Glu Val Lys Phe Asn Trp Tyr
370                 375                 380

Val Asp Gly Val Glu Val His Asn Ala Lys Thr Lys Pro Arg Glu Glu
385                 390                 395                 400

Gln Tyr Asn Ser Thr Tyr Arg Val Val Ser Val Leu Thr Val Leu His
            405                 410                 415

Gln Asp Trp Leu Asn Gly Lys Glu Tyr Lys Cys Lys Val Ser Asn Lys
            420                 425                 430

Ala Leu Pro Ala Pro Ile Glu Lys Thr Ile Ser Lys Ala Lys Gly Gln
            435                 440                 445

Pro Arg Glu Pro Gln Val Tyr Thr Leu Pro Pro Ser Arg Asp Glu Leu
450                 455                 460

Thr Lys Asn Gln Val Ser Leu Thr Cys Leu Val Lys Gly Phe Tyr Pro
465                 470                 475                 480

Ser Asp Ile Ala Val Glu Trp Glu Ser Asn Gly Gln Pro Glu Asn Asn
            485                 490                 495

Tyr Lys Thr Thr Pro Pro Val Leu Asp Ser Asp Gly Ser Phe Phe Leu
            500                 505                 510

Tyr Ser Lys Leu Thr Val Asp Lys Ser Arg Trp Gln Gln Gly Asn Val
            515                 520                 525

Phe Ser Cys Ser Val Met His Glu Ala Leu His Asn His Tyr Thr Gln
            530                 535                 540

Lys Ser Leu Ser Leu Ser Pro Gly Lys
545                 550

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Gly Gly Ser Gly Gly Gly Gly Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Gly Gly Gly Ser Gly Gly Gly Ser
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 17

Gly Gly Gly Gly Ser
1               5

<210> SEQ ID NO 18
<211> LENGTH: 11
<212> TYPE: PRT
<213> ORGANISM: Bos sp.

<400> SEQUENCE: 18

Thr Ser Val His Gln Glu Thr Lys Lys Tyr Gln
1               5                   10

<210> SEQ ID NO 19
<211> LENGTH: 9
<212> TYPE: PRT
<213> ORGANISM: Bos sp.

<400> SEQUENCE: 19

Val His Gln Glu Thr Lys Lys Tyr Gln
1               5

<210> SEQ ID NO 20
<211> LENGTH: 5
<212> TYPE: PRT
<213> ORGANISM: Bos sp.

<400> SEQUENCE: 20

Thr Thr Val His Gln
1               5

<210> SEQ ID NO 21
<211> LENGTH: 5
<212> TYPE: PRT
<213> ORGANISM: Bos sp.

<400> SEQUENCE: 21

Thr Ser Val His Gln
1               5

<210> SEQ ID NO 22
<211> LENGTH: 3
<212> TYPE: PRT
<213> ORGANISM: Bos sp.

<400> SEQUENCE: 22

Val His Gln
1

<210> SEQ ID NO 23
<211> LENGTH: 3
<212> TYPE: PRT
<213> ORGANISM: Bos sp.

<400> SEQUENCE: 23

Lys Lys Gln
1

<210> SEQ ID NO 24
<211> LENGTH: 3
<212> TYPE: PRT
<213> ORGANISM: Bos sp.

<400> SEQUENCE: 24

```
Val Tyr Gln
1

<210> SEQ ID NO 25
<211> LENGTH: 7
<212> TYPE: PRT
<213> ORGANISM: Bos sp.
<220> FEATURE:
<221> NAME/KEY: MOD_RES
<222> LOCATION: (7)..(7)
<223> OTHER INFORMATION: Any amino acid

<400> SEQUENCE: 25

Cys Thr Thr Val His Gln Xaa
1               5

<210> SEQ ID NO 26
<211> LENGTH: 7
<212> TYPE: PRT
<213> ORGANISM: Bos sp.
<220> FEATURE:
<221> NAME/KEY: MOD_RES
<222> LOCATION: (7)..(7)
<223> OTHER INFORMATION: Any amino acid

<400> SEQUENCE: 26

Cys Thr Ser Val His Gln Xaa
1               5

<210> SEQ ID NO 27
<211> LENGTH: 6
<212> TYPE: PRT
<213> ORGANISM: Bos sp.
<220> FEATURE:
<221> NAME/KEY: MOD_RES
<222> LOCATION: (2)..(5)
<223> OTHER INFORMATION: Any amino acid

<400> SEQUENCE: 27

Cys Xaa Xaa Xaa Xaa Gln
1               5

<210> SEQ ID NO 28
<211> LENGTH: 5
<212> TYPE: PRT
<213> ORGANISM: Bos sp.
<220> FEATURE:
<221> NAME/KEY: MOD_RES
<222> LOCATION: (1)..(2)
<223> OTHER INFORMATION: Any amino acid

<400> SEQUENCE: 28

Xaa Xaa Val His Gln
1               5

<210> SEQ ID NO 29
<211> LENGTH: 6
<212> TYPE: PRT
<213> ORGANISM: Bos sp.
<220> FEATURE:
<221> NAME/KEY: MOD_RES
<222> LOCATION: (2)..(3)
<223> OTHER INFORMATION: Any amino acid

<400> SEQUENCE: 29

Cys Xaa Xaa Val His Gln
1               5
```

```
<210> SEQ ID NO 30
<211> LENGTH: 5
<212> TYPE: PRT
<213> ORGANISM: Bos sp.
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid

<400> SEQUENCE: 30

Xaa Xaa Val Xaa Gln
1               5

<210> SEQ ID NO 31
<211> LENGTH: 6
<212> TYPE: PRT
<213> ORGANISM: Bos sp.
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid

<400> SEQUENCE: 31

Cys Xaa Xaa Val Xaa Gln
1               5

<210> SEQ ID NO 32
<211> LENGTH: 5
<212> TYPE: PRT
<213> ORGANISM: Bos sp.
<220> FEATURE:
<221> NAME/KEY: MOD_RES
<222> LOCATION: (1)..(2)
<223> OTHER INFORMATION: Any amino acid

<400> SEQUENCE: 32

Xaa Xaa Lys Lys Gln
1               5

<210> SEQ ID NO 33
<211> LENGTH: 6
<212> TYPE: PRT
<213> ORGANISM: Bos sp.
<220> FEATURE:
<221> NAME/KEY: MOD_RES
<222> LOCATION: (2)..(3)
<223> OTHER INFORMATION: Any amino acid

<400> SEQUENCE: 33

Cys Xaa Xaa Lys Lys Gln
1               5

<210> SEQ ID NO 34
<211> LENGTH: 7
<212> TYPE: PRT
<213> ORGANISM: Bos sp.

<400> SEQUENCE: 34

Tyr Thr Tyr Asn Tyr Glu Trp
1               5
```

```
<210> SEQ ID NO 35
<211> LENGTH: 6
<212> TYPE: PRT
<213> ORGANISM: Bos sp.

<400> SEQUENCE: 35

Tyr Thr Tyr Asn Tyr Glu
1               5

<210> SEQ ID NO 36
<211> LENGTH: 7
<212> TYPE: PRT
<213> ORGANISM: Bos sp.

<400> SEQUENCE: 36

Tyr Leu Tyr Thr Tyr Glu His
1               5

<210> SEQ ID NO 37
<211> LENGTH: 6
<212> TYPE: PRT
<213> ORGANISM: Bos sp.

<400> SEQUENCE: 37

Tyr Leu Tyr Thr Tyr Glu
1               5

<210> SEQ ID NO 38
<211> LENGTH: 4
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid

<400> SEQUENCE: 38

Tyr Xaa Tyr Xaa
1

<210> SEQ ID NO 39
<211> LENGTH: 5
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid

<400> SEQUENCE: 39

Tyr Xaa Tyr Xaa Tyr
1               5

<210> SEQ ID NO 40
<211> LENGTH: 6
<212> TYPE: PRT
<213> ORGANISM: Bos sp.
<220> FEATURE:
<221> NAME/KEY: MOD_RES
<222> LOCATION: (2)..(2)
```

```
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 40

Tyr Xaa Tyr Xaa Tyr Xaa
1               5

<210> SEQ ID NO 41
<211> LENGTH: 7
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(7)
<223> OTHER INFORMATION: Any amino acid

<400> SEQUENCE: 41

Tyr Xaa Tyr Xaa Tyr Xaa Xaa
1               5

<210> SEQ ID NO 42
<211> LENGTH: 3
<212> TYPE: PRT
<213> ORGANISM: Bos sp.
<220> FEATURE:
<221> NAME/KEY: MOD_RES
<222> LOCATION: (3)..(3)
<223> OTHER INFORMATION: Any amino acid

<400> SEQUENCE: 42

Tyr Glu Xaa
1

<210> SEQ ID NO 43
<211> LENGTH: 3
<212> TYPE: PRT
<213> ORGANISM: Bos sp.
<220> FEATURE:
<221> NAME/KEY: MOD_RES
<222> LOCATION: (3)..(3)
<223> OTHER INFORMATION: Any amino acid

<400> SEQUENCE: 43

Tyr Asp Xaa
1

<210> SEQ ID NO 44
<211> LENGTH: 3
<212> TYPE: PRT
<213> ORGANISM: Bos sp.
<220> FEATURE:
<221> NAME/KEY: MOD_RES
<222> LOCATION: (1)..(1)
<223> OTHER INFORMATION: Any amino acid

<400> SEQUENCE: 44
```

```
Xaa Tyr Glu
1

<210> SEQ ID NO 45
<211> LENGTH: 3
<212> TYPE: PRT
<213> ORGANISM: Bos sp.
<220> FEATURE:
<221> NAME/KEY: MOD_RES
<222> LOCATION: (1)..(1)
<223> OTHER INFORMATION: Any amino acid

<400> SEQUENCE: 45

Xaa Tyr Asp
1

<210> SEQ ID NO 46
<211> LENGTH: 5
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Glu or Asp
<220> FEATURE:
<221> NAME/KEY: MOD_RES
<222> LOCATION: (3)..(4)
<223> OTHER INFORMATION: Any amino acid

<400> SEQUENCE: 46

Tyr Xaa Xaa Xaa Trp
1               5

<210> SEQ ID NO 47
<211> LENGTH: 8
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Glu or Asp
<220> FEATURE:
<221> NAME/KEY: MOD_RES
<222> LOCATION: (3)..(7)
<223> OTHER INFORMATION: Any amino acid

<400> SEQUENCE: 47

Tyr Xaa Xaa Xaa Xaa Xaa Xaa Trp
1               5

<210> SEQ ID NO 48
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(17)
<223> OTHER INFORMATION: Any amino acid
<220> FEATURE:
<221> NAME/KEY: MOD_RES
<222> LOCATION: (19)..(23)
<223> OTHER INFORMATION: Any amino acid
<220> FEATURE:
<221> NAME/KEY: MOD_RES
```

```
<222> LOCATION: (25)..(25)
<223> OTHER INFORMATION: Any amino acid
<220> FEATURE:
<221> NAME/KEY: MOD_RES
<222> LOCATION: (27)..(33)
<223> OTHER INFORMATION: Any amino acid

<400> SEQUENCE: 48

Cys Xaa Xaa Xaa Xaa Xaa Xaa Xaa Xaa Xaa Cys Xaa Xaa Xaa Xaa
1               5                   10                  15

Xaa Cys Xaa Xaa Xaa Xaa Xaa Cys Xaa Cys Xaa Xaa Xaa Xaa Xaa
            20                  25                  30

Xaa Cys

<210> SEQ ID NO 49
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(42)
<223> OTHER INFORMATION: Any amino acid

<400> SEQUENCE: 49

Cys Xaa Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Cys Xaa Xaa Xaa Xaa Xaa
            20                  25                  30

Xaa Xaa Xaa Xaa Xaa Xaa Xaa Xaa Xaa Xaa Cys
            35                  40

<210> SEQ ID NO 50
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(12)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (16)..(20)
<223> OTHER INFORMATION: Any amino acid

<400> SEQUENCE: 50
```

```
Cys Xaa Xaa Xaa Xaa Xaa Xaa Xaa Xaa Xaa Xaa Cys Xaa Cys Xaa
1               5                   10                  15

Xaa Xaa Xaa Xaa Cys
            20
```

<210> SEQ ID NO 51
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(12)
<223> OTHER INFORMATION: Any amino acid
<220> FEATURE:
<221> NAME/KEY: MOD_RES
<222> LOCATION: (14)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(34)
<223> OTHER INFORMATION: Any amino acid

<400> SEQUENCE: 51

```
Cys Xaa Xaa Xaa Xaa Xaa Xaa Xaa Xaa Xaa Xaa Cys Xaa Xaa Xaa
1               5                   10                  15

Xaa Xaa Cys Xaa Xaa Xaa Xaa Xaa Cys Xaa Cys Xaa Xaa Xaa Xaa Xaa
            20                  25                  30

Xaa Xaa Cys
        35
```

<210> SEQ ID NO 52
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(40)
<223> OTHER INFORMATION: Any amino acid

<400> SEQUENCE: 52

```
Cys Xaa Xaa Xaa Xaa Xaa Xaa Xaa Xaa Xaa Xaa Cys Xaa Xaa Xaa Xaa
```

```
                1               5                   10                  15
Xaa Xaa Cys Xaa Xaa Xaa Xaa Xaa Cys Xaa Cys Xaa Xaa Xaa Xaa
                        20                  25                  30
Xaa Xaa Xaa Xaa Xaa Xaa Xaa Xaa Cys
                35                  40

<210> SEQ ID NO 53
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(17)
<223> OTHER INFORMATION: Any amino acid
<220> FEATURE:
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (21)..(24)
<223> OTHER INFORMATION: Any amino acid
<220> FEATURE:
<221> NAME/KEY: MOD_RES
<222> LOCATION: (26)..(33)
<223> OTHER INFORMATION: Any amino acid

<400> SEQUENCE: 53

Cys Xaa Xaa Xaa Xaa Xaa Xaa Xaa Xaa Xaa Xaa Cys Xaa Xaa Xaa Xaa
1               5                   10                  15
Xaa Cys Xaa Cys Xaa Xaa Xaa Xaa Cys Xaa Xaa Xaa Xaa Xaa Xaa Xaa
                        20                  25                  30
Xaa Cys

<210> SEQ ID NO 54
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(25)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (29)..(35)
<223> OTHER INFORMATION: Any amino acid

<400> SEQUENCE: 54

Cys Xaa Xaa Xaa Xaa Xaa Xaa Xaa Xaa Xaa Xaa Cys Xaa Xaa Xaa Xaa
```

```
                1               5                   10                  15
Xaa Xaa Cys Xaa Xaa Xaa Xaa Xaa Xaa Cys Xaa Cys Xaa Xaa Xaa
                        20                  25                  30
Xaa Xaa Xaa Cys
        35
```

<210> SEQ ID NO 55
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(35)
<223> OTHER INFORMATION: Any amino acid

<400> SEQUENCE: 55

```
Cys Xaa Xaa Xaa Xaa Xaa Xaa Xaa Xaa Xaa Cys Xaa Xaa Xaa Xaa
1               5                   10                  15
Cys Xaa Xaa Xaa Xaa Xaa Xaa Xaa Cys Xaa Cys Xaa Xaa Xaa Xaa
                        20                  25                  30
Xaa Xaa Xaa Cys
        35
```

<210> SEQ ID NO 56
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(34)
<223> OTHER INFORMATION: Any amino acid

<400> SEQUENCE: 56

```
Cys Xaa Xaa Xaa Xaa Xaa Xaa Xaa Xaa Cys Xaa Xaa Xaa Xaa
1               5                   10                  15

Cys Xaa Xaa Xaa Xaa Xaa Xaa Xaa Cys Xaa Cys Xaa Xaa Xaa Xaa
                20                  25                  30

Xaa Xaa Cys
        35

<210> SEQ ID NO 57
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(14)
<223> OTHER INFORMATION: Any amino acid
<220> FEATURE:
<221> NAME/KEY: MOD_RES
<222> LOCATION: (16)..(23)
<223> OTHER INFORMATION: Any amino acid
<220> FEATURE:
<221> NAME/KEY: MOD_RES
<222> LOCATION: (25)..(32)
<223> OTHER INFORMATION: Any amino acid

<400> SEQUENCE: 57

Cys Xaa Xaa Xaa Xaa Xaa Xaa Xaa Xaa Xaa Xaa Xaa Xaa Xaa Cys Xaa
1               5                   10                  15

Xaa Xaa Xaa Xaa Xaa Xaa Xaa Cys Xaa Xaa Xaa Xaa Xaa Xaa Xaa Xaa
                20                  25                  30

Cys

<210> SEQ ID NO 58
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(34)
<223> OTHER INFORMATION: Any amino acid

<400> SEQUENCE: 58

Cys Xaa Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Cys Xaa Xaa Xaa Xaa Xaa
                20                  25                  30

Xaa Xaa Cys
        35
```

```
<210> SEQ ID NO 59
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(17)
<223> OTHER INFORMATION: Any amino acid
<220> FEATURE:
<221> NAME/KEY: MOD_RES
<222> LOCATION: (19)..(23)
<223> OTHER INFORMATION: Any amino acid

<400> SEQUENCE: 59

Cys Xaa Xaa Xaa Xaa Xaa Xaa Xaa Xaa Xaa Xaa Cys Xaa Xaa Xaa Xaa
1               5                   10                  15

Xaa Cys Xaa Xaa Xaa Xaa Xaa Cys
            20

<210> SEQ ID NO 60
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(17)
<223> OTHER INFORMATION: Any amino acid
<220> FEATURE:
<221> NAME/KEY: MOD_RES
<222> LOCATION: (19)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(34)
<223> OTHER INFORMATION: Any amino acid

<400> SEQUENCE: 60

Cys Xaa Xaa Xaa Xaa Xaa Xaa Xaa Xaa Xaa Xaa Cys Xaa Xaa Xaa Xaa
1               5                   10                  15

Xaa Cys Xaa Xaa Xaa Xaa Xaa Xaa Cys Xaa Cys Xaa Xaa Xaa Xaa Xaa
            20                  25                  30

Xaa Xaa Cys
        35

<210> SEQ ID NO 61
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(32)
<223> OTHER INFORMATION: Any amino acid
<220> FEATURE:
<221> NAME/KEY: MOD_RES
<222> LOCATION: (34)..(42)
<223> OTHER INFORMATION: Any amino acid

<400> SEQUENCE: 61

Cys Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Xaa Xaa Xaa Xaa Xaa
            20                  25                  30

Cys Xaa Xaa Xaa Xaa Xaa Xaa Xaa Xaa Xaa Cys
        35                  40

<210> SEQ ID NO 62
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(10)
<223> OTHER INFORMATION: Any amino acid
<220> FEATURE:
<221> NAME/KEY: MOD_RES
<222> LOCATION: (12)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(34)
<223> OTHER INFORMATION: Any amino acid

<400> SEQUENCE: 62

Cys Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Cys Xaa Xaa Xaa Xaa
            20                  25                  30

Xaa Xaa Cys
        35

<210> SEQ ID NO 63
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(36)
<223> OTHER INFORMATION: Any amino acid

<400> SEQUENCE: 63

Cys Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Cys Xaa Xaa Xaa Xaa
            20                  25                  30

Xaa Xaa Xaa Xaa Cys
        35

<210> SEQ ID NO 64
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (15)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(36)
<223> OTHER INFORMATION: Any amino acid

<400> SEQUENCE: 64

Cys Xaa Xaa Xaa Xaa Xaa Xaa Xaa Xaa Xaa Xaa Cys Xaa Cys Xaa Xaa
1               5                   10                  15

Xaa Xaa Cys Xaa Xaa Xaa Xaa Xaa Cys Xaa Xaa Xaa Xaa Xaa Xaa Xaa
            20                  25                  30

Xaa Xaa Xaa Xaa Cys
        35

<210> SEQ ID NO 65
<211> LENGTH: 45
<212> TYPE: PRT
<213> ORGANISM: Artificial Sequence
<220> FEATURE:
<223> OTHER INFORMATION: Description of Artificial Sequence: Synthetic
```

```
              polypeptide
<220> FEATURE:
<221> NAME/KEY: MOD_RES
<222> LOCATION: (2)..(8)
<223> OTHER INFORMATION: Any amino acid
<220> FEATURE:
<221> NAME/KEY: MOD_RES
<222> LOCATION: (10)..(12)
<223> OTHER INFORMATION: Any amino acid
<220> FEATURE:
<221> NAME/KEY: MOD_RES
<222> LOCATION: (14)..(19)
<223> OTHER INFORMATION: Any amino acid
<220> FEATURE:
<221> NAME/KEY: MOD_RES
<222> LOCATION: (21)..(25)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (29)..(33)
<223> OTHER INFORMATION: Any amino acid
<220> FEATURE:
<221> NAME/KEY: MOD_RES
<222> LOCATION: (35)..(44)
<223> OTHER INFORMATION: Any amino acid

<400> SEQUENCE: 65

Cys Xaa Xaa Xaa Xaa Xaa Xaa Xaa Cys Xaa Xaa Xaa Cys Xaa Xaa Xaa
1               5                   10                  15

Xaa Xaa Xaa Cys Xaa Xaa Xaa Xaa Xaa Cys Xaa Cys Xaa Xaa Xaa Xaa
                20                  25                  30

Xaa Cys Xaa Xaa Xaa Xaa Xaa Xaa Xaa Xaa Xaa Xaa Cys
        35                  40                  45

<210> SEQ ID NO 66
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (15)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(29)
<223> OTHER INFORMATION: Any amino acid
<220> FEATURE:
<221> NAME/KEY: MOD_RES
<222> LOCATION: (31)..(33)
<223> OTHER INFORMATION: Any amino acid

<400> SEQUENCE: 66
```

```
Cys Xaa Xaa Xaa Xaa Xaa Xaa Xaa Xaa Xaa Cys Xaa Cys Xaa Xaa
1               5                   10                  15

Xaa Xaa Cys Xaa Xaa Xaa Xaa Xaa Cys Xaa Cys Xaa Cys Xaa Xaa
            20                  25                  30

Xaa Cys
```

<210> SEQ ID NO 67
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(17)
<223> OTHER INFORMATION: Any amino acid
<220> FEATURE:
<221> NAME/KEY: MOD_RES
<222> LOCATION: (19)..(23)
<223> OTHER INFORMATION: Any amino acid
<220> FEATURE:
<221> NAME/KEY: MOD_RES
<222> LOCATION: (25)..(25)
<223> OTHER INFORMATION: Any amino acid

<400> SEQUENCE: 67

```
Cys Xaa Xaa Xaa Xaa Xaa Xaa Xaa Xaa Xaa Xaa Xaa Xaa Xaa Xaa
1               5                   10                  15

Xaa Cys Xaa Xaa Xaa Xaa Xaa Cys Xaa Cys
            20                  25
```

<210> SEQ ID NO 68
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(7)
<223> OTHER INFORMATION: Any amino acid
<220> FEATURE:
<221> NAME/KEY: MOD_RES
<222> LOCATION: (9)..(12)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (16)..(19)
<223> OTHER INFORMATION: Any amino acid
<220> FEATURE:
<221> NAME/KEY: MOD_RES
<222> LOCATION: (21)..(25)
<223> OTHER INFORMATION: Any amino acid

<400> SEQUENCE: 68

```
Cys Xaa Xaa Xaa Xaa Xaa Xaa Cys Xaa Xaa Xaa Xaa Cys Xaa Cys Xaa
1               5                   10                  15

Xaa Xaa Xaa Cys Xaa Xaa Xaa Xaa Xaa Cys
            20                  25
```

<210> SEQ ID NO 69
<211> LENGTH: 35
<212> TYPE: PRT

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(12)
<223> OTHER INFORMATION: Any amino acid
<220> FEATURE:
<221> NAME/KEY: MOD_RES
<222> LOCATION: (14)..(17)
<223> OTHER INFORMATION: Any amino acid
<220> FEATURE:
<221> NAME/KEY: MOD_RES
<222> LOCATION: (19)..(23)
<223> OTHER INFORMATION: Any amino acid
<220> FEATURE:
<221> NAME/KEY: MOD_RES
<222> LOCATION: (25)..(30)
<223> OTHER INFORMATION: Any amino acid
<220> FEATURE:
<221> NAME/KEY: MOD_RES
<222> LOCATION: (32)..(34)
<223> OTHER INFORMATION: Any amino acid

<400> SEQUENCE: 69

Cys Xaa Xaa Xaa Xaa Xaa Xaa Xaa Xaa Xaa Xaa Cys Xaa Xaa Xaa
1               5                   10                  15

Xaa Cys Xaa Xaa Xaa Xaa Xaa Cys Xaa Xaa Xaa Xaa Xaa Xaa Cys Xaa
            20                  25                  30

Xaa Xaa Cys
        35

<210> SEQ ID NO 70
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(9)
<223> OTHER INFORMATION: Any amino acid
<220> FEATURE:
<221> NAME/KEY: MOD_RES
<222> LOCATION: (11)..(12)
<223> OTHER INFORMATION: Any amino acid
<220> FEATURE:
<221> NAME/KEY: MOD_RES
<222> LOCATION: (14)..(19)
<223> OTHER INFORMATION: Any amino acid
<220> FEATURE:
<221> NAME/KEY: MOD_RES
<222> LOCATION: (21)..(25)
<223> OTHER INFORMATION: Any amino acid

<400> SEQUENCE: 70

Cys Xaa Xaa Xaa Xaa Xaa Xaa Xaa Xaa Cys Xaa Xaa Cys Xaa Xaa Xaa
1               5                   10                  15

Xaa Xaa Xaa Cys Xaa Xaa Xaa Xaa Xaa Cys
            20                  25

<210> SEQ ID NO 71
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

```
<222> LOCATION: (2)..(11)
<223> OTHER INFORMATION: Any amino acid
<220> FEATURE:
<221> NAME/KEY: MOD_RES
<222> LOCATION: (13)..(17)
<223> OTHER INFORMATION: Any amino acid
<220> FEATURE:
<221> NAME/KEY: MOD_RES
<222> LOCATION: (19)..(23)
<223> OTHER INFORMATION: Any amino acid
<220> FEATURE:
<221> NAME/KEY: MOD_RES
<222> LOCATION: (25)..(25)
<223> OTHER INFORMATION: Any amino acid
<220> FEATURE:
<221> NAME/KEY: MOD_RES
<222> LOCATION: (27)..(36)
<223> OTHER INFORMATION: Any amino acid

<400> SEQUENCE: 71

Cys Xaa Xaa Xaa Xaa Xaa Xaa Xaa Xaa Xaa Xaa Cys Xaa Xaa Xaa Xaa
1               5                   10                  15

Xaa Cys Xaa Xaa Xaa Xaa Xaa Cys Xaa Cys Xaa Xaa Xaa Xaa Xaa Xaa
            20                  25                  30

Xaa Xaa Xaa Xaa Cys
        35

<210> SEQ ID NO 72
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (15)..(20)
<223> OTHER INFORMATION: Any amino acid
<220> FEATURE:
<221> NAME/KEY: MOD_RES
<222> LOCATION: (22)..(25)
<223> OTHER INFORMATION: Any amino acid
<220> FEATURE:
<221> NAME/KEY: MOD_RES
<222> LOCATION: (27)..(27)
<223> OTHER INFORMATION: Any amino acid

<400> SEQUENCE: 72

Cys Xaa Xaa Xaa Xaa Xaa Xaa Xaa Xaa Xaa Xaa Cys Xaa Cys Xaa Xaa
1               5                   10                  15

Xaa Xaa Xaa Xaa Cys Xaa Xaa Xaa Xaa Cys Xaa Cys
            20                  25

<210> SEQ ID NO 73
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(11)
<223> OTHER INFORMATION: Any amino acid
```

```
<220> FEATURE:
<221> NAME/KEY: MOD_RES
<222> LOCATION: (13)..(17)
<223> OTHER INFORMATION: Any amino acid
<220> FEATURE:
<221> NAME/KEY: MOD_RES
<222> LOCATION: (19)..(23)
<223> OTHER INFORMATION: Any amino acid
<220> FEATURE:
<221> NAME/KEY: MOD_RES
<222> LOCATION: (25)..(25)
<223> OTHER INFORMATION: Any amino acid
<220> FEATURE:
<221> NAME/KEY: MOD_RES
<222> LOCATION: (27)..(28)
<223> OTHER INFORMATION: Any amino acid

<400> SEQUENCE: 73

Cys Xaa Xaa Xaa Xaa Xaa Xaa Xaa Xaa Xaa Cys Xaa Xaa Xaa Xaa
1               5                   10                  15

Xaa Cys Xaa Xaa Xaa Xaa Xaa Cys Xaa Cys Xaa Xaa Cys
            20                  25

<210> SEQ ID NO 74
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(15)
<223> OTHER INFORMATION: Any amino acid
<220> FEATURE:
<221> NAME/KEY: MOD_RES
<222> LOCATION: (17)..(18)
<223> OTHER INFORMATION: Any amino acid
<220> FEATURE:
<221> NAME/KEY: MOD_RES
<222> LOCATION: (20)..(22)
<223> OTHER INFORMATION: Any amino acid
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid

<400> SEQUENCE: 74

Cys Xaa Xaa Xaa Xaa Xaa Xaa Xaa Xaa Xaa Xaa Xaa Xaa Xaa Xaa Cys
1               5                   10                  15

Xaa Xaa Cys Xaa Xaa Xaa Cys Xaa Cys Xaa Cys
            20                  25

<210> SEQ ID NO 75
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(16)
<223> OTHER INFORMATION: Any amino acid
<220> FEATURE:
<221> NAME/KEY: MOD_RES
<222> LOCATION: (18)..(22)
<223> OTHER INFORMATION: Any amino acid
<220> FEATURE:
```

```
<221> NAME/KEY: MOD_RES
<222> LOCATION: (24)..(24)
<223> OTHER INFORMATION: Any amino acid

<400> SEQUENCE: 75

Cys Xaa Xaa Xaa Xaa Xaa Xaa Xaa Xaa Xaa Xaa Xaa Xaa Xaa Xaa
1               5                   10                  15

Cys Xaa Xaa Xaa Xaa Xaa Cys Xaa Cys
            20                  25

<210> SEQ ID NO 76
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(5)
<223> OTHER INFORMATION: Any amino acid
<220> FEATURE:
<221> NAME/KEY: MOD_RES
<222> LOCATION: (7)..(12)
<223> OTHER INFORMATION: Any amino acid
<220> FEATURE:
<221> NAME/KEY: MOD_RES
<222> LOCATION: (14)..(22)
<223> OTHER INFORMATION: Any amino acid
<220> FEATURE:
<221> NAME/KEY: MOD_RES
<222> LOCATION: (24)..(25)
<223> OTHER INFORMATION: Any amino acid
<220> FEATURE:
<221> NAME/KEY: MOD_RES
<222> LOCATION: (27)..(37)
<223> OTHER INFORMATION: Any amino acid

<400> SEQUENCE: 76

Cys Xaa Xaa Xaa Xaa Cys Xaa Xaa Xaa Xaa Xaa Xaa Cys Xaa Xaa
1               5                   10                  15

Xaa Xaa Xaa Xaa Xaa Xaa Cys Xaa Xaa Cys Xaa Xaa Xaa Xaa Xaa
            20                  25                  30

Xaa Xaa Xaa Xaa Xaa Cys
        35

<210> SEQ ID NO 77
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(7)
<223> OTHER INFORMATION: Any amino acid
<220> FEATURE:
<221> NAME/KEY: MOD_RES
<222> LOCATION: (9)..(12)
<223> OTHER INFORMATION: Any amino acid
<220> FEATURE:
<221> NAME/KEY: MOD_RES
<222> LOCATION: (14)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(37)
```

<223> OTHER INFORMATION: Any amino acid

<400> SEQUENCE: 77

Cys Xaa Xaa Xaa Xaa Xaa Xaa Cys Xaa Xaa Xaa Xaa Cys Xaa Xaa Xaa
1               5                   10                  15

Xaa Xaa Cys Xaa Xaa Xaa Xaa Xaa Cys Xaa Xaa Xaa Xaa Xaa Xaa Xaa
            20                  25                  30

Xaa Xaa Xaa Xaa Xaa Cys
        35

<210> SEQ ID NO 78
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(8)
<223> OTHER INFORMATION: Any amino acid
<220> FEATURE:
<221> NAME/KEY: MOD_RES
<222> LOCATION: (10)..(12)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (18)..(21)
<223> OTHER INFORMATION: Any amino acid
<220> FEATURE:
<221> NAME/KEY: MOD_RES
<222> LOCATION: (23)..(27)
<223> OTHER INFORMATION: Any amino acid
<220> FEATURE:
<221> NAME/KEY: MOD_RES
<222> LOCATION: (29)..(37)
<223> OTHER INFORMATION: Any amino acid

<400> SEQUENCE: 78

Cys Xaa Xaa Xaa Xaa Xaa Xaa Xaa Cys Xaa Xaa Xaa Cys Xaa Cys Xaa
1               5                   10                  15

Cys Xaa Xaa Xaa Xaa Cys Xaa Xaa Xaa Xaa Cys Xaa Xaa Xaa Xaa Xaa
            20                  25                  30

Xaa Xaa Xaa Xaa Xaa Cys
        35

<210> SEQ ID NO 79
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid

<400> SEQUENCE: 79

Cys Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys
            20                  25

<210> SEQ ID NO 80
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(8)
<223> OTHER INFORMATION: Any amino acid
<220> FEATURE:
<221> NAME/KEY: MOD_RES
<222> LOCATION: (10)..(12)
<223> OTHER INFORMATION: Any amino acid
<220> FEATURE:
<221> NAME/KEY: MOD_RES
<222> LOCATION: (14)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(34)
<223> OTHER INFORMATION: Any amino acid

<400> SEQUENCE: 80

Cys Xaa Xaa Xaa Xaa Xaa Xaa Xaa Cys Xaa Xaa Xaa Cys Xaa Xaa Xaa
1               5                   10                  15

Xaa Xaa Cys Xaa Xaa Xaa Xaa Xaa Cys Xaa Xaa Xaa Xaa Xaa Xaa Xaa
            20                  25                  30

Xaa Xaa Cys
        35

<210> SEQ ID NO 81
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(8)
<223> OTHER INFORMATION: Any amino acid
<220> FEATURE:
<221> NAME/KEY: MOD_RES
<222> LOCATION: (10)..(14)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (18)..(19)
<223> OTHER INFORMATION: Any amino acid

<400> SEQUENCE: 81

Cys Xaa Xaa Xaa Xaa Xaa Xaa Xaa Cys Xaa Xaa Xaa Xaa Xaa Cys Xaa

```
1               5                   10                  15

Cys Xaa Xaa Cys
            20

<210> SEQ ID NO 82
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (15)..(20)
<223> OTHER INFORMATION: Any amino acid

<400> SEQUENCE: 82

Cys Xaa Xaa Xaa Xaa Xaa Xaa Xaa Xaa Xaa Xaa Cys Xaa Cys Xaa Xaa
1               5                   10                  15

Xaa Xaa Xaa Xaa Cys
            20

<210> SEQ ID NO 83
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(15)
<223> OTHER INFORMATION: Any amino acid
<220> FEATURE:
<221> NAME/KEY: MOD_RES
<222> LOCATION: (17)..(19)
<223> OTHER INFORMATION: Any amino acid
<220> FEATURE:
<221> NAME/KEY: MOD_RES
<222> LOCATION: (21)..(25)
<223> OTHER INFORMATION: Any amino acid
<220> FEATURE:
<221> NAME/KEY: MOD_RES
<222> LOCATION: (27)..(33)
<223> OTHER INFORMATION: Any amino acid
<220> FEATURE:
<221> NAME/KEY: MOD_RES
<222> LOCATION: (35)..(35)
<223> OTHER INFORMATION: Any amino acid
<220> FEATURE:
<221> NAME/KEY: MOD_RES
<222> LOCATION: (37)..(42)
<223> OTHER INFORMATION: Any amino acid

<400> SEQUENCE: 83

Cys Xaa Xaa Xaa Xaa Xaa Xaa Xaa Xaa Xaa Xaa Cys Xaa Xaa Xaa Cys
1               5                   10                  15

Xaa Xaa Xaa Cys Xaa Xaa Xaa Xaa Xaa Cys Xaa Xaa Xaa Xaa Xaa Xaa
            20                  25                  30
```

Xaa Cys Xaa Cys Xaa Xaa Xaa Xaa Xaa Xaa Cys
        35                  40

<210> SEQ ID NO 84
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(22)
<223> OTHER INFORMATION: Any amino acid
<220> FEATURE:
<221> NAME/KEY: MOD_RES
<222> LOCATION: (24)..(35)
<223> OTHER INFORMATION: Any amino acid
<220> FEATURE:
<221> NAME/KEY: MOD_RES
<222> LOCATION: (37)..(38)
<223> OTHER INFORMATION: Any amino acid

<400> SEQUENCE: 84

Cys Xaa Xaa Xaa Xaa Xaa Xaa Xaa Xaa Xaa Xaa Cys Xaa Xaa Xaa Xaa
1               5                   10                  15

Cys Xaa Xaa Xaa Xaa Xaa Cys Xaa Xaa Xaa Xaa Xaa Xaa Xaa Xaa Xaa
            20                  25                  30

Xaa Xaa Xaa Cys Xaa Xaa Cys
        35

<210> SEQ ID NO 85
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(13)
<223> OTHER INFORMATION: Any amino acid
<220> FEATURE:
<221> NAME/KEY: MOD_RES
<222> LOCATION: (15)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(28)
<223> OTHER INFORMATION: Any amino acid
<220> FEATURE:
<221> NAME/KEY: MOD_RES
<222> LOCATION: (30)..(38)
<223> OTHER INFORMATION: Any amino acid
<220> FEATURE:
<221> NAME/KEY: MOD_RES
<222> LOCATION: (40)..(42)
<223> OTHER INFORMATION: Any amino acid

<400> SEQUENCE: 85

Cys Xaa Xaa Xaa Xaa Xaa Xaa Xaa Xaa Xaa Xaa Xaa Cys Xaa Xaa
1               5                   10                  15

Xaa Xaa Cys Xaa Xaa Xaa Xaa Cys Xaa Cys Xaa Cys Xaa Xaa Xaa
            20                  25                  30

Xaa Xaa Xaa Xaa Xaa Xaa Cys Xaa Xaa Xaa Cys
        35                  40

<210> SEQ ID NO 86
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(13)
<223> OTHER INFORMATION: Any amino acid
<220> FEATURE:
<221> NAME/KEY: MOD_RES
<222> LOCATION: (15)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(37)
<223> OTHER INFORMATION: Any amino acid
<220> FEATURE:
<221> NAME/KEY: MOD_RES
<222> LOCATION: (39)..(40)
<223> OTHER INFORMATION: Any amino acid

<400> SEQUENCE: 86

Cys Xaa Xaa Xaa Xaa Xaa Xaa Xaa Xaa Xaa Xaa Xaa Cys Xaa Xaa
1               5                   10                  15

Xaa Xaa Cys Xaa Xaa Xaa Xaa Cys Xaa Xaa Xaa Xaa Xaa Xaa Xaa
            20                  25                  30

Xaa Xaa Xaa Xaa Xaa Cys Xaa Xaa Cys
        35                  40

<210> SEQ ID NO 87
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(38)

<223> OTHER INFORMATION: Any amino acid

<400> SEQUENCE: 87

Cys Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Cys Xaa Cys Xaa Xaa Xaa Xaa Xaa
            20                  25                  30

Xaa Xaa Xaa Xaa Xaa Xaa Cys
        35

<210> SEQ ID NO 88
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(17)
<223> OTHER INFORMATION: Any amino acid
<220> FEATURE:
<221> NAME/KEY: MOD_RES
<222> LOCATION: (19)..(23)
<223> OTHER INFORMATION: Any amino acid
<220> FEATURE:
<221> NAME/KEY: MOD_RES
<222> LOCATION: (25)..(25)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (29)..(42)
<223> OTHER INFORMATION: Any amino acid

<400> SEQUENCE: 88

Cys Xaa Xaa Xaa Xaa Xaa Xaa Xaa Xaa Xaa Xaa Xaa Xaa Xaa Xaa
1               5                   10                  15

Xaa Xaa Cys Xaa Xaa Xaa Xaa Xaa Cys Xaa Cys Xaa Cys Xaa Xaa Xaa Xaa
            20                  25                  30

Xaa Xaa Xaa Xaa Xaa Xaa Xaa Xaa Xaa Xaa Cys
        35                  40

<210> SEQ ID NO 89
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(17)
<223> OTHER INFORMATION: Any amino acid
<220> FEATURE:
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (21)..(28)
<223> OTHER INFORMATION: Any amino acid
<220> FEATURE:
<221> NAME/KEY: MOD_RES

```
<222> LOCATION: (30)..(35)
<223> OTHER INFORMATION: Any amino acid

<400> SEQUENCE: 89

Cys Xaa Xaa Xaa Xaa Xaa Xaa Xaa Xaa Xaa Cys Xaa Xaa Xaa Xaa
1               5                   10                  15

Xaa Cys Xaa Cys Xaa Xaa Xaa Xaa Xaa Xaa Xaa Cys Xaa Xaa Xaa
            20                  25                  30

Xaa Xaa Xaa Cys
        35

<210> SEQ ID NO 90
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(13)
<223> OTHER INFORMATION: Any amino acid
<220> FEATURE:
<221> NAME/KEY: MOD_RES
<222> LOCATION: (15)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(33)
<223> OTHER INFORMATION: Any amino acid
<220> FEATURE:
<221> NAME/KEY: MOD_RES
<222> LOCATION: (35)..(36)
<223> OTHER INFORMATION: Any amino acid

<400> SEQUENCE: 90

Cys Xaa Xaa Xaa Xaa Xaa Xaa Xaa Xaa Xaa Xaa Xaa Xaa Cys Xaa Xaa
1               5                   10                  15

Xaa Xaa Cys Xaa Xaa Xaa Xaa Xaa Cys Xaa Xaa Xaa Xaa Xaa Xaa Xaa
            20                  25                  30

Xaa Cys Xaa Xaa Cys
        35

<210> SEQ ID NO 91
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(13)
<223> OTHER INFORMATION: Any amino acid
<220> FEATURE:
<221> NAME/KEY: MOD_RES
<222> LOCATION: (15)..(19)
<223> OTHER INFORMATION: Any amino acid
<220> FEATURE:
<221> NAME/KEY: MOD_RES
<222> LOCATION: (21)..(25)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
```

```
<221> NAME/KEY: MOD_RES
<222> LOCATION: (29)..(36)
<223> OTHER INFORMATION: Any amino acid

<400> SEQUENCE: 91

Cys Xaa Xaa Xaa Xaa Xaa Xaa Xaa Xaa Xaa Xaa Xaa Cys Xaa Xaa
1               5                   10                  15

Xaa Xaa Xaa Cys Xaa Xaa Xaa Xaa Cys Xaa Cys Xaa Xaa Xaa Xaa
                20                  25                  30

Xaa Xaa Xaa Xaa Cys
        35

<210> SEQ ID NO 92
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(31)
<223> OTHER INFORMATION: Any amino acid
<220> FEATURE:
<221> NAME/KEY: MOD_RES
<222> LOCATION: (33)..(33)
<223> OTHER INFORMATION: Any amino acid
<220> FEATURE:
<221> NAME/KEY: MOD_RES
<222> LOCATION: (35)..(43)
<223> OTHER INFORMATION: Any amino acid

<400> SEQUENCE: 92

Cys Xaa Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Cys Xaa Xaa Xaa Xaa Cys
                20                  25                  30

Xaa Cys Xaa Xaa Xaa Xaa Xaa Xaa Xaa Xaa Xaa Cys
        35                  40

<210> SEQ ID NO 93
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(12)
<223> OTHER INFORMATION: Any amino acid
<220> FEATURE:
<221> NAME/KEY: MOD_RES
<222> LOCATION: (14)..(17)
<223> OTHER INFORMATION: Any amino acid
```

```
<220> FEATURE:
<221> NAME/KEY: MOD_RES
<222> LOCATION: (19)..(23)
<223> OTHER INFORMATION: Any amino acid
<220> FEATURE:
<221> NAME/KEY: MOD_RES
<222> LOCATION: (25)..(32)
<223> OTHER INFORMATION: Any amino acid
<220> FEATURE:
<221> NAME/KEY: MOD_RES
<222> LOCATION: (34)..(35)
<223> OTHER INFORMATION: Any amino acid

<400> SEQUENCE: 93

Cys Xaa Xaa Xaa Xaa Xaa Xaa Xaa Xaa Xaa Xaa Cys Xaa Xaa Xaa
1               5                   10                  15

Xaa Cys Xaa Xaa Xaa Xaa Xaa Cys Xaa Xaa Xaa Xaa Xaa Xaa Xaa
            20                  25                  30

Cys Xaa Xaa Cys
        35

<210> SEQ ID NO 94
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(33)
<223> OTHER INFORMATION: Any amino acid
<220> FEATURE:
<221> NAME/KEY: MOD_RES
<222> LOCATION: (35)..(36)
<223> OTHER INFORMATION: Any amino acid

<400> SEQUENCE: 94

Cys Xaa Xaa Xaa Xaa Xaa Xaa Xaa Xaa Xaa Xaa Cys Xaa Xaa Xaa
1               5                   10                  15

Xaa Xaa Cys Xaa Xaa Xaa Xaa Xaa Cys Xaa Xaa Xaa Xaa Xaa Xaa
            20                  25                  30

Xaa Cys Xaa Xaa Cys
        35

<210> SEQ ID NO 95
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
```

<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(35)
<223> OTHER INFORMATION: Any amino acid

<400> SEQUENCE: 95

Cys Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Cys Xaa Xaa Xaa Xaa
            20                  25                  30

Xaa Xaa Xaa Cys
        35

<210> SEQ ID NO 96
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(30)
<223> OTHER INFORMATION: Any amino acid
<220> FEATURE:
<221> NAME/KEY: MOD_RES
<222> LOCATION: (32)..(39)
<223> OTHER INFORMATION: Any amino acid
<220> FEATURE:
<221> NAME/KEY: MOD_RES
<222> LOCATION: (41)..(42)
<223> OTHER INFORMATION: Any amino acid

<400> SEQUENCE: 96

Cys Xaa Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Cys Xaa Xaa Xaa Cys Xaa
            20                  25                  30

Xaa Xaa Xaa Xaa Xaa Xaa Xaa Cys Xaa Xaa Cys
        35                  40

<210> SEQ ID NO 97
<211> LENGTH: 43
<212> TYPE: PRT
<213> ORGANISM: Artificial Sequence
<220> FEATURE:

```
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(29)
<223> OTHER INFORMATION: Any amino acid
<220> FEATURE:
<221> NAME/KEY: MOD_RES
<222> LOCATION: (31)..(36)
<223> OTHER INFORMATION: Any amino acid
<220> FEATURE:
<221> NAME/KEY: MOD_RES
<222> LOCATION: (38)..(42)
<223> OTHER INFORMATION: Any amino acid

<400> SEQUENCE: 97

Cys Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Cys Xaa Xaa Cys Xaa Xaa
            20                  25                  30

Xaa Xaa Xaa Xaa Cys Xaa Xaa Xaa Xaa Xaa Cys
        35                  40

<210> SEQ ID NO 98
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(28)
<223> OTHER INFORMATION: Any amino acid
<220> FEATURE:
<221> NAME/KEY: MOD_RES
<222> LOCATION: (30)..(37)
<223> OTHER INFORMATION: Any amino acid

<400> SEQUENCE: 98

Cys Xaa Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Xaa Xaa Cys Xaa Xaa Xaa
            20                  25                  30
```

Xaa Xaa Xaa Xaa Xaa Cys
           35

<210> SEQ ID NO 99
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(8)
<223> OTHER INFORMATION: Any amino acid
<220> FEATURE:
<221> NAME/KEY: MOD_RES
<222> LOCATION: (10)..(15)
<223> OTHER INFORMATION: Any amino acid
<220> FEATURE:
<221> NAME/KEY: MOD_RES
<222> LOCATION: (17)..(19)
<223> OTHER INFORMATION: Any amino acid
<220> FEATURE:
<221> NAME/KEY: MOD_RES
<222> LOCATION: (21)..(23)
<223> OTHER INFORMATION: Any amino acid
<220> FEATURE:
<221> NAME/KEY: MOD_RES
<222> LOCATION: (25)..(33)
<223> OTHER INFORMATION: Any amino acid

<400> SEQUENCE: 99

Cys Xaa Xaa Xaa Xaa Xaa Xaa Xaa Cys Xaa Xaa Xaa Xaa Xaa Xaa Cys
1               5                   10                  15

Xaa Xaa Xaa Cys Xaa Xaa Xaa Cys Xaa Xaa Xaa Xaa Xaa Xaa Xaa Xaa
            20                  25                  30

Xaa Cys

<210> SEQ ID NO 100
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(10)
<223> OTHER INFORMATION: Any amino acid
<220> FEATURE:
<221> NAME/KEY: MOD_RES
<222> LOCATION: (12)..(19)
<223> OTHER INFORMATION: Any amino acid
<220> FEATURE:
<221> NAME/KEY: MOD_RES
<222> LOCATION: (21)..(25)
<223> OTHER INFORMATION: Any amino acid
<220> FEATURE:
<221> NAME/KEY: MOD_RES
<222> LOCATION: (27)..(32)
<223> OTHER INFORMATION: Any amino acid
<220> FEATURE:
<221> NAME/KEY: MOD_RES
<222> LOCATION: (34)..(38)
<223> OTHER INFORMATION: Any amino acid

<400> SEQUENCE: 100

Cys Xaa Xaa Xaa Xaa Xaa Xaa Xaa Xaa Xaa Cys Xaa Xaa Xaa Xaa Xaa
1               5                   10                  15

Xaa Xaa Xaa Cys Xaa Xaa Xaa Xaa Xaa Cys Xaa Xaa Xaa Xaa Xaa Xaa
            20                  25                  30

Cys Xaa Xaa Xaa Xaa Xaa Cys
        35

<210> SEQ ID NO 101
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(14)
<223> OTHER INFORMATION: Any amino acid
<220> FEATURE:
<221> NAME/KEY: MOD_RES
<222> LOCATION: (16)..(17)
<223> OTHER INFORMATION: Any amino acid
<220> FEATURE:
<221> NAME/KEY: MOD_RES
<222> LOCATION: (19)..(25)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (29)..(39)
<223> OTHER INFORMATION: Any amino acid
<220> FEATURE:
<221> NAME/KEY: MOD_RES
<222> LOCATION: (41)..(45)
<223> OTHER INFORMATION: Any amino acid

<400> SEQUENCE: 101

Cys Xaa Xaa Xaa Xaa Xaa Xaa Xaa Xaa Xaa Xaa Cys Xaa Xaa Cys Xaa
1               5                   10                  15

Xaa Cys Xaa Xaa Xaa Xaa Xaa Xaa Xaa Cys Xaa Cys Xaa Xaa Xaa Xaa
            20                  25                  30

Xaa Xaa Xaa Xaa Xaa Xaa Xaa Cys Xaa Xaa Xaa Xaa Xaa Cys
        35                  40                  45

<210> SEQ ID NO 102
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(11)
<223> OTHER INFORMATION: Any amino acid
<220> FEATURE:
<221> NAME/KEY: MOD_RES
<222> LOCATION: (13)..(18)
<223> OTHER INFORMATION: Any amino acid
<220> FEATURE:
<221> NAME/KEY: MOD_RES
<222> LOCATION: (20)..(24)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (28)..(29)
<223> OTHER INFORMATION: Any amino acid

```
<220> FEATURE:
<221> NAME/KEY: MOD_RES
<222> LOCATION: (31)..(38)
<223> OTHER INFORMATION: Any amino acid
<220> FEATURE:
<221> NAME/KEY: MOD_RES
<222> LOCATION: (40)..(43)
<223> OTHER INFORMATION: Any amino acid

<400> SEQUENCE: 102

Cys Xaa Xaa Xaa Xaa Xaa Xaa Xaa Xaa Xaa Cys Xaa Xaa Xaa Xaa
1               5                   10                  15

Xaa Xaa Cys Xaa Xaa Xaa Xaa Xaa Cys Xaa Cys Xaa Xaa Cys Xaa Xaa
            20                  25                  30

Xaa Xaa Xaa Xaa Xaa Xaa Cys Xaa Xaa Xaa Xaa Cys
        35                  40

<210> SEQ ID NO 103
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(25)
<223> OTHER INFORMATION: This sequence may encompass 1-5 "Gly Gly Gly
      Gly Ser" repeating units wherein some positions may be absent

<400> SEQUENCE: 103

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 104
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ile Glu Gly Arg
1

<210> SEQ ID NO 105
<211> LENGTH: 6
<212> TYPE: PRT
<213> ORGANISM: Bos sp.
<220> FEATURE:
<221> NAME/KEY: MOD_RES
<222> LOCATION: (3)..(3)
<223> OTHER INFORMATION: Thr or Ser

<400> SEQUENCE: 105

Cys Thr Xaa Val His Gln
1               5

<210> SEQ ID NO 106
<211> LENGTH: 14
<212> TYPE: PRT
<213> ORGANISM: Bos sp.
<220> FEATURE:
<221> NAME/KEY: MOD_RES
<222> LOCATION: (3)..(3)
```

```
<223> OTHER INFORMATION: Thr or Ser
<220> FEATURE:
<221> NAME/KEY: MOD_RES
<222> LOCATION: (7)..(14)
<223> OTHER INFORMATION: Any amino acid and this region may encompass
      1-8 residues

<400> SEQUENCE: 106

Cys Thr Xaa Val His Gln Xaa Xaa Xaa Xaa Xaa Xaa Xaa Xaa
1               5                   10

<210> SEQ ID NO 107
<211> LENGTH: 6
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Thr, Ser, Ala or Gly
<220> FEATURE:
<221> NAME/KEY: MOD_RES
<222> LOCATION: (3)..(3)
<223> OTHER INFORMATION: Thr, Ser, Ala, Pro or Ile
<220> FEATURE:
<221> NAME/KEY: MOD_RES
<222> LOCATION: (4)..(4)
<223> OTHER INFORMATION: Val or Lys
<220> FEATURE:
<221> NAME/KEY: MOD_RES
<222> LOCATION: (5)..(5)
<223> OTHER INFORMATION: His, Lys or Tyr

<400> SEQUENCE: 107

Cys Xaa Xaa Xaa Xaa Gln
1               5

<210> SEQ ID NO 108
<211> LENGTH: 5
<212> TYPE: PRT
<213> ORGANISM: Bos sp.
<220> FEATURE:
<221> NAME/KEY: MOD_RES
<222> LOCATION: (1)..(1)
<223> OTHER INFORMATION: Thr, Ser, Ala or Gly
<220> FEATURE:
<221> NAME/KEY: MOD_RES
<222> LOCATION: (2)..(2)
<223> OTHER INFORMATION: Thr, Ser, Ala, Pro or Ile

<400> SEQUENCE: 108

Xaa Xaa Val His Gln
1               5

<210> SEQ ID NO 109
<211> LENGTH: 6
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Thr, Ser, Ala or Gly
<220> FEATURE:
<221> NAME/KEY: MOD_RES
<222> LOCATION: (3)..(3)
<223> OTHER INFORMATION: Thr, Ser, Ala, Pro or Ile

<400> SEQUENCE: 109

Cys Xaa Xaa Val His Gln
1               5

<210> SEQ ID NO 110
```

```
<211> LENGTH: 5
<212> TYPE: PRT
<213> ORGANISM: Bos sp.
<220> FEATURE:
<221> NAME/KEY: MOD_RES
<222> LOCATION: (1)..(1)
<223> OTHER INFORMATION: Thr, Ser, Ala or Gly
<220> FEATURE:
<221> NAME/KEY: MOD_RES
<222> LOCATION: (2)..(2)
<223> OTHER INFORMATION: Thr, Ser, Ala, Pro or Ile
<220> FEATURE:
<221> NAME/KEY: MOD_RES
<222> LOCATION: (4)..(4)
<223> OTHER INFORMATION: His, Tyr or Lys

<400> SEQUENCE: 110

Xaa Xaa Val Xaa Gln
1               5

<210> SEQ ID NO 111
<211> LENGTH: 6
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Thr, Ser, Ala or Gly
<220> FEATURE:
<221> NAME/KEY: MOD_RES
<222> LOCATION: (3)..(3)
<223> OTHER INFORMATION: Thr, Ser, Ala, Pro or Ile
<220> FEATURE:
<221> NAME/KEY: MOD_RES
<222> LOCATION: (5)..(5)
<223> OTHER INFORMATION: His, Tyr or Lys

<400> SEQUENCE: 111

Cys Xaa Xaa Val Xaa Gln
1               5

<210> SEQ ID NO 112
<211> LENGTH: 5
<212> TYPE: PRT
<213> ORGANISM: Bos sp.
<220> FEATURE:
<221> NAME/KEY: MOD_RES
<222> LOCATION: (1)..(1)
<223> OTHER INFORMATION: Thr, Ser, Ala or Gly
<220> FEATURE:
<221> NAME/KEY: MOD_RES
<222> LOCATION: (2)..(2)
<223> OTHER INFORMATION: Thr, Ser, Ala, Pro or Ile

<400> SEQUENCE: 112

Xaa Xaa Lys Lys Gln
1               5

<210> SEQ ID NO 113
<211> LENGTH: 6
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Thr, Ser, Ala or Gly
<220> FEATURE:
<221> NAME/KEY: MOD_RES
<222> LOCATION: (3)..(3)
<223> OTHER INFORMATION: Thr, Ser, Ala, Pro or Ile

<400> SEQUENCE: 113
```

Cys Xaa Xaa Lys Lys Gln
1               5

<210> SEQ ID NO 114
<211> LENGTH: 4
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Thr, Ser, Asn or Ile
<220> FEATURE:
<221> NAME/KEY: MOD_RES
<222> LOCATION: (4)..(4)
<223> OTHER INFORMATION: Glu or Asp

<400> SEQUENCE: 114

Tyr Xaa Tyr Xaa
1

<210> SEQ ID NO 115
<211> LENGTH: 5
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Leu, Ser, Thr or Arg
<220> FEATURE:
<221> NAME/KEY: MOD_RES
<222> LOCATION: (4)..(4)
<223> OTHER INFORMATION: Thr, Ser, Asn or Ile

<400> SEQUENCE: 115

Tyr Xaa Tyr Xaa Tyr
1               5

<210> SEQ ID NO 116
<211> LENGTH: 6
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Leu, Ser, Thr or Arg
<220> FEATURE:
<221> NAME/KEY: MOD_RES
<222> LOCATION: (4)..(4)
<223> OTHER INFORMATION: Thr, Ser, Asn or Ile
<220> FEATURE:
<221> NAME/KEY: MOD_RES
<222> LOCATION: (6)..(6)
<223> OTHER INFORMATION: Glu or Asp

<400> SEQUENCE: 116

Tyr Xaa Tyr Xaa Tyr Xaa
1               5

<210> SEQ ID NO 117
<211> LENGTH: 7
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Leu, Ser, Thr or Arg
<220> FEATURE:
<221> NAME/KEY: MOD_RES
<222> LOCATION: (4)..(4)
<223> OTHER INFORMATION: Thr, Ser, Asn or Ile
<220> FEATURE:
<221> NAME/KEY: MOD_RES

```
<222> LOCATION: (6)..(6)
<223> OTHER INFORMATION: Glu or Asp
<220> FEATURE:
<221> NAME/KEY: MOD_RES
<222> LOCATION: (7)..(7)
<223> OTHER INFORMATION: His, Trp, Asn, Phe, Ile or Tyr

<400> SEQUENCE: 117

Tyr Xaa Tyr Xaa Tyr Xaa Xaa
1               5

<210> SEQ ID NO 118
<211> LENGTH: 3
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Glu or Asp
<220> FEATURE:
<221> NAME/KEY: MOD_RES
<222> LOCATION: (3)..(3)
<223> OTHER INFORMATION: His, Trp, Asn, Phe, Ile or Tyr

<400> SEQUENCE: 118

Tyr Xaa Xaa
1

<210> SEQ ID NO 119
<211> LENGTH: 3
<212> TYPE: PRT
<213> ORGANISM: Bos sp.
<220> FEATURE:
<221> NAME/KEY: MOD_RES
<222> LOCATION: (1)..(1)
<223> OTHER INFORMATION: Thr, Ser, Asn or Ile
<220> FEATURE:
<221> NAME/KEY: MOD_RES
<222> LOCATION: (3)..(3)
<223> OTHER INFORMATION: Glu or Asp

<400> SEQUENCE: 119

Xaa Tyr Xaa
1

<210> SEQ ID NO 120
<211> LENGTH: 8
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Glu or Asp
<220> FEATURE:
<221> NAME/KEY: MOD_RES
<222> LOCATION: (3)..(3)
<223> OTHER INFORMATION: His, Trp, Asn, Phe, Ile or Tyr
<220> FEATURE:
<221> NAME/KEY: MOD_RES
<222> LOCATION: (4)..(7)
<223> OTHER INFORMATION: Any amino acid and this region may encompass
     1-4 residues

<400> SEQUENCE: 120

Tyr Xaa Xaa Xaa Xaa Xaa Xaa Trp
1               5

<210> SEQ ID NO 121
<211> LENGTH: 8
<212> TYPE: PRT
<213> ORGANISM: Bos sp.
```

```
<220> FEATURE:
<221> NAME/KEY: MOD_RES
<222> LOCATION: (2)..(2)
<223> OTHER INFORMATION: Glu or Asp
<220> FEATURE:
<221> NAME/KEY: MOD_RES
<222> LOCATION: (3)..(3)
<223> OTHER INFORMATION: His, Trp, Asn, Phe, Ile or Tyr
<220> FEATURE:
<221> NAME/KEY: MOD_RES
<222> LOCATION: (4)..(4)
<223> OTHER INFORMATION: Tyr, His, Gly or Asn
<220> FEATURE:
<221> NAME/KEY: MOD_RES
<222> LOCATION: (5)..(5)
<223> OTHER INFORMATION: Val, Ile or Ala
<220> FEATURE:
<221> NAME/KEY: MOD_RES
<222> LOCATION: (6)..(6)
<223> OTHER INFORMATION: Asp, Asn, Thr or Glu
<220> FEATURE:
<221> NAME/KEY: MOD_RES
<222> LOCATION: (7)..(7)
<223> OTHER INFORMATION: Ala, Val, Ser or Thr

<400> SEQUENCE: 121

Tyr Xaa Xaa Xaa Xaa Xaa Xaa Trp
1               5

<210> SEQ ID NO 122
<211> LENGTH: 7
<212> TYPE: PRT
<213> ORGANISM: Bos sp.
<220> FEATURE:
<221> NAME/KEY: MOD_RES
<222> LOCATION: (3)..(3)
<223> OTHER INFORMATION: Thr or Ser
<220> FEATURE:
<221> NAME/KEY: MOD_RES
<222> LOCATION: (7)..(7)
<223> OTHER INFORMATION: Any amino acid

<400> SEQUENCE: 122

Cys Thr Xaa Val His Gln Xaa
1               5

<210> SEQ ID NO 123
<211> LENGTH: 3
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Glu or Asp
<220> FEATURE:
<221> NAME/KEY: MOD_RES
<222> LOCATION: (3)..(3)
<223> OTHER INFORMATION: Any amino acid

<400> SEQUENCE: 123

Tyr Xaa Xaa
1

<210> SEQ ID NO 124
<211> LENGTH: 3
<212> TYPE: PRT
<213> ORGANISM: Bos sp.
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
```

```
<222> LOCATION: (3)..(3)
<223> OTHER INFORMATION: Glu or Asp

<400> SEQUENCE: 124

Xaa Tyr Xaa
1

<210> SEQ ID NO 125
<211> LENGTH: 5
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Glu or Asp
<220> FEATURE:
<221> NAME/KEY: MOD_RES
<222> LOCATION: (3)..(4)
<223> OTHER INFORMATION: Any amino acid

<400> SEQUENCE: 125

Tyr Xaa Xaa Xaa Trp
1               5

<210> SEQ ID NO 126
<211> LENGTH: 8
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Glu or Asp
<220> FEATURE:
<221> NAME/KEY: MOD_RES
<222> LOCATION: (3)..(7)
<223> OTHER INFORMATION: Any amino acid

<400> SEQUENCE: 126

Tyr Xaa Xaa Xaa Xaa Xaa Xaa Trp
1               5

<210> SEQ ID NO 127
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Pro or Ser

<400> SEQUENCE: 127

Cys Xaa Asp Gly
1

<210> SEQ ID NO 128
<211> LENGTH: 5
<212> TYPE: PRT
<213> ORGANISM: Bos sp.
<220> FEATURE:
<221> NAME/KEY: MOD_RES
<222> LOCATION: (2)..(2)
<223> OTHER INFORMATION: Ser or Thr

<400> SEQUENCE: 128

Thr Xaa Val His Gln
1               5
```

```
<210> SEQ ID NO 129
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 129

Gly Gly Gly Gly Ser
1               5
```